US009919299B2

(12) United States Patent
Ondi et al.

(10) Patent No.: US 9,919,299 B2
(45) Date of Patent: Mar. 20, 2018

(54) METATHESIS CATALYSTS AND REACTIONS USING THE CATALYSTS

(71) Applicant: XiMo AG, Horw/Lucerne (CH)

(72) Inventors: Levente Ondi, Veresegyhaz (HU); Jeno Varga, Budapest (HU); Agota Bucsai, Budapest (HU); Florian Toth, Magyarhertelend (HU); Krisztian Lorincz, Budapest (HU); Csaba Hegedus, Gyal (HU); Emmanuel Robe, Tatabanya (HU); Georg Emil Frater, Schwand (CH)

(73) Assignee: Ximo AG, Horw/Lucerne (CH)

( * ) Notice: Subject to any disclaimer, the term of this patent is extended or adjusted under 35 U.S.C. 154(b) by 0 days.

(21) Appl. No.: 14/774,404

(22) PCT Filed: Mar. 13, 2014

(86) PCT No.: PCT/EP2014/000671
§ 371 (c)(1),
(2) Date: Sep. 10, 2015

(87) PCT Pub. No.: WO2014/139679
PCT Pub. Date: Sep. 18, 2014

(65) Prior Publication Data

US 2016/0030936 A1 Feb. 4, 2016

Related U.S. Application Data

(60) Provisional application No. 61/781,120, filed on Mar. 14, 2013.

(30) Foreign Application Priority Data

Mar. 14, 2013 (EP) .................................... 13001297

(51) Int. Cl.
*B01J 31/22* (2006.01)
*C07C 6/04* (2006.01)
(Continued)

(52) U.S. Cl.
CPC ......... *B01J 31/2265* (2013.01); *B01J 31/143* (2013.01); *B01J 31/1608* (2013.01); *B01J 31/181* (2013.01); *B01J 31/1805* (2013.01); *B01J 31/223* (2013.01); *B01J 31/2208* (2013.01); *B01J 31/2226* (2013.01);
(Continued)

(58) Field of Classification Search
CPC ............................... B01J 31/2265; C07C 6/04
See application file for complete search history.

(56) References Cited

U.S. PATENT DOCUMENTS 3,696,161 A 1/1972 Kobetz et al.
4,637,197 A 1/1987 Banfield et al.
(Continued)

FOREIGN PATENT DOCUMENTS

EP 0116408 1/1984
EP 2703081 3/2014
(Continued)

OTHER PUBLICATIONS

Office Action dated Oct. 9, 2013 for U.S. Appl. No. 14/011,811.
Allen, et al., "Preparation of High Purity, Anionic Polymerization Grade Alkyl Mathacrylate Monomers", Polymer Bulletin, 15, 1986, pp. 127-134.
Bailey, et al., "Evaluation of Molybdenum and Tungsten Metathesis Catalysts for Homogeneous Tandem Alkane Metathesis", Organometallics, vol. 28, 2009, pp. 355-360.
Blanc, et al., "Direct Observation of Reaction Intermediates for a Well Defined Heterogeneous Alkene Metathesis Catalyst", PNAS, vol. 105 No. 34, Aug. 26, 2008, pp. 12123-12127.
(Continued)

*Primary Examiner* — Shawquia Jackson
(74) *Attorney, Agent, or Firm* — Stoel Rives LLP

(57) ABSTRACT

The invention relates to a method of forming an olefin from a first olefin and a second olefin in a metathesis reaction, comprising step (i): (i) reacting the first olefin with the second olefin in the presence of a compound that catalyzes said metathesis reaction such that the molar ratio of said compound to the first or the second olefin is from 1:500 or less, and the conversion of the first or the second olefin to said olefin is at least 50%, characterized in that as compound that catalyzes said metathesis reaction a compound of formula (A) is used: wherein M is Mo or W; $R^1$ is aryl, heteroaryl, alkyl, or heteroalkyl; optionally substituted; $R^2$ and $R^3$ can be the same or different and are hydrogen, alkyl, alkenyl, heteroalkyl, heteroalkenyl, aryl, or heteroaryl; optionally substituted; $R^5$ is alkyl, alkoxy, heteroalkyl, aryl, heteroaryl, silylalkyl, silyloxy, optionally substituted; and $R^4$ is a residue $R^6$—X—, wherein X═O and $R^6$ is aryl, optionally substituted; or X═S and $R^6$ is aryl, optionally substituted; or X═O and $R^6$ is ($R^7$, $R^8$, $R^9$)Si; wherein $R^7$, $R^8$, $R^9$ are alkyl or phenyl, optionally substituted; or X═O and $R^6$ is ($R^{10}$, $R^{11}$, $R^{12}$)C, wherein $R^{10}$, $R^{11}$, $R^{12}$ are independently selected from phenyl, alkyl; optionally substituted; and to the catalysts used in the method.

(A)

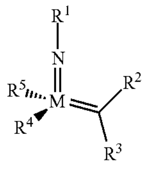

15 Claims, No Drawings

(51) Int. Cl.

| | |
|---|---|
| ***B01J 31/16*** | (2006.01) |
| ***B01J 31/18*** | (2006.01) |
| ***C07F 11/00*** | (2006.01) |
| ***B01J 31/14*** | (2006.01) |
| ***C08G 61/08*** | (2006.01) |
| ***C07C 67/293*** | (2006.01) |
| ***C07C 67/347*** | (2006.01) |

(52) U.S. Cl.

CPC .............. *C07C 6/04* (2013.01); *C07C 67/293* (2013.01); *C07C 67/347* (2013.01); *C07F 11/00* (2013.01); *C08G 61/08* (2013.01); *B01J 2231/543* (2013.01); *B01J 2531/0266* (2013.01); *B01J 2531/0288* (2013.01); *B01J 2531/64* (2013.01); *B01J 2531/66* (2013.01); *B01J 2540/20* (2013.01); *B01J 2540/22* (2013.01); *B01J 2540/225* (2013.01); *C07C 2531/12* (2013.01); *C07C 2531/22* (2013.01); *C07C 2601/10* (2017.05); *C08G 2261/418* (2013.01)

(56) References Cited

U.S. PATENT DOCUMENTS

| | | | |
|---|---|---|---|
| 5,378,783 | A | 1/1995 | Okumura et al. |
| 6,121,473 | A | 9/2000 | Schrock et al. |
| 8,993,470 | B2 | 3/2015 | Fuerstner et al. |
| 9,079,173 | B2 | 7/2015 | Schrock et al. |
| 2003/0135080 | A1 | 7/2003 | Botha et al. |
| 2005/0107529 | A1 | 5/2005 | Datta et al. |
| 2005/0124839 | A1 | 6/2005 | Gartside et al. |
| 2008/0119678 | A1 | 5/2008 | Hock et al. |
| 2011/0015430 | A1 | 1/2011 | Schrock et al. |
| 2011/0077421 | A1 | 3/2011 | Schrock et al. |
| 2011/0160472 | A1 | 6/2011 | Lemke et al. |
| 2011/0263917 | A1 | 10/2011 | Van Hal et al. |
| 2012/0316057 | A1 | 12/2012 | Taoufik et al. |
| 2013/0006012 | A1 | 1/2013 | Firth et al. |
| 2013/0035502 | A1 | 2/2013 | Cohen et al. |
| 2013/0144102 | A1 | 6/2013 | Fuerstner et al. |
| 2013/0217906 | A1 | 8/2013 | Kunz et al. |
| 2014/0275595 | A1 | 9/2014 | Wampler et al. |
| 2014/0309466 | A1 | 10/2014 | Ondi et al. |
| 2016/0122375 | A1 | 5/2016 | Coperet et al. |

FOREIGN PATENT DOCUMENTS

| | | | |
|---|---|---|---|
| WO | 2008066754 | | 6/2008 |
| WO | 2009094201 | A1 | 7/2009 |
| WO | 2011007742 | A1 | 1/2011 |
| WO | 2011097642 | | 8/2011 |
| WO | 2011097642 | A1 | 8/2011 |

OTHER PUBLICATIONS

Blanc, et al., "'Highly Active, Stable, and Selective Well-Defined Silica Supported Mo Imido Olefin Metathesis Catalysts'", JACS, 2007, vol. 129 No. 5, pp. 1044-1045.

EP13003540.5, Extended European Search Report, dated Dec. 11, 2013.

Heppekausen, et al., "Practical New Sulyloxy-Based Alkyne Metathesis Catalysts with Optimized Activity and Selectivity Profiles", J Am Chem Soc., vol. 132 No. 32, 2010, pp. 11045-11057.

Jiang, et al., "Highly Z-Selective Metathesis Homocoupling of Terminal Olefins", Journal of the American Chemical SocietyACS Publications, US, vol. 131 No. 46, Nov. 25, 2009, pp. 16630-16631.

Lee, et al., "Endo-Selective Enyne Ring-Closing Metathesis Promoted by Steriogenetic-at-Mo Monoalkoxide and Momoaryloxide Complexes Efficient Synthesis of Cyclic Dienes Not Accessible Through Reactions with Ru Carbenes", Journal of the American Chemical Society, vol. 131, 2009, pp. 10652-10661.

Marinescu, et al., "Ethenolysis Reactions Catalyzed by Imido Alkylinene Monoaryloxide Monopyrrolide (MAP) Complexes of Molybdenum", Journal of the American Chemical Society, ACS Publications, US, vol. 131 No. 31, Aug. 12, 2009, pp. 10840-10841.

Marinescu, et al., "Simple Molybdenum (IV) Olefin Complexes of the Type Mo )NR) (X) (Y) (olefin)", Organometiallics, vol. 29 No. 24, Dec. 2, 2010, pp. 6816-6828.

PCT/EP2014/001910, International Search Report and Written Opinion, dated Sep. 24, 2014.

Schrock, "Recent Advances in High Oxidation State Mo and W Imido Alkylidene Chemistry", Chemical Reviews, vol. 109 No. 8, Mar. 13, 2009, pp. 3211-3226.

Tsai, et al., "Facile Synthesis of Trialkoxymolybdenum (VI) Alkylidyne Complexes for Alkyne Metathesis", Organmetallics, vol. 19 No. 25, 2000, pp. 5260-5262.

Yu, et al., "Enol Ethers and Substrates for Efficient Z- and Enantioselective Ring-Opening/Cross-Metathesis Reactions Promoted by Stereogenic-at-Mo Complexes: Utility in chemical Synthesis and Mecahnistic Attributes—Supporting Information Part A", J Am Chem Soc. vol. 134, 2012, pp. SIA-2-SIA-26.

Yu, et al., "Enol Ethers as Substrates for Efficient Z- and Enantioselective Ring-Opening/Cross-Metathesis Reactions Promoted by Steriogenic-at-Mo Complexes: Utility in chemical Synthesis and Mechanistic Attributes", Journal of the American Chemical Society, vol. 134, 2012, pp. 2788-2799.

Yu, "Synthesis of Macrocyclic Natural Products by Catalyst-Controlled Stereoselective Ring-Closing Metathesis", Nature, vol. 479 No. 7371, Nov. 2, 2011, pp. 89-93.

Office Action dated Feb. 10, 2017 for U.S. Appl. No. 14/209,313.

Blanc, et al., "Dramatic Improvements of Well-Defined Silica Supported Mo-Based Olefin Metathesis Catalysts by Tuning the N-Containing Ligands", J Am Chem Soc., 129(27), 2007, 8434-8435.

Blanc, et al., "Highly Active, Stable, and Selective Well-Defined Silica Supported Mo Imido Olefin Metathesis Catalysts", J Am Chem Soc., 129(17), 2007, 1044-1045.

U.S. Appl. No. 13/639,067, Notice of Allowance, dated Jan. 21, 2015, 19 pages.

U.S. Appl. No. 14/001,811, Non-Final Office Action, dated Jun. 30, 2015, 14 pages.

U.S. Appl. No. 14/011,811, Office Action, dated Oct. 9, 2015.

Bailey, et al., "Evaluation of Molybdenum and Tungsten Metathesis Catalysts for Homogeneous Tandem Alkane Metathesis", Organometallics, 28, 2009, pp. 355-360.

Blanc, et al., "Dramatic Improvements of Well-Defined Silica Supported Mo-Based Olefin Metathesis Catalysts by Tuning the N-Containing Ligands", JACS, vol. 129 No. 27, 2007, pp. 8434-8435.

EP13003541.3, European Search Report, dated Nov. 25, 2013.

Fox, et al., "Synthesis of Five- and Six-Coordinate Alkylidene Complexes of the Type Mo (CHR) (NAr) [OCMe (CF3) 2Sx and Their Use as Living ROMP Initiators or Wittig Reagents", American Chemical Society, Organometallics, 12, 1993, pp. 759-768.

Heppekausen, et al., "Rendering Schrock-type Molybdenum Alkylidene Complexes Air Stable: User-Friendly Precatalysts for Alkene Metathesis", Angewandte Chemie (International Ed.) vol. 123, No. 34, Aug. 16, 2011, pp. 7975-7978.

Lee, et al., "Endo-Selective Enyne Ring-Closing Metathesis Promoted by Stereogenic-at-Mo Monoalkoxide and Monoaryloxide Complexes. Efficient Synthesis of Cyclic Dienes Not Accessible Through Reactions with Ru Carbines", J Am Chem Soc., 131(30), Aug. 5, 2009, 10652-10661.

PCT/DE2011/000348, International Search Report and Written Opinion with English Translation, dated Jul. 22, 2011, 10 pages.

PCT/DE2011/000348, International Preliminary Report on Patentability, dated Oct. 9, 2012, 5 pages.

PCT/DE2012/100047, International Search Report and Written Opinion (with English translation), Jul. 24, 2012, 10 pages.

PCT/DE2012/100047, International Preliminary Report on Patentability, dated Sep. 3, 2013, 6 pages.

PCT/EP2014/001909, International Search Report and Written Opinion, dated Aug. 7, 2014.

(56) References Cited

OTHER PUBLICATIONS

Rendon, et al., “Well-Defined Silica-Supported No-Alkylidene Catalyst Precursors Containing One or Subsitituent: Methods of Preparation and Structure-Reactivity Relationship in Alkene Metathesis”, Chem. Euro. J., 15, 2009, pp. 5083-5089.
Totland, et al., “Ring Opening Metathesis Polymerization with Binaphtholate or Bibhenolate Complexes of Molybdenum”, American Chemical Society, Macromolecules, 29, 1996, pp. 6114-6125.
Tsai, et al., “Facile Synthesis of Trialkoxymolybdenum(VI) Alkylidyne Complexes for Alkyne Metathesis”, Organometallics, 19, 2000, 5260-5262.
Yu, et al., “Enol Ethers as Substrates for Effecient Z- and Enentioselective Ring-Opening/Cross-Metathesis Reactions Promoted by Sterogenis-at-Mo Complexes: Utility in Chemical Synthesis and Mechanistice Atrributes”, J. Chem. Soc., 134, 2012, 2788-2799.
Arndt, et al., “Synthesis and Reactions of Tungsten Alkylidene Complexes that Contain the 2,6-Dichlorophenylimido Ligand”, Organometallics, 26, 2007, pp. 1279-1290.
Bindl, et al., “Molybdenum Nitride Complexes with Ph3SiO Ligands are Exceedingly Practical and Tolerant Precatalysts for Alkyne Metathesis and Efficient Nitrogen Transfer Agents”, J Am Chem Soc., 1321(27), Jul. 15, 2009, pp. 9468-9470.
Dolman, et al., “Enantioselective Synthesis of Cyclic Secondary Amines through Mo-Catalyzed Asymmetric Ring-Closing Metathesis (ARCM)”, Organic Letters col. 5, No. 25, 2003, pp. 4899-4902.
Flook, et al., “Z-Selective and Syndioselective Ring-Opening Metathesis Polymerization (ROMP) Initiated by Monoaryloxidepryrrolide (MAP) Catalysts”, Macromolecules vol. 43 No. 18, 2010, pp. 7515-7522.
Jiang, et al., “Fundamental Studies of Tungsten Alkylidene Imido Monoalkoxidepyrrolide Complexes”, J. Am. Chem. Soc. vol. 131, 2009, pp. 7770-7780.
Malcolmson, et al., “Highly efficient molybdenum-based catalysts for enantioselective alkene metathesis”, Nature, vol. 456, Dec. 25, 2008, pp. 933-937.
Marinescu, et al., “Syntheses of Variations of Stereogenic-at-Metal Imido Alkylidene Complexes of Molybdenum”, Organometallics, vol. 31 No. 17, 2012, pp. 6336-6343.
Mazoyer, et al., “Development of the First Well-Defined Tungsten Oxo Alkyl Derivatives Supported on Silica by SOMC: towards a Model of WO3/SiO2 Olefin Metathesis Catalyst”, Chem. Commun., 46, 2010, pp. 8944-8946.
Merle, et al., “On the Track to Silica-Supported Tungsten Oxo Metathesis Catalysts: Input from O Solid-State NMR”, Inorg. Chem., 52, 2013, pp. 10119-10130.
Oskam, et al., “Rational Isomers of Mo(VI) Alkylidene Complexes and Cis/Trans Polymer Structure: Investigations in Ring-Opening Metathesis Polymerization”, J. Am. Chem. Soc. 115, 1993, pp. 11831-11845.
PCT/EP2014/002654, International Search Report and Written Opinion, dated Dec. 17, 2014, 10 pages.
Peryshkov, et al., “Synthesis of Tungsten Oxo Alkylidene Complexes”, Organometallics, 31, 2012, pp. 7278-7286.
Peryshkov, et al., “Z-Selective Olefin Metathesis Reactions Promoted by Tungsten Oxo Alkylidene Complexes”, JACS, 133, 2011, pp. 20754-20757.
Rhers, et al., “A Well-Defined, Silica-Supported Tungsten Imido Alkylidene Olefin Metathesis Catalyst”, Organometallics, 25, 2006, 3554-3557.
Schrock, et al., “Further Studies of Imido Alkylidene Complexes of Tungsten, Well-Characterized Olefin Metathesis Catalysts with Controllable Activity”, Organometallics, 9(8), 1990, pp. 2262-2275.
Schrock, “High Oxidation State Multiple Metal-Carbon Bonds”, Chem Rev., 102, 2002, pp. 145-179.
Schrock, “Multiple Metal-Carbon Bonds for Catalytic Metathesis Reactions (Nobel Lecture)”, Angew Chem Int Ed Engl, 45(23), 2006, pp. 748-3759.
Schrock, et al., “Recent Advances in the Syntheses and Applications of Molybdenum and Tungsten Alkylidene and Alkylidene Catalysts for the Metathesis of Alkenes and Alkynes”, Adv Sys Catal., 349, 2007, 55 pages.
Singh, et al., “Synthesis of Monoalkoxide Monopyrrolyl Complexes Mo(NR)(CHR')(OR")(pyrrolyl) Enyne Metathesis with High Oxidation State Catalysts”, J. Am. Chem. Soc. 129, 2007, pp. 12654-12655.
Yuan, “Pentafluorophenylimido Alkylidene Complexes of Molybdenum and Tungsten”, Organometallics, vol. 31, 2012, pp. 4650-4653.
Office Action dated Aug. 24, 2017 for U.S. Appl. No. 14/209,313.
Meek, et al.,Catalytic Z-Selective Olefin Cross-Metathesis for Natural Product Synthesis, Nature 471 ,2011 ,461-466.
Blanc, et al., Surface versus Molecular Siloxy Ligands in Well-Defined Olefin Metathesis Catalysts: [{(RO)3SiO}Mo(=NAr)(=CHtBu)(CH2tBu)], Angew. Chem. Int. Ed. 2007, 45, 1216-1220.
Chabanas, et al., A Highly Active Well-Defined Rhenium Heterogenous Catalyst for Olefin Metathesis Prepared via Surface Organometallic Chemsitry, J. Am Chem Soc. 2001, 123, 2062-2063.
Frater, et al., Office Action dated Jun. 9, 2017 for U.S. Appl. No. 14/903,119.
Jiang, et al., Highly Z-Selective Metathesis Homocoupling of Terminal Olefins, J Am Chem Soc., 131 (46), 2009, 16630-16631.
Malcolmson, et al., Highly Efficient Molybdenum-Based Catalyst for Enantioselective Alkene Metathesis, Nature, 456(7224), Epub Nov. 16, 2008, Dec. 18, 2008, 933-937.
Solans-Monfort, et al., d0 Based Olefin Metathesis Catalysts, Re(=CR)(=CHR)(X)(Y): The Key Role of X and Y Ligands for Efficient Active Sites, J. Am. Chem. Soc. 2005, 127 14015-14025.
Wang, et al., Molybdenum-Based Complexes with Two Aryloxides and a Pentafluoroimido Ligand: Catalysts for Efficient Z-Selective Synthesis of a Macrocyclic Trisubstituted alkene by Ring-Closing Metathesis, Angew Chem Int Ed Engl, 52(7), 2013, 1939-1943.
Office Action dated Jan. 11, 2018 for U.S. Appl. No. 14/903,119.

METATHESIS CATALYSTS AND REACTIONS USING THE CATALYSTS

This invention relates to alkene metathesis reactions and metathesis catalysts suitable for use in said reactions.

Alkene metathesis (olefin metathesis) is a reaction between alkenes or olefinic groups, in which formally alkylidene groups are exchanged between the alkenes or olefinic groups. Examples of metathesis reactions include cross metathesis, i.e. the reaction between two different olefins forming a new olefin or new olefins, the ring opening metathesis of a cyclic diene, which may also proceed under polymerization, the ring closing metathesis of a diene, the ethenolysis of an olefin having an internal olefinic double bond to form an olefin having a terminal olefinic double bond, and the formation of internal olefin(s) from terminal olefin(s) via homo-metathesis reactions. The latter reaction may be regarded as a cross metathesis between two identical olefins. More generally, any two identical olefins may be reacted in a homo cross metathesis reaction.

US 2011/007742 Al relates generally to catalysts and processes for the Z-selective formation of internal olefin(s) from terminal olefin(s) via homo-metathesis reactions. The method comprises reacting a first molecule comprising a terminal double bond and a second, identical molecule via a homo-metathesis reaction to produce a product comprising an internal double bond, wherein the internal double bond of the product comprises one carbon atom from the terminal double bond of the first molecule and one carbon atom from the terminal double bond of the second carbon atom, and wherein at least about 60% of the internal double bond of the product is formed as the Z-isomer. This reaction is catalyzed by a compound of formula

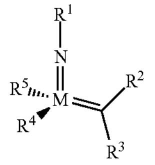

wherein M is Mo or W, $R^1$ is aryl, heteroaryl, alkyl, heteroalkyl, optionally substituted, $R^2$ and $R^3$ can be the same or different and are hydrogen, alkyl, alkenyl, heteroalkyl, heteroalkenyl, aryl, or heteroaryl, optionally substituted, and $R^4$ and $R^5$ can be the same or different and are alkyl, heteroalkyl, aryl, heteroaryl, silylalkyl, or silyloxy, optionally substituted, wherein at least one of $R^4$ or $R^5$ is a ligand containing oxygen bound to M. Preferably, bidentate structures may be used as ligand $R^4$.

Further compounds based on Mo and W useful as catalysts in metathesis reaction are known from U.S. Pat. No. 6,121,473, US 2008/0119678 and US 2011/0015430.

Such catalysts usually are applied or have to be applied in a metathesis reaction in a relatively high molar amount with respect to the molar amount of olefin or olefins in order to achieve a sufficient degree of conversion of the olefin(s) used as starting material. It is known that a molar ratio up to 1:500 with respect to the applied olefin(s) (molar ratio catalyst:olefin(s)) is necessary in order to achieve a conversion of 30% or more. Accordingly, and since these catalysts are relatively costive, such reactions are costive at an industrial scale, and thus often lack industrial applicability.

It is an object of the invention to provide a process for the manufacture of an olefin in a metathesis reaction and compounds useful as metathesis catalysts that perform metathesis in a molar amount as low as possible with respect to the molar amount of the applied olefin(s) and still allow for a high conversion while optionally providing for a specific stereoselectivity, and further optionally not only allowing for increased formation of Z-isomers in a homo-metathesis reaction, but which may beneficially catalyze other metathesis reactions such as cross metathesis or ethenolysis of an olefin having an internal olefinic bond. Accordingly, the process and the compounds should be able to allow for a conversion in a metathesis reaction of at least 30% when applied in a molar ratio of less than 1:500 with respect to the olefin(s) to be reacted. Such conversion and molar ratio are considered to allow for a beneficial reaction at an industrial scale.

First Aspect of the Invention—Metathesis Reactions According to the Invention and Compounds Used in the Metathesis Reactions According to the Invention According to a first aspect, this object is achieved with a method of forming an olefin from a first olefin and a second olefin in a metathesis reaction, comprising step (i):

(i) reacting the first olefin with the second olefin in the presence of a compound that catalyzes said metathesis reaction such that the molar ratio of said compound to the first or the second olefin is less than 1:500, and the conversion is at least 30%, wherein as compound that catalyzes said metathesis reaction a compound of the following general formula is used:

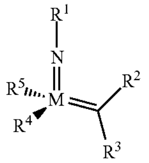

wherein M=Mo or W, and $R^1$, $R^2$, $R^3$, $R^5$ are selected among residues commonly used for catalysts of the above formula, and $R^4$ is selected such to be a residue $R^6$—X—, wherein X═O and $R^6$ is aryl, optionally substituted; or X═S and $R^6$ is aryl, optionally substituted; or X═O and $R^6$ is silyl; or X═O and $R^6$ is a residue, which is bound to the oxygen atom via a tertiary carbon atom;

or $R^4$ and $R^5$ are linked together and are bound to M via oxygen, respectively.

In one embodiment, $R^1$ to $R^5$ are selected such that a conversion of at least 30%, or at least 40%, or at least 50%, or at least 60%, or at least 70%, or at least 80% or at least 90% is achieved.

In one embodiment, $R^1$ to $R^5$ are selected such that the molar ratio of the compound of the above formula to first or the second olefin is 1:1,000 or less, or 1:2,500 or less, or 1:5,000 or less, or 1:7,500 or less, or 1:10,000 or less in order to achieve the object of the invention.

In one embodiment, $R^1$ to $R^5$ are selected such that the molar ratio is less than 1:500, and the corresponding conversion is at least 30%, or at least 40%, or at least 50%, or at least 60%, or at least 70%, or at least 80%, or at least 90%.

In one embodiment, $R^1$ to $R^5$ are selected such that the molar ratio is 1:1,000 or less, and the corresponding conversion is at least 30%, or at least 40%, or at least 50%, or at least 60%, or at least 70%, or at least 80%, or at least 90%.

In one embodiment, $R^1$ to $R^5$ are selected such that the molar ratio is 1:2,500 or less, and the corresponding conversion is at least 30%, or at least 40%, or at least 50%, or at least 60%, or at least 70%, or at least 80%, or at least 90%.

In one embodiment, $R^1$ to $R^5$ are selected such that the molar ratio is 1:5,000 or less, and the corresponding conversion is at least 30%, or at least 40%, or at least 50%, or at least 60%, or at least 70%, or at least 80%, or at least 90%.

In one embodiment, $R^1$ to $R^5$ are selected such that the molar ratio is 1:7,500 or less, and the corresponding conversion is at least 30%, or at least 40%, or at least 50%, or at least 60%, or at least 70%, or at least 80%, or at least 90%.

In one embodiment, $R^1$ to $R^5$ are selected such that the molar ratio is 1:10,000 or less, and the corresponding conversion is at least 30%, or at least 40%, or at least 50%, or at least 60%, or at least 70%, or at least 80%, or at least 90%.

In one embodiment, $R^1$ to $R^5$ are selected such that the molar ratio is 1:20,000 or less, or 1:50,000 or less, or 1:100,000 or less, or 1:500,000 or less, or 1:1,000,000 or less, and the corresponding conversion is at least 30%, or at least 40%, or at least 50%, or at least 60%, or at least 70%, or at least 80%, or at least 90%, respectively.

In one embodiment, the upper limit of the molar ratio of said compound, which catalyzes said metathesis reaction, to the first or second olefin is 1:2,000,000.

In other embodiments, $R^1$ to $R^5$ are selected such that the molar ratio is from less than 1:500 to 1:50,000 or less, and the corresponding conversion is from 30 to 100%, or from 50 to 100%, or 60 to 100%.

In one embodiment, $R^1$ to $R^5$ are selected such that the molar ratio is from 1:1,000 to 1:40,000 or less, and the corresponding conversion is from 30 to 100%, or from 50 to 100%, or 60 to 100%.

In one embodiment, $R^1$ to $R^5$ are selected such that the molar ratio is from 1:2,500 to 1:30,000 or less, and the corresponding conversion is from 30 to 100%, or from 50 to 100%, or 60 to 100%.

In one embodiment, $R^1$ to $R^5$ are selected such that the molar ratio is from 1:5,000 to 1:30,000 or less, or from 1:10,000 to 1:30,000, or from 1:15,000 to 1:30,000, and the corresponding conversion is from 30 to 100%, or from 50 to 100%, or 60 to 100%, respectively.

In one embodiment, the method consists of step (i).

In one embodiment, the first olefin has a terminal olefinic double bond, and the second olefin has a terminal olefinic double bond, wherein the first and the second olefin are identical. Accordingly, this reaction may be denoted as a homo-metathesis reaction. This reaction results in an olefin having an internal olefinic double bond, which is made from an olefin having a terminal olefinic double bond. Such reaction may also be termed as a cross-metathesis reaction between two identical olefins (homo-cross metathesis reaction).

Accordingly, in this embodiment, the invention relates to a method of forming an olefin having an internal olefinic double bond from an olefin having a terminal olefinic double bond in a metathesis reaction, comprising step (i.1):

(i.1) reacting the first olefin with the second olefin in the presence of a compound that catalyzes said metathesis reaction such that the molar ratio of said compound to the first or the second olefin is less than 1:500, and the conversion is at least 30%, wherein the first and the second olefin are identical, wherein as compound that catalyzes said metathesis reaction a compound of the following formula is used:

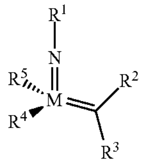

wherein M=Mo or W, and $R^1$ to $R^5$ are selected such to achieve the object of the invention.

The reaction as defined in step (i.1) may be performed according to methods and conditions known from the prior art, e.g. known from US 2011/0077421.

In one embodiment, at least 50% of the internal double bond is formed as the Z-isomer, further preferred more than 60%, still more preferred more than 70%, or more than 80%, or more than 90%.

In another embodiment, the first and the second olefin are different from one another. Such reaction may be termed as a cross-metathesis reaction between two different olefins.

Thus, in another embodiment, the invention relates to a method of forming an olefin (or olefins) from a first olefin and a second olefin in a metathesis reaction, comprising step (i.2):

(i.2) reacting the first olefin with the second olefin in the presence of a compound that catalyzes said metathesis reaction such that the molar ratio of said compound to the first or the second olefin is less than 1:500, and the conversion is at least 30%, wherein the first and the second olefin are different from one another;

wherein as compound that catalyzes said metathesis reaction a compound of the following formula is used:

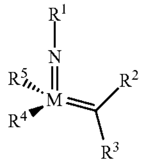

wherein M=Mo or W, and $R^1$ to $R^5$ are selected such to achieve the object of the invention.

In one embodiment, the first and the second olefin have an internal olefinic double bond, respectively.

In another embodiment, the first and the second olefin have a terminal olefinic double bond, respectively.

In another embodiment, the first olefin has a terminal olefinic double bond, and the second olefin has an internal olefinic group, or vice versa.

In one embodiment, the first olefin is an olefin having an internal olefinic double bond and the second olefin is ethylene. Such metathesis reaction may be termed as ethenolysis. This ethenolysis reaction results in an olefin or olefins having a terminal olefinic double bond, respectively.

Thus, in another embodiment, the invention relates to a method of forming an olefin having a terminal olefinic double bond from a first olefin having an internal olefinic double bond and a second olefin, wherein the second olefin is ethylene, comprising step (i.3):

(i.3) reacting the first olefin with the second olefin in the presence of a compound that catalyzes said metathesis reaction such that the molar ratio of said compound to the first or the second olefin is less than 1:500, and the conversion is at least 30%, wherein the first and the second olefin are different from one another;

wherein as compound that catalyzes said metathesis reaction a compound of the following formula is used:

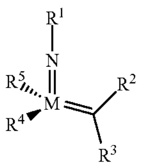

wherein M=Mo or W, and $R^1$ to $R^5$ are selected such to achieve the object of the invention.

In one embodiment, the first olefin is a cyclic olefin and the second olefin is a cyclic olefin, wherein the metathesis reaction is a ring opening polymerization metathesis.

Thus, in one embodiment, the invention relates to a method of forming a polymer comprising internal olefinic double bonds from a first cyclic olefin and a second cyclic olefin in a ring opening polymerization metathesis, comprising step (i.4):

(i.4) reacting the first cyclic olefin with the second cyclic olefin in the presence of a compound that catalyzes said metathesis reaction such that the molar ratio of said compound to the first or the second olefin is less than 1:500, and the conversion is at least 30%, wherein the first and the second olefin are identical or are different from one another;

wherein as compound that catalyzes said metathesis reaction a compound of the following formula is used:

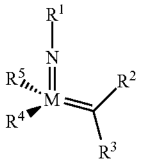

wherein M=Mo or W, and $R^1$ to $R^5$ are selected such to achieve the object of the invention.

In one embodiment, the first olefin is identical to the second olefin. In one embodiment, the olefin is selected from norbornene or cyclopentadiene.

In one embodiment, the method consists of step (i.1) or step (i.2) or step (i.3) or step (i.4).

In a more specific embodiment, the invention relates to a method of forming an olefin from a first olefin and a second olefin in a metathesis reaction, comprising step (i):

(i) reacting the first olefin with the second olefin in the presence of a compound that catalyzes said metathesis reaction such that the molar ratio of said compound to the first or the second olefin is less than 1:500, and the conversion of the first or the second olefin to said olefin is at least 30%, wherein as compound that catalyzes said metathesis reaction a compound of the following formula is used:

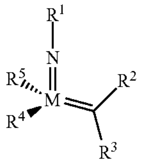

wherein

M=Mo or W; $R^1$ is aryl, heteroaryl, alkyl, or heteroalkyl; optionally substituted; $R^2$ and $R^3$ can be the same or different and are hydrogen, alkyl, alkenyl, heteroalkyl, heteroalkenyl, aryl, or heteroaryl; optionally substituted;

$R^5$ is alkyl, alkoxy, heteroalkyl, aryl, aryloxy, heteroaryl, silylalkyl, silyloxy, optionally substituted; and $R^4$ is a residue $R^6$—X—, wherein X═O and $R^6$ is aryl, optionally substituted; or X═S and $R^6$ is aryl, optionally substituted; or X═O and $R^6$ is ($R^7$, $R^8$, $R^9$)Si; wherein $R^7$, $R^8$, $R^9$ are alkyl or phenyl, optionally substituted; or X═O and $R^6$ is ($R^{10}$, $R^{11}$, $R^{12}$)C, wherein $R^{10}$, $R^{11}$, $R^{12}$ are independently selected from phenyl, alkyl; optionally substituted;

or $R^4$ and $R^5$ are linked together and are bound to M via oxygen, respectively.

In one embodiment, M=Mo or W; $R^1$ is aryl, or adamant-1-yl; optionally substituted; $R^2$ is an alkyl or cycloalkyl moiety which is bound to M via a tertiary carbon atom such as $—C(CH_3)_2C_6H_5$ or $—C(CH_3)_3$; $R^3$ is H; $R^5$ is alkoxy, heteroaryl, silyloxy; aryloxy; optionally substituted; and $R^4$ is a residue $R^6$—X—, wherein X═O and $R^6$ is phenyl substituted with up to five substituents independently selected from alkyl, preferably $C_1$-$C_4$ alkyl such as methyl, isopropyl or t-butyl, alkoxy, preferably $C_1$-$C_4$ alkoxy, halogen, phenoxy, optionally substituted. phenyl, optionally substituted; or X═S and $R^6$ is phenyl substituted with up to five substituents independently selected from alkyl, preferably $C_1$-$C_4$ alkyl such as methyl, isopropyl or t-butyl, alkoxy, preferably $C_1$-$C_4$ alkoxy, halogen, phenyl, optionally substituted, phenoxy, optionally substituted; or X═O and $R^6$ is triphenylsilyl; optionally substituted; or triisopropylsilyl; or X═O and $R^6$ is triphenylmethyl; optionally substituted; or X═O and $R^6$ is 9-phenyl-fluorene-9-yl; or X═O and $R^6$ is 2-phenyl-1,1,1,3,3,3-hexafluoro-prop-2-yl, or 2-methyl-1,1,1,3,3,3-hexafluoro-prop-2-yl; or X═O and $R^6$ is t-butyl.

In one embodiment, M=Mo or W; $R^1$ is selected from 2,6-dimethylphenyl, 2,6-diisopropylphenyl, 2,6-di-t-butylphenyl, 2,6-dichlorophenyl, adamant-1-yl; $R^2$ is $—C(CH_3)_2C_6H_5$ or $—C(CH_3)_3$; $R^3$ is H; $R^5$ is selected from pyrrol-1-yl; 2,5-dimethyl-pyrrol-1-yl; triphenylsilyloxy; triisopropylsilyloxy; 2-phenyl-1,1,1,3,3,3-hexafluoro-prop-2-yloxy; 2-methyl-1,1,1,3,3,3-hexafluoro-prop-2-yloxy; 9-phenyl-fluorene-9-yloxy; 2,6-diphenylphenoxy; t-butyloxy; and $R^4$ is $R^6$—X—, wherein X═O and $R^6$ is phenyl substituted with up to five substituents independently selected from alkyl, preferably $C_1$-$C_4$ alkyl such as methyl, isopropyl or t-butyl, alkoxy, preferably $C_1$-$C_4$ alkoxy, phenoxy, phenyl, halogen, optionally substituted; or X═S and $R^6$ is phenyl substituted with up to five substituents independently selected from alkyl, preferably $C_1$-$C_4$ alkyl such as methyl, isopropyl or t-butyl, alkoxy, preferably $C_1$-$C_4$ alkoxy, halogen, phenyl, optionally substituted, phenoxy, optionally substituted; or X═O and $R^6$ is triphenylsilyl; optionally substituted; or triisopropylsilyl; or X═O and $R^6$ is triphenylmethyl; optionally substituted; or X═O and $R^6$ is 9-phenyl-fluorene-9-yl; or X═O and $R^6$ is 2-phenyl-1,1,1,3,3,3-hexafluoro-prop-2-yl or 2-methyl-1,1,1,3,3,3-hexafluoro-prop-2-yl; or X═O and $R^6$ is t-butyl.

In one embodiment, M=Mo or W; $R^1$ is selected from 2,6-dimethylphenyl, 2,6-diisopropylphenyl, 2,6-dichlorophenyl, adamant-1-yl; $R^2$ is —$C(CH_3)_2C_6H_5$ or —$C(CH_3)_3$; $R^3$ is H; $R^5$ is selected from pyrrol-1-yl and 2,5-dimethyl-pyrrol-1-yl; and $R^4$ is $R^6$—X—, wherein X═O and $R^6$ is phenyl substituted with up to five substituents independently selected from alkyl, preferably $C_1$-$C_4$ alkyl such as methyl, isopropyl or t-butyl, alkoxy, preferably $C_1$-$C_4$ alkoxy, halogen, phenoxy, optionally substituted, phenyl, optionally substituted; or X═S and $R^6$ is phenyl substituted with up to five substituents independently selected from alkyl, preferably $C_1$-$C_4$ alkyl such as methyl, isopropyl or t-butyl, alkoxy, preferably $C_1$-$C_4$ alkoxy, halogen phenoxy, optionally substituted, phenyl, optionally substituted; or X═O and $R^6$ is triphenylsilyl; or triisopropylsilyl; or X═O and $R^6$ is triphenylmethyl or tri(4-methylphenyl) methyl; or X═O and $R^6$ is 9-phenyl-fluorene-9-yl; or X═O and $R^6$ is 2-phenyl-1,1,1,3,3,3-hexafluoro-prop-2-yl or 2-methyl-1,1,1,3,3,3-hexafluoro-prop-2-yl; or X═O and $R^6$ is t-butyl.

In one embodiment, M=Mo or W; $R^1$ is selected from 2,6-dimethylphenyl, 2,6-diisopropylphenyl, 2,6-dichlorophenyl, adamant-1-yl; $R^2$ is —$C(CH_3)_2C_6H_5$ or —$C(CH_3)_3$; $R^3$ is H; $R^5$ is selected from triphenylsilyloxy or triisopropylsilyloxy; and $R^4$ is $R^6$—X—, wherein X═O and $R^6$ is phenyl substituted with up to five substituents independently selected from alkyl, preferably $C_1$-$C_4$ alkyl such as methyl, isopropyl or t-butyl, alkoxy, preferably $C_1$-$C_4$ alkoxy, halogen, phenoxy, optionally substituted, phenyl, optionally substituted; or X═S and $R^6$ is phenyl substituted with up to five substituents independently selected from alkyl, preferably $C_1$-$C_4$ alkyl such as methyl, isopropyl or t-butyl, alkoxy, preferably $C_1$-$C_4$ alkoxy, halogen, phenyl, optionally substituted, phenoxy, optionally substituted; or X═O and $R^6$ is triphenylsilyl or triisopropylsilyl; or X═O and $R^6$ is triphenylmethyl or tri(4-methylphenyl) methyl; or X═O and $R^6$ is 9-phenyl-fluorene-9-yl; or X═O and $R^6$ is 2-phenyl-1,1,1,3,3,3-hexafluoro-prop-2-yl or 2-methyl-1,1,1,3,3,3-hexafluoro-prop-2-yl; or X═O and $R^6$ is t-butyl.

In one embodiment, M=Mo or W; $R^1$ is selected from 2,6-dimethylphenyl, 2,6-diisopropylphenyl, 2,6-dichlorophenyl, adamant-1-yl; $R^2$ is —$C(CH_3)_2C_6H_5$ or —$C(CH_3)_3$; $R^3$ is H; $R^5$ is selected from 9-phenyl-fluorene-9-yloxy; and $R^4$ is $R^6$—X—, wherein X═O and $R^6$ is phenyl substituted with up to five substituents independently selected from alkyl, preferably $C_1$-$C_4$ alkyl such as methyl, isopropyl or t-butyl, alkoxy, preferably $C_1$-$C_4$ alkoxy, halogen, phenoxy, optionally substituted, phenyl, optionally substituted; or X═S and $R^6$ is phenyl substituted with up to five substituents independently selected from alkyl, preferably $C_1$-$C_4$ alkyl such as methyl, isopropyl or t-butyl, alkoxy, preferably $C_1$-$C_4$ alkoxy, halogen, phenoxy, optionally substituted, phenyl, optionally substituted; or X═O and $R^6$ is triphenylsilyl or triisopropylsilyl; or X═O and $R^6$ is triphenylmethyl or tri(4-methylphenyl) methyl; or X═O and $R^6$ is 9-phenyl-fluorene-9-yl; or X═O and $R^6$ is 2-phenyl-1,1,1,3,3,3-hexafluoro-prop-2-yl or 2-methyl-1,1,1,3,3,3-hexafluoro-prop-2-yl; or X═O and $R^6$ is t-butyl.

In one embodiment, M=Mo or W; $R^1$ is selected from 2,6-dimethylphenyl, 2,6-diisopropylphenyl, 2,6-dichlorophenyl, adamant-1-yl; $R^2$ is —$C(CH_3)_2C_6H_5$ or —$C(CH_3)_3$; $R^3$ is H; $R^5$ is selected from 2-phenyl-1,1,1,3,3,3-hexafluoro-prop-2-yloxy or 2-methyl-1,1,1,3,3,3-hexafluoro-prop-2-yloxy; and $R^4$ is $R^6$—X—, wherein X═O and $R^6$ is phenyl substituted with up to five substituents independently selected from alkyl, preferably $C_1$-$C_4$ alkyl such as methyl, isopropyl or t-butyl, alkoxy, preferably $C_1$-$C_4$ alkoxy, halogen, phenoxy, optionally substituted, phenyl, optionally substituted; or X═S and $R^6$ is phenyl substituted with up to five substituents independently selected from alkyl, preferably $C_1$-$C_4$ alkyl such as methyl, isopropyl or t-butyl, alkoxy, preferably $C_1$-$C_4$ alkoxy, halogen, phenoxy, optionally substituted, phenyl, optionally substituted; or X═O and $R^6$ is triphenylsilyl or triisopropylsilyl; or X═O and $R^6$ is triphenylmethyl or tri(4-methylphenyl) methyl; or X═O and $R^6$ is 9-phenyl-fluorene-9-yl; or X═O and $R^6$ is 2-phenyl-1,1,1,3,3,3-hexafluoro-prop-2-yl or 2-methyl-1,1,1,3,3,3-hexafluoro-prop-2-yl; or X═O and $R^6$ is t-butyl.

In one embodiment, M=Mo or W; $R^1$ is selected from 2,6-dimethylphenyl, 2,6-diisopropylphenyl, 2,6-dichlorophenyl, adamant-1-yl; $R^2$ is —$C(CH_3)_2C_6H_5$ or —$C(CH_3)_3$; $R^3$ is H; $R^5$ is selected from pyrrol-1-yl; 2,5-dimethyl-pyrrol-1-yl; triphenylsilyloxy; triisopropylsilyloxy; 2-phenyl-1,1,1,3,3,3-hexafluoro-prop-2-yloxy; 2-methyl-1,1,1,3,3,3-hexafluoro-prop-2-yloxy; 2,6-diphenylphenoxy; 9-phenyl-fluorene-9-yloxy; t-butyloxy; and $R^4$ is $R^6$—X—, wherein X═O and $R^6$ is phenyl which bears two substituents in ortho position with respect to O, or which bears two substituents in ortho position with respect to O and at least a further substituent in para position with respect to O;

X═O and $R^6$ is triphenylsilyl; optionally substituted; or triisopropylsilyl; or X═O and $R^6$ is triphenylmethyl or tri(4-methylphenyl) methyl; or X═O and $R^6$ is 9-phenyl-fluorene-9-yl; or X═O and $R^6$ is 2-phenyl-1,1,1,3,3,3-hexafluoro-prop-2-yl or 2-methyl-1,1,1,3,3,3-hexafluoro-prop-2-yl; or X═O and $R^6$ is t-butyl.

In one embodiment, M=Mo or W; $R^1$ is selected from 2,6-dimethylphenyl, 2,6-diisopropylphenyl, 2,6-dichlorophenyl, adamant-1-yl; $R^2$ is —$C(CH_3)_2C_6H_5$ or —$C(CH_3)_3$; $R^3$ is H; $R^5$ is selected from pyrrol-1-yl; 2,5-dimethyl-pyrrol-1-yl; triphenylsilyloxy; triisopropylsilyloxy; 2-phenyl-1,1,1,3,3,3-hexafluoro-prop-2-yloxy; 2-methyl-1,1,1,3,3,3-hexafluoro-prop-2-yloxy; 2,6-diphenylphenoxy; 9-phenyl-fluorene-9-yloxy; t-butyloxy; and $R^4$ is selected from 4-bromo-2,6-diphenylphenoxy, 4-fluoro-2,6-diphenylphenoxy, 4-methyl-2,6-diphenylphenoxy, 4-methoxy-2,6-diphenylphenoxy, 2,4,6-triphenylphenoxy, 4-fluoro-2,6-dimesitylphenoxy, 4-bromo-2,6-di-tert.-butylphenoxy, 4-methoxy-2,6-di-tert.butylphenoxy, 4-methyl-2,6-di-tert.-butylphenoxy, 4-dimethylaminophenyl-2,6-diphenylphenoxy, 2,4,6-tri-tert.-butylphenoxy, 4-bromo-2,3,5,6-tetraphenylphenoxy; 4-bromo-2,6-di(4-bromophenyl)-3,5-diphenylphenoxy; or

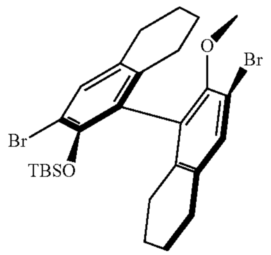

wherein TBS is t-butyldimethylsilyl; or

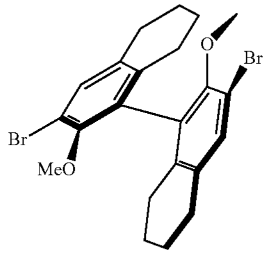

wherein Me=methyl; or
2,6-diphenylphenoxy, 2,3,5,6-tetraphenylphenoxy, 2,6-di(tert.-butyl)phenoxy; 2,6-di(2,4,6-triisopropylphenyl)phenoxy; or
triphenylsilyloxy or triisopropylsilyloxy; or
triphenylmethyloxy or tri(4-methyphenyl)methyloxy; or
2-phenyl-1,1,1,3,3,3-hexafluoro-prop-2-yloxy or 2-methyl-1,1,1,3,3,3-hexafluoro-prop-2-yloxy; or
9-phenyl-fluorene-9-yloxy; or
t-butyloxy.

In one embodiment, residues $R^4$ and $R^5$ are linked and are bound to M via oxygen, respectively. An example of such a linked residue is the corresponding residue in compounds 105 and 114:

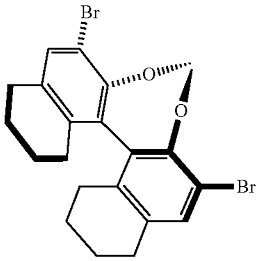

The catalysts may be prepared according to known methods or methods e.g. known from US 2011/0077421 A1, U.S. Pat. No. 6,121,473, US 2008/0119678 and US 2011/0015430.

The compounds may be advantageously used in metathesis reactions specified above. Without being bound by theory, it is believed that in particular $R^4$ as selected and defined provides for a high yield and stereoselectivity in the various types of metathesis reactions. Furthermore, the starting materials of the catalysts, in particular the starting materials used to introduce residue $R^4$ into the Mo or W-compound are mostly commercially available or may be simply prepared according to known methods. This makes the selected catalysts particularly applicable for industrial purposes, i.e. for alkene metathesis reactions performed at an industrial scale.

Accordingly, said catalysts may advantageously be applied in various types of metathesis reactions.

In one embodiment of the method according to the invention, the first olefin has a terminal olefinic double bond, and the second olefin has a terminal olefinic double bond, wherein the first and the second olefin are identical.

In another embodiment, the first and the second olefin are different from one another.

In still another embodiment, the first olefin has an internal olefinic double bond and the second olefin is ethylene.

In one embodiment, when M=Mo; $R^1$ is 2,6-diisopropylphenyl; $R^2$ is —$C(CH_3)_2C_6H_5$; $R^3$ is H; $R^4$ is 1-(4-bromo-2,6-diphenylphenoxy); $R^5$ is 2,5-dimethyl-pyrrol-1-yl; or when M is Mo; $R^1$ is 2,6-dimethylphenyl; $R^2$ is —$C(CH_3)_2C_6H_5$; $R^3$ is H; $R^4$ is 4-bromo-2,3,5,6-tetraphenylphenoxy; $R^5$ is 2,5-dimethyl-pyrrol-1-yl; the catalysts allow for ethenolysis resulting in a high yield of an olefin having a terminal olefinic double bond.

Other preferred compounds have the following structures:

M=Mo; $R^1$ is 2,6-dimethylphenyl; $R^2$ is —$C(CH_3)_2C_6H_5$; $R^3$ is H; $R^4$ is 4-bromo-2,3-diphenylphenoxy; $R^5$ is 2,5-dimethyl-pyrrol-1-yl; or M is Mo; $R^1$ is 2,6-diisopropylphenyl; $R^2$ is —$C(CH_3)_2C_6H_5$; $R^3$ is H; $R^4$ is 4-bromo-2,3,5,6-tetraphenylphenoxy; $R^5$ is 2,5-dimethyl-pyrrol-1-yl; or M is Mo; $R^1$ is 2,6-diisopropylphenyl; $R^2$ is —$C(CH_3)_2C_6H_5$; $R^3$ is H; $R^4$ is 4-methyl-2,3-di-t-butylphenoxy; $R^5$ is pyrrol-1-yl; or M is Mo; $R^1$ is 2,6-diisopropylphenyl; $R^2$ is —$C(CH_3)_2C_6H_5$; $R^3$ is H; $R^4$ is 4-bromo-2,3-di-t-butylphenoxy; $R^5$ is pyrrol-1-yl; or M is Mo; $R^1$ is 2,6-diisopropylphenyl; $R^2$ is —$C(CH_3)_2C_6H_5$; $R^3$ is H; $R^4$ is 2,4,6-tri-t-butylphenoxy; $R^5$ is pyrrol-1-yl; or M is Mo; $R^1$ is 2,6-diisopropylphenyl; $R^2$ is —$C(CH_3)_2C_6H_5$; $R^3$ is H; $R^4$ is 4-methoxy-2,3-di-t-butylphenoxy; $R^5$ is pyrrol-1-yl.

Further preferred compounds used as catalysts in the method according to the invention are the following compounds 1 to 291:

1

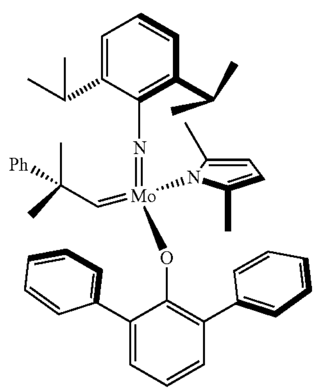

-continued
2
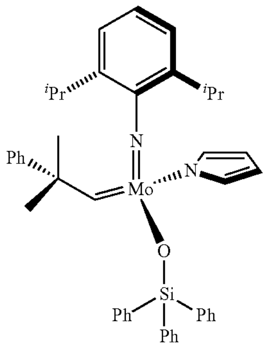
3
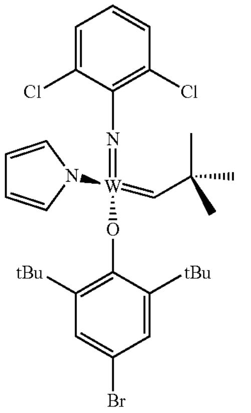
4
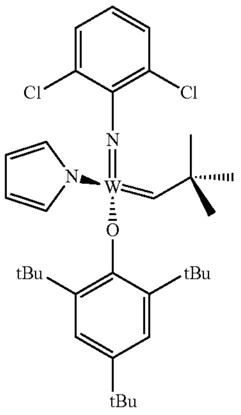
5
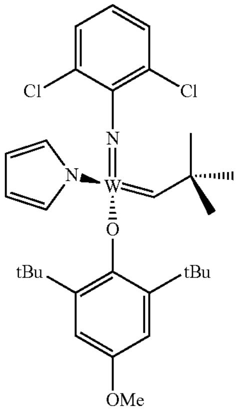
-continued
6
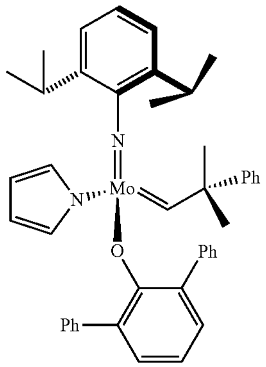
7
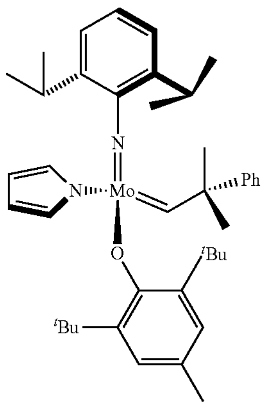
8
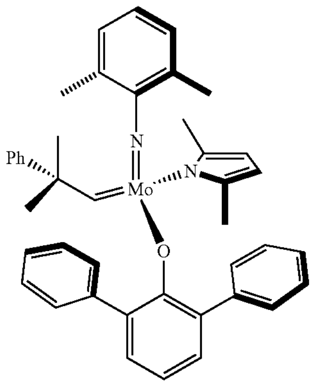
9
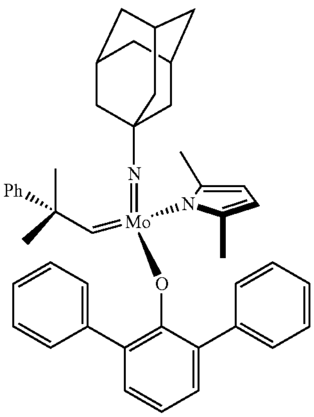

10
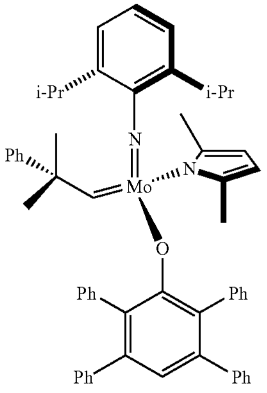
11
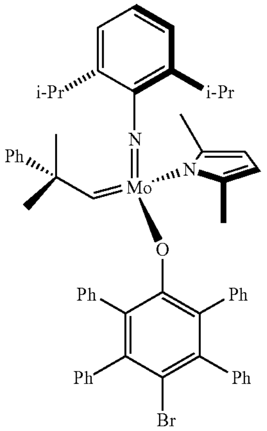
12
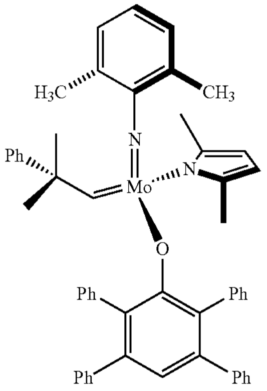
13
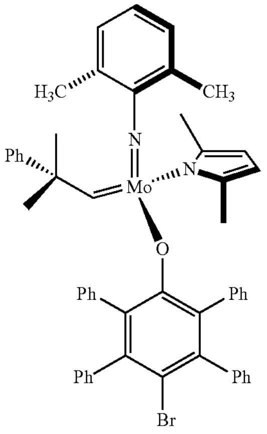
14
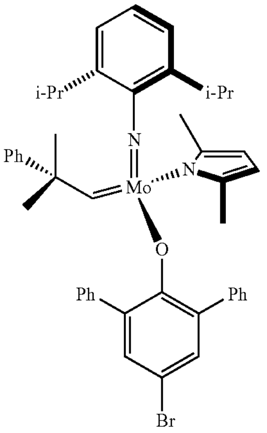
15
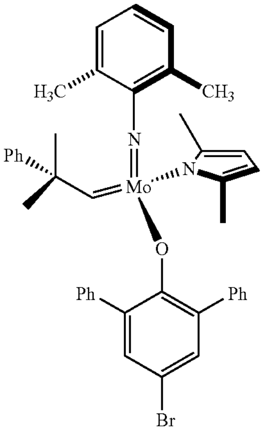
16
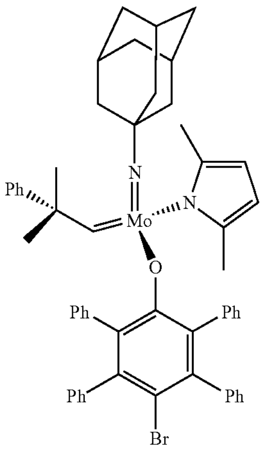

-continued
17
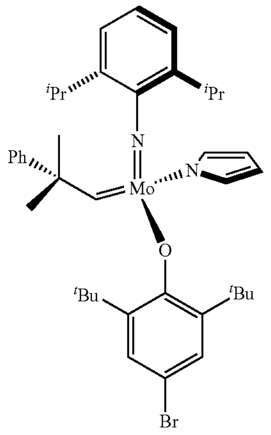
18
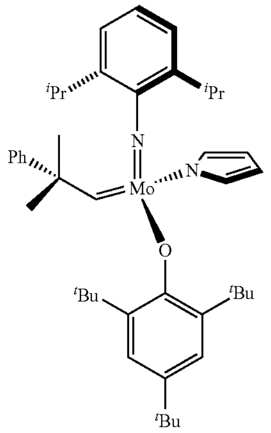
19
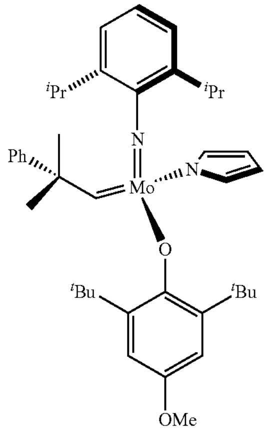
20
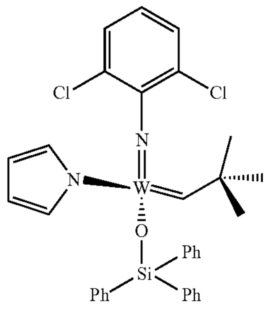
-continued
21
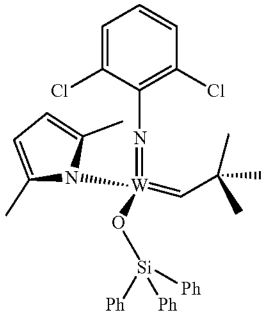
22
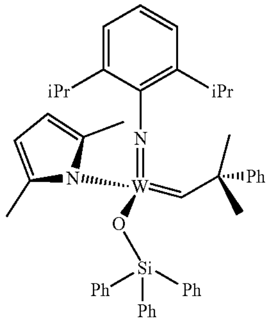
23
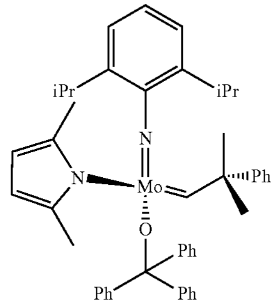
24
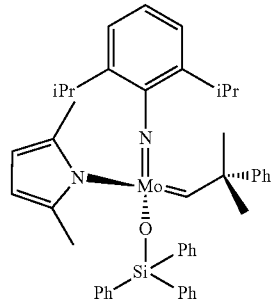
25
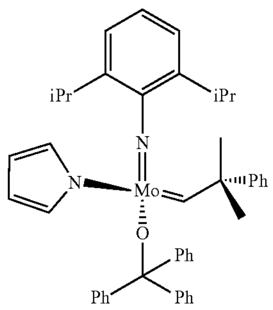

-continued
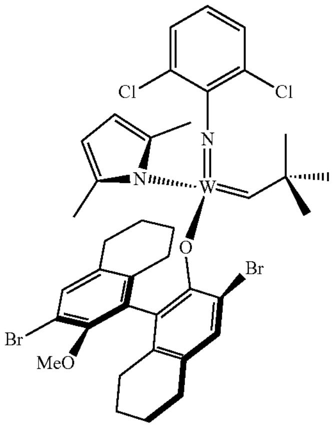
27
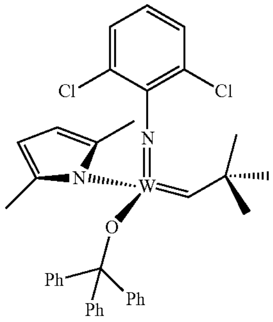
28
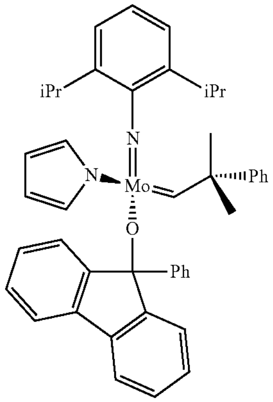
29
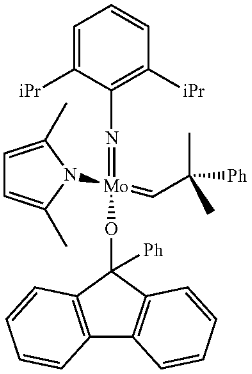
-continued
30
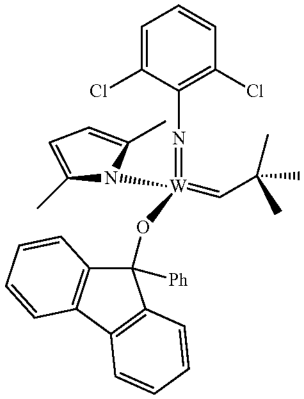
31
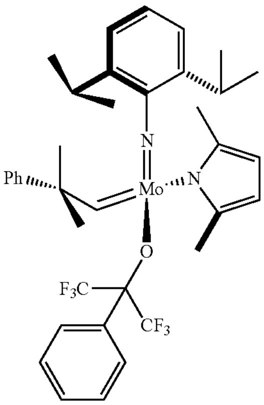
32
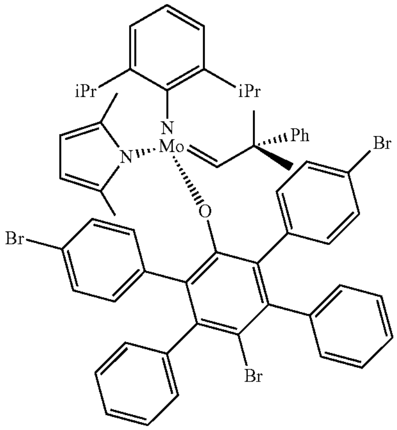

-continued
33
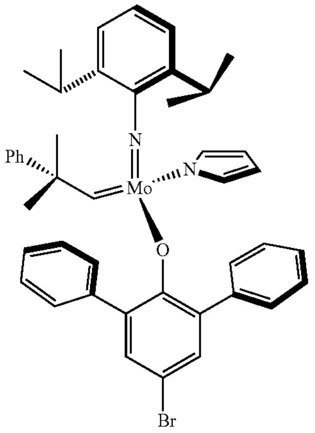
34
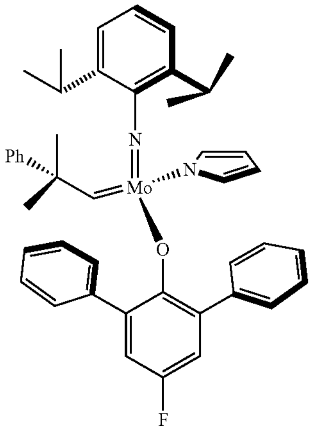
35
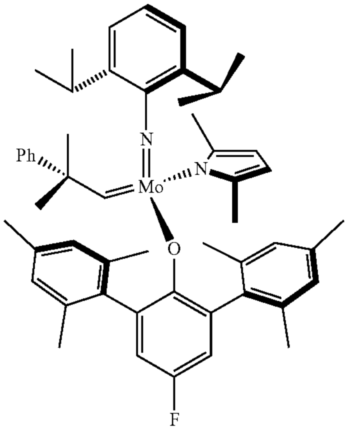
-continued
36
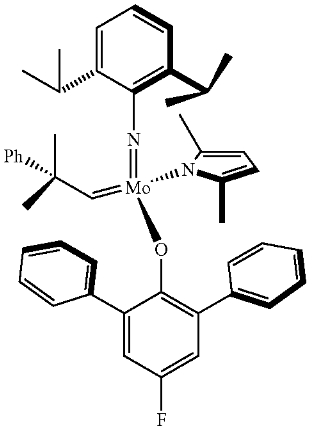
37
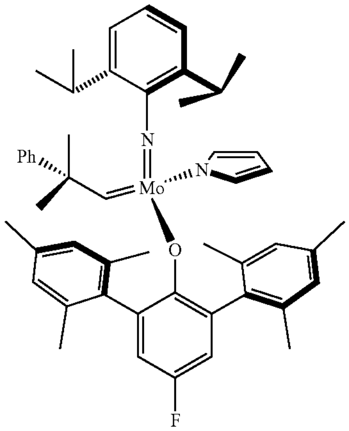
38
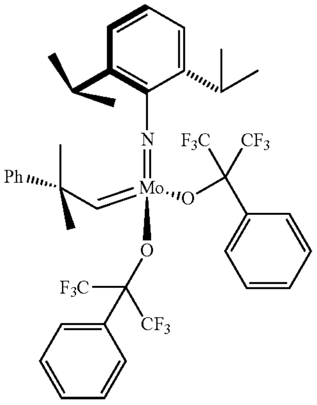

-continued
39
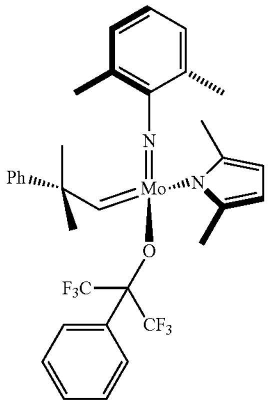
40
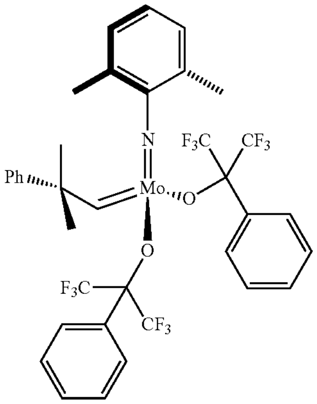
41
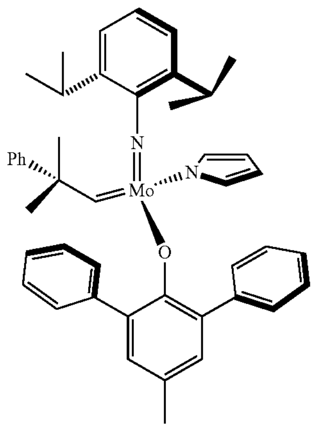
-continued
42
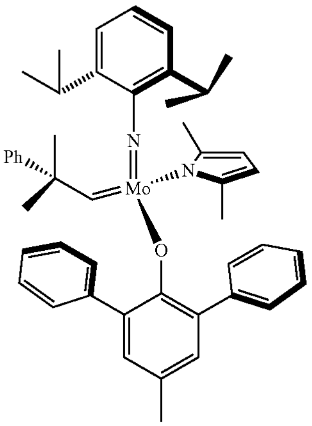
43
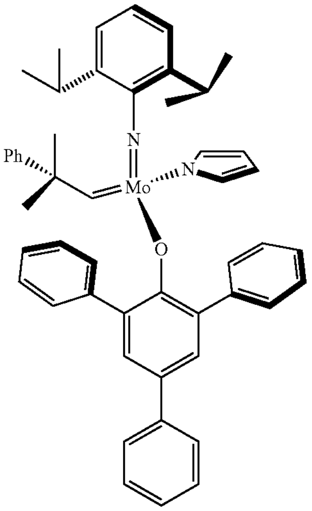
44
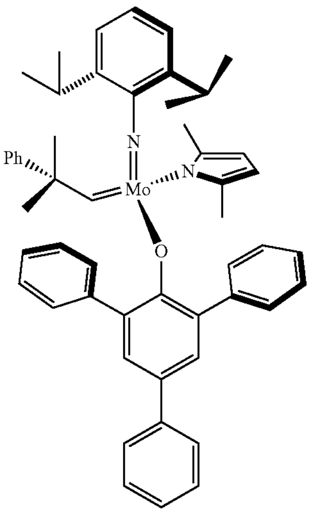

-continued
45
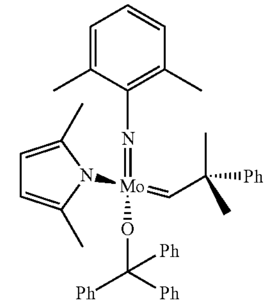
46
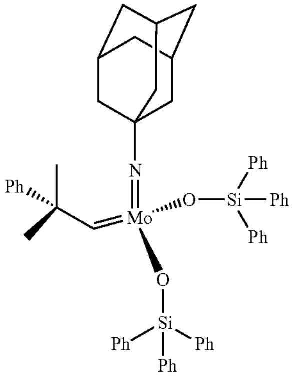
47
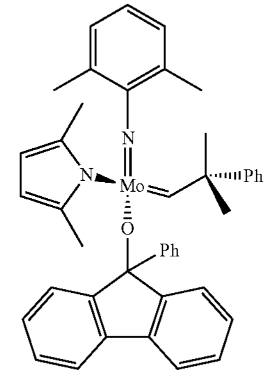
48
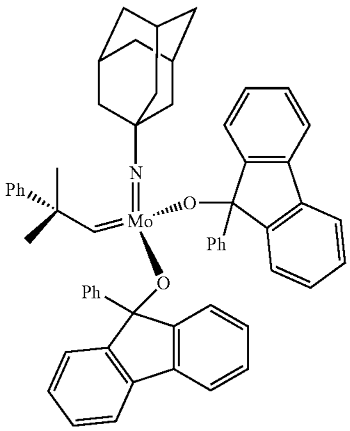
-continued
49
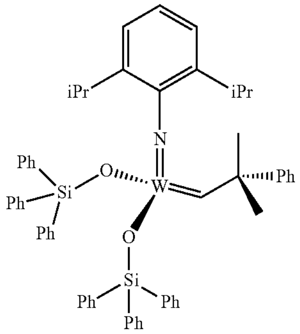
50
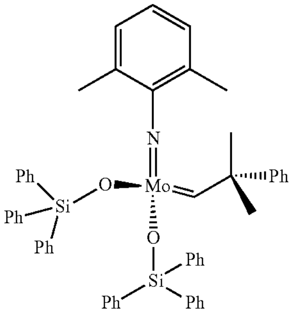
51
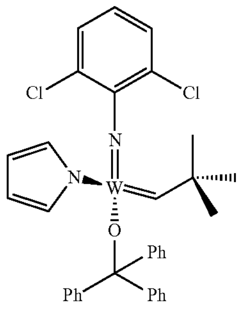
52
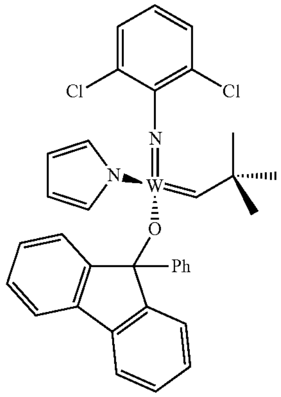

-continued
53
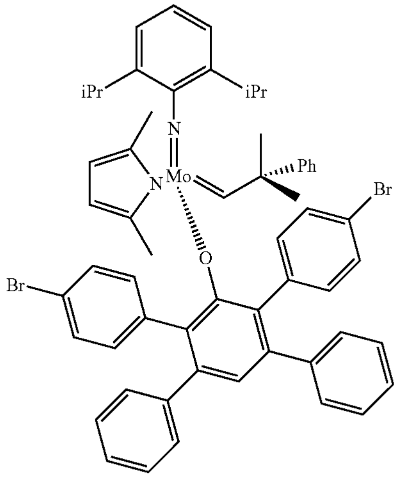
54
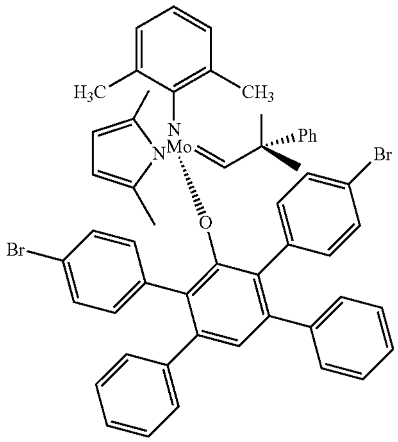
55
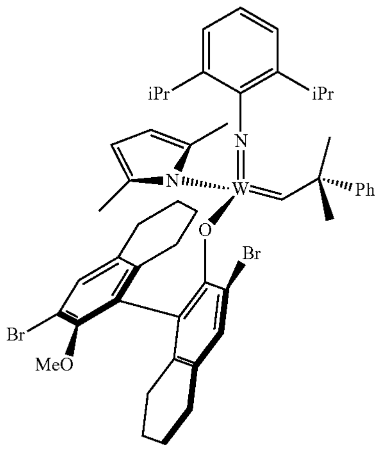
-continued
56
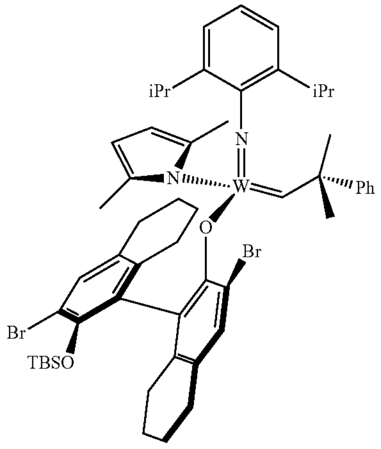
57
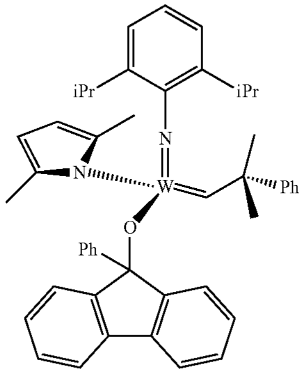
58
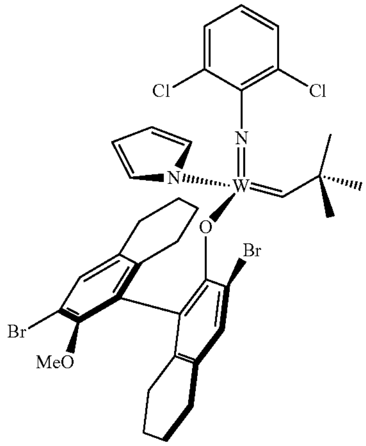
59
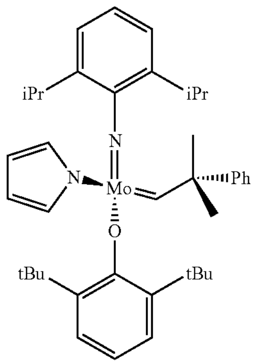

-continued
60
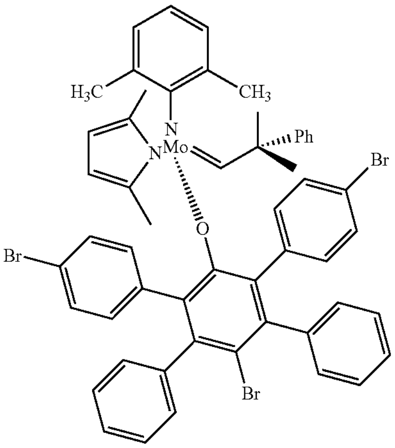
61
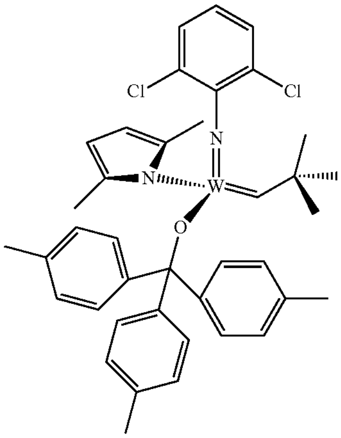
62
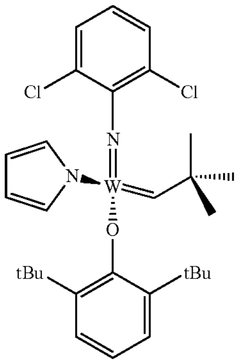
-continued
63
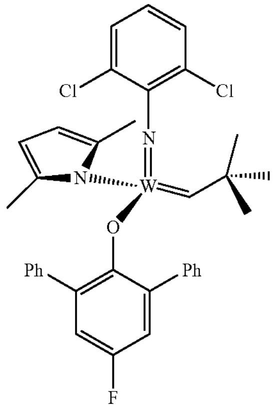
64
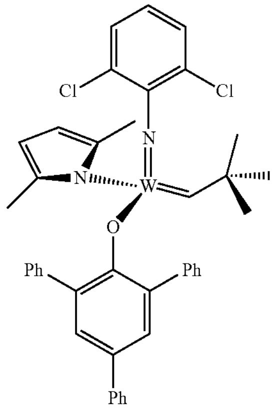
65
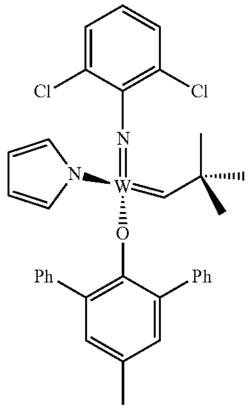
66
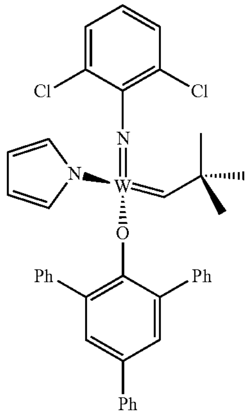

67
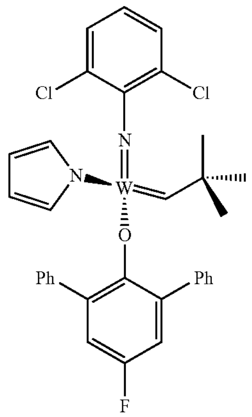
68
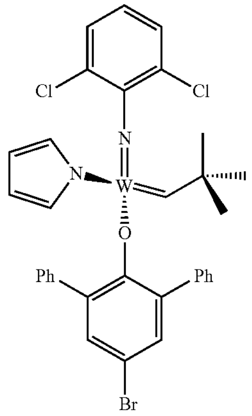
69
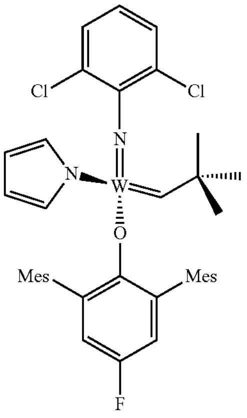
70
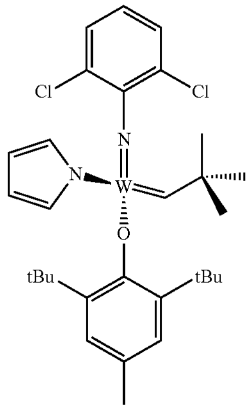
71
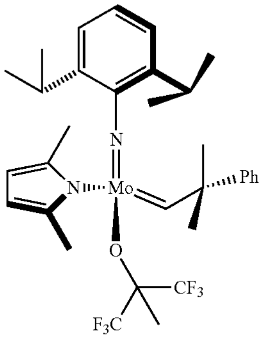
72
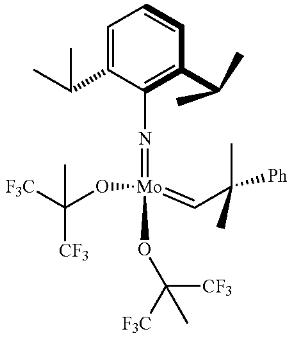
73
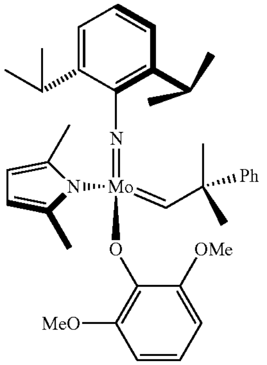

-continued
74
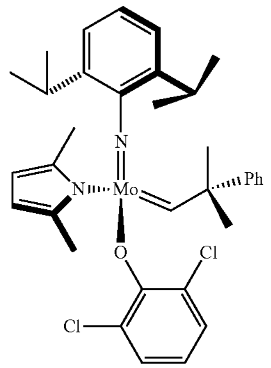
75
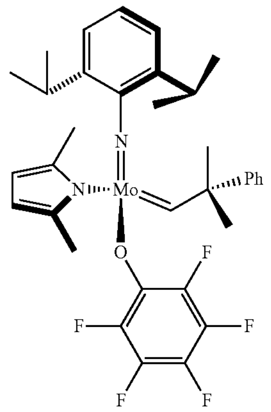
76
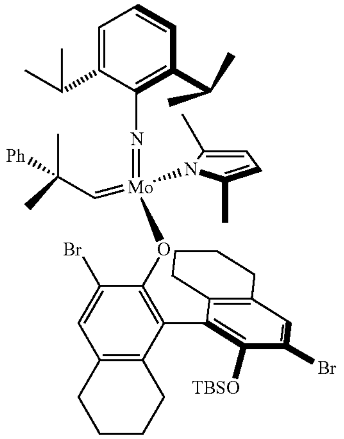
-continued
77
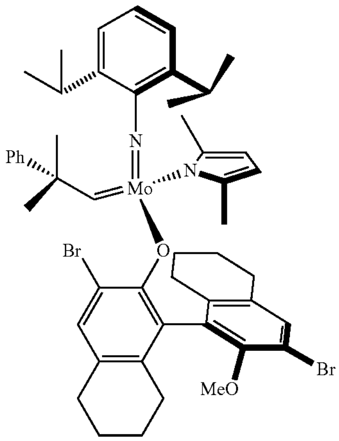
78
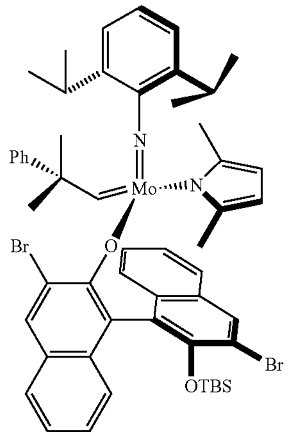
79
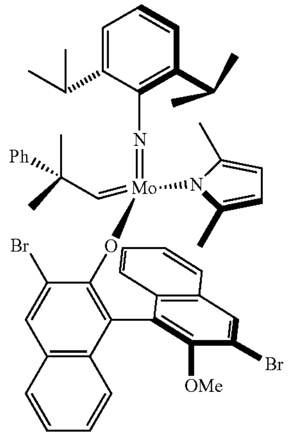

-continued
80
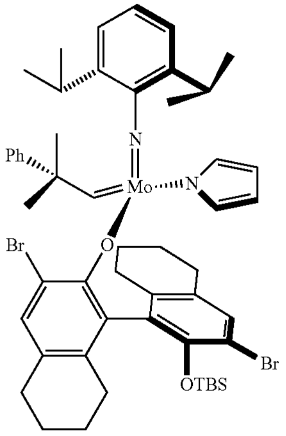
81
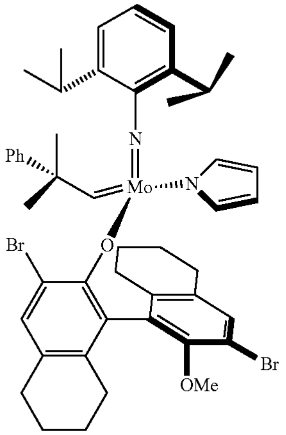
82
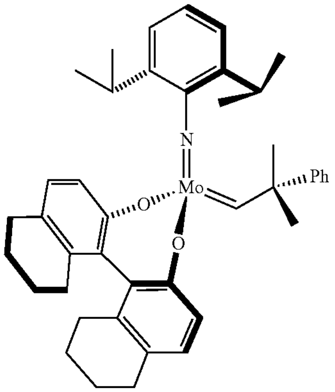
-continued
83
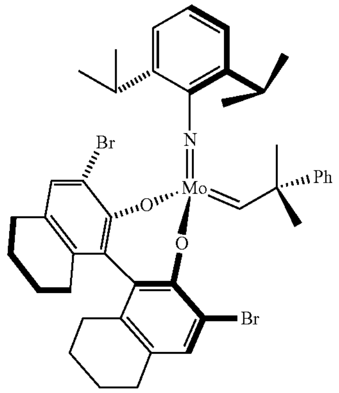
84
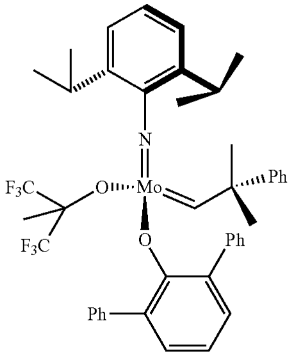
85
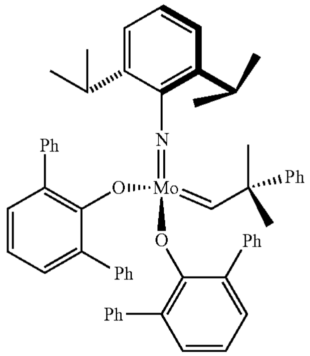
86
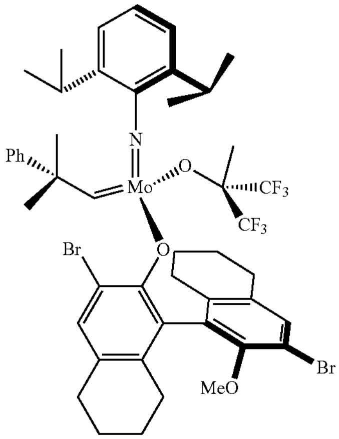

-continued
87
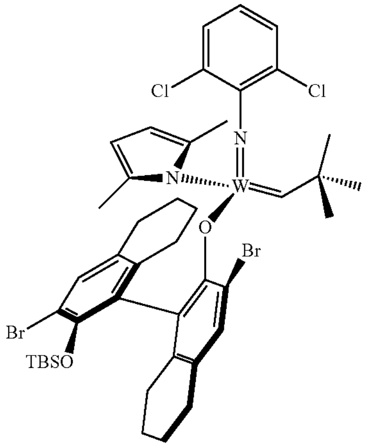
88
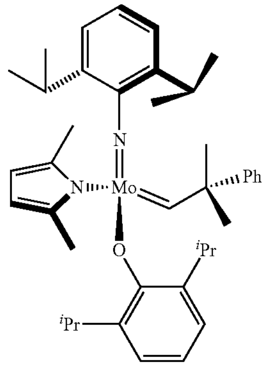
89
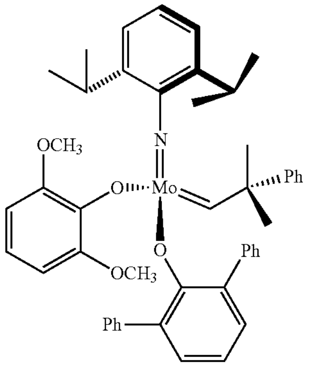
90
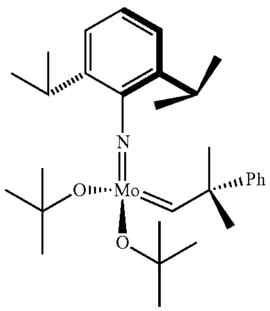
-continued
91
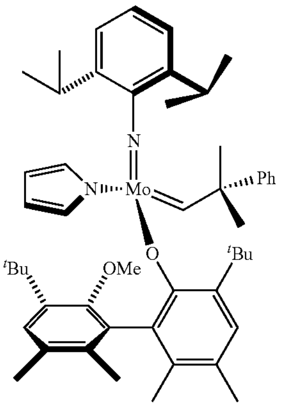
92
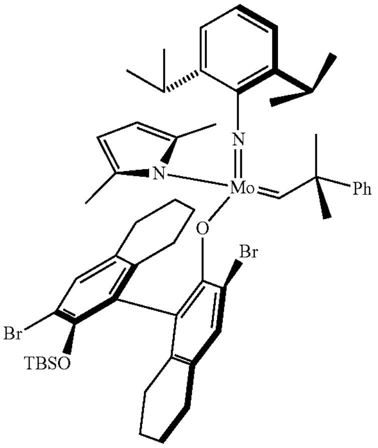
93
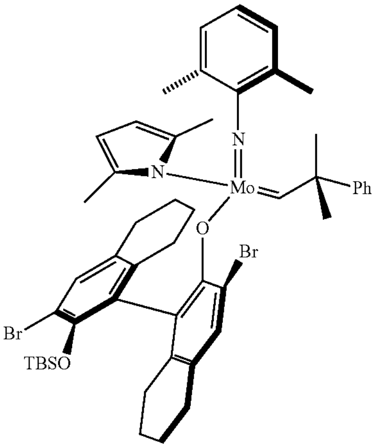

-continued
94
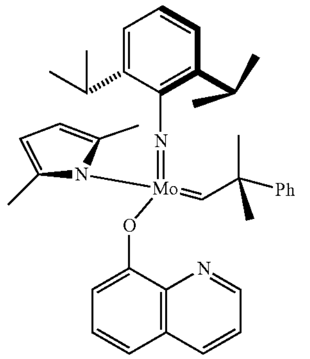
95
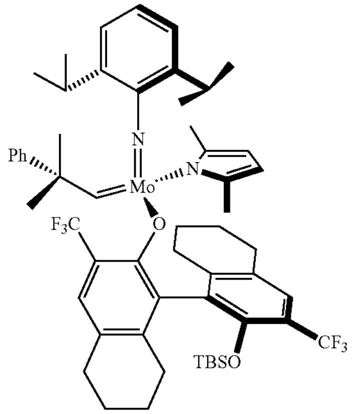
96
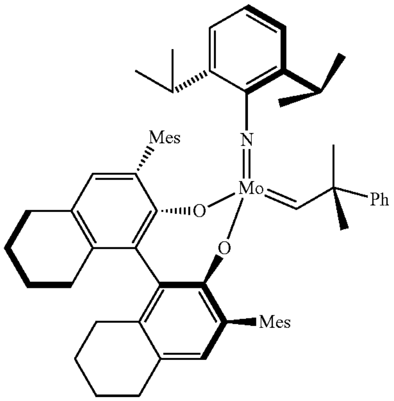
97
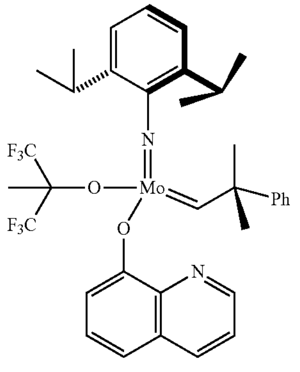
-continued
98
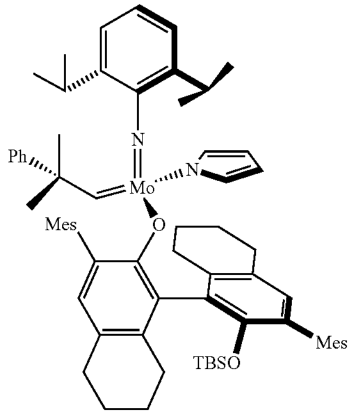
99
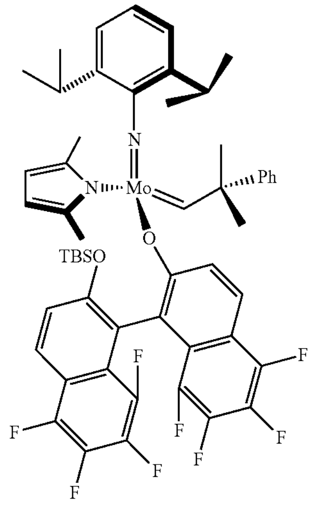
100
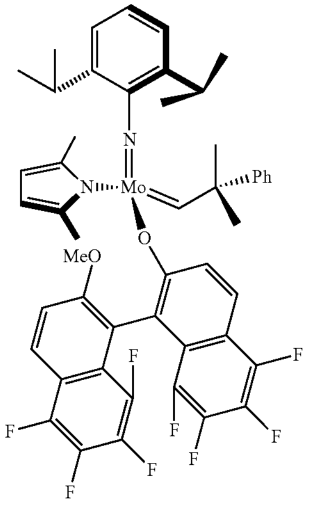

-continued
101
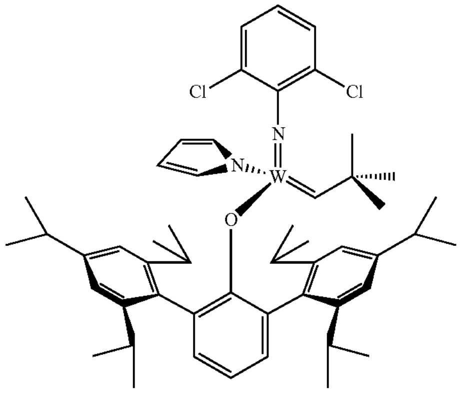
102
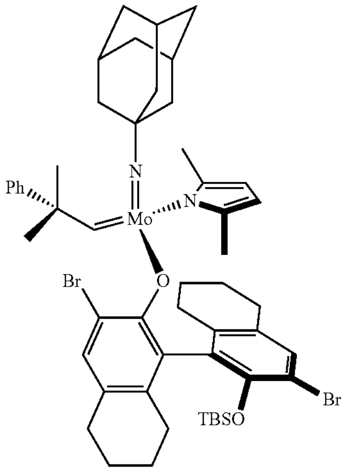
103
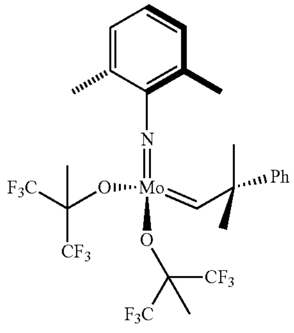
104
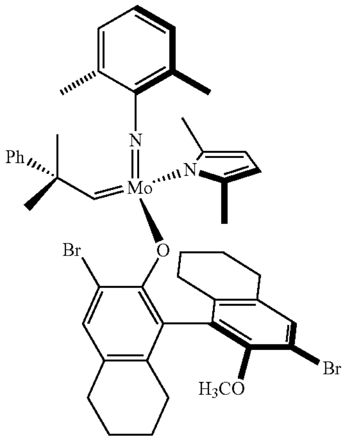
-continued
105
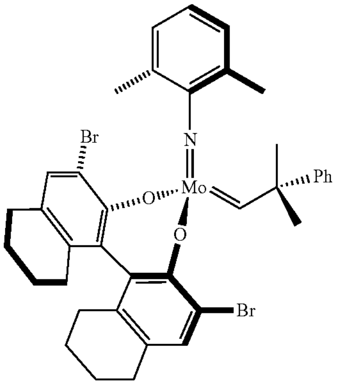
106
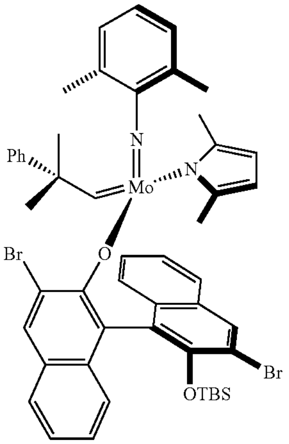
107
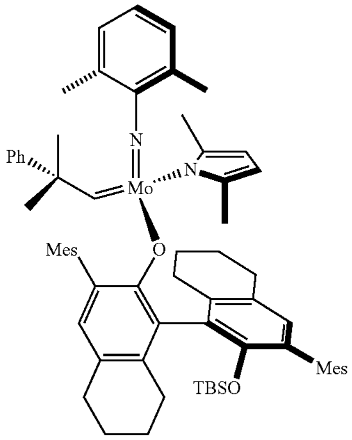

-continued
108
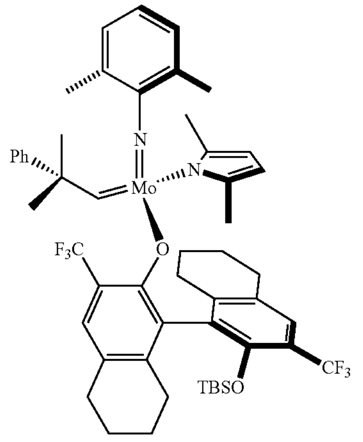
109
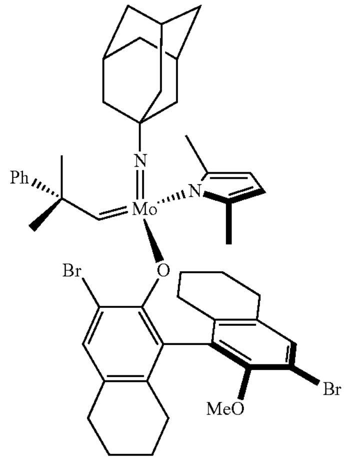
110
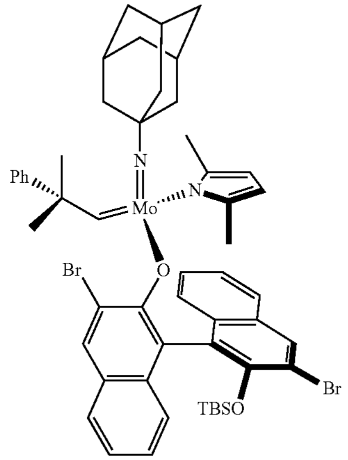
-continued
111
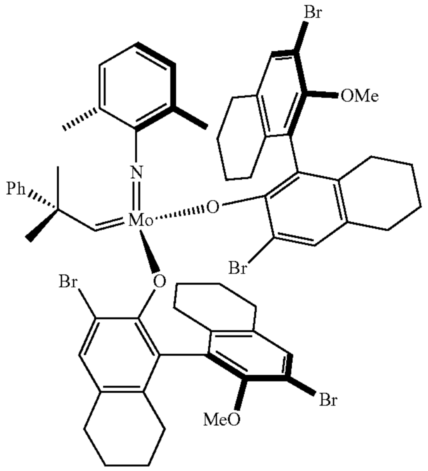
112
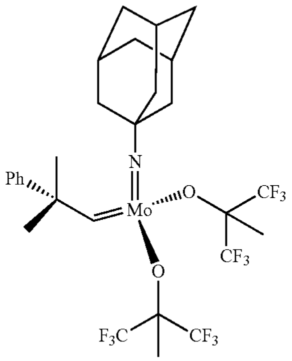
113
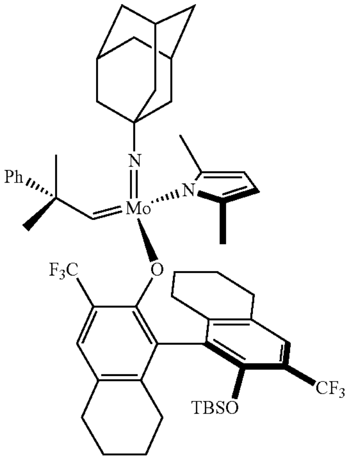

114
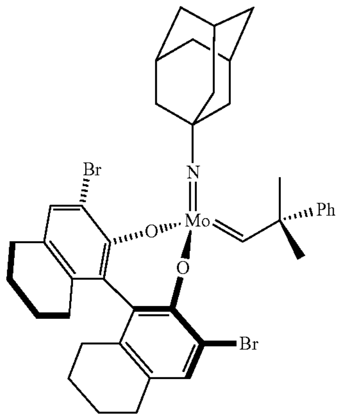
115
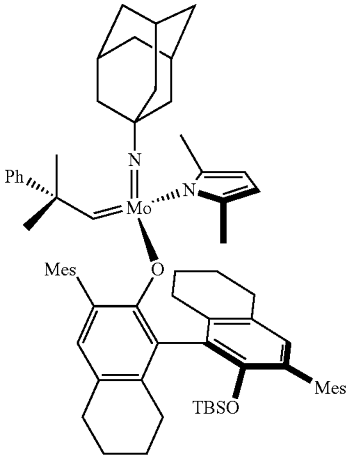
116
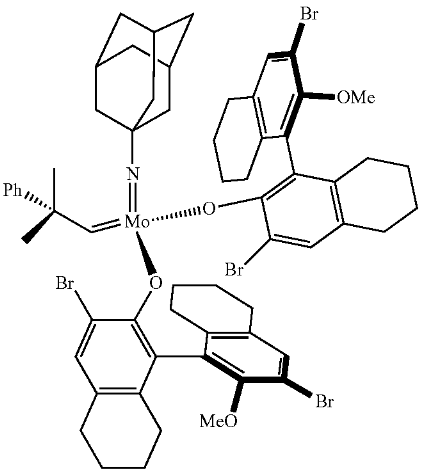
117
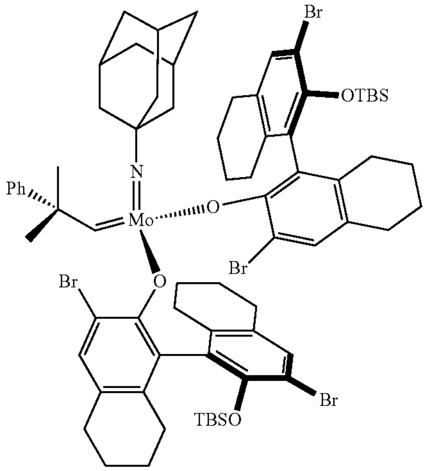
118
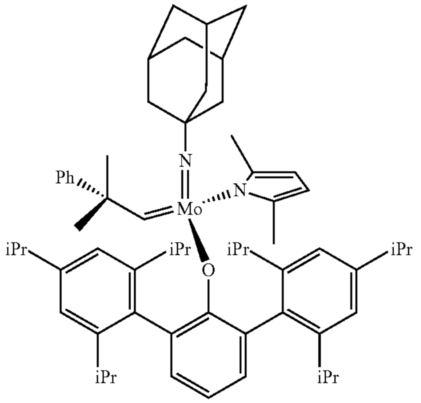
119
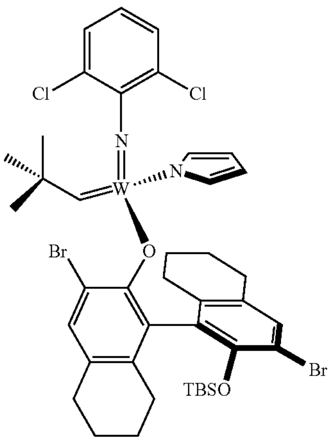

-continued
120
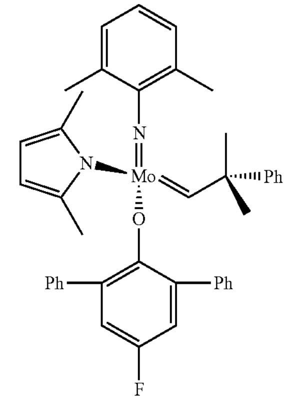
121
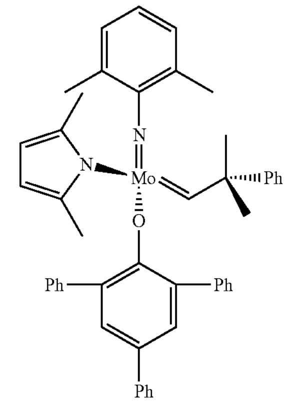
122
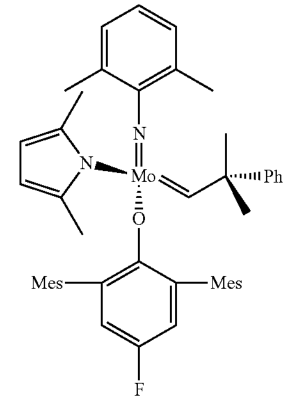
123
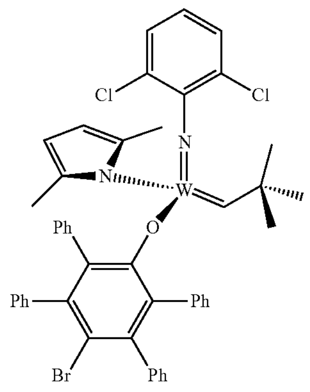
-continued
124
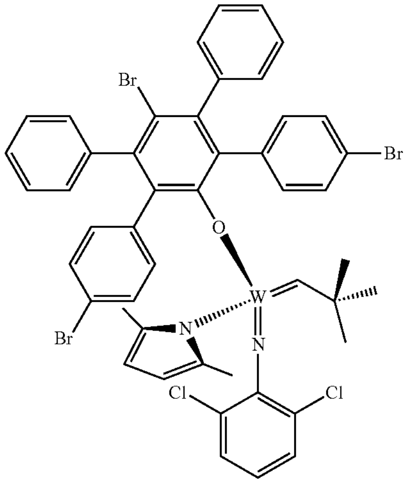
125
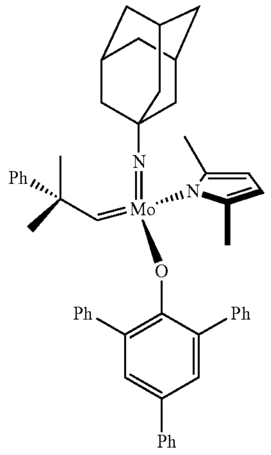
126
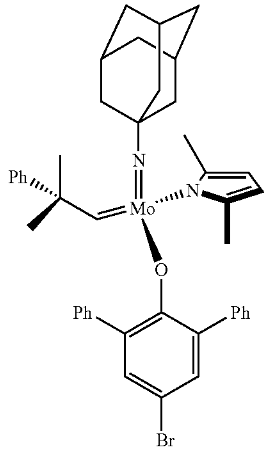

-continued
127
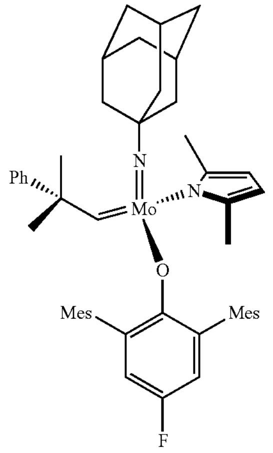
128
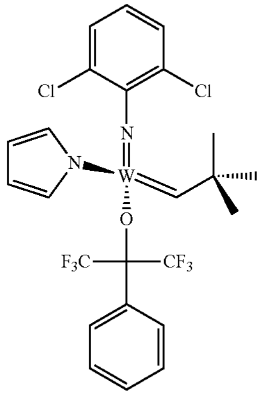
129
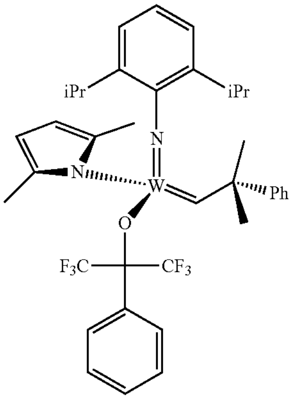
130
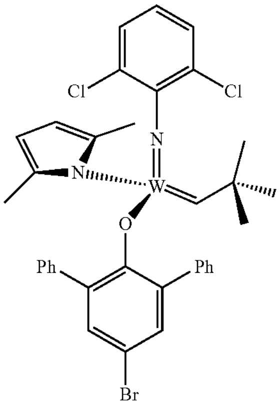
-continued
131
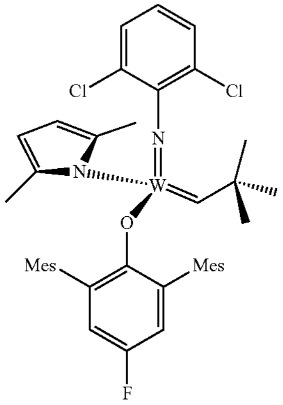
132
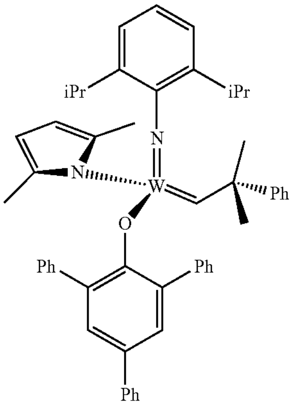
133
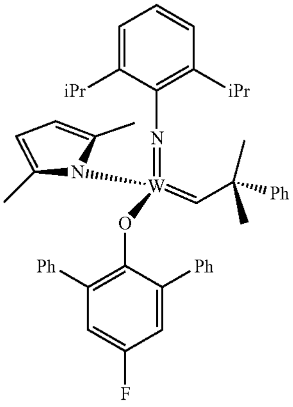
134
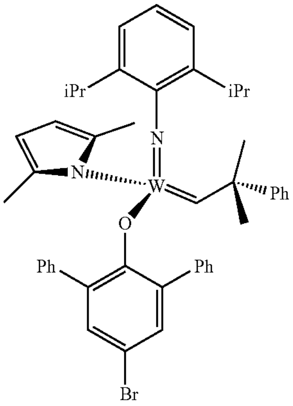

-continued
135
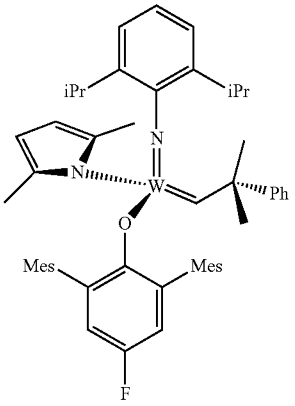
136
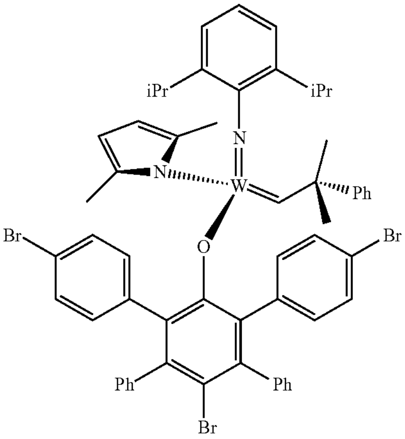
137
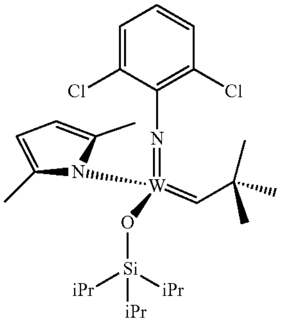
138
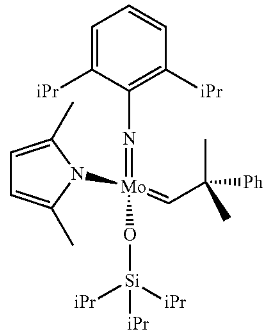
-continued
139
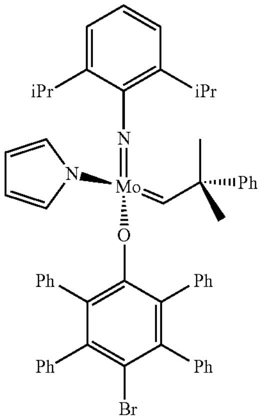
140
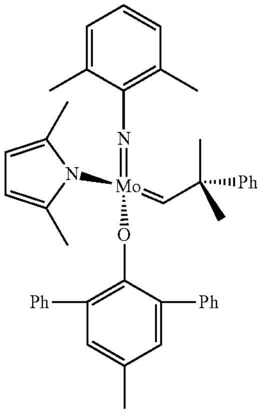
141
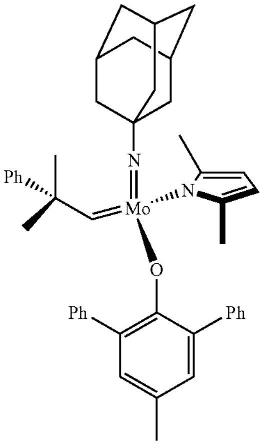

142
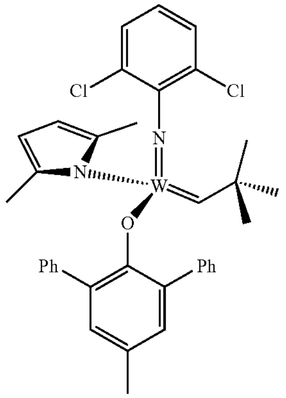
143
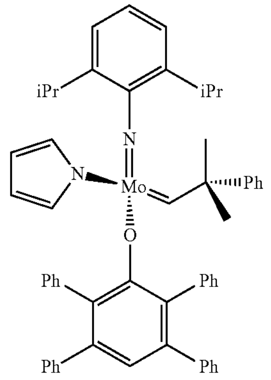
144
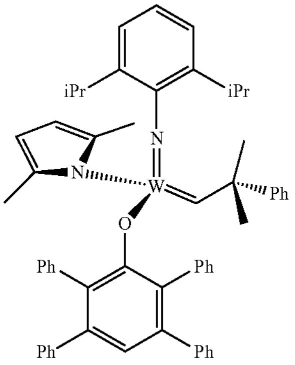
145
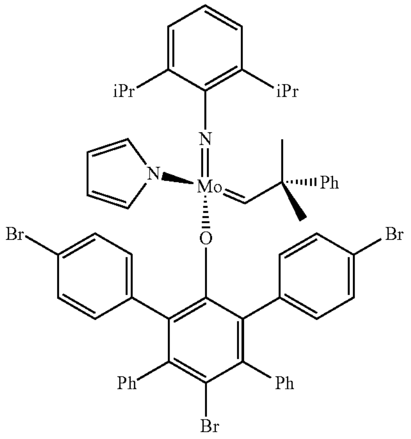
146
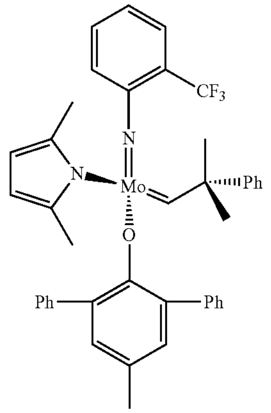
147
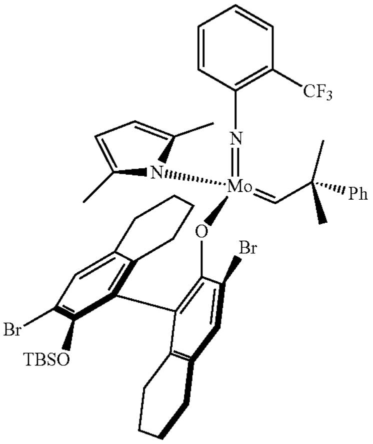
148
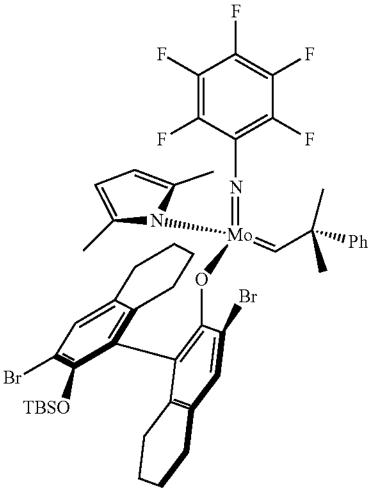

-continued
149
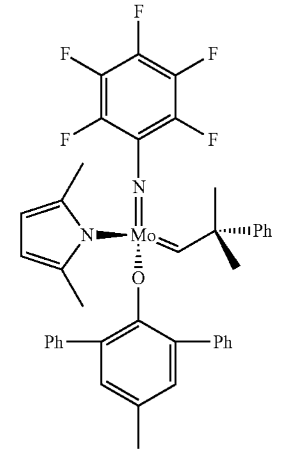
150
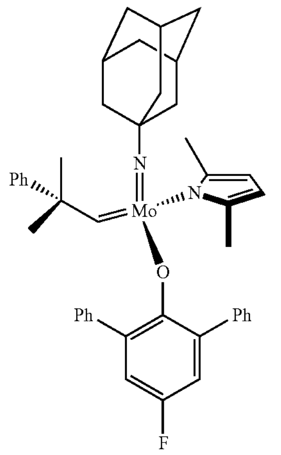
151
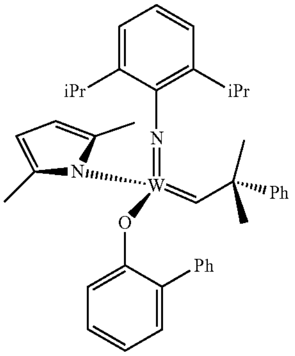
152
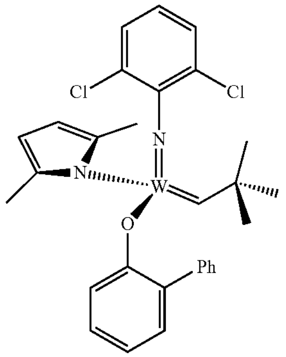
-continued
153
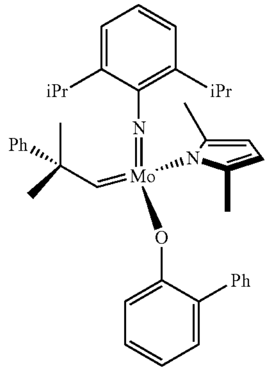
154
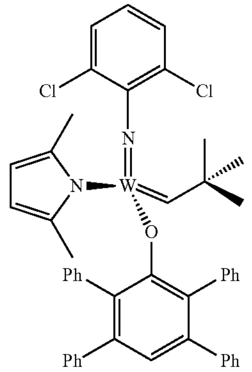
155
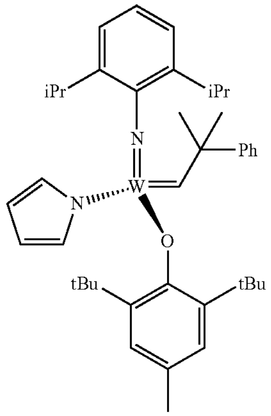
156
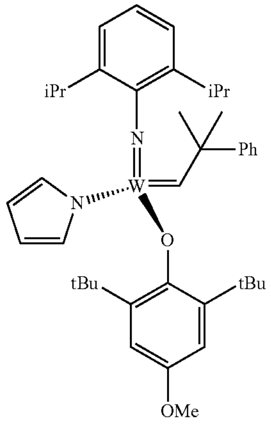

-continued
157
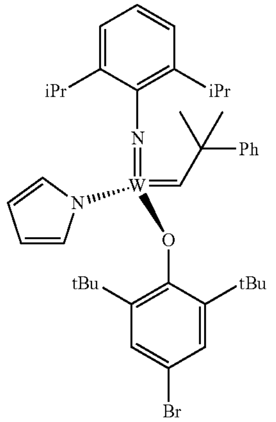
158
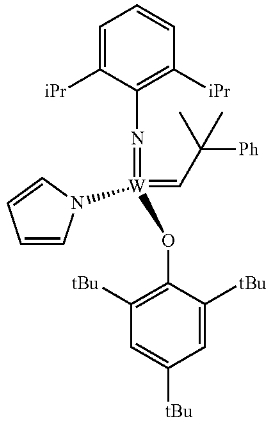
159
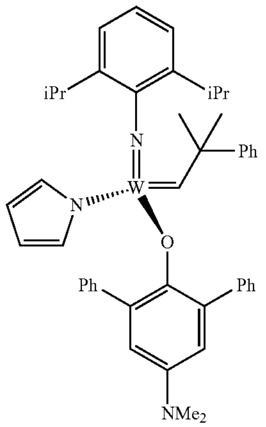
-continued
160
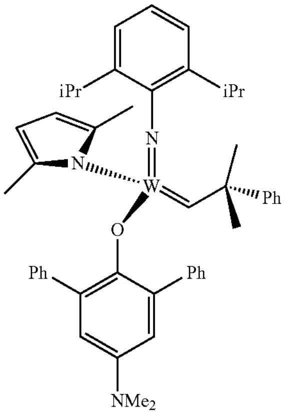
161
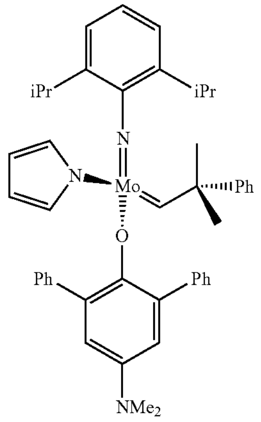
162
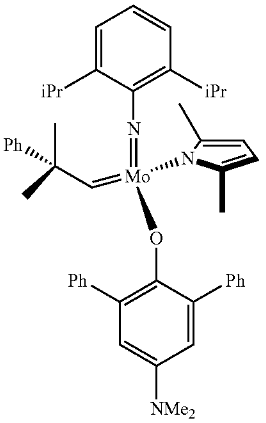

-continued
163
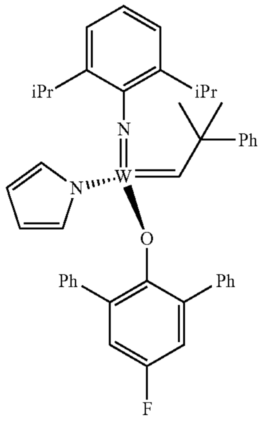
164
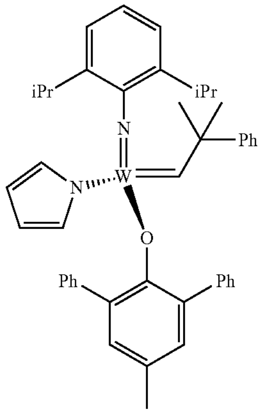
165
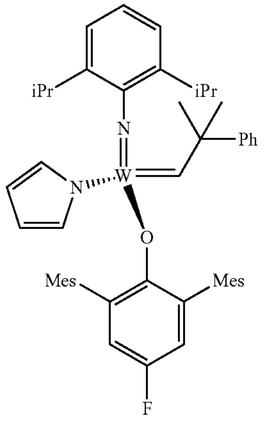
-continued
166
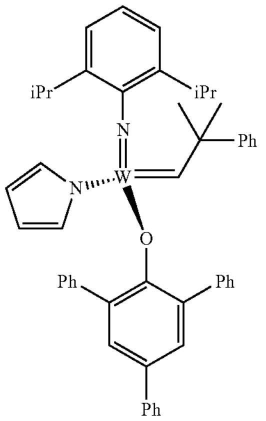
167
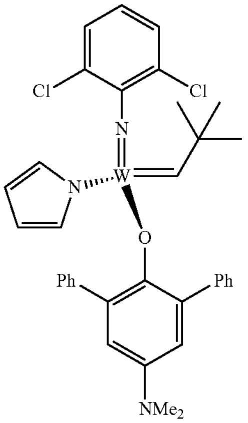
168
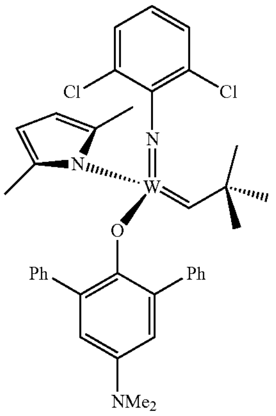

169
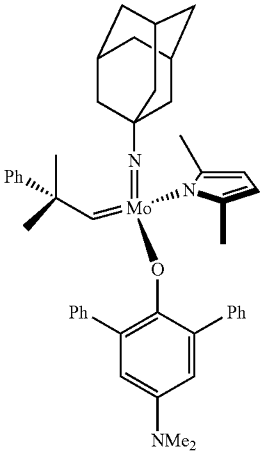
170
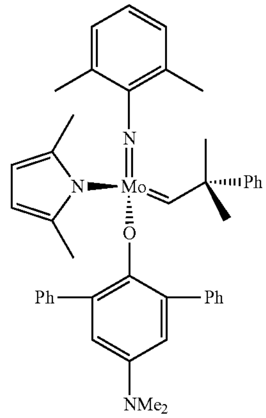
171
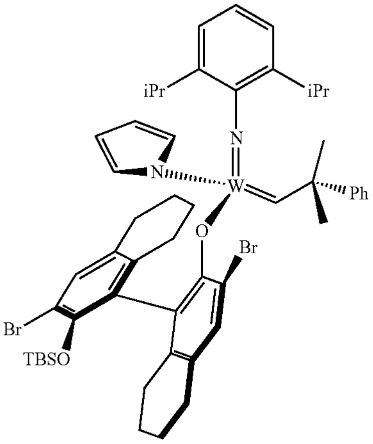
172
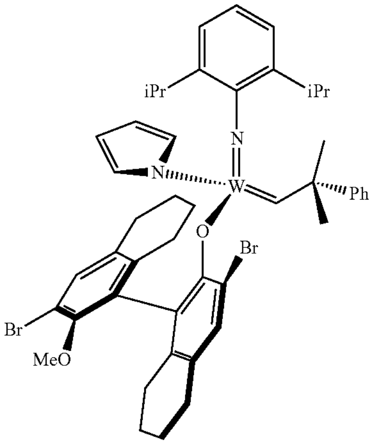
173
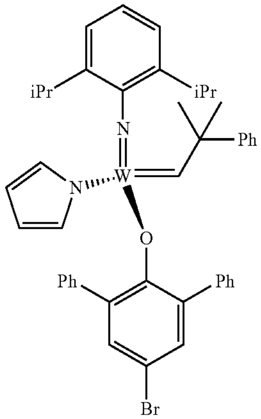
174
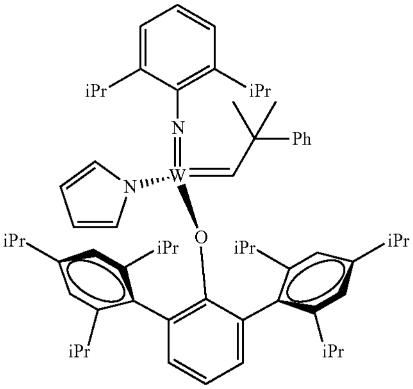
175
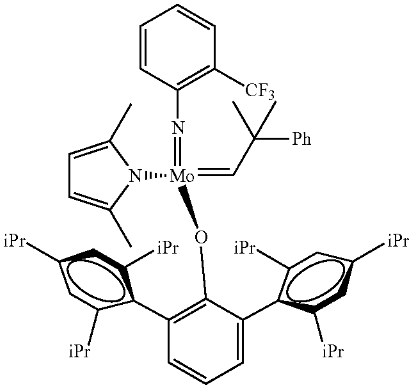

-continued
176
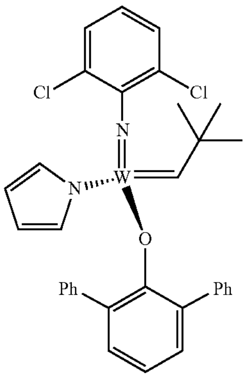
177
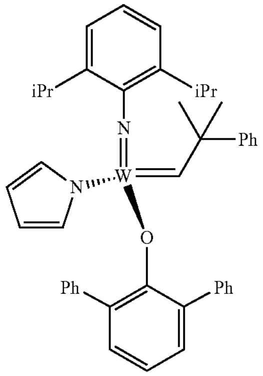
178
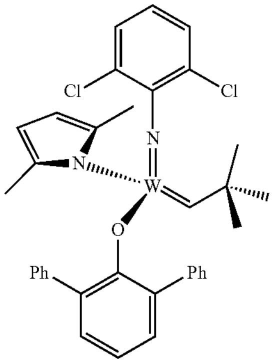
179
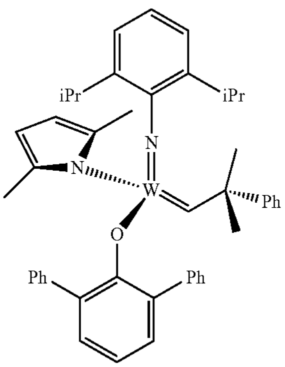
-continued
180
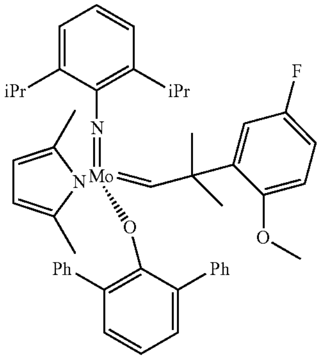
C47H51FMoN2O2
790.87
10.9
181
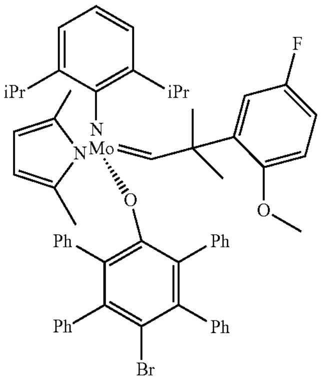
C59H58BrFMoN2O2
1021.96
11.73
182
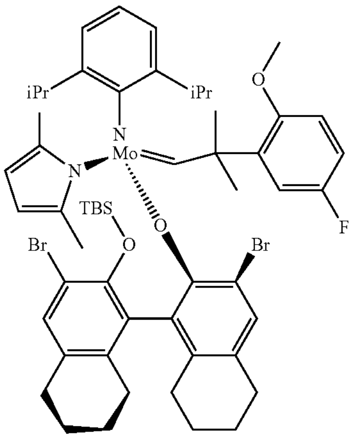
C55H71Br2FMoN2O3Si
1111.01
12.99, 13.55

-continued
183
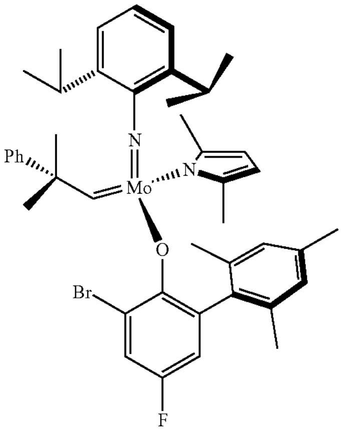
C43H50BrFMoN2O
805.71
11.62
184
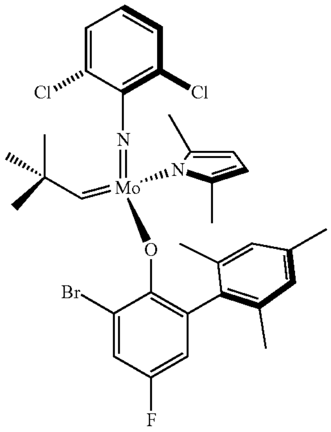
C32H34BrCl2FN2OW
814.07
8.43
185
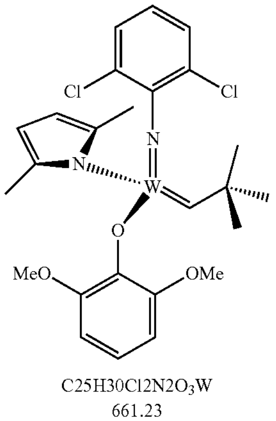
C25H30Cl2N2$O_3$W
661.23
9.17
-continued
186
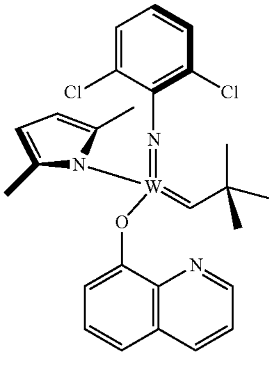
C26H27Cl2N3OW
652.26
10.34
187
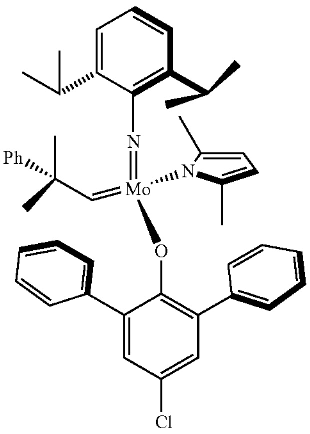
C46H49ClMoN2O
777.29
11.7
188
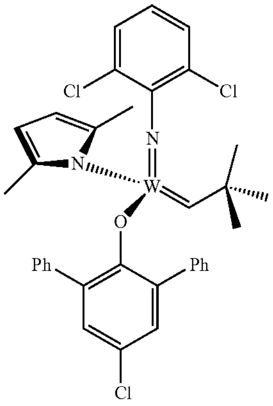
C35H33Cl3N2OW
787.25
8.04

189
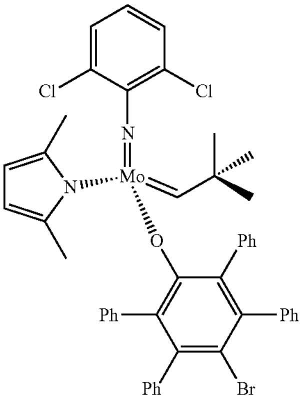
C47H41BrCl2MoN2O
896.6
10.73
190
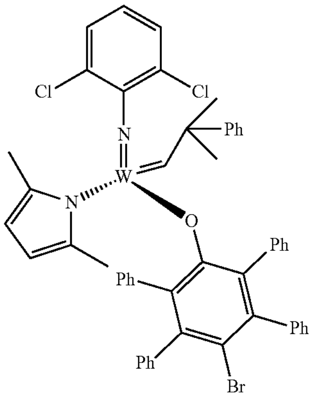
C52H43BrCl2N2OW
1046.56
7.98
191
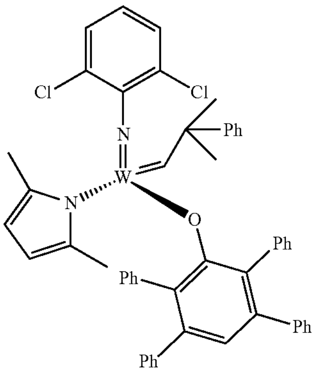
C52H44Cl2N2OW
967.66
01.aug
192
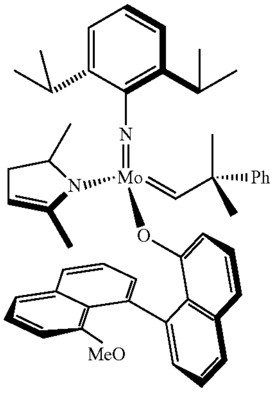
$C_{49}H_{52}MoN_2O_2$
796.89
10.82
193
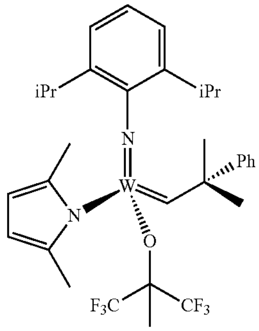
$C_{32}H_{40}F_6N_2OW$
766.5
9.39
194
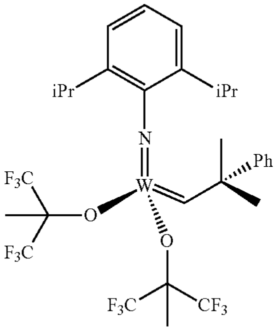
$C_{30}H_{35}F_{12}O_2W$
853.43
8.93

-continued
195
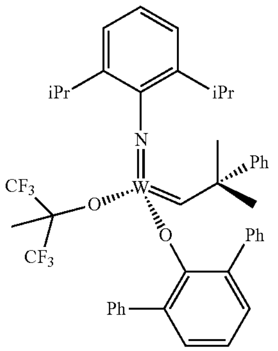
$C_{44}H_{45}F_6NO_2W$
917.66
8.44
196
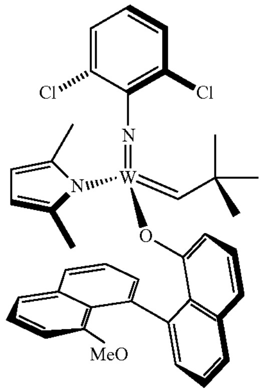
$C_{38}H_{36}Cl_2N_2O_2W$
807.45
overlapped with the aromatic protons
197
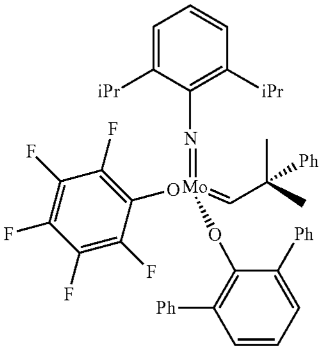
$C_{46}H_{42}F_5MoNO_2$
831.76
11.72
-continued
198
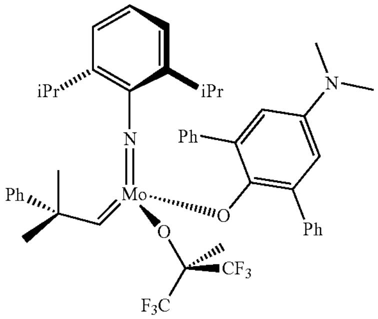
$C_{46}H_{50}F_6MoN_2O_2$
872.85
11.58
199
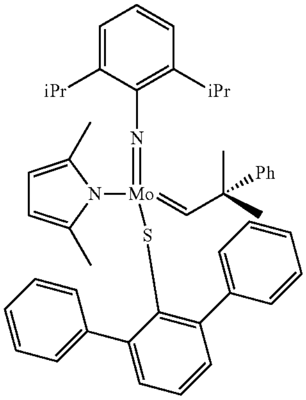
$C_{46}H_{50}MoN_2S$
760.91
11.99
200
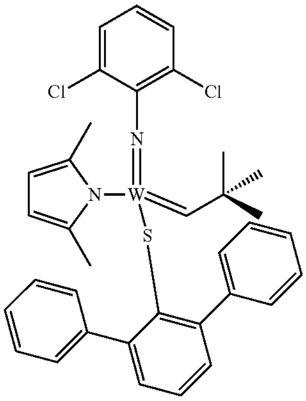
$C_{35}H_{34}Cl_2N_2SW$
769.47
8.479

201
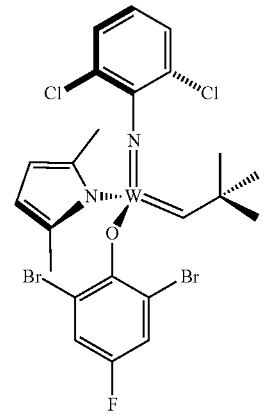
$C_{23}H_{23}Br_2Cl_2FN_2OW$
776.99
9.42
202
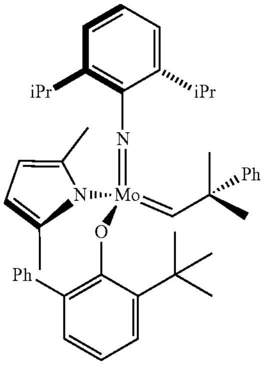
$C_{44}H_{54}MoN_2O$
722.87
11.86
203
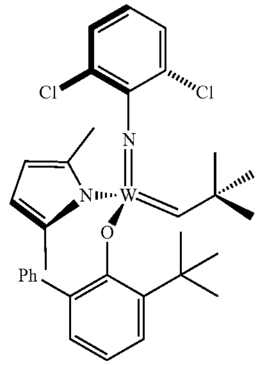
$C_{33}H_{38}Cl_2N_2OW$
733.42
8.34
204
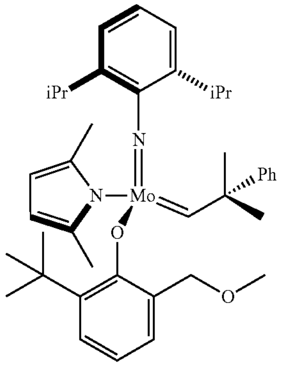
$C_{40}H_{34}MoN_2O_2$
690.82
13.74
205
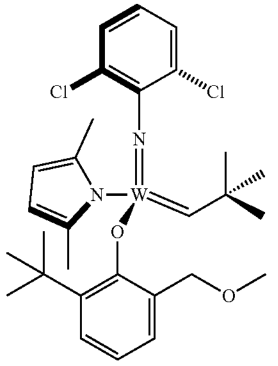
$C_{29}H_{38}Cl_2N_2O_2W$
701.38
11.02
207
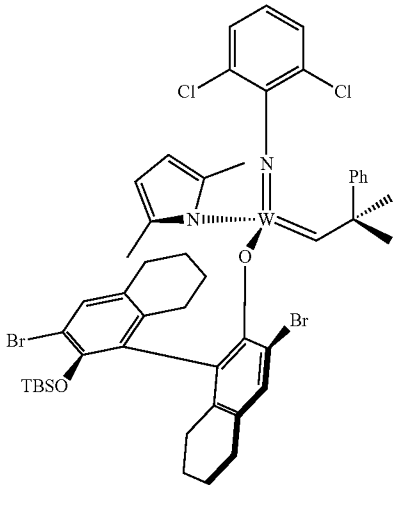
$C_{48}H_{56}Br_2Cl_2N_2O_2SiW$
1135.61
9.97, 9.72

208
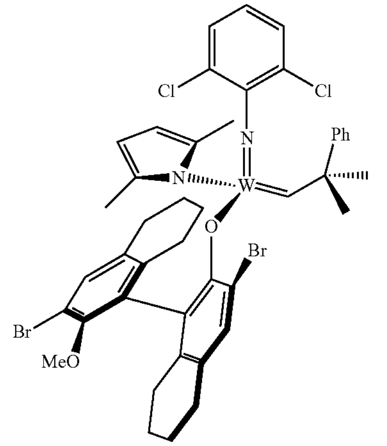
$C_{43}H_{44}Br_2Cl_2N_2O_2W$
1035.38
9.99, 9.60
209
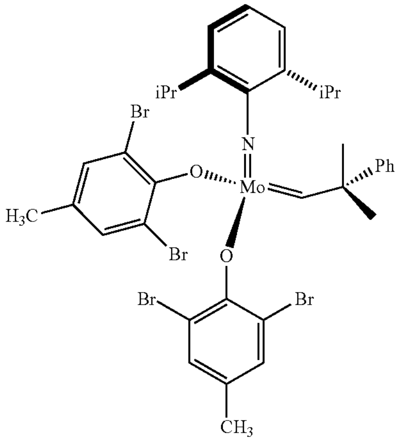
$C_{36}H_{39}Br_4MoNO_2$
933.27
11.78
210
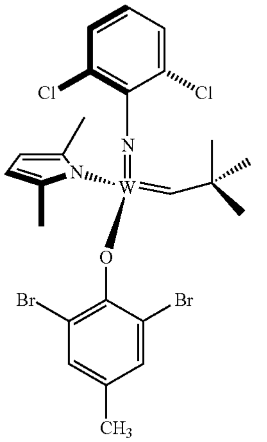
$C_{24}H_{26}Br_2Cl_2N_2OW$
773.04
9.54
212
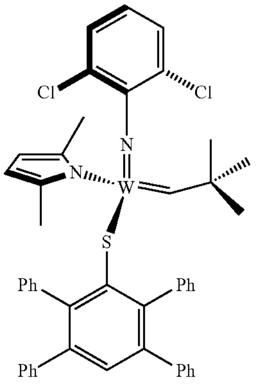
$C_{47}H_{42}Cl_2N_2SW$
921.68
8.69
213
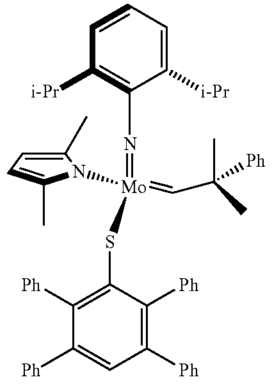
$C_{58}H_{58}MoN_2S$
911.12
11.81
214
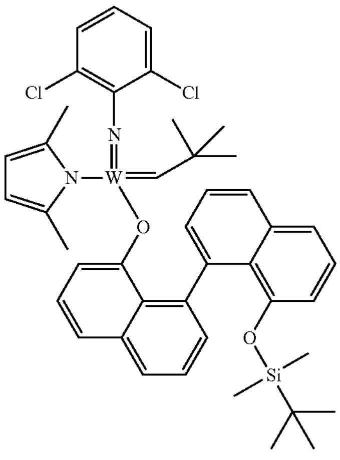
$C_{43}H_{48}Cl_2N_2O_2SiW$
907.7
7.9, 7.65

-continued
216
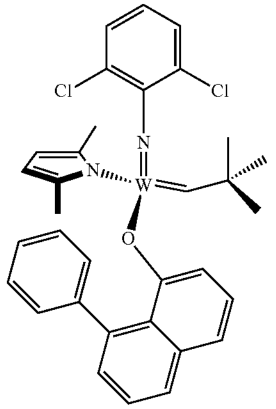
$C_{33}H_{32}Cl_2N_2OW$
726.14
8.54
217
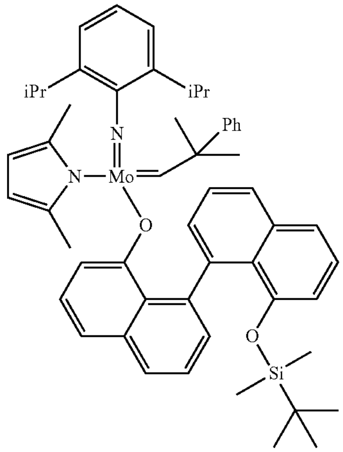
$C_{54}H_{64}MoN_2O_2Si$
897.12
11.16, 11.02
218
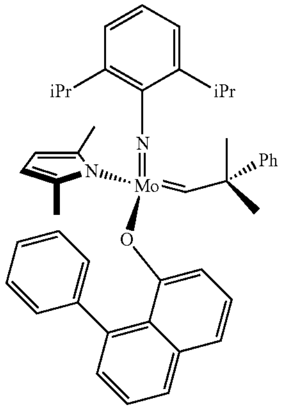
$C_{44}H_{48}MoN_2O$
716.8
11.71 (2), 10.55 (3)
-continued
219
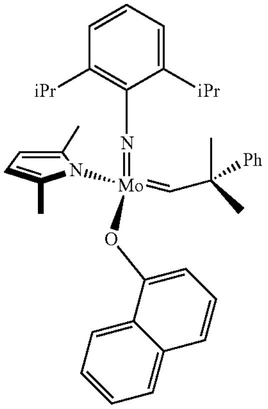
$C_{38}H_{44}MoN_2O$
640.7
12.2
220
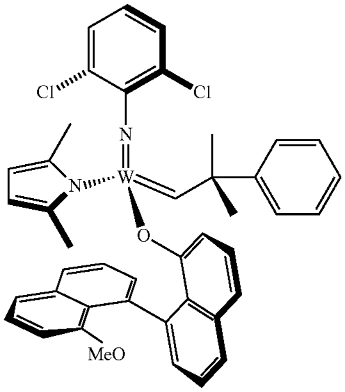
$C_{43}H_{38}Cl_2N_2O_2W$
869.52
7.88, 7.65
232
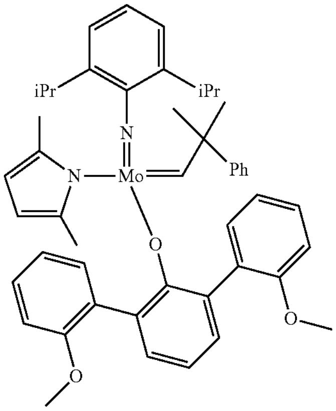
$C_{48}H_{54}MoN_2O_3$
802.91
11.71

-continued
233
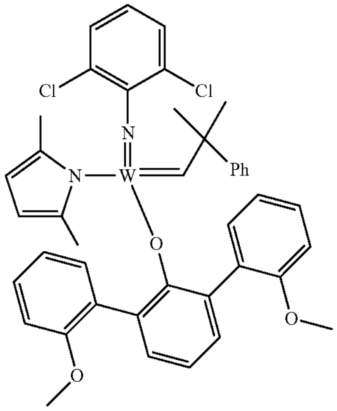
$C_{42}H_{40}Cl_2N_2O_3W$
875.54
8.65
246
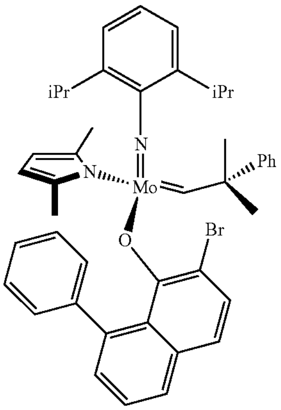
$C_{44}H_{47}BrMoN_2O$
795.71
12.00
247
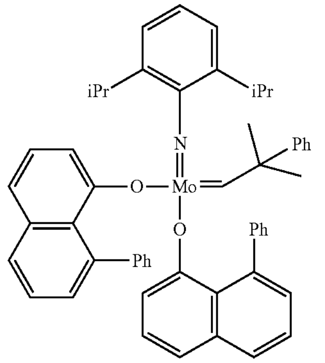
$C_{54}H_{51}MoNO_2$
841.94
10.5
-continued
261
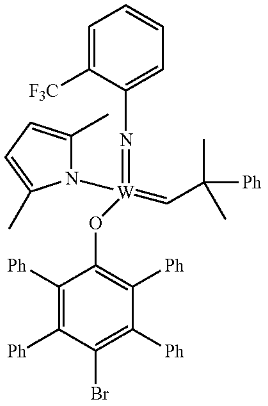
C53H44BrF3N2OW
1045.67
8.18 (2); 8.02 (debrominated)
262
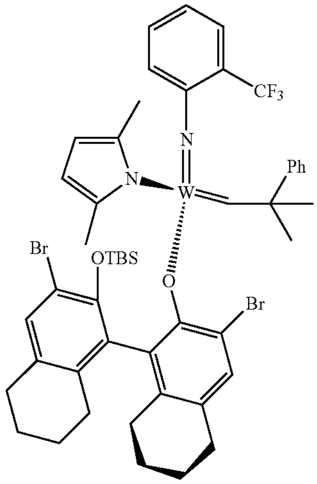
C49H57Br2F3N2O2SiW
1134.72
9.94 (2); 9.39 (2)
263
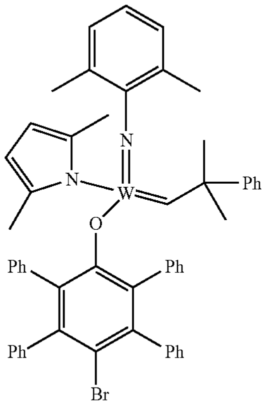
C54H49BrN2OW
1005.72
8.45 (2)

-continued
264
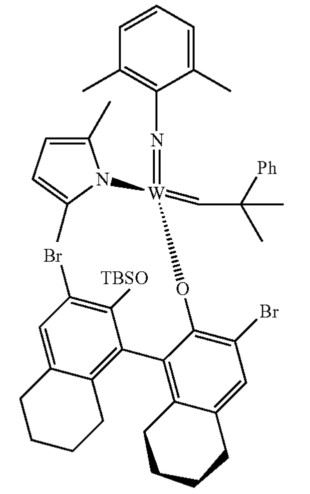
C50H62Br2N2O2SiW
1094.77
10.09 (2)
269
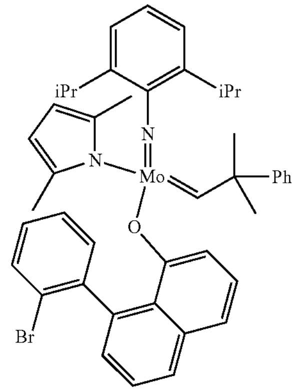
$C_{44}H_{47}BrMoN_2O$
795.71
12.6, 11.69
270
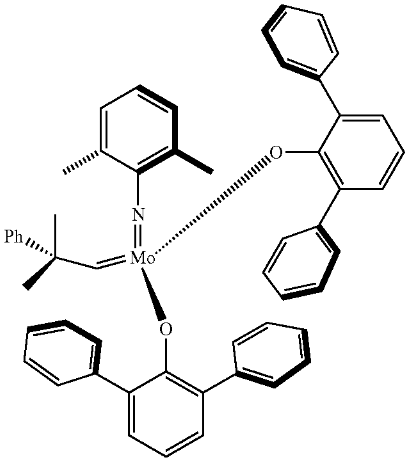
$C_{54}H_{47}MoNO_2$
837.90
11.29
-continued
271
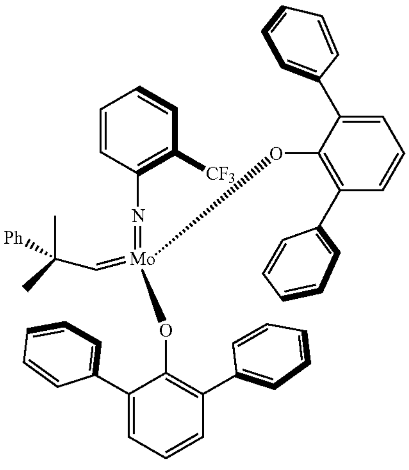
$C_{53}H_{42}F_3MoNO_2$
877.84
11.81 (11.88 MAP)
272
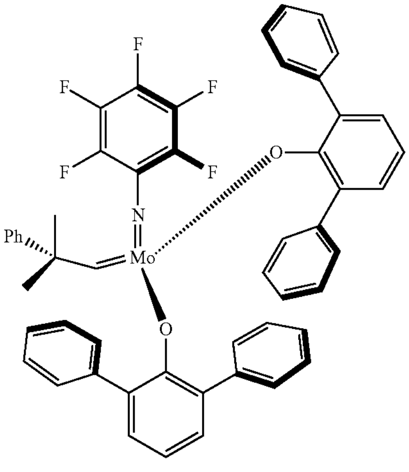
$C_{52}H_{38}F_5MoNO_2$
899.80
10.68
273
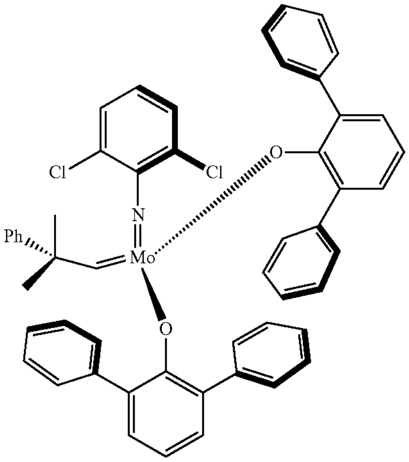
$C_{52}H_{41}Cl_2MoNO_2$
878.73
11.37, (11.19 MAPIII)

-continued
274
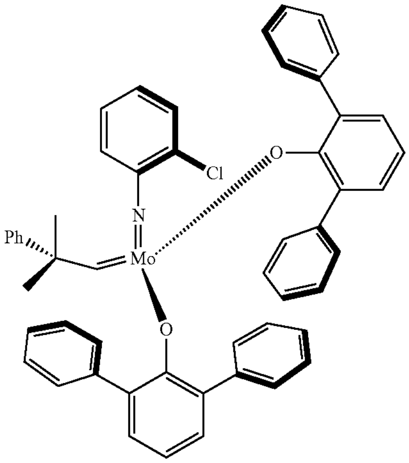
$C_{52}H_{42}ClMoNO_2$
844.29
11.04
280
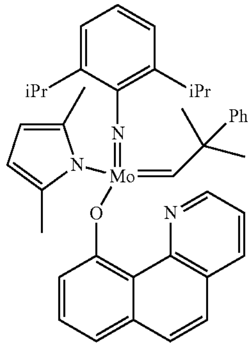
$C_{41}H_{45}MoN_3O$
691.78
11.92 (MAP) and 14.85 (BIS)
281
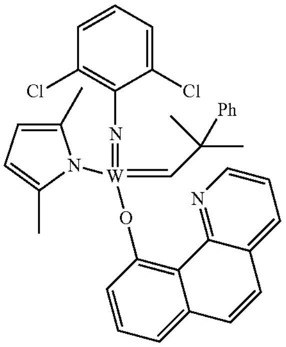
$C_{35}H_{31}Cl_2N_3OW$
764.39
12.98 and 10.82
-continued
282
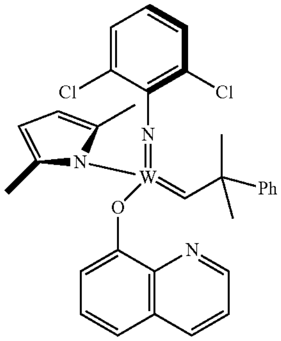
$C_{31}H_{29}Cl_2N_3OW$
714.34
10.44
283
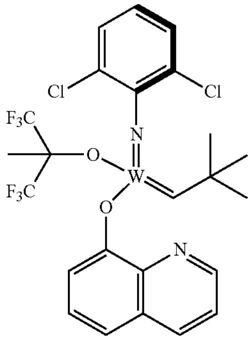
$C_{24}H_{22}Cl_2F_6N_2O_2W$
739.19
9.81 and 11.60
284
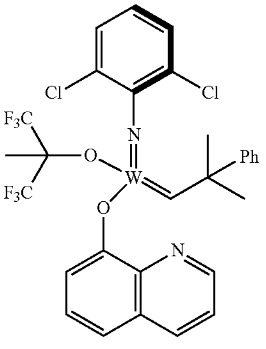
$C_{29}H_{24}Cl_2F_6N_2O_2W$
801.26
9.99 and 11.56

-continued

288

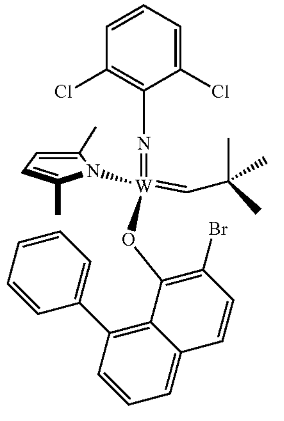

C33H31BrCl2N2OW
806.27
9.37

289

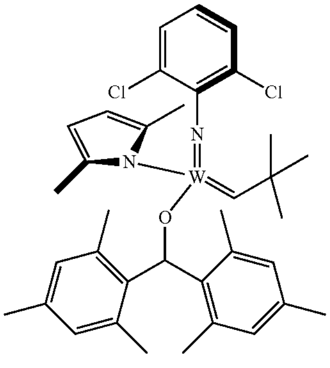

$C_{36}H_{44}Cl_2N_2OW$
775.5
7.78

290

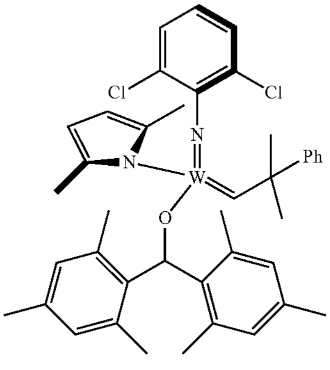

$C_{41}H_{46}Cl_2N_2OW$
837.57
8.00

-continued

291

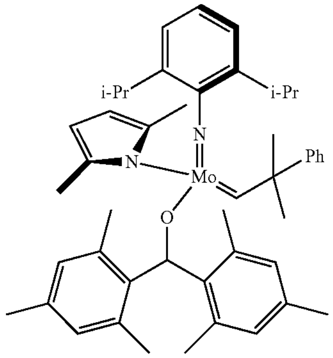

$C_{47}H_{60}MoN_2O$
764.95
11.11

The following compounds are known:

| | |
|---|---|
| 1 | J. Am. Chem. Soc. 2009, vol. 131, 10652-10661 |
| 9 | WO 2011/097642 |
| 10 | J. Amer. Chem. Soc. 2009, 131, 10652-10661 |
| 22 | Organometallics, 2009, vol. 28, 355-360 |
| 24 | Organometallics 2009, 28, 355-360; Organometallics 2010, 29, 6816-6828 |
| 49 | Organometallics 2012, 31, 4650-4653; Organometallics, 2009, vol. 28, 355-360 |
| 56 | J. Amer. Chem. Soc., 2009, vol. 131(46), 16630-16631 |
| 71 | J. Amer. Chem. Soc., 2009, 131, 10652-10661 |
| 72 | Plurality of references |
| 76 | WO 2009/094201; US 20120302710; Nature (London, United Kingdom) 456 (7224)933-937 (2008) |
| 78 | WO 2009/094201; US 2011/65915; Nature 456 (7224), 933-937(2008) |
| 80 | WO 2009/094201 |
| 87 | WO 2011/097642 |
| 88 | J. Amer. Chem. Soc. 2007, 129, 12654-12655 |
| 90 | variety of references |
| 92 | WO 2009/094201; Nature 456 (7224), 933-937(2008) |
| 93 | WO 2011/097642; J. Amer. Chem. Soc. 2012, 134(5), 2788-2799 |
| 96 | Organic Letters 2003, 5(25), 4899-4902 |
| 98 | J. Amer. Chem. Soc. 2009, 131, 16630-16631 |
| 101 | WO 2011/040963; US 2011/0077421 |
| 102 | J. Amer. Chem. Soc. 2012, 134, 2788-2799 |
| 103 | J. Amer. Chem. Soc. 1993, 115(25), 11831-45 |
| 110 | WO 2011/097642; Nature 479(7371), 88-93 (2011) |
| 112 | Organometallics 2012, 31(17), 6336-6343 |
| 113 | WO 2011/097642 |
| 118 | J. Amer. Chem. Soc., 2009, vol. 131, 16630-16631 |
| 143 | Macromolecules (2010), 43(18), 7515-7522 |
| 144 | J. Amer. Chem. Soc. 2009, 131, 7770-7780 |
| 147 | WO 2011/097642 |
| 153 | J. Amer. Chem. Soc. 2009, 131(30), 10652-10661 |
| 154 | WO 2011/040963; US 2011/0077421 |
| 174 | J. Amer. Chem. Soc. 2009, 131(30), 16630-16631 |
| 193 | Organometallics, 2009, 28, 355-361 |
| 194 | Organometallics, 2009, 28, 355-361 |

Purification of the First and/or Second Olefin, Respectively Purification of a Feedstock Comprising Said First and/or Second Olefin It has further been surprisingly found that the molar ratio of metathesis catalyst and first or second olefin or first and second olefin can be further decreased if the feedstock comprising said first and/or said second olefin that are to be subjected to said metathesis reaction is purified prior to its reaction at the catalyst.

In one embodiment, purification is performed such that by-products (contaminants) being contained in said feedstock are subjected to a physical purification. Preferably, the term "physical purification" encompasses: distilling said by-products off, or distilling the feedstock, or adsorbing said by-products. Accordingly, said by-products may be partially or completely removed from the feedstock such that they do not negatively affect the catalyst to be employed.

Possible by-products accompanying said first and said second olefin, which are comprised in said feedstock, are e.g. water, alcohols, aldehydes, peroxides, hydroperoxides, protic materials, polar materials, Lewis base (basic) catalyst poisons and two or more thereof. Accordingly, the by-products are selected from the group consisting of water, alcohols, aldehydes, peroxides, hydroperoxides, peroxide decomposition products, protic materials, polar materials, Lewis basic catalyst poisons, and two or more thereof.

In a further embodiment, purification is a chemical purification. Preferably, the term "chemical purification" encompasses: subjecting the by-products to a chemical reaction.

Accordingly, by means of a suitable reaction, the by-product(s) may be converted to another compound, which does not negatively affect the catalyst to be employed.

In one embodiment, physical purification comprises means selected from the group consisting of heat (preferably distillation), molecular sieves, alumina, silica gel, montmorillonite clay, Fuller's earth, bleaching clay, diatomaceous earth, zeolites, kaolin, activated metals, metal sulfates, metal halides, metal silicates, activated carbon, and soda ash.

In one embodiment, chemical purification comprises means selected from the group consisting of metal carbonates and metal hydrogen carbonates, acid anhydrides, metal hydrides, phosphorous pentoxide, metal aluminum hydrides, alkyl aluminum hydrides, trialkyl aluminums, metal borohydrides, organometallic reagents, metal amides, and combinations thereof.

In one embodiment, a by-product is a compound that contains at least one proton that is suitable to react with a compound selected from the group consisting of metal carbonates and metal hydrogen carbonates, acid anhydrides, metal hydrides, phosphorous pentoxide, metal aluminum hydrides, alkyl aluminum hydrides, trialkyl aluminums, metal borohydrides, organometallic reagents, metal amides, and combinations thereof.

In a further embodiment, purification is performed by means selected from the group consisting of optionally heat-treated molecular sieves, optionally heat-treated activated alumina, optionally heat-treated activated acidic alumina, optionally heat-treated activated neutral alumina, optionally heat-treated activated basic alumina, alkaline earth metal hydrides, alkaline earth metal sulfates, alkali metal sulfates, alkali earth metal halides, alkali metal aluminum hydrides, alkali metal borohydrides, Grignard reagents; organolithium reagents, trialkyl aluminums, metal bis(trimethylsilyl)amides, and combinations thereof.

In a further embodiment, purification is performed by means selected from the group consisting of $CaH_2$, activated Cu, activated Mg, acetic anhydride, calcium sulfate, magnesium sulfate, potassium sulfate, aluminum sulfate, potassium magnesium sulfate, sodium sulfate, calcium carbonate, sodium carbonate, magnesium silicate, potassium chloride, $LiAlH_4$, $NaAlH_4$, $iBu_2AlH$, n-butyl lithium, t-butyl lithium, sec-butyl lithium, triethyl aluminum, tributyl aluminum, triisopropyl aluminum, trioctyl aluminum, lithium diisopropyl amide, KHMDS, and combinations thereof.

Accordingly, in one embodiment, wherein said first and said second olefin are comprised in a feedstock, wherein said feedstock further comprises at least one by-product selected from the group consisting of water, alcohols, aldehydes, peroxides, hydroperoxides, peroxide decomposition products, protic materials, polar materials, Lewis basic catalyst poisons, or a mixture of two or more thereof, the method further comprises step (0) prior to step (i):

(0) subjecting said feedstock to a physical or chemical or physical and chemical purification step, preferably wherein said physical purification is performed prior to the chemical purification step,
  wherein the physical purification step comprises: distilling at least one of said by-products off, or distilling said feedstock, or adsorbing at least one of said by-products; and
  wherein the chemical purification step comprises: subjecting at least one of said by-products to a chemical reaction.

In one embodiment, said first and said second olefin are comprised in a feedstock, wherein said feedstock further comprises at least one by-product selected from the group consisting of water, alcohols, aldehydes, peroxides and hydroperoxides, peroxide decomposition products, protic materials, polar materials, Lewis basic catalyst poisons, or a mixture of two or more thereof, the method further comprising step (0) prior to step (i)

(0) subjecting at least one of the by-products in said feedstock to a chemical reaction.

In one embodiment, the first and the second olefin are identical.

In one embodiment, the feedstock comprises at least 99% by weight of the first and the second olefin based on the total weight of the feedstock, the remainder being by-products, or at least 99.5% by weight.

After the purification step, in one embodiment, the feedstock comprises at least 99.9% by weight of the first and the second olefin, or at least 99.99% by weight, or at least 99.999%.

Without being bound by theory, it is believed that said step (0) transfers by-products being contained in the olefin and which may react with a metathesis catalyst and thus may destroy activity thereof, into non-reactive species, thereby further favorably decreasing the molar ratio of catalyst to olefin.

In one embodiment, the by-products of the feedstock are subjected to an anhydride of an organic acid. Suitable anhydrides are preferably the anhydrides of aliphatic, cyclic, alicyclic organic acids having from 1 to 10 carbon atoms, or an aromatic organic acid having from 6 to 10 carbon atoms. Such compounds are known in the art or may be produced according to known methods.

In one embodiment, the organic anhydride is acetic anhydride.

In another embodiment, the by-products of the feedstock are subjected to an organometallic compound of aluminum.

In one embodiment, the organometallic compound is of formula $R_1R_2R_3Al$, wherein $R_1$, $R_2$, and $R_3$ are independently selected from an aliphatic, cyclic, alicyclic residue having from 1 to 10 carbon atoms, or from aromatic residues having from 6 to 10 carbon atoms. Such compounds are known in the art or may be produced according to known methods.

In one embodiment, the organometallic compound of aluminum is triethyl aluminum, tributyl aluminum, triisobutyl aluminum, triisopropyl aluminum, or trioctyl.

Trioctyl aluminum is particularly preferred since said compound is stable in contact with air, i.e. is not-flammable in contact with air, contrary to e.g. triethyl aluminum. This renders said compound particularly suitable for applications at an industrial scale.

For the practical realization of the chemical purification step, in one embodiment, the amount of by-products may be determined, e.g. by known methods such as chromatographical methods. Then, the theoretical amount of compound needed to convert reactive groups of the by-products into non-reactive groups, preferably organic anhydride or organometallic aluminum compound, is added.

In one embodiment, per mole of by-product, a slight excess of organic anhydride or organometallic aluminum compound, preferably a trialkyl aluminum compound, preferably trioctyl aluminum, is added in order to convert said by-product into a species which is not reactive towards the catalyst.

In one embodiment, if a trialkyl aluminum compound, preferably trioctyl aluminum, is used in the chemical purification step, per 1 mole of by-product, preferably 1 to 0.2 mole of trialkyl aluminum compound, preferably trioctyl aluminum, is used, preferably 1 to 1.5 mole, more preferred 1 to 1.25 mole.

In another embodiment, any excess of organometallic aluminum compound may be destroyed or removed.

In one embodiment, step (0) and step (i) may be performed spatially separated from each other. Thus, step (0) may be performed in one place or in one reaction vessel, and step (i) is performed at another place or in another reaction vessel.

In another embodiment, step (0) and step (i) are performed spatially not separated from each other. Thus, step (0) is performed in one place or in one reaction vessel, and step (i) is performed in the same place or in the same reaction vessel.

Typically, there are several choices of different and oftentimes complementary means from which to choose when preparing to purify a contaminated feedstock comprising said first and said second olefin prior to a metathesis reaction according to the invention.

While neither desiring to be bound by any particular theory nor intending to limit in any measure the scope of the appended claims or their equivalents, it is presently believed that the following non-exhaustive and non-limiting list of representative purification methodologies can be useful in treating feedstocks that contain besides the first and the second olefin the specified contaminants [provided the means are compatible with any functional groups on the feedstock and/or with the by-products (contaminants) themselves, etc.]: (a) a thermal treatment—for example, heating (and/or distilling) a feedstock or a by-product (e.g., between about 100° C. and about 250° C., or around 200° C. in some embodiments—depending on the feedstock's boiling point, optionally with a purge of an inert gas such as $N_2$ and/or the like) and/or treatment with an adsorbent (e.g., alumina and the like) can be useful both in decomposing peroxide contaminants and/or decomposition products thereof or adsorbing contaminants; (b) treatment with an acid anhydride (e.g., acetic anhydride, $Ac_2O$) can be useful in removing moisture, active hydroxyl-containing materials (e.g., alcohols), and hydroperoxides (via acetylation); (c) treatment with a desiccant (e.g., silica gel, alumina, molecular sieves, magnesium sulfate, calcium sulfate, and the like, and combinations thereof) and/or an organometallic reagent (e.g., t-butyl lithium, triethyl aluminum, tributyl aluminum, triisobutyl aluminum, triisopropyl aluminum, trioctyl aluminum, and the like, and combinations thereof) and/or metal hydrides (e.g., $CaH_2$ and the like) and/or acid anhydrides (e.g., acetic anhydride and the like) can be useful in removing moisture; (d) treatment with an adsorbent (e.g., alumina, silica gel, and the like, and combinations thereof) and/or an organometallic reagent (e.g., t-butyl lithium, triethyl aluminum, tributyl aluminum, triisobutyl aluminum, triisopropyl aluminum, trioctyl aluminum, and the like, and combinations thereof) and/or a metal amide (e.g., LDA, KHMDA, and the like) can be useful in removing protic materials; (e) treatment with an adsorbent (e.g., alumina, silica gel, activated charcoal, and the like, and combinations thereof) can be useful in removing polar materials; (f) treatment with an organometallic reagent (e.g., t-butyl lithium, triethyl aluminum, tributyl aluminum, triisobutyl aluminum, triisopropyl aluminum, trioctyl aluminum, and the like, and combinations thereof) can be useful in removing Lewis basic catalyst poisons; etc.

In some embodiments, the means used to purify said feedstock prior to a metathesis reaction comprises an adsorbent which, in some embodiments, is selected from the group consisting of silica gel, alumina, bleaching clay, activated carbon, molecular sieves, zeolites, Fuller's earth, diatomaceous earth, and the like, and combinations thereof. In some embodiments, the means is selected from the group consisting of optionally heat-treated molecular sieves, optionally heat-treated alumina, and a combination thereof. In some embodiments, the adsorbent comprises optionally heat-treated activated alumina which, in some embodiments, is selected from the group consisting of optionally heat-treated activated acidic alumina, optionally heat-treated activated neutral alumina, optionally heat-treated activated basic alumina, and combinations thereof. In some embodiments, the absorbent comprises optionally heat-treated activated neutral alumina, which can be useful in treating substrates (e.g., olefins) that are susceptible to acid-catalyzed isomerization and/or rearrangement.

For embodiments in which the means for purification comprises an adsorbent (e.g., molecular sieves, alumina, etc.), it is presently believed that the treating of the feedstock with the adsorbent is more effectively performed by flowing the feedstock through the means for purification using a percolation- or flow-type system (e.g., chromatography column) as opposed to simply adding the adsorbent to the substrate in a container. In some embodiments, about 20 wt % of alumina is used in a column. While neither desiring to be bound by any particular theory nor intending to limit in any measure the scope of the appended claims or their equivalents, it is presently believed that treating a feedstock with alumina on about a 5-to-1 weight-to-weight basis is effective for some embodiments. However, it is to be understood that the amount of alumina used is not restricted and will be both feedstock- and impurity dependent in addition to being impacted by the form of the alumina, its activation process, and the precise treatment method (e.g., flow through a column vs. direct addition to container). In some embodiments, the means used for purifying the feedstock prior to a metathesis reaction comprises a trialkyl aluminum which, in some embodiments, is selected from the group consisting of triethyl aluminum, tributyl aluminum, triisobutyl aluminum, triisopropyl aluminum, trioctyl aluminum, and the like, and combinations thereof. While neither desiring to be bound by any particular theory nor intending to limit in any measure the scope of the appended claims or their equivalents, it is presently believed that the treatment of a substrate with a trialkyl aluminum greatly improves feedstock conversions at low concentrations of metathesis catalyst but that in the presence of excess trialkyl aluminum, catalyst performance is adversely affected. Thus, in some embodiments, a successive agent used to treat the substrate can comprise an adsorbent which can remove excess trialkyl aluminum. In other embodiments, the amount of trialkyl aluminum used for treatment of the feedstock can be reduced by first treating the feedstock with a different means of a type described herein (e.g., an adsorbent including but not limited to molecular sieves, alumina, and/or the like), and then introducing the trialkyl aluminum as a second (or subsequent) means to remove residual contaminants. In any event, while neither desiring to be bound by any particular theory nor intending to limit in any measure the scope of the appended claims or their equivalents, it is presently believed that removal of excess trialkyl aluminum from organic products should be performed with great caution since use of the wrong adsorbent might be unsafe.

In some embodiments, molecular sieves can be used as a means for bulk drying a feedstock, “high heat-treated” alumina can then be used as a second means to remove additional moisture, and finally molecular sieves can be used at the end as a third means for removing still further residual moisture. In other embodiments, molecular sieves can be used as a first means for bulk drying a substrate, “high heat-treated” alumina can then be used as a second means to remove additional moisture, and finally a trialkyl aluminum (e.g., triethyl aluminum, tributyl aluminum, triisobutyl aluminum, triisopropyl aluminum, trioctyl aluminum, and the like, and combinations thereof) can be used as a third means for removing any further residual moisture.

In one particular embodiment, activated copper powder is used alone or in combination with another treatment. For example, in some embodiments, activated copper powder is used in combination with heat (e.g., 200° C. for at least 2 hours under nitrogen gas), molecular sieves, and/or a trialkyl aluminum treatment. In another embodiment, activated magnesium turnings are used alone or in combination with another treatment. For example, in some embodiments, activated magnesium turnings are used in combination with heat (e.g., 200° C. for at least 2 hours under nitrogen gas), molecular sieves, and/or a trialkyl aluminum treatment.

In another particular embodiment, acetic anhydride is used alone or in combination with another treatment/means. For example, in some embodiments, acetic anhydride is used in combination with alumina (aluminum oxide) and/or a trialkyl aluminum treatment. In other embodiments, acetic anhydride is used in combination with alumina, distillation, molecular sieves, and/or a trialkyl aluminum treatment. Further, percolation on activated alumina or molecular sieves can be applied before or instead of the trialkyl aluminum treatment.

In another embodiment, alumina is used alone or in combination with another treatment/agent. In one embodiment, alumina is used in combination with a palladium on carbon (Pd/C) catalyst and/or a trialkyl aluminum treatment.

It has further been unexpectedly found that the purification period of the feedstock may significantly influence efficacy of the chemical purification step. Accordingly, prolonged purification periods may improve catalytic activity of the compounds used as catalysts in the metathesis reactions according to the invention.

In one embodiment, preferably when a trialkyl aluminum compound is used for purification, preferably trioctyl aluminum, the feedstock is subjected to said compound for a period of from 2 to 100 h, preferably 5 to 90 h, more preferred 10 to 80 h, and still more preferred 15 to 70 h.

In some embodiments, the purification of the feedstock reduces the level of the at least one by-product by an amount sufficient to enable the metathesis reaction to proceed at a molar ratio of the compound of the above formula to the first and/or the second olefin of 1:1,000 or less, or 1:2,500 or less, or 1:5,000 or less, or 1:7,500 or less, or 1:10,000 or less.

In one embodiment, the purification of the feedstock reduces the level of the at least one by-product by an amount sufficient to enable the metathesis reaction to proceed at a molar ratio of the compound of the above formula to the first and/or the second olefin of less than 1:500, and the corresponding conversion is at least 30%, or at least 40%, or at least 50%, or at least 60%, or at least 70%, or at least 80%, or at least 90%.

In one embodiment, the purification of the feedstock reduces the level of the at least one by-product by an amount sufficient to enable the metathesis reaction to proceed at a molar ratio of the compound of the above formula to the first and/or the second olefin of 1:1,000 or less, and the corresponding conversion is at least 30%, or at least 40%, or at least 50%, or at least 60%, or at least 70%, or at least 80%, or at least 90%.

In one embodiment, the purification of the feedstock reduces the level of the at least one by-product by an amount sufficient to enable the metathesis reaction to proceed at a molar ratio of the compound of the above formula to the first and/or the second olefin of 1:2,500 or less, and the corresponding conversion is at least 30%, or at least 40%, or at least 50%, or at least 60%, or at least 70%, or at least 80%, or at least 90%.

In one embodiment, the purification provides a molar ratio of 1:5,000 or less, and the corresponding conversion is at least 30%, or at least 40%, or at least 50%, or at least 60%, or at least 70%, or at least 80%, or at least 90%.

In one embodiment, the purification of the feedstock reduces the level of the at least one by-product by an amount sufficient to enable the metathesis reaction to proceed at a molar ratio of the compound of the above formula to the first and/or the second olefin of 1:7,500 or less, and the corresponding conversion is at least 30%, or at least 40%, or at least 50%, or at least 60%, or at least 70%, or at least 80%, or at least 90%.

In one embodiment, the purification of the feedstock reduces the level of the at least one by-product by an amount sufficient to enable the metathesis reaction to proceed at a molar ratio of the compound of the above formula to the first and/or the second olefin of 1:10,000 or less, and the corresponding conversion is at least 30%, or at least 40%, or at least 50%, or at least 60%, or at least 70%, or at least 80%, or at least 90%.

In one embodiment, the purification of the feedstock reduces the level of the at least one by-product by an amount sufficient to enable the metathesis reaction to proceed at a molar ratio of the compound of the above formula to the first and/or the second olefin of 1:20,000 or less, or 1:50,000 or less, or 1:100,000 or less, or 1:500,000 or less, or 1:1,000,000 or less, and the corresponding conversion is at least 30%, or at least 40%, or at least 50%, or at least 60%, or at least 70%, or at least 80%, or at least 90%, respectively.

In one embodiment, the purification provides for a lower limit of the compound of the above formula to the first and/or the second olefin of the molar ratio of 1:2,000,000, or 1:3,000,000 or 1:4,000,000, respectively.

In other embodiments, the purification of the feedstock reduces the level of the at least one by-product by an amount sufficient to enable the metathesis reaction to proceed at a molar ratio of the compound of the above formula to the first and/or the second olefin of less than 1:500 to 1:50,000 or less, and the corresponding conversion is from 30 to 100%, or from 50 to 100%, or 60 to 100%.

In one embodiment, the purification of the feedstock reduces the level of the at least one by-product by an amount sufficient to enable the metathesis reaction to proceed at a molar ratio of the compound of the above formula to the first and/or the second olefin of from 1:1,000 to 1:40,000 or less, and the corresponding conversion is from 30 to 100%, or from 50 to 100%, or 60 to 100%.

In one embodiment, the purification of the feedstock reduces the level of the at least one by-product by an amount sufficient to enable the metathesis reaction to proceed at a molar ratio of the compound of the above formula to the first and/or the second olefin of from 1:2,500 to 1:30,000 or less, and the corresponding conversion is from 30 to 100%, or from 50 to 100%, or 60 to 100%.

In one embodiment, the purification of the feedstock reduces the level of the at least one by-product by an amount sufficient to enable the metathesis reaction to proceed at a molar ratio of the compound of the above formula to the first and/or the second olefin of from 1:5,000 to 1:30,000 or less, or from 1:10,000 to 1:30,000, or from 1:15,000 to 1:30,000, and the corresponding conversion is from 30 to 100%, or from 50 to 100%, or 60 to 100%, respectively.

In one embodiment, said method consists of steps (0) and (i).

Mode of Addition of the Catalyst to the Feedstock Comprising the First Olefin and/or the Second Olefin In another embodiment, it has further been unexpectedly found that the efficacy of the compound of the above formula used as metathesis catalyst may be improved through slow addition of the catalyst to the first and/or second olefin. The efficacy may be e.g. evaluated by calculating the turn-over-number (TON). In some embodiments, the overall catalyst loading may be decreased by at least 10%, at least 20%, or at least 30% in comparison to achieve the same TON as a single, full batch loading. The slow addition of overall catalyst loading may comprise adding fractional catalyst loadings to the substrate at an average rate of approximately 10 ppmwt catalyst per hour (ppmwt/hr), 5 ppmwt/hr, 1 ppmwt/hr, 0.5 ppmwt/hr, 0.1 ppmwt/hr, 0.05 ppmwt/hr, or 0.01 ppmwt/hr. In other embodiments, the catalyst is slowly added at a rate of between about 0.01-10 ppmwt/hr, 0.05-5 ppmwt/hr, or 0.1-1 ppmwt/hr. The slow addition of the catalyst may be conducted in batch loadings at frequencies of every 5 minutes, 15 minutes, 30 minutes, 1 hour, 2 hours, 4 hours, 12 hours, or 1 day. In other embodiments, the slow addition is conducted in a continuous addition process.

In one embodiment, the catalyst is slowly added to the substrate at a rate of from 0.01-10 ppmwt catalyst per hour.

In one embodiment, the catalyst is added in portions.

In some embodiments, the feedstock comprising the first and/or second olefin is purified with at least one means as described in detail above prior to the slow addition of the catalyst. In other embodiments, the slow addition of the catalyst improves the efficacy of the catalyst independent of any treatment of the substrate.

In one embodiment, the feedstock is purified applying prolonged purification periods followed by a slow addition of the catalyst.

Second Aspect of the Invention—Selected Compounds Suitable for Use in Metathesis Reactions and Metathesis Reactions According to the Invention According to a second aspect, the invention relates to compounds that may be used in the method as defined in the first aspect of the invention and in any embodiment defined therein.

In one embodiment, the invention relates to a compound of formula

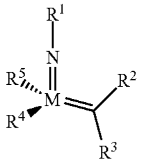

wherein

M is Mo or W;

$R^1$ is selected from 2,6-dimethylphenyl, 2,6-diisopropylphenyl, 2,6-di-t-butylphenyl, 2,6-dichlorophenyl, adamant-1-yl;

$R^2$ is —$C(CH_3)_2C_6H_5$ or —$C(CH_3)_3$;

$R^3$ is H;

$R^5$ is selected from pyrrol-1-yl; 2,5-dimethyl-pyrrol-1-yl; triphenylsilyloxy; triisopropylsilyloxy; 2-phenyl-1,1,1,3,3,3-hexafluoro-prop-2-yloxy; 2-methyl-1,1,1,3,3,3-hexafluoro-prop-2-yloxy; 9-phenyl-fluorene-9-yloxy; 2,6-diphenylphenoxy; t-butyloxy; and $R^4$ is $R^6$—X—, wherein X═O and $R^6$ is phenyl which bears at least two substituents, or which bears two substituents in ortho position with respect to O, or which bears two substituents in ortho position with respect to O and a substituent in para position with respect to O;

X═O and $R^6$ is triphenylsilyl; optionally substituted; or triisopropylsilyl; or X═O and $R^6$ is triphenylmethyl; optionally substituted; or X═O and $R^6$ is 9-phenyl-fluorene-9-yl; or X═O and $R^6$ is 2-phenyl-1,1,1,3,3,3-hexafluoro-prop-2-yl or 2-methyl-1,1,1,3,3,3-hexafluoro-prop-2-yl; or X═O and $R^6$ is t-butyl with the proviso that following compounds are excluded:

M=Mo; $R^1$=2,6-diisopropylphenyl; $R^2$═—$C(CH_3)_2C_6H_5$; $R^3$═H; $R^5$=2,5-dimethylpyrrol-1-yl; $R^4$=2,6-diphenylphenoxy;

M=Mo; $R^1$=2,6-diisopropylphenyl; $R^2$═—$C(CH_3)_2C_6H_5$; $R^3$═H; $R^5$=2,5-dimethylpyrrol-1-yl; $R^4$=2,3,5,6-tetraphenylphenoxy;

M=W; $R^1$=2,6-diisopropylphenyl; $R^2$═—$C(CH_3)_2C_6H_5$; $R^3$═H; $R^5$=2,5-dimethylpyrrol-1-yl; $R^4$=triphenylsilyloxy; and M=Mo; $R^1$=2,6-diisopropylphenyl; $R^2$═—$C(CH_3)_2C_6H_5$; $R^3$═H; $R^5$=2,5-dimethylpyrrol-1-yl; $R^4$=triphenylsilyloxy; and M=W; $R^1$=2,6-diisopropylphenyl; $R^2$═—$C(CH_3)_2C_6H_5$; $R^3$═H; $R^5$=2,5-dimethylpyrrol-1-yl; and $R^4$=

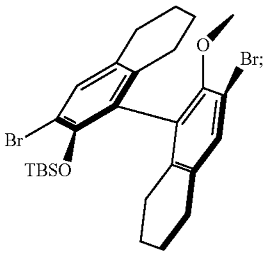

and

-continued

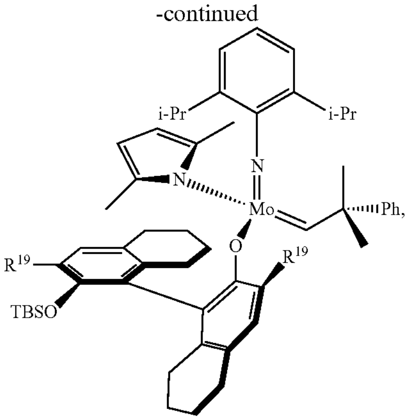

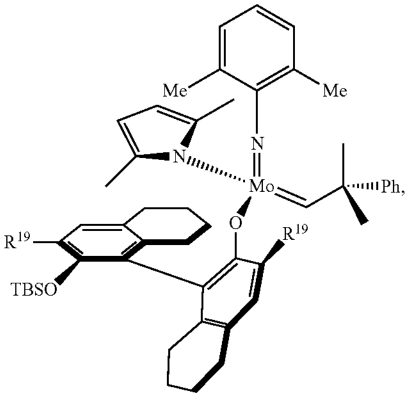

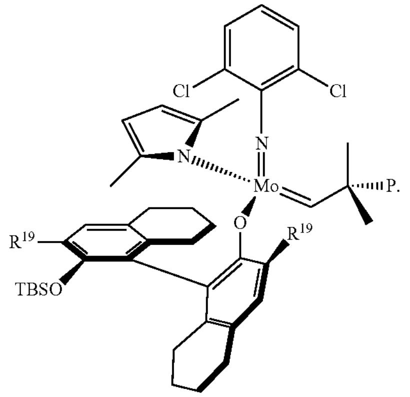

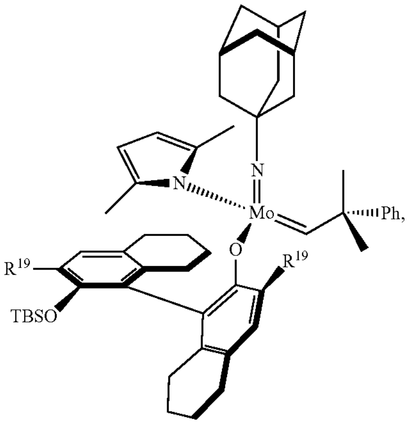

wherein $R^{19}$ is F, Cl, Br, or I.

In one embodiment, $R^6$ is phenyl, which bears two substituents in ortho position with respect to O, or which bears two substituents in ortho position with respect to O and a substituent in para position with respect to O, wherein the two substituents in ortho position are identical.

In one embodiment,

M=Mo or W;

$R^1$ is selected from 2,6-dimethylphenyl, 2,6-diisopropylphenyl, 2,6-dichlorophenyl, adamant-1-yl;

$R^2$ is —$C(CH_3)_2C_6H_5$ or —$C(CH_3)_3$;

$R^3$ is H;

$R^5$ is selected from pyrrol-1-yl; 2,5-dimethyl-pyrrol-1-yl; triphenylsilyloxy; triisopropylsilyloxy; 2-phenyl-1,1,1,3,3,3-hexafluoro-prop-2-yloxy; 2-methyl-1,1,1,3,3,3-hexafluoro-prop-2-yloxy; 9-phenyl-fluorene-9-yloxy; 2,6-diphenylphenoxy; t-butyloxy; and $R^4$ is selected from 4-bromo-2,6-diphenylphenoxy, 4-fluoro-2,6-diphenylphenoxy, 4-methyl-2,6-diphenylphenoxy, 4-dimethylamino-2,6-diphenylphenoxy, 4-methoxy-2,6-diphenylphenoxy, 2,4,6-triphenylphenoxy, 4-fluoro-2,6-dimesitylphenoxy, 4-bromo-2,6-di-tert.-butylphenoxy, 4-methoxy-2,6-di-tert.-butylphenoxy, 4-methyl-2,6-di-tert.butylphenoxy, 2,4,6-tri-tert.-butylphenoxy, 4-bromo-2,3,5,6-tetraphenylphenoxy; 4-bromo-2,6-di(4-bromophenyl)-3,5-diphenylphenoxy.

In one embodiment,

M=Mo or W;

$R^1$ is selected from 2,6-dimethylphenyl, 2,6-diisopropylphenyl, 2,6-dichlorophenyl, adamant-1-yl;

$R^2$ is —$C(CH_3)_2C_6H_5$ or —$C(CH_3)_3$;

$R^3$ is H;

$R^5$ is selected from pyrrol-1-yl; 2,5-dimethyl-pyrrol-1-yl; triphenylsilyoxy; triisopropylsilyloxy; 2-phenyl-1,1,1,3,3,3-hexafluoro-prop-2-yloxy; 9-phenyl-fluorene-9-yloxy; 2-methyl-1,1,1,3,3,3-hexafluoro-prop-2-yloxy; 2,6-diphenylphenoxy; and $R^4$ is selected from

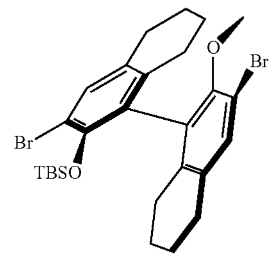

wherein TBS is t-butyldimethylsilyl;

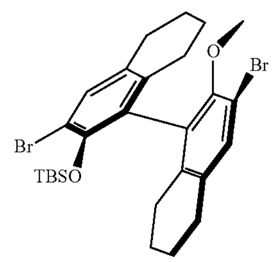

wherein Me=methyl;

with the proviso that following compounds are excluded: M=W; $R^1$=2,6-diisopropylphenyl; $R^2$=—$C(CH_3)_2C_6H_5$; $R^3$=H; $R^5$=2,5-dimethylpyrrol-1-yl; and $R^4$=

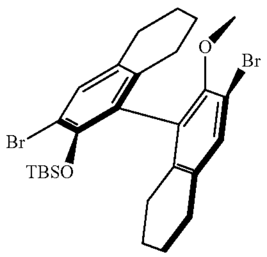

wherein TBS is t-butyldimethylsilyl; and

M=Mo; $R^1$=2,6-diisopropylphenyl, 2,6-dimethylphenyl, 2,6-dichlorophenyl, adamant-1-yl; $R^2$=—$C(CH_3)_2C_6H_5$; $R^3$=H; $R^5$=2,5-dimethylpyrrol-1-yl; and $R^4$=

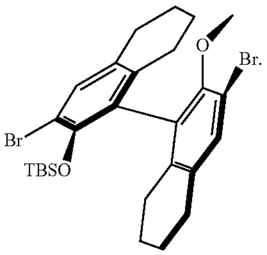

In one embodiment,

M is Mo or W;

$R^1$ is 2,6-dimethylphenyl, 2,6-diisopropylphenyl, 2,6-dichlorophenyl, adamant-1-yl;

$R^2$ is —$C(CH_3)_2C_6H_5$ or —$C(CH_3)_3$;

$R^3$ is H;

$R^5$ is selected from pyrrol-1-yl; 2,5-dimethyl-pyrrol-1-yl; triphenylsilyloxy; triisopropylsilyloxy; 2-phenyl-1,1,1,3,3,3-hexafluoro-prop-2-yloxy; 2-methyl-1,1,1,3,3,3-hexafluoro-prop-2-yloxy; 9-phenyl-fluorene-9-yloxy; 2,6-diphenylphenoxy; t-butyloxy; and $R^4$ is selected from 2,6-diphenylphenoxy, 2,3,5,6-tetraphenylphenoxy, 2,6-di(tert.butyl)phenoxy;

with the proviso that following compounds are excluded:

M=Mo; $R^1$=2,6-diisopropylphenyl; $R^2$=—$C(CH_3)_2C_6H_5$; $R^3$=H; $R^5$=2,5-dimethylpyrrol-1-yl; $R^4$=2,6-diphenylphenoxy; and M=Mo; $R^1$=2,6-diisopropylphenyl; $R^2$=—$C(CH_3)_2C_6H_5$; $R^3$=H; $R^5$=2,5-dimethylpyrrol-1-yl; $R^4$=2,3,5,6-tetraphenylphenoxy.

In one embodiment,

M is Mo or W;

$R^1$ is selected from 2,6-dimethylphenyl, 2,6-diisopropylphenyl, 2,6-dichlorophenyl, adamant-1-yl;

$R^2$ is —$C(CH_3)_2C_6H_5$ or —$C(CH_3)_3$;

$R^3$ is H;

$R^5$ is selected from pyrrol-1-yl; 2,5-dimethyl-pyrrol-1-yl; triphenylsilyloxy; triisopropylsilyloxy; 2-phenyl-1,1,1,3,3,3-hexafluoro-prop-2-yloxy; 2-methyl-1,1,1,3,3,3-hexafluoro-prop-2-yloxy; 9-phenyl-fluorene-9-yloxy; 2,6-diphenylphenoxy; t-butyloxy; and $R^4$ is a residue $R^6$—X—, wherein X=O and $R^6$ is triphenylsilyl;

with the proviso that following compounds are excluded:

M=W; $R^1$=2,6-diisopropylphenyl; $R^2$=—$C(CH_3)_2C_6H_5$; $R^3$=H; $R^5$=2,5-dimethylpyrrol-1-yl; $R^4$=triphenylsilyloxy; and M=Mo; $R^1$=2,6-diisopropylphenyl; $R^2$=—$C(CH_3)_2C_6H_5$; $R^3$=H; $R^5$=2,5-dimethylpyrrol-1-yl; $R^4$=triphenylsilyloxy.

In one embodiment,

M is Mo or W;

$R^1$ is selected from 2,6-dimethylphenyl, 2,6-diisopropylphenyl, 2,6-dichlorophenyl, adamant-1-yl;

$R^2$ is —$C(CH_3)_2C_6H_5$ or —$C(CH_3)_3$;

$R^3$ is H;

$R^5$ is selected from pyrrol-1-yl; 2,5-dimethyl-pyrrol-1-yl; triphenylsilyloxy; triisopropylsilyloxy; 2-phenyl-1,1,1,3,3,3-hexafluoro-prop-2-yloxy; 2-methyl-1,1,1,3,3,3-hexafluoro-prop-2-yloxy; 9-phenyl-fluorene-9-yloxy; t-butyloxy; and $R^4$ is a residue $R^6$—X—, wherein X=O and $R^6$ is selected from triphenylmethyl or tri(4-methyphenyl)methyl; 1,1,1,3,3,3-hexafluoro-prop-2-yl; 9-phenyl-fluorene-9-yl.

In a further embodiment, the invention relates to a compound of formula

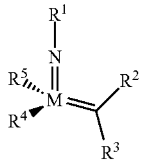

wherein M is Mo or W; $R^1$ is aryl, or adamant-1-yl; optionally substituted; $R^2$ is —$C(CH_3)_2C_6H_5$ or —$C(CH_3)_3$; $R^3$ is H; $R^5$ is alkoxy, heteroaryl, silyloxy; optionally substituted; and $R^4$ is a residue $R^6$—X—, wherein X=O and $R^6$ is an aryl residue, which bears a substituent in para-position with respect to O.

In one embodiment, $R^1$ is selected from 2,6-dimethylphenyl, 2,6-diisopropylphenyl, 2,6-di-t-butylphenyl, 2,6-dichlorophenyl, adamant-1-yl; $R^2$ is —$C(CH_3)_2C_6H_5$ or —$C(CH_3)_3$; $R^3$ is H; $R^5$ is selected from pyrrol-1-yl; 2,5-dimethyl-pyrrol-1-yl; triphenylsilyloxy; triisopropylsilyloxy; 2-phenyl-1,1,1,3,3,3-hexafluoro-prop-2-yloxy; 2-methyl-1,1,1,3,3,3-hexafluoro-prop-2-yloxy; 9-phenyl-fluorene-9-yloxy; t-butyloxy; and $R^4$ is $R^6$—X—, wherein $R^6$=phenyl substituted in para-position with respect to O and with up to four further substituents, wherein the substituents are independently selected from alkyl, preferably $C_1$-$C_4$ alkyl such as methyl, isopropyl or t-butyl, alkoxy, preferably $C_1$-$C_4$ alkoxy, halogen phenoxy, optionally substituted phenyl, optionally substituted.

In one embodiment, $R^4$ is selected from 4-bromo-2,6-diphenylphenoxy, 4-fluoro-2,6-diphenylphenoxy, 4-methyl-2,6-diphenylphenoxy, 4-methoxy-2,6-diphenylphenoxy, 2,4,6-triphenylphenoxy, 4-fluoro-2,6-dimesitylphenoxy, 4-bromo-2,6-di-tert.-butylphenoxy, 4-methoxy-2,6-di-tert.-butylphenoxy, 4-methyl-2,6-di-tert.-butylphenoxy, 2,4,6-tri-tert.butylphenoxy, 4-bromo-2,3,5,6-tetraphenylphenoxy, 4-bromo-2,6-di(4-bromophenyl)-3,5-diphenylphenoxy;

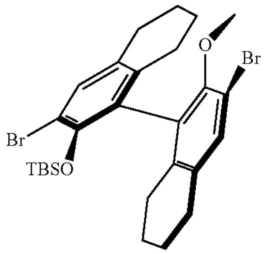

wherein TBS is t-butyldimethylsilyl;

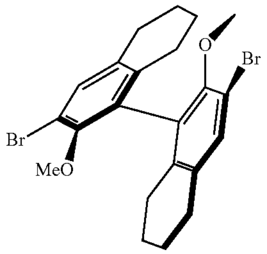

wherein Me=methyl.

In one embodiment, $R^4$ is selected from 4-bromo-2,6-diphenylphenoxy, 4-fluoro-2,6-diphenylphenoxy, 4-methyl-2,6-diphenylphenoxy, 4-methoxy-2,6-diphenylphenoxy, 2,4,6-triphenylphenoxy, 4-fluoro-2,6-dimesitylphenoxy, 4-bromo-2,6-di-tert.-butylphenoxy, 4-methoxy-2,6-di-tert.-butylphenoxy, 4-methyl-2,6-di-tert.-butylphenoxy, 2,4,6-tri-tert.butylphenoxy, 4-bromo-2,3,5,6-tetraphenylphenoxy, 4-bromo-2,6-di(4-bromophenyl)-3,5-diphenylphenoxy.

In one embodiment, the invention relates to a compound of formula

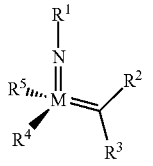

wherein M is Mo or W; $R^1$ is aryl, or adamant-1-yl; optionally substituted; $R^2$ is —$C(CH_3)_2C_6H_5$ or —$C(CH_3)_3$; $R^3$ is H; $R^5$ is alkoxy, heteroaryl, silyloxy; optionally substituted; and $R^4$ is a residue $R^6$—X—, wherein X═O and $R^6$ is an aryl residue, which bears two substituents in ortho-position with respect to O;

with the proviso that following compounds are excluded:

M=Mo; $R^1$=2,6-diisopropylphenyl; $R^2$═—$C(CH_3)_2C_6H_5$; $R^3$═H; $R^5$=2,5-dimethylpyrrol-1-yl; $R^4$=2,6-diphenylphenoxy (compound 1); M=Mo; $R^1$=2,6-diisopropylphenyl; $R^2$═—$C(CH_3)_2C_6H_5$; $R^3$═H; $R^5$=2,5-dimethylpyrrol-1-yl; $R^4$=2,3,5,6-tetraphenylphenoxy (compound 10).

In one embodiment, $R^1$ is selected from 2,6-dimethylphenyl, 2,6-diisopropylphenyl, 2,6-di-t-butylphenyl, 2,6-dichlorophenyl, adamant-1-yl; $R^5$ is selected from pyrrol-1-yl; 2,5-dimethyl-pyrrol-1-yl; triphenylsilyloxy; triisopropylsilyloxy; 2-phenyl-1,1,1,3,3,3-hexafluoro-prop-2-yloxy; 2-methyl-1,1,1,3,3,3-hexafluoro-prop-2-yloxy; 9-phenyl-fluorene-9-yloxy; t-butyloxy; and $R^4$ is $R^6$—X—, wherein X═O and $R^6$ is phenyl substituted with up to two further substituents in ortho-position with respect to O, and wherein all substituents are independently selected from alkyl, preferably $C_1$-$C_4$ alkyl such as methyl, isopropyl or t-butyl, alkoxy, preferably $C_1$-$C_4$ alkoxy, phenoxy, phenyl, halogen, optionally substituted.

In one embodiment, $R^4$ is selected from 2,6-diphenylphenoxy, 2,3,5,6-tetraphenylphenoxy, 2,6-di(tert.-butyl)phenoxy.

In one embodiment, the invention relates to a compound of formula

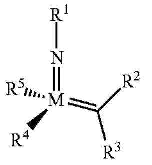

wherein

M=Mo or W; $R^1$ is aryl, or adamant-1-yl; optionally substituted; $R^2$ is —$C(CH_3)_2C_6H_5$ or —$C(CH_3)_3$; $R^3$ is H; $R^5$ is alkoxy, heteroaryl, silyloxy; optionally substituted; and $R^4$ is a residue $R^6$—X—, wherein X═O and $R^6$ is triphenylsilyl or triisopropylsilyl;

with the proviso that following compounds are excluded:

M=W; $R^1$=2,6-diisopropylphenyl; $R^2$═—$C(CH_3)_2C_6H_5$; $R^3$═H; $R^5$=2,5-dimethylpyrrol-1-yl; $R^4$=triphenylsilyloxy; and M=Mo; $R^1$=2,6-diisopropylphenyl; $R^2$═—$C(CH_3)_2C_6H_5$; $R^3$═H; $R^5$=2,5-dimethylpyrrol-1-yl; $R^4$=triphenylsilyloxy.

In one embodiment, $R^1$ is selected from 2,6-dimethylphenyl, 2,6-diisopropylphenyl, 2,6-dichlorophenyl, adamant-1-yl; $R^5$ is selected from pyrrol-1-yl; 2,5-dimethyl-pyrrol-1-yl; triphenylsilyl; triisopropylsilyl; 2-phenyl-1,1,1,3,3,3-hexafluoro-prop-2-yloxy; 2-methyl-1,1,1,3,3,3-hexafluoro-prop-2-yloxy; 9-phenyl-fluorene-9-yloxy; t-butyloxy.

In one embodiment, the invention relates to a compound of formula

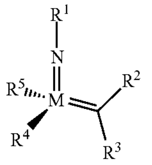

wherein M=Mo or W; $R^1$ is aryl, or adamant-1-yl; optionally substituted; $R^2$ is —$C(CH_3)_2C_6H_5$ or —$C(CH_3)_3$; $R^3$ is H; $R^5$ is alkoxy, heteroaryl, silyloxy; optionally substituted; and $R^4$ is a residue $R^6$—X—, wherein X═O and $R^6$ is selected from triphenylmethyl or tri(4-methyphenyl)methyl; 1,1,1,3,3,3-hexafluoro-prop-2-yl; 9-phenyl-fluorene-9-yl.

In one embodiment, $R^1$ is selected from 2,6-dimethylphenyl, 2,6-diisopropylphenyl, 2,6-dichlorophenyl, adamant-1-yl; $R^5$ is selected from pyrrol-1-yl; 2,5-dimethyl-pyrrol-1-yl; triphenylsilyl; triisopropylsilyl; 2-phenyl-1,1,1,3,3,3-hexafluoro-prop-2-yloxy; 2-methyl-1,1,1,3,3,3-hexafluoro-prop-2-yloxy; 9-phenyl-fluorene-9-yloxy; t-butyloxy.

In one embodiment, M=Mo or W; $R^1$ is selected from 2,6-dimethylphenyl, 2,6-diisopropylphenyl, 2,6-dichlorophenyl; $R^2$ is —$C(CH_3)_2C_6H_5$ or —$C(CH_3)_3$; $R^3$ is H; $R^5$ is selected from pyrrol-1-yl and 2,5-dimethyl-pyrrol-1-yl; $R^4$ is $R^6$—X—, wherein $R^6$—X— is selected from 1-(2,6-di-t-butylphenoxy); wherein the phenyl moiety of the phenoxy residue preferably bears up to three substituents independently selected from alkyl, preferably $C_1$-$C_4$ alkyl such as methyl, isopropyl or t-butyl, alkoxy, such as $C_1$-$C_4$ alkoxy, phenoxy, phenyl, halogen.

In one embodiment, M=Mo or W; $R^1$ is selected from 2,6-dimethylphenyl, 2,6-diisopropylphenyl, 2,6-dichlorophenyl; $R^2$ is —$C(CH_3)_2C_6H_5$ or —$C(CH_3)_3$; $R^3$ is H; $R^5$ is selected from pyrrol-1-yl and 2,5-dimethyl-pyrrol-1-yl; $R^4$ is $R^6$—X—, wherein $R^6$—X— is selected from 4-methyl-2,6-di-t-butylphenoxy or 4-methoxy-2,6-di-t-butylphenoxy or 4-bromo-2,6-di-t-butylphenoxy or 2,4,6-tri-t-butylphenoxy.

In one embodiment, M=W; $R^1$ is 2,6-dichlorophenyl; $R^2$ is —$C(CH_3)_2C_6H_5$ or —$C(CH_3)_3$; $R^3$ is H; $R^5$ is pyrrol-1-yl; $R^4$ is 4-bromo-2,6-di-t-butylphenoxy or 2,4,6-tri-t-butylphenoxy or 4-methoxy-2,6-di-t-butylphenoxy.

In one embodiment, M=Mo; $R^1$ is 2,6-diisopropylphenyl; $R^2$ is —$C(CH_3)_2C_6H_5$ or —$C(CH_3)_3$; $R^3$ is H; $R^5$ is pyrrol-1-yl; $R^4$ is 4-methyl-2,6-di-t-butylphenoxy or 4-bromo-2,6-di-t-butylphenoxy or 2,4,6-tri-t-butylphenoxy or 4-methoxy-2,6-di-t-butylphenoxy.

In one embodiment, M=Mo or W; $R^1$ is selected from 2,6-dimethylphenyl, 2,6-diisopropylphenyl, 2,6-dichlorophenyl; $R^2$ is —$C(CH_3)_2C_6H_5$ or —$C(CH_3)_3$; $R^3$ is H; $R^5$ is selected from pyrrol-1-yl and 2,5-dimethyl-pyrrol-1-yl; $R^4$ is $R^6$—X—, wherein $R^6$—X— is selected from 2,6-di-phenylphenoxy; wherein the phenyl moiety of the phenoxy residue preferably bears up to three substituents independently selected from alkyl, preferably $C_1$-$C_4$ alkyl such as methyl, isopropyl or t-butyl, alkoxy, such as $C_1$-$C_4$ alkoxy, halogen, phenoxy, phenyl, optionally substituted, respectively.

In one embodiment, M=Mo or W; $R^1$ is selected from 2,6-dimethylphenyl, 2,6-diisopropylphenyl, 2,6-dichlorophenyl; $R^2$ is —$C(CH_3)_2C_6H_5$ or —$C(CH_3)_3$; $R^3$ is H; $R^5$ is selected from pyrrol-1-yl and 2,5-dimethyl-pyrrol-1-yl; $R^4$ is $R^6$—X—, wherein $R^6$—X— is selected from 2,6-diphenylphenoxy, 4-chloro-2,6-diphenylphenoxy, 4-bromo-2,6-diphenylphenoxy, 4-fluoro-2,6-diphenylphenoxy, 4-fluoro-2,6-di(2,4,6-trimethylphenyl)phenoxy, 2,3,5,6-tetraphenylphenoxy or 4-chloro-2,3,5,6-tetraphenylphenoxy or 4-bromo-2,3,5,6-tetraphenylphenoxy or 4-fluoro-2,3,5,6-tetraphenylphenoxy or 4-bromo-3,5-diphenyl-2,6-di(4-bromophenyl)phenoxy or 4-dimethylaminophenyl-2,6-diphenylphenoxy or 2,6-di(2,4,6-triisopropylphenyl)phenoxy.

In one embodiment, M=Mo; $R^1$ is selected from 2,6-diisopropylphenyl; $R^2$ is —$C(CH_3)_2C_6H_5$ or —$C(CH_3)_3$; $R^3$ is H; $R^5$ is pyrrol-1-yl; $R^4$ is 2,6-diphenylphenoxy, 4-bromo-2,6-diphenylphenoxy, 4-fluoro-2,6-diphenylphenoxy, 4-fluoro-2,6-di(2,4,6-trimethylphenyl)phenoxy.

In one embodiment, M=Mo; $R^1$ is selected from 2,6-dimethylphenyl; $R^2$ is —$C(CH_3)_2C_6H_5$ or —$C(CH_3)_3$; $R^3$ is H; $R^5$ is 2,5-dimethyl-pyrrol-1-yl; $R^4$ is selected from 2,6-diphenylphenoxy, 4-fluoro-2,6-di(2,4,6-trimethylphenyl) phenoxy.

In one embodiment, M=Mo; $R^1$ is selected from adamant-1-yl; $R^2$ is —$C(CH_3)_2C_6H_5$ or —$C(CH_3)_3$; $R^3$ is H; $R^5$ is 2,5-dimethyl-pyrrol-1-yl; $R^4$ is 2,6-diphenylphenoxy.

In one embodiment, M=Mo; $R^1$ is 2,6-dimethylphenyl; $R^2$ is —$C(CH_3)_2C_6H_5$ or —$C(CH_3)_3$; $R^3$ is H; $R^5$ is 2,5-dimethyl-pyrrol-1-yl; $R^4$ is selected from 4-bromo-2,6-diphenylphenoxy, 4-fluoro-2,6-di(2,4,6-trimethylphenyl)phenoxy.

In one embodiment, M=Mo; $R^1$ is 2,6-dimethylphenyl; $R^2$ is —$C(CH_3)_2C_6H_5$ or —$C(CH_3)_3$; $R^3$ is H; $R^5$ is selected from pyrrol-1-yl; 2,5-dimethyl-pyrrol-1-yl; $R^4$ is 9-phenyl-fluorene-9-yloxy.

In one embodiment, M is Mo; $R^1$ is 2,6-dichlorophenyl; $R^2$ is —$C(CH_3)_2C_6H_5$ or —$C(CH_3)_3$; $R^3$ is H; $R^5$ is selected from pyrrol-1-yl; 2,5-dimethyl-pyrrol-1-yl; $R^4$ is 9-phenyl-fluorene-9-yloxy.

In one embodiment, M=Mo; $R^1$ is 2,6-diisopropylphenyl; $R^2$ is —$C(CH_3)_2C_6H_5$ or —$C(CH_3)_3$; $R^3$ is H; $R^5$ is selected from pyrrol-1-yl; 2,5-dimethyl-pyrrol-1-yl; $R^4$ is 2-phenyl-1,1,1,3,3,3-hexafluoroprop-2-yloxy.

In one embodiment, M=Mo; $R^1$ is 2,6-diisopropylphenyl; $R^2$ is —$C(CH_3)_2C_6H_5$ or —$C(CH_3)_3$; $R^3$ is H; $R^5$ is selected from pyrrol-1-yl; 2,5-dimethyl-pyrrol-1-yl; $R^4$ is triphenylsilyloxy.

In one embodiment, M=W; $R^1$ is selected from 2,6-diisopropylphenyl, 2,6-dichlorophenyl; $R^2$ is —$C(CH_3)_2C_6H_5$ or —$C(CH_3)_3$; $R^3$ is H; $R^5$ is 2,5-dimethyl-pyrrol-1-yl; $R^4$ is triphenylsilyloxy.

In one embodiment, M=Mo; $R^1$ is selected from 2,6-diisopropylphenyl; 2,6-dichlorophenyl; $R^2$ is —$C(CH_3)_2C_6H_5$ or —$C(CH_3)_3$; $R^3$ is H; $R^5$ is pyrrol-1-yl; $R^4$ is triphenylmethyloxy.

In one embodiment, M=Mo; $R^1$ is 2,6-dichlorophenyl; $R^2$ is —$C(CH_3)_2C_6H_5$ or —$C(CH_3)_3$; $R^3$ is H; $R^5$ is 2,5-dimethyl-pyrrol-1-yl; $R^4$ is triphenylmethyloxy.

In one embodiment, $R^1$ is 2,6-dimethylphenyl or 2,6-diisopropylphenyl; $R^2$ is —$C(CH_3)_2C_6H_5$ or —$C(CH_3)_3$; $R^3$ is H; $R^4$ is 4-bromo-2,6-diphenylphenoxy or 4-bromo-2,3,5,6-tetraphenylphenoxy; $R^5$ is pyrrol-1-yl or 2,5-dimethyl-pyrrol-1-yl.

In one embodiment, M=Mo; $R^1$ is 2,6-dimethylphenyl or 2,6-diisopropylphenyl; $R^2$ is —$C(CH_3)_2C_6H_5$ or —$C(CH_3)_3$; $R^3$ is H; $R^4$ is 4-bromo-2,6-diphenylphenoxy; $R^5$ is 2,5-dimethyl-pyrrol-1-yl.

In still another embodiment, M=Mo; $R^1$ is 2,6-dimethylphenyl or 2,6-diisopropylphenyl; $R^2$ is —$C(CH_3)_2C_6H_5$ or —$C(CH_3)_3$; $R^3$ is H; $R^4$ is 4-bromo-2,3,5,6-tetraphenylphenoxy; $R^5$ is 2,5-dimethyl-pyrrol-1-yl.

In one embodiment, M=Mo; $R^1$ is 2,6-diisopropylphenyl; $R^2$ is —$C(CH_3)_2C_6H_5$ or —$C(CH_3)_3$; $R^3$ is H; $R^4$ is 2,6-di-t-butylphenoxy; wherein the phenyl moiety of the phenoxy residue preferably bears up to three substituents independently selected from alkyl, preferably $C_1$-$C_4$ alkyl such as methyl or t-butyl, alkoxy, such as $C_1$-$C_4$ alkoxy, phenoxy, phenyl, halogen; $R^5$ is pyrrol-1-yl.

In one embodiment, M=Mo; $R^1$ is 2,6-diisopropylphenyl; $R^2$ is —$C(CH_3)_2C_6H_5$ or —$C(CH_3)_3$; $R^3$ is H; $R^4$ is 4-methyl-2,6-di-t-butylphenoxy or 4-methoxy-2,6-di-t-butylphenoxy or 4-bromo-2,6-di-t-butylphenoxy or 2,4,6-tri-t-butylphenoxy; $R^5$ is pyrrol-1-yl.

In one embodiment, M=W; $R^1$ is 2,6-dichlorophenyl; $R^2$ is —$C(CH_3)_3$; $R^3$ is H; $R^5$ is pyrrol-1-yl; $R^4$ is 4-methoxy-2,6-di-t-butylphenoxy or 4-bromo-2,6-di-t-butylphenoxy or 2,4,6-tri-t-butylphenoxy.

Each of these three W-based compounds of the aforementioned embodiment, when used as a catalyst in a cross metathesis reaction, may provide for excellent Z-selectivity, which may be around 90% Z and around 10% E.

In one embodiment, M=Mo; $R^1$ is 2,6-diisopropylphenyl; $R^2$ is —$C(CH_3)_2C_6H_5$ or —$C(CH_3)_3$; $R^3$ is H; $R^4$ is 4-bromo-2,6-diphenylphenoxy or 4-bromo-2,3,5,6-tetraphenylphenoxy; $R^5$ is pyrrol-1-yl.

In one embodiment, M=Mo; or W; $R^1$ is selected from 2,6-dimethylphenyl; 2,6-diisopropylphenyl; or 2,6-dichlorophenyl; $R^2$ is —$C(CH_3)_2C_6H_5$ or —$C(CH_3)_3$; $R^3$ is H; $R^4$ is 2,6-diphenylphenoxy or 2,6-di-t-butylphenoxy; wherein the phenyl moiety of the phenoxy residue preferably additionally to the two phenyl or t-butyl residues bears up to three substituents independently selected from alkyl, preferably $C_1$-$C_4$ alkyl such as methyl or t-butyl, alkoxy, such as $C_1$-$C_4$ alkoxy, phenoxy, phenyl, halogen; $R^5$ is pyrrol-1-yl; 2,5-dimethyl-pyrrol-1-yl.

In one embodiment, M=Mo; or W; is selected from 2,6-dimethylphenyl; 2,6-diisopropylphenyl; or 2,6-dichlorophenyl; $R^2$ is —$C(CH_3)_2C_6H_5$; —$C(CH_3)_3$; $R^3$ is H; $R^4$ is 2,6-diphenylphenoxy or 2,6-di-t-butylphenoxy; wherein the phenyl moiety of the phenoxy residue additionally to the two phenyl or t-butyl residues bears up to three substituents independently selected from alkyl, preferably $C_1$-$C_4$ alkyl such as methyl or t-butyl, alkoxy, such as $C_1$-$C_4$ alkoxy, halogen, phenoxy, phenyl, optionally substituted, respectively; $R^5$ is pyrrol-1-yl; 2,5-dimethyl-pyrrol-1-yl.

In one embodiment, M is Mo or W; $R^1$ is selected from 2,6-dimethylphenyl, 2,6-diisopropylphenyl, 2,6-di-t-butylphenyl, 2,6-dichlorophenyl, adamant-1-yl; $R^2$ is —$C(CH_3)_2C_6H_5$ or —$C(CH_3)_3$; $R^3$ is H; $R^5$ is selected from triphenylsilyloxy; and $R^4$ is $R^6$—X—, wherein X═O and $R^6$ is triphenylmethyl; optionally substituted; or X═O and $R^6$ is 9-phenyl-fluorene-9-yl; or X═O and $R^6$ is 2-phenyl-1,1,1,3,3,3-hexafluoro-prop-2-yl or 2-methyl-1,1,1,3,3,3-hexafluoro-prop-2-yloxy.

In one embodiment, M=Mo or W; $R^1$ is selected from 2,6-dimethylphenyl, 2,6-diisopropylphenyl, 2,6-di-t-butylphenyl, 2,6-dichlorophenyl, adamant-1-yl; $R^2$ is —$C(CH_3)_2C_6H_5$ or —$C(CH_3)_3$; $R^3$ is H; $R^5$ is selected from 9-phenyl-fluorene-9-yloxy; and $R^4$ is $R^6$—X—, wherein X═O and $R^6$ is triphenylmethyl; optionally substituted; or X═O and $R^6$ is 9-phenyl-fluorene-9-yl; or X═O and $R^6$ is 2-phenyl-1,1,1,3,3,3-hexafluoro-prop-2-yl or 2-methyl-1,1,1,3,3,3-hexafluoro-prop-2-yloxy.

In one embodiment, M=Mo or W; $R^1$ is selected from 2,6-dimethylphenyl, 2,6-diisopropylphenyl, 2,6-di-t-butylphenyl, 2,6-dichlorophenyl, adamant-1-yl; $R^2$ is —$C(CH_3)_2C_6H_5$ or —$C(CH_3)_3$; $R^3$ is H; $R^5$ is selected from 2-phenyl-1,1,1,3,3,3-hexafluoro-prop-2-oxy or 2-methyl-1,1,1,3,3,3-hexafluoro-prop-2-yloxy; and $R^4$ is $R^6$—X—, wherein X═O and $R^6$ is triphenylmethyl; optionally substituted; or X═O and $R^6$ is 9-phenyl-fluorene-9-yl; or X═O and $R^6$ is 2-phenyl-1,1,1,3,3,3-hexafluoro-prop-2-yl or 2-methyl-1,1,1,3,3,3-hexafluoro-prop-2-yloxy; or t-butyloxy.

In one embodiment, M=W; $R^1$ is selected from 2,6-dimethylphenyl, 2,6-diisopropylphenyl, 2,6-dichlorophenyl, adamant-1-yl; $R^2$ is —$C(CH_3)_3$; $R^3$ is H; $R^5$ is selected from pyrrol-1-yl; 2,5-dimethyl-pyrrol-1-yl;

$R^4$ is

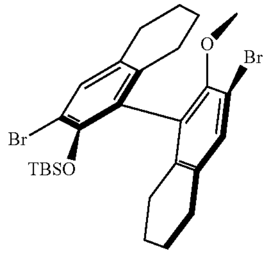

wherein TBS is t-butyldimethylsilyl;

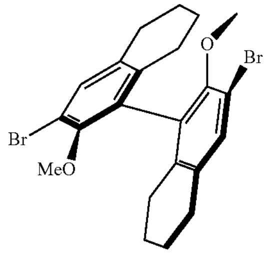

wherein M=methyl;

In one embodiment, M=Mo or W; $R^1$ is selected from 2,6-dimethylphenyl, 2,6-diisopropylphenyl, 2,6-dichlorophenyl, adamant-1-yl; $R^2$ is —$C(CH_3)_3$; $R^3$ is H; $R^5$ is selected from pyrrol-1-yl; 2,5-dimethyl-pyrrol-1-yl; triphenylsilyloxy; 9-phenyl-fluorene-9-yloxy; 2-phenyl-1,1,1,3,3,3-hexafluoroprop-2-yloxy; $R^4$ is $R^6$—X—, wherein X═O and $R^6$ is phenyl substituted with up to five substituents independently selected from alkyl, preferably $C_1$-$C_4$ alkyl such as methyl, isopropyl or t-butyl, alkoxy, preferably $C_1$-$C_4$ alkoxy, halogen, phenoxy, phenyl, optionally substituted, respectively; or X═S and $R^6$ is phenyl substituted with up to five substituents independently selected from alkyl, preferably $C_1$-$C_4$ alkyl such as methyl, isopropyl or t-butyl, alkoxy, preferably $C_1$-$C_4$ alkoxy, halogen, phenoxy, phenyl, optionally substituted, respectively; or X═O and $R^6$ is triphenylsilyl or triisopropylsilyl; or X═O and $R^6$ is triphenylmethyl or tri(4-methylphenyl)methyl; or X═O and $R^6$ is 9-phenyl-fluorene-9-yl; or X═O and $R^6$ is 2-phenyl-1,1,1,3,3,3-hexafluoro-prop-2-yl or 2-methyl-1,1,1,3,3,3-hexafluoro-prop-2-yloxy; or X═O and $R^6$ is t-butyloxy.

In one embodiment, M=Mo or W; $R^1$ is selected from 2,6-dimethylphenyl, 2,6-diisopropylphenyl, 2,6-dichlorophenyl; $R^2$ is —$C(CH_3)_3$; $R^3$ is H; $R^5$ is selected from pyrrol-1-yl; 2,5-dimethyl-pyrrol-1-yl; $R^4$ is selected from 2,6-diphenylphenoxy, 4-bromo-2,6-diphenylphenoxy, 4-fluoro-2,6-diphenylphenoxy, 4-methyl-2,6-diphenylphenoxy, 4-dimethylamino-2,6-diphenylphenoxy, 2,6-di(2,4,6-triisopropylphenyl)phenoxy, 4-fluoro-2,6-dimesityiphenoxy, 2,6-di-tert.-butylphenoxy, 4-bromo-2,6-di-tert.-butylphenoxy, 4-methoxy-2,6-di-tert.-butylphenoxy, 4-methyl-2,6-di-tert.-butylphenoxy, 2,4,6-tri-tert.butylphenoxy, 2,3,5,6-tetraphenylphenoxy, 4-bromo-2,3,5,6-tetraphenylphenoxy, 2,6-di(4-bromophenyl)-3,5-diphenylphenoxy, 4-bromo-2,6-di(4-bromophenyl)-3,5-diphenylphenoxy,

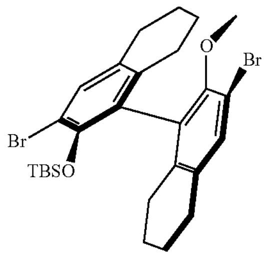

wherein TBS denotes a t-butyldimethylsilyl group, and

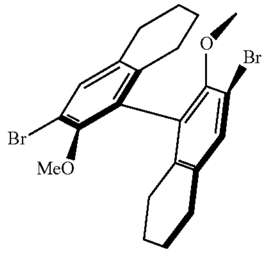

wherein Me denotes a methyl group;

or $R^4$ is $R^6$—X—, wherein

X=O and $R^6$ is triphenylsilyl or triisopropylsilyl; or

X=O and $R^6$ is triphenylmethyl or tri(4-methylphenyl) methyl; or

X=O and $R^6$ is 9-phenyl-fluorene-9-yl; or

X=O and $R^6$ is 2-phenyl-1,1,1,3,3,3-hexafluoro-prop-2-yl or 2-methyl-1,1,1,3,3,3-hexafluoro-prop-2-yloxy; or X=O and $R^6$ is t-butyl.

In one embodiment, the invention relates to a compound of structure 2, 3, 4, 5, 6, 7, 8, 11, 12, 13, 14, 15, 16, 17, 18, 19, 20, 21, 23, 25, 26, 27, 28, 29, 30, 31, 32, 33, 34, 35, 36, 37, 38, 39, 40, 41, 42, 43, 44, 45, 46, 47, 48, 50, 51, 52, 53, 54, 55, 57, 58, 59, 60, 61, 62, 63, 64, 65, 66, 67, 68, 69, 70, 73, 74, 75, 77, 79, 81, 82, 83, 84, 85, 86, 89, 91, 94, 95, 97, 99, 100, 104, 105, 107, 108, 109, 111, 114, 115, 116, 117,119, 120, 121, 122, 123, 124, 125, 126, 127, 128, 129, 130, 131, 132, 133, 134, 135, 136, 137, 138, 139, 140, 141, 142, 145, 146, 148, 149, 150, 151, 152, 155, 156, 157, 158, 159, 160, 161, 162, 163, 164, 165, 166, 167, 168, 169, 170, 171, 172, 173, 175, 176, 177, 178, 179, 180, 181, 182, 183, 184, 185, 186, 187, 188, 189, 190, 191, 192, 195, 196, 197, 198, 199, 200, 201, 202, 203, 204, 205, 207, 208, 209, 210, 212, 213, 214, 216, 217, 218, 219, 220, 232, 233, 246, 247, 261, 262, 263, 264, 269, 270, 271, 272, 273, 274, 280, 281, 282, 283, 284, 288, 289, 290, 291.

In one embodiment, compounds are preferably selected from the group consisting of structures 11, 32, 36, and 162. Also preferred are compounds selected from the group consisting of structures 30, 123, 142, 154, 168, and 178. Also preferred is the compound of structure 21.

Third Aspect of the Invention—Use of the Compounds as Defined in the Second Aspect of the Invention According to a third aspect, the invention relates to the use of a compound as defined in the second aspect or in any embodiment of the second aspect as catalyst, preferably wherein the catalyst catalyzes a metathesis reaction. Accordingly, the compounds may be used in a metathesis reaction or as catalyst in a metathesis reaction.

In one embodiment, the metathesis reaction is selected from cross metathesis, ring opening metathesis, ring opening polymerization metathesis, ring closing metathesis, ethenolysis, homo-metathesis.

Cross metathesis may e.g. be performed as a homo cross metathesis, i.e. the metathesis reaction between identical olefins (HCM) or as a hetereo cross metathesis reaction, i.e. the reaction between two different olefins.

Fourth Aspect of the Invention—Use of the Compounds in a Kit

According to a fourth aspect, the invention relates to a kit comprising an organometallic compound of aluminum of formula $R_1R_2R_3Al$, wherein $R_1$, $R_2$, and $R_3$ are independently selected from an aliphatic, cyclic, alicyclic residue having from 1 to 10 carbon atoms, or from aromatic residues having from 6 to 10 carbon atoms; and a compound used in the method of the invention, preferably a compound selected from one or more of the structures 1 to 291.

In one embodiment, the organometallic compound of aluminum used in the kit is trioctу aluminum.

In one embodiment, the invention relates to a kit consisting of said organometallic compound of aluminum of formula $R_1R_2R_3Al$ and said compound selected from one or more of said structures 1 to 291.

Fifth Aspect of the Invention—Method of Purifying an Olefin

According to a fifth aspect, the invention relates to a method of purifying a feedstock comprising a first and a second olefin, which may be identical or which may be different from one another, and by-products, which are selected from the group consisting of water, alcohols, aldehydes, peroxides, hydroperoxides, peroxide decomposition products, protic materials, polar materials, Lewis basic catalyst poisons, or a mixture of two or more thereof, comprising:

(0) subjecting said feedstock to a physical or chemical or physical and chemical purification step, preferably wherein said physical purification is performed prior to the chemical purification step,
 wherein the physical purification step comprises: distilling said by-products off, or distilling the feedstock, or adsorbing said by-products; and wherein the chemical purification step comprises: subjecting at least one of the by-products to a chemical reaction;

or (0) subjecting at least one of the by-products in said feedstock to a chemical reaction.

In one embodiment, the by-products in the feedstock are subjected to an anhydride of an organic acid; preferably wherein said anhydrides are the anhydrides of aliphatic, cyclic, alicyclic organic acids having from 1 to 10 carbon atoms, or an aromatic organic acid having from 6 to 10 carbon atoms;

In a further embodiment, the by-products in the feedstock are subjected to an organometallic compound of aluminum; preferably wherein the organometallic compound of aluminum is of formula $R_1R_2R_3Al$, wherein $R_1$, $R_2$, and $R_3$ are independently selected from an aliphatic, cyclic, alicyclic residue having from 1 to 10 carbon atoms, or from aromatic residues having from 6 to 10 carbon atoms.

In one embodiment, the anhydride of an organic acid is acetic acid; or the organometallic compound of aluminum is trioctyl aluminum.

In one embodiment, said method consists of step (0).

Sixth Aspect of the Invention—Composition Comprising a Compound that Catalyzes Metathesis of a First and/or a Second Olefin and a Purified Feedstock According to a sixth aspect, the invention relates to a composition comprising a compound as defined in any one of the embodiments according to the first aspect or a compound defined in any one of the embodiments according to the second aspect that catalyzes metathesis of a first and/or a second olefin, and a first and/or a second olefin, which are comprised in a feedstock, wherein said feedstock further comprises at least one by-product selected from the group consisting of water, alcohols, aldehydes, peroxides, hydroperoxides, peroxide decomposition products, protic materials, polar materials, Lewis basic catalyst poisons, or a mixture of two or more thereof, and wherein said feedstock has been subjected to a purification step as defined in any one of the respective embodiments according to the first aspect.

In one embodiment, the invention relates to a composition consisting of said compound and said first and/or second ole; or consisting of said compound and a feedstock which contains said first and/or second olefin.

Seventh Aspect of the Invention—Method of Increasing Reactivity of a Compound that Catalyzes a Metathesis Reaction According to a seventh aspect, the invention relates to a method of increasing the reactivity of a compound as defined in any one of the embodiments according to the first aspect that catalyzes a metathesis reaction of a first and a second olefin such that the molar ratio of said compound to the first or the second olefin is less than 1:500, and the conversion of the first or the second olefin is at least 30%, wherein said first and said second olefin are comprised in a feedstock, wherein said feedstock further comprises at least one by-product selected from the group consisting of water, alcohols, aldehydes, peroxides, hydroperoxides, peroxide decomposition products, protic materials, polar materials, Lewis basic catalyst poisons, or a mixture of two or more thereof, comprising step (0) and, optionally, subsequent to step (0), the following step (i):

(0) subjecting said feedstock to a physical or chemical or physical and chemical purification step, preferably wherein said physical purification is performed prior to the chemical purification step,
  wherein the physical purification step comprises: distilling at least one of said by-products off, or distilling said feedstock, or adsorbing at least one of said by-products; and
  wherein the chemical purification step comprises: subjecting at least one of said by-products to a chemical reaction;

(i) reacting the first olefin with the second olefin in the presence of said compound that catalyzes said metathesis reaction.

In one embodiment, preferably when a trialkyl aluminum compound is used for purification, preferably trioctyl aluminum, the feedstock is subjected to said compound for a period of from 2 to 100 h, preferably 5 to 90 h, more preferred 10 to 80 h, and still more preferred 15 to 70 h.

In another embodiment of this aspect, the catalyst is slowly added to the substrate at a rate of from 0.01-10 ppmwt catalyst per hour.

In one embodiment, said method consists of steps (0) and (i).

Eighth Aspect of the Invention-Method of Metathesizing

According to an eighth aspect, the invention relates to a method of metathesizing a first olefin and/or a second olefin, comprising at least steps (i) to (iii):

(i) providing at least one compound for use as metathesis catalyst as defined in any one of the embodiments according to the first aspect of the invention, or according to the second aspect of the invention;

(ii) providing a first olefin and/or a second olefin; and (iii) slowly adding the catalyst to the first and/or second olefin to metathesize the first and/or second olefin;

wherein the slowly adding step of the catalyst to the first and/or second olefin allows the metathesis reaction to proceed at a molar ratio of catalyst to first and/or second olefin of less than 1:7,500.

In one embodiment, the catalyst is slowly added to the first and/or second olefin at a rate of from 0.01-10 ppmwt catalyst per hour, or any other rate as defined in the first aspect of the invention.

In one embodiment, the catalyst is added at a rate to enable the metathesis reaction to proceed at a molar ratio of the catalyst to the first and/or the second olefin of 1:7,500 or less, and the corresponding conversion is at least 30%, or at least 40%, or at least 50%, or at least 60%, or at least 70%, or at least 80%, or at least 90%.

In one embodiment, the catalyst is added at a rate to enable the metathesis reaction to proceed at a molar ratio of the catalyst to the first and/or the second olefin of 1:10,000 or less, and the corresponding conversion is at least 30%, or at least 40%, or at least 50%, or at least 60%, or at least 70%, or at least 80%, or at least 90%.

In one embodiment, the catalyst is added at a rate to enable the metathesis reaction to proceed at a molar ratio of the catalyst to the first and/or the second olefin of 1:20,000 or less, or 1:50,000 or less, or 1:100,000 or less, or 1:500,000 or less, or 1:1,000,000 or less, and the corresponding conversion is at least 30%, or at least 40%, or at least 50%, or at least 60%, or at least 70%, or at least 80%, or at least 90%, respectively.

In one embodiment, the catalyst is added at a rate to enable the metathesis reaction to proceed at a molar ratio of the catalyst to the first and/or the second olefin of a lower limit of 1:2,000,000, or 1:3,000,000 or 1:4,000,000, respectively.

In other embodiments, the catalyst is added at a rate to enable the metathesis reaction to proceed at a molar ratio of the catalyst to the first and/or the second olefin of 1:500 to 1:50,000 or less, and the corresponding conversion is from 30 to 100%, or from 50 to 100%, or 60 to 100%.

In one embodiment, the catalyst is added at a rate to enable the metathesis reaction to proceed at a molar ratio of the catalyst to the first and/or the second olefin of 1:1,000 to 1:40,000 or less, and the corresponding conversion is from 30 to 100%, or from 50 to 100%, or 60 to 100%.

In one embodiment, the catalyst is added at a rate to enable the metathesis reaction to proceed at a molar ratio of the catalyst to the first and/or the second olefin of from 1:2,500 to 1:30,000 or less, and the corresponding conversion is from 30 to 100%, or from 50 to 100%, or 60 to 100%.

In one embodiment, the catalyst is added at a rate to enable the metathesis reaction to proceed at a molar ratio of the catalyst to the first and/or the second olefin of 1:5,000 to 1:30,000 or less, or from 1:10,000 to 1:30,000, or from 1:15,000 to 1:30,000, and the corresponding conversion is from 30 to 100%, or from 50 to 100%, or 60 to 100%, respectively.

In one embodiment, said method consists of steps (i) to (iii).

Further Preferred Embodiments and Compounds

In a ninth aspect, the invention relates to a compound of formula:

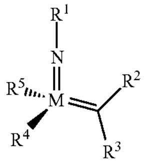

wherein

M=Mo or W;

$R^1$ is aryl, heteroaryl, alkyl, or heteroalkyl; optionally substituted;

$R^2$ and $R^3$ can be the same or different and are hydrogen, alkyl, alkenyl, heteroalkyl, heteroalkenyl, aryl, or heteroaryl; optionally substituted;

$R^5$ is alkyl, alkoxy, heteroalkyl, aryl, aryloxy, heteroaryl, silylalkyl, silyloxy, optionally substituted; and $R^4$ is a residue $R^6$—X—, wherein X═O and $R^6$ is a phenyl ring which is at least substituted in 4-position (para-position) with respect to O; or X═S and $R^6$ is a phenyl ring which is at least substituted in 4-position with respect to S.

In a first embodiment, $R^6$ is substituted in 2- and 4-position with respect to O.

In a second embodiment, $R^6$ is substituted in 3- and 4-position.

In a third embodiment, $R^6$ is substituted in 2-, 3- and 4-position.

In fourth embodiment, $R^6$ is substituted in 2-, 5- and 4-position.

In a fifth embodiment, $R^6$ is substituted in 3-, 5- and 4-position.

In a sixth embodiment, $R^6$ is substituted 2-, 6- and 4-position.

In a seventh embodiment, $R^6$ is substituted in 2-, 3-, 5- and 4-position.

In an eighth embodiment, $R^6$ is substituted in 2-, 3-, 6- and 4-position.

In a ninth embodiment, $R^6$ is substituted in 2-, 3-, 5-, 6- and 4-position.

The substituent of residue $R^6$ in 4-position may be independently selected from the group consisting of: halogen, dialkylamino, cyano, optionally substituted alkyl, optionally substituted alkyloxy, optionally substituted aryl, optionally substituted aryloxy.

The further substituents of residue $R^6$, if any, i.e. a substituent 2-position with respect to O, or in 3-position, or substituents in 2- and 3-position, or in 2- and 5-position, or in 6- and 5-position, or in 2- and 6-position, or in 2-, 3- and 5-position, or in 2-, 3- and 6-position, or in 2-, 3-, 5- and 6-position, may be the same or may be different from the substituent in 4-position and may be independently selected from the group consisting of: halogen, dialkylamino, cyano, optionally substituted alkyl, optionally substituted alkyloxy, optionally substituted aryl, optionally substituted aryloxy.

In one embodiment, $R^1$ is phenyl or alkyl; optionally substituted; $R^2$ and $R^3$ can be the same or different and are hydrogen, optionally substituted alkyl; $R^5$ is alkyl, alkoxy, heteroalkyl, aryl, aryloxy, heteroaryl, silylalkyl, silyloxy, optionally substituted; and the substituent of residue $R^6$ in 4-position may be independently selected from the group consisting of: halogen, $C_{1-4}$ dialkylamino, optionally substituted $C_{1-4}$ alkyl, optionally substituted $C_{1-4}$ alkyloxy, optionally substituted phenyl, optionally substituted phenyloxy; and the further substituents of residue $R^6$, i.e. a substituent in 2-position with respect to O, or in 3-position, or in 2- and 3-position, or in 2- and 5-position, or in 3- and 5-position, or in 2- and 6-position, or in 2-, 3- and 5-position, or in 2-, 3- and 6-position, or in 2-, 3-, 5- and 6-position, may be the same or may be different from the substituent in 4-position and may be independently selected from the group consisting of halogen, $C_{1-4}$ dialkylamino, optionally substituted $C_{1-4}$ alkyl, optionally substituted $C_{1-4}$ alkyloxy, optionally substituted phenyl, optionally substituted phenyloxy.

In one embodiment, $R^1$ is phenyl or alkyl, optionally independently substituted with halogen, $C_{1-4}$ dialkylamino, $C_{1-4}$ alkyl, $C_{1-4}$ alkyloxy, optionally substituted phenyl, optionally substituted phenyloxy, respectively; $R^2$ and $R^3$ can be the same or different and are hydrogen or optionally substituted alkyl; $R^5$ is alkyl, alkoxy, heteroalkyl, aryl, aryloxy, heteroaryl, silylalkyl, silyloxy, optionally substituted; and the substituent of residue $R^6$ in 4-position may be independently selected from the group consisting of: halogen, $C_{1-4}$ dialkylamino, optionally substituted $C_{1-4}$ alkyl, optionally substituted $C_{1-4}$ alkyloxy, optionally substituted phenyl, optionally substituted phenyloxy; and the further substituents of residue $R^6$, i.e. a substituent in 2-position with respect to O, or in 3-position, or in 2- and 3-position, or in 2- and 5-position, or in 3-, and 5-position, or in 2- and 6-position, or in 2-, 3- and 5-position, or in 2-, 3- and 6-position, or in 2-, 3-, 5- and 6-position, may be the same or may be different from the substituent in 4-position and may be independently selected from the group consisting of halogen, $C_{1-4}$ dialkylamino, optionally substituted $C_{1-4}$ alkyl, optionally substituted $C_{1-4}$ alkyloxy, optionally substituted phenyl, optionally substituted phenyloxy.

In one embodiment, $R^1$ is phenyl or alkyl, optionally independently substituted with halogen, $C_{1-4}$ dialkylamino, $C_{1-4}$ alkyl, $C_{1-4}$ alkyloxy, optionally substituted phenyl, optionally substituted phenyloxy;

$R^2$ and $R^3$ can be the same or different and are hydrogen, $C(CH_3)_3$ or $C(CH_3)_2C_6H_5$;

$R^5$ is alkyl, alkoxy, heteroalkyl, aryl, aryloxy, heteroaryl, silylalkyl, silyloxy, optionally substituted; and the substituent of residue $R^6$ in 4-position may be independently selected from the group consisting of: halogen, $C_{1-4}$ dialkylamino, optionally substituted $C_{1-4}$ alkyl, optionally substituted $C_{1-4}$ alkyloxy, optionally substituted phenyl, optionally substituted phenyloxy;

and the further substituents of residue $R^6$, i.e. a substituent in 2-position with respect to O, or in 3-position, or in 2- and 3-position, or in 2- and 5-position, or in 3- and 5-position, or in 2- and 6-position, or in 2-, 3- and 5-position, or in 2-, 3- and 6-position, or in 2-, 3-, 5- and 6-position, may be the same or may be different from the substituent in 4-position and may be independently selected from the group consisting of halogen, $C_{1-4}$ dialkylamino, optionally substituted $C_{1-4}$ alkyl, optionally substituted $C_{1-4}$ alkyloxy, optionally substituted phenyl, optionally substituted phenyloxy.

In one embodiment, M=Mo or W;

$R^1$ is selected from 2,6-dimethylphenyl, 2,6-diisopropylphenyl, 2,6-dichlorophenyl, 2,3,4,5,6-pentafluorophenly, 2-trifluoromethyl, 2,6-di(trifluoromethyl)phenyl, adamant-1-yl;

$R^2$ is $—C(CH_3)_2C_6H_5$ or $—C(CH_3)_3$;

$R^3$ is H;

$R^5$ is selected from pyrrol-1-yl; 2,5-dimethyl-pyrrol-1-yl; triphenylsilyloxy; triisopropylsilyloxy; 2-phenyl-1,1,1,3,3,3-hexafluoro-prop-2-yloxy; 2-methyl-1,1,1,3,3,3-hexafluoro-prop-2-yloxy; 2,6-diphenylphenoxy; 9-phenyl-fluorene-9-yloxy; t-butyloxy; and the substituent of residue $R^6$ in 4-position may be independently selected from the group consisting of: halogen, $C_{1-4}$ dialkylamino, optionally substituted $C_{1-4}$ alkyl, optionally substituted $C_{1-4}$ alkyloxy, optionally substituted phenyl, optionally substituted phenyloxy; and the further substituents of residue $R^6$, i.e. a substituent in 2-position with respect to O, or in 3-position, or substituents in 2- and 3-position, or in 2- and 5-position, or in 3- and 5-position, or in 2- and 6-position, or in 2-, 3- and 5-position, or in 2-, 3- and 6-position, or in 2-, 3-, 5- and 6-position, may be the same or may be different from the substituent in 4-position and may be independently selected from the group consisting of halogen, $C_{1-4}$ dialkylamino, optionally substituted $C_{1-4}$ alkyl, optionally substituted $C_{1-4}$ alkyloxy, optionally substituted phenyl, optionally substituted phenyloxy.

In one embodiment, the substituent of $R^6$ in 4-position may be independently selected from the group consisting of: fluoro, chloro, bromo, dimethylamino, diethylamino, methyl, ethyl, propyl, isopropyl, butyl, t-butyl, methoxy, ethoxy, propyloxy, butyloxy, t-butyloxy, trifluoromethyl, phenyl optionally substituted with halogen, alkyl, alkyloxy, phenyl, phenoxy: phenoxy optionally substituted with halogen, alkyl, alkyloxy, phenyl, phenoxy; and the further substituents of residue $R^6$, i.e. a substituent in 2-position with respect to O, or in 3-position, or in 2- and 3-position, or in 2- and 5-position, or in 3- and 5-position, or in 2- and 6-position, or in 2-, 3- and 5-position, or in 2-, 3- and 6-position, or in 2-, 3-, 5- and 6-position, may be the same or may be different from the substituent in 4-position and may be independently selected from the group consisting of fluoro, chloro, bromo, dimethylamino, diethylamino, methyl, ethyl, propyl, isopropyl, butyl, t-butyl, methoxy, ethoxy, propyloxy, butyloxy, t-butyloxy, trifluoromethyl, phenyl optionally substituted with halogen, alkyl, alkyloxy, phenyl, phenoxy; phenoxy optionally substituted with halogen, alkyl, alkyloxy, phenyl, phenoxy.

In a preferred embodiment according to the sixth embodiment, residue $R^6$ is a phenyl ring which is substituted in 2- and 4-position independently with halogen and in 6-position with phenyl, which optionally may be substituted with halogen, alkyl, alkyloxy, phenyl, optionally substituted with halogen, alkyl, alkyloxy, phenyl, phenoxy, phenoxy, optionally substituted with halogen, alkyl, alkyloxy, phenyl, phenoxy.

In one embodiment, M=Mo or W;

$R^1$ is selected from 2,6-diisopropylphenyl, 2,6-dichlorophenyl;

$R^2$ is —$C(CH_3)_2C_6H_5$ or —$C(CH_3)_3$;

$R^3$ is H;

$R^5$ is selected from pyrrol-1-yl; 2,5-dimethyl-pyrrol-1-yl; triphenylsilyloxy; triisopropylsilyloxy;

$R^4$ is a residue $R^6$—X—, wherein X═O and $R^6$ is substituted in 2- and 4-position independently with halogen and in 6-position with phenyl, which optionally may be substituted with halogen, alkyl, alkyloxy, phenyl, optionally substituted with halogen, alkyl, alkyloxy, phenyl, phenoxy; phenoxy, optionally substituted with halogen, alkyl, alkyloxy, phenyl, phenoxy.

This type of catalyst according to the invention is e.g. represented by compounds 183 and 184.

In further embodiments, said phenyl ring $R^6$ may bear—besides the substituents in 2, 6 and 4-position with respect to O—also substituents in 3- and/or 5-position.

Accordingly, in one embodiment, M=Mo or W;

$R^1$ is aryl, heteroaryl, alkyl, or heteroalkyl; optionally substituted;

$R^2$ and $R^3$ can be the same or different and are hydrogen, alkyl, alkenyl, heteroalkyl, heteroalkenyl, aryl, or heteroaryl; optionally substituted;

$R^5$ is alkyl, alkoxy, heteroalkyl, aryl, aryloxy, heteroaryl, silylalkyl, silyloxy, optionally substituted; and $R^4$ is a residue $R^6$—X—, wherein X═O and $R^6$ is a phenyl ring which bears at least three substituents, wherein said phenyl ring is substituted in 2- and 4-position independently with halogen and in 6-position with phenyl, which optionally may be substituted with halogen, alkyl, alkyloxy, phenyl, phenoxy; phenoxy, optionally substituted with halogen, alkyl, alkyloxy, phenyl, phenoxy.

In a further preferred embodiment according to the sixth embodiment, $R^6$ is a phenyl ring which is substituted in 2- and 6-position by substituents via carbon atoms, and in 4-position by a substituent via any atom.

The term “any atom” used herein encompasses halogen, carbon, nitrogen, oxygen.

Accordingly, in one embodiment, M=Mo or W;

$R^1$ is aryl, heteroaryl, alkyl, or heteroalkyl; optionally substituted;

$R^2$ and $R^3$ can be the same or different and are hydrogen, alkyl, alkenyl, heteroalkyl, heteroalkenyl, aryl, or heteroaryl; optionally substituted;

$R^5$ is alkyl, alkoxy, heteroalkyl, aryl, aryloxy, heteroaryl, silylalkyl, silyloxy, optionally substituted; and $R^4$ is a residue $R^6$—X—, wherein X═O and $R^6$ is a phenyl ring which is substituted in 2- and 6-position by substituents via carbon atoms, and in 4-position by a substituent via any atom.

In one embodiment, M=Mo or W;

$R^1$ is phenyl or alkyl, optionally independently substituted with halogen, $C_{1-4}$ dialkylamino, $C_{1-4}$ alkyl, $C_{1-4}$ alkyloxy, optionally substituted phenyl, optionally substituted phenyloxy;

$R^2$ and $R^3$ can be the same or different and are hydrogen, $C(CH_3)_3$, or $C(CH_3)_2C_6H_5$;

$R^5$ is alkyl, alkoxy, heteroalkyl, aryl, aryloxy, heteroaryl, silylalkyl, silyloxy, optionally substituted; and the substituent of residue $R^6$ in 4-position may be selected from the group consisting of: halogen, $C_{1-4}$ dialkylamino, optionally substituted $C_{1-4}$ alkyl, optionally substituted $C_{1-4}$ alkyloxy, optionally substituted phenyl, optionally substituted phenyloxy; and the further substituents of residue $R^6$, i.e. substituents in 2- and 6-position with respect to O, may be the same or may be different from one another, and may be selected from the group consisting of optionally substituted $C_{1-4}$ alkyl, optionally substituted $C_{1-4}$ alkyloxy, optionally substituted phenyl, optionally substituted phenyloxy.

In one embodiment, M=Mo or W;

$R^1$ is selected from 2,6-dimethylphenyl, 2,6-diisopropylphenyl, 2,6-dichlorophenyl, 2,3,4,5,6-pentafluorophenly, 2-trifluoromethyl, 2,6-di(trifluoromethyl)phenyl, adamant-1-yl;

$R^2$ is —$C(CH_3)_2C_6H_5$ or —$C(CH_3)_3$;

$R^3$ is H;

$R^5$ is selected from pyrrol-1-yl; 2,5-dimethyl-pyrrol-1-yl; triphenylsilyloxy; triisopropylsilyloxy;

the substituent of residue $R^6$ in 4-position may be selected from the group consisting of: halogen, $C_{1-4}$ dialkylamino, optionally substituted $C_{1-4}$ alkyl, optionally substituted $C_{1-4}$ alkyloxy, optionally substituted phenyl, optionally substituted phenyloxy;

and the further substituents of residue $R^6$, i.e. substituents in 2- and 6-position, may be the same or may be different from one another, and may be selected from the group consisting of optionally substituted $C_{1-4}$ alkyl, optionally substituted $C_{1-4}$ alkyloxy, optionally substituted phenyl, optionally substituted phenyloxy.

Examples are compounds 3, 4, 5, 7, 14, 15, 17, 18, 19, 70, 33, 34, 35, 36, 37, 41, 42, 43, 44, 63, 64, 65, 66, 67, 68, 69, 120, 121, 122, 125, 126, 127, 130, 131, 132, 133, 134, 135, 140, 141, 142, 146, 149, 150, 155, 156, 157, 158, 159, 160, 161, 162, 163, 164, 165, 166, 167, 168, 169, 170, 173, 187, 188.

These compounds are particularly effective in ethenolysis.

In further embodiments, said phenyl ring $R^6$ may bear—besides the substituents in 2-, band 4-position with respect to O—also substituents in 3- and/or 5-position.

Accordingly, in one embodiment, M=Mo or W;

$R^1$ is aryl, heteroaryl, alkyl, or heteroalkyl; optionally substituted;

$R^2$ and $R^3$ can be the same or different and are hydrogen, alkyl, alkenyl, heteroalkyl, heteroalkenyl, aryl, or heteroaryl; optionally substituted;

$R^5$ is alkyl, alkoxy, heteroalkyl, aryl, aryloxy, heteroaryl, silylalkyl, silyloxy, optionally substituted; and $R^4$ is a residue $R^6$—X—, wherein X═O and $R^6$ is a phenyl ring which bears at least three substituents, wherein said phenyl ring is substituted in 2- and 6-position by substituents via carbon atoms, and in 4-position and 3- and/or 5-position by a substituent via any atom, respectively.

In one embodiment, M=Mo or W;

$R^1$ is phenyl or alkyl, optionally independently substituted with halogen, $C_{1-4}$ dialkylamino, $C_{1-4}$ alkyl, $C_{1-4}$ alkyloxy, optionally substituted phenyl, optionally substituted phenyloxy;

$R^2$ and $R^3$ can be the same or different and are hydrogen, $C(CH_3)_3$, $C(CH_3)_2C_6H_5$;

$R^5$ is alkyl, alkoxy, heteroalkyl, aryl, aryloxy, heteroaryl, silylalkyl, silyloxy, optionally substituted; and the substituent of residue $R^6$ in 4-position may be selected from the group consisting of: halogen, $C_{1-4}$ dialkylamino, optionally substituted $C_{1-4}$ alkyl, optionally substituted $C_{1-4}$ alkyloxy, optionally substituted phenyl, optionally substituted phenyloxy;

and the substituents of residue $R^6$ in 2- and 6-position may be the same or may be different from one another, and may be selected from the group consisting of optionally substituted $C_{1-4}$ alkyl, optionally substituted $C_{1-4}$ alkyloxy, optionally substituted phenyl, optionally substituted phenyloxy;

and the further substituents in 3- or/and 5-position may be selected from the group consisting of: halogen, $C_{1-4}$ dialkylamino, optionally substituted $C_{1-4}$ alkyl, optionally substituted $C_{1-4}$ alkyloxy, optionally substituted phenyl, optionally substituted phenyloxy In one embodiment, M=Mo or W;

$R^1$ is selected from 2,6-dimethylphenyl, 2,6-diisopropylphenyl, 2,6-dichlorophenyl, 2,3,4,5,6-pentafluorophenly, 2-trifluoromethyl, 2,6-di(trifluoromethyl)phenyl, adamant-1-yl;

$R^2$ is —$C(CH_3)_2C_6H_5$ or —$C(CH_3)_3$;

$R^3$ is H;

$R^5$ is selected from pyrrol-1-yl; 2,5-dimethyl-pyrrol-1-yl; triphenylsilyloxy; triisopropylsilyloxy; and the substituent of residue $R^6$ in 4-position may be selected from the group consisting of: halogen, $C_{1-4}$ dialkylamino, optionally substituted $C_{1-4}$ alkyl, optionally substituted $C_{1-4}$ alkyloxy, optionally substituted phenyl, optionally substituted phenyloxy; and the substituents of residue $R^6$ in 2- and 6-position may be the same or may be different from one another, and may be selected from the group consisting of optionally substituted $C_{1-4}$ alkyl, optionally substituted $C_{1-4}$ alkyloxy, optionally substituted phenyl, optionally substituted phenyloxy;

and the further substituents in 3- or/and 5-position may be selected from the group consisting of: halogen, $C_{1-4}$ dialkylamino, optionally substituted $C_{1-4}$ alkyl, optionally substituted $C_{1-4}$ alkyloxy, optionally substituted phenyl, optionally substituted phenyloxy.

In a further preferred specific embodiment according to the ninth embodiment, M=Mo or W;

$R^1$ is aryl, heteroaryl, alkyl, or heteroalkyl; optionally substituted;

$R^2$ and $R^3$ can be the same or different and are hydrogen, alkyl, alkenyl, heteroalkyl, heteroalkenyl, aryl, or heteroaryl; optionally substituted;

$R^5$ is alkyl, alkoxy, heteroalkyl, aryl, aryloxy, heteroaryl, silylalkyl, silyloxy, optionally substituted; and $R^4$ is a residue $R^6$—X—, wherein X═O and $R^6$ is a phenyl ring which is substituted in 4-position with halogen, preferably bromine, and in 2-, 3-, 5- and 6-position with phenyl, respectively, wherein said phenyl residues may be independently substituted with fluoro, chloro, bromo, dimethylamino, diethylamino, methyl, ethyl, propyl, isopropyl, butyl, t-butyl, methoxy, ethoxy, propyloxy, butyloxy, t-butyloxy, trifluoromethyl, phenyl optionally substituted with halogen, alkyl, alkyloxy, phenyl, phenoxy; phenoxy optionally substituted with halogen, alkyl, alkyloxy, phenyl, phenoxy.

In a preferred embodiment, embodiment, M=Mo or W;

$R^1$ is selected from 2,6-dimethylphenyl, 2,6-diisopropylphenyl, 2,6-dichlorophenyl, 2,3,4,5,6-pentafluorophenly, 2-trifluoromethyl, 2,6-di(trifluoromethyl)phenyl, adamant-1-yl;

$R^2$ is —$C(CH_3)_2C_6H_5$ or —$C(CH_3)_3$;

$R^3$ is H;

$R^5$ is selected from pyrrol-1-yl; 2,5-dimethyl-pyrrol-1-yl; triphenylsilyloxy; triisopropylsilyloxy;

$R^4$ is a residue $R^6$—X—, wherein X═O and $R^6$ is a phenyl ring which is substituted in 4-position with bromine and in 2-, 3-, 5- and 6-position with phenyl, respectively, wherein said phenyl residues may be independently substituted with fluoro, chloro, bromo, dimethylamino, diethylamino, methyl, ethyl, propyl, isopropyl, butyl, t-butyl, methoxy, ethoxy, propyloxy, butyloxy, t-butyloxy, trifluoromethyl, phenyl optionally substituted with halogen, alkyl, alkyloxy, phenyl, phenoxy; phenoxy optionally substituted with halogen, alkyl, alkyloxy, phenyl, phenoxy.

Examples are compounds 11, 13, 16, 32, 60, 123, 136, 145, 189, 261,

Such compounds, which bear a 4-bromo-(2,3,5,6-tetraphenyl)phenyl moiety may have a positive impact on catalytic activity compared to their debromo analogues, i.e. which are substituted in 4-position with hydrogen. This positive impact may result in a higher conversion in the range of from 10 to 30%.

Moreover, such compounds exhibit good activity in ethenolysis.

In a tenth aspect, the invention relates to a compound of formula:

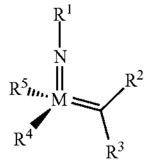

wherein

M=Mo or W;

$R^1$ is aryl, heteroaryl, alkyl, or heteroalkyl; optionally substituted;

$R^2$ and $R^3$ can be the same or different and are hydrogen, alkyl, alkenyl, heteroalkyl, heteroalkenyl, aryl, or heteroaryl; optionally substituted;

$R^5$ is alkyl, alkoxy, heteroalkyl, aryl, aryloxy, heteroaryl, silylalkyl, silyloxy, optionally substituted; and $R^4$ is a residue $R^6$—X—, wherein X═O and $R^6$ is a phenyl ring which is substituted in 2- and 6-position with phenyl, respectively, optionally substituted; or X═S and $R^6$ is phenyl ring which is substituted in 2- and 6-position with phenyl, respectively, optionally substituted.

In one embodiment, M=Mo or W;

$R^1$ is selected from 2,6-dimethylphenyl, 2,6-diisopropylphenyl, 2,6-dichlorophenyl, 2,3,4,5,6-pentafluorophenly, 2-trifluoromethyl, 2,6-di(trifluoromethyl)phenyl, adamant-1-yl;

$R^2$ is —$C(CH_3)_2C_6H_5$ or —$C(CH_3)_3$;

$R^3$ is H;

$R^5$ is selected from pyrrol-1-yl; 2,5-dimethyl-pyrrol-1-yl; triphenylsilyloxy; triisopropylsilyloxy;

$R^4$ is a residue $R^6$—X—, wherein X═O and $R^6$ is substituted in 2- and 6-position with phenyl, which optionally may be independently substituted with halogen, alkyl, preferably $C_{1-4}$ alky, alkyloxy, preferably $C_{1-4}$ alkyoxy, phenyl, optionally substituted with halogen, alkyl, alkyloxy, dialylamino, phenyl, phenoxy; phenoxy, optionally substituted with halogen, alkyl, alkyloxy, dialkylamino, phenyl, phenoxy Such compounds exhibit good activity in ethenolysis.

Compounds are e.g. compounds 178 and 233.

In an eleventh aspect, the invention relates to a compound of formula

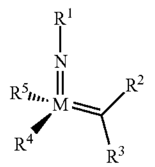

wherein
M=Mo or W;
$R^1$ is aryl, heteroaryl, alkyl, or heteroalkyl; optionally substituted;
$R^2$ and $R^3$ can be the same or different and are hydrogen, alkyl, alkenyl, heteroalkyl, heteroalkenyl, aryl, or heteroaryl; optionally substituted;
$R^5$ is alkyl, alkoxy, heteroalkyl, aryl, aryloxy, heteroaryl, silylalkyl, silyloxy, optionally substituted; and
$R^4$ is [8-(naphthalene-1-yl)naphthalene-1-yl]oxy, optionally substituted.

The term "[8-(naphthalene-1-yl)-naphthalene-1-yl]oxy, optionally substituted" encompasses the substitution of one or both of the naphthyl rings with one or more substituents selected from the group consisting of: halogen, hydroxyl, protected hydroxyl, $C_{1-4}$ dialkylamino, optionally substituted $C_{1-4}$ alkyl, optionally substituted $C_{1-4}$ alkyloxy, optionally substituted phenyl, optionally substituted phenyloxy.

In one embodiment, M=Mo or W;
$R^1$ is phenyl or alkyl, optionally independently substituted with halogen, $C_{1-4}$ dialkylamino, $C_{1-4}$ alkyl, $C_{1-4}$ alkyloxy, optionally substituted phenyl, optionally substituted phenyloxy;
$R^2$ and $R^3$ can be the same or different and are hydrogen, $C(CH_3)_3$, or $C(CH_3)_2C_6H_5$;
$R^5$ is alkyl, alkoxy, heteroalkyl, aryl, aryloxy, heteroaryl, silylalkyl, silyloxy, optionally substituted; and
$R^4$ is [8-(naphthalene-1-yl)-naphthalene-1-yl]oxy, optionally substituted.

In one embodiment, M=Mo or W;
$R^1$ is selected from 2,6-dimethylphenyl, 2,6-diisopropylphenyl, 2,6-dichlorophenyl, 2,3,4,5,6-pentafluorophenly, 2-trifluoromethyl, 2,6-di(trifluoromethyl)phenyl, adamant-1-yl;
$R^2$ is $—C(CH_3)_2C_6H_5$ or $—C(CH_3)_3$;
$R^3$ is H;
$R^5$ is selected from pyrrol-1-yl; 2,5-dimethyl-pyrrol-1-yl; triphenylsilyloxy; triisopropylsilyloxy;
$R^4$ is [8-(naphthalene-1-yl)naphthalene-1-yl]oxy, optionally substituted.

Examples are compounds 192, 196, 214, 217, 220.

Such compounds may have a positive impact on catalytic activity regarding ethenolysis, cross metathesis and homo metathesis.

In a twelfth aspect, the invention relates to a compound of formula

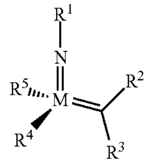

wherein
M=Mo or W;
$R^1$ is aryl, heteroaryl, alkyl, or heteroalkyl; optionally substituted;
$R^2$ and $R^3$ can be the same or different and are hydrogen, alkyl, alkenyl, heteroalkyl, heteroalkenyl, aryl, or heteroaryl; optionally substituted;
$R^5$ is alkyl, alkoxy, heteroalkyl, aryl, aryloxy, heteroaryl, silylalkyl, silyloxy, optionally substituted; and
$R^4$ is (8-phenlynaphthalene-1-yl)oxy, optionally substituted.

The term "8-phenlynaphthalene-1-yl)oxy, optionally substituted" encompasses the substitution of the phenyl ring or the naphthyl ring or the phenyl and the naphthyl ring with one or more substituents selected from the group consisting of: halogen, hydroxyl, protected hydroxyl, $C_{1-4}$ dialkylamino, optionally substituted $C_{1-4}$ alkyl, optionally substituted $C_{1-4}$ alkyloxy, optionally substituted phenyl, optionally substituted phenyloxy.

In one embodiment, M=Mo or W;
$R^1$ is selected from 2,6-dimethylphenyl, 2,6-diisopropylphenyl, 2,6-dichlorophenyl, 2,3,4,5,6-pentafluorophenly, 2-trifluoromethyl, 2,6-di(trifluoromethyl)phenyl, adamant-1-yl;
$R^2$ is $—C(CH_3)_2C_6H_5$ or $—C(CH_3)_3$;
$R^3$ is H;
$R^5$ is selected from pyrrol-1-yl; 2,5-dimethyl-pyrrol-1-yl; triphenylsilyloxy; triisopropylsilyloxy; (8-phenlynaphthalene-1-yl)oxy, optionally substituted;
$R^4$ is (8-phenlynaphthalene-1-yl)oxy, optionally substituted.

Examples are compounds 218, 216, 247, 246, 288, 269.

In a thirteenth aspect, the invention relates to a compound of formula:

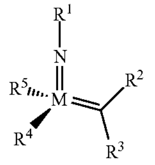

wherein
M=Mo or W;
$R^1$ is aryl, heteroaryl, alkyl, or heteroalkyl; optionally substituted;
$R^2$ and $R^3$ can be the same or different and are hydrogen, alkyl, alkenyl, heteroalkyl, heteroalkenyl, aryl, or heteroaryl; optionally substituted;
$R^5$ is alkyl, alkoxy, heteroalkyl, aryl, aryloxy, heteroaryl, silylalkyl, silyloxy, optionally substituted; and
$R^4$ is a residue $R^6—X—$, wherein
X═O and $R^6$ is a quinoline-8-yl, optionally substituted.

The term "quinoline-8-yl, optionally substituted" encompasses the substitution of the ring system with one or more substituents selected from the group consisting of: halogen, hydroxyl, protected hydroxyl, $C_{1-4}$ dialkylamino, optionally substituted $C_{1-4}$ alkyl, optionally substituted $C_{1-4}$ alkyloxy, optionally substituted phenyl, optionally substituted phenyloxy.

In one embodiment, M=Mo or W;
$R^1$ is selected from 2,6-dimethylphenyl, 2,6-diisopropylphenyl, 2,6-dichlorophenyl, 2,3,4,5,6-pentafluorophenly, 2-trifluoromethyl, 2,6-di(trifluoromethyl)phenyl, adamant-1-yl;
$R^2$ is $—C(CH_3)_2C_6H_5$ or $—C(CH_3)_3$;
$R^3$ is H;
$R^5$ is selected from pyrrol-1-yl; 2,5-dimethyl-pyrrol-1-yl; triphenylsilyloxy; triisopropylsilyloxy; $R^4$ is a residue $R^6—X—$, wherein
X═O and $R^6$ is a quinoline-8-yl, optionally substituted.

In a fourteenth aspect, the invention relates to a compound of formula:

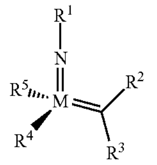

wherein

M=Mo or W;

$R^1$ is aryl, heteroaryl, alkyl, or heteroalkyl; optionally substituted;

$R^2$ and $R^3$ can be the same or different and are hydrogen, alkyl, alkenyl, heteroalkyl, heteroalkenyl, aryl, or heteroaryl; optionally substituted;

$R^5$ is alkyl, alkoxy, heteroalkyl, aryl, aryloxy, heteroaryl, silylalkyl, silyloxy, optionally substituted; and $R^4$ is a residue $R^6$—X—, wherein X═O and $R^6$ is a phenyl ring substituted in 2-position with respect to O; under the proviso that compound 153 is excluded The substituent in 2-position may be selected from the group consisting of: halogen, hydroxyl, protected hydroxyl, $C_{1-4}$ dialkylamino, optionally substituted $C_{1-4}$ alkyl, optionally substituted $C_{1-4}$ alkyloxy, optionally substituted phenyl, optionally substituted phenyloxy.

In one embodiment, M=Mo or W;

$R^1$ is selected from 2,6-dimethylphenyl, 2,6-diisopropylphenyl, 2,6-dichlorophenyl, 2,3,4,5,6-pentafluorophenly, 2-trifluoromethyl, 2,6-di(trifluoromethyl)phenyl, adamant-1-yl;

$R^2$ is —$C(CH_3)_2C_6H_5$ or —$C(CH_3)_3$;

$R^3$ is H;

$R^5$ is selected from pyrrol-1-yl; 2,5-dimethyl-pyrrol-1-yl; triphenylsilyloxy; triisopropylsilyloxy; 2-phenyl-1,1,1,3,3,3-hexafluoro-prop-2-yloxy; 2-methyl-1,1,1,3,3,3-hexafluoro-prop-2-yloxy; 9-phenyl-fluorene-9-yloxy; 2,6-diphenylphenoxy; t-butyloxy $R^4$ is a residue $R^6$—X—, wherein X═O and $R^6$ is phenyl substituted in 2-position with respect to O, wherein the substituent is selected from the group consisting of: halogen, hydroxyl, protected hydroxyl, $C_{1-4}$ dialkylamino, optionally substituted $C_{1-4}$alkyl, optionally substituted $C_{1-4}$ alkyloxy, optionally substituted phenyl, optionally substituted phenyloxy;

under the proviso that compound 153 is excluded

An exemplary compound is compound 152.

In a fifteenth aspect, the invention relates to a compound of formula:

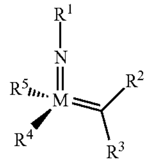

wherein

M=Mo or W;

$R^1$ is aryl, heteroaryl, alkyl, or heteroalkyl; optionally substituted;

$R^2$ and $R^3$ can be the same or different and are hydrogen, alkyl, alkenyl, heteroalkyl, heteroalkenyl, aryl, or heteroaryl; optionally substituted;

$R^5$ is alkyl, alkoxy, heteroalkyl, aryl, aryloxy, heteroaryl, silylalkyl, silyloxy, optionally substituted; and $R^4$ is a residue $R^6$—X—, wherein X═O and $R^6$ is a phenyl ring substituted in 2- and 6-position with respect to O; under the proviso that compounds 1, 9, 88, 101, 118, 174 are excluded.

The substituents in 2- and 6-position may be independently selected from the group consisting of: halogen, hydroxyl, protected hydroxyl, $C_{1-4}$ dialkylamino, optionally substituted $C_{1-4}$ alkyl, optionally substituted $C_{1-4}$ alkyloxy, optionally substituted phenyl, optionally substituted phenyloxy.

In one embodiment, M=Mo or W;

$R^1$ is selected from 2,6-dimethylphenyl, 2,6-diisopropylphenyl, 2,6-dichlorophenyl, 2,3,4,5,6-pentafluorophenly, 2-trifluoromethyl, 2,6-di(trifluoromethyl)phenyl, adamant-1-yl;

$R^2$ is —$C(CH_3)_2C_6H_5$ or —$C(CH_3)_3$;

$R^3$ is H;

$R^5$ is selected from pyrrol-1-yl; 2,5-dimethyl-pyrrol-1-yl; triphenylsilyloxy; triisopropylsilyloxy; 2-phenyl-1,1,1,3,3,3-hexafluoro-prop-2-yloxy; 2-methyl-1,1,1,3,3,3-hexafluoro-prop-2-yloxy; 9-phenyl-fluorene-9-yloxy; 2,6-diphenylphenoxy; t-butyloxy;

$R^4$ is a residue $R^6$—X—, wherein

X═O and $R^6$ is a phenyl ring substituted in 2- and 6-position with respect to O, wherein the substituents in 2- and 6-position may be independently selected from the group consisting of: halogen, hydroxyl, protected hydroxyl, $C_{1-4}$ dialkylamino, optionally substituted $C_{1-4}$ alkyl, optionally substituted $C_{1-4}$ alkyloxy, optionally substituted phenyl, optionally substituted phenyloxy, under the proviso that compounds 1, 9, 88, 101, 118, 174 are excluded.

Exemplary compounds are compounds 73, 74, 84, 85, 89, 6, 8, 62, 175, 176, 177, 178, 179, 185, 195, 199, 202, 203, 204, 205, 232, 233, 270, 271, 272, 273, 274.

DEFINITIONS USED IN THE MEANING OF THE INVENTION

The term "metathesis" refers to alkene (olefin) metathesis.

The term "cross metathesis" encompasses the reaction between two different olefins.

The term "ring opening metathesis" encompasses the ring opening of a cyclic olefin.

The term "ring opening polymerization metathesis" encompasses the ring opening of a cyclic olefin, wherein the ring-opened product polymerizes in a chain-growth polymerization to form a polymer containing olefinic bonds.

The term "ring closing metathesis" encompasses the ring closing of a diene.

The term "ethenolysis" encompasses the reaction of an olefin having an internal olefinic bond with ethylene.

The term "homo-metathesis" encompasses the formation of an internal olefin from two identical olefins.

The term "conversion" or "conversion degree" is defined as 100−[final moles of first or second olefin*100%/initial moles of first or second olefin].

The term "olefinic double bond" refers to a carbon-carbon double bond or ethylenic double bond.

The term "olefin" refers to any species having at least one ethylenic double bond such as normal and branched chain aliphatic olefins, cycloaliphatic olefins, or aryl substituted olefins. Olefins may comprise terminal double bond(s) ("terminal olefin") and/or internal double bond(s) ("internal olefin") and can be cyclic or acyclic, linear or branched, optionally substituted. The total number of carbon atoms can be from 1 to 100, or from 1 to 40; the double bonds of a terminal olefin may be mono- or bi-substituted and the double bond of an internal olefin may be bi-, tri-, or tetrasubstituted. In some cases, an internal olefin is bisubstituted.

Non-limiting examples of molecules comprising terminal olefins are substituted and unsubstituted linear alkyl internal olefins such as $C_4$-$C_{30}$ olefins (e.g., 1-butene, 1-pentene, 1-hexene, 1-heptene, 1-octene, 1-decene, 1-dodecene, 1-tetradecene, 1-hexadecene, 1-octadecene, 1-eicosene, allylbenzene, allyltrimethylsilane, methyl-10-undecenoate, allylboronic acid pincol ester, allylbenzylether, N-allyl-4-methylbenzenesulfonamide, allylaniline, methyl-9-decenoate, allyloxy(tert-butyl)dimethyl silane, allylcyclohexane, etc.).

In one embodiment, the olefin having a terminal olefinic double bond is of formula $RCH{=}CH_2$, wherein R is selected from H, alkyl, alkenyl, aryl, heteroalkyl, heteroalkenyl, heteroaryl, or acyl, optionally substituted.

The term "cyclic olefin" refers to any cyclic species comprising at least one ethylenic double bond in a ring. The atoms of the ring may be optionally substituted. The ring may comprise any number of carbon atoms and/or heteroatoms. In some cases, the cyclic olefin may comprise more than one ring. A ring may comprise at least 3, at least 4, at least 5, at least 6, at least 7, at least 8, or more, atoms. Non-limiting examples of cyclic olefins include norbornene, dicyclopentadiene, bicyclo compounds, oxabicyclo compounds, and the like, all optionally substituted. "Bicyclo compounds" are a class of compounds consisting of two rings only, having two or more atoms in common. "Oxabicyclo compounds" are a class of compounds consisting of two rings only, having two or more atoms in common, wherein at least one ring comprises an oxygen atom.

The term "substituted" is contemplated to include all permissible substituents of organic compounds, "permissible" being in the context of the chemical rules of valence known to those of ordinary skill in the art. Examples of substituents include, but are not limited to, alkyl, aryl, arylalkyl, cyclic alkyl, heterocycloalkyl, hydroxy, alkoxy, aryloxy, perhaloalkoxy, arylalkoxy, heteroaryl, heteroaryloxy, heteroarylalkyl, heteroarylalkoxy, azido, amino, halogen, alkylthio, oxo, acylalkyl, carboxy esters, carboxyl, -carboxamido, nitro, acyloxy, aminoalkyl, alkylaminoaryl, alkylaryl, alkylaminoalkyl, alkoxyaryl, arylamino, arylalkylamino, alkylsulfonyl, -carboxamidoalkylaryl, -carboxamidoaryl, hydroxyalkyl, haloalkyl, alkylaminoalkylcarboxy-, aminocarboxamidoalkyl-, cyano, alkoxyalkyl, perhaloalkyl, arylalkyloxyalkyl.

The term "alkyl" encompasses saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer. Likewise, cycloalkyls have from about 3 to about 10 carbon atoms in their ring structure, and alternatively about 5, 6 or 7 carbons in the ring structure. In some embodiments, an alkyl group may be a lower alkyl group, wherein a lower alkyl group comprises 10 or fewer carbon atoms in its backbone (e.g., $C_1$-$C_{10}$ for straight chain lower alkyls).

In one embodiment, the term "alky" encompasses $C_1$-$C_4$ alkyl such as methyl, isopropyl or t-butyl.

The term "alkyl" also encompasses bridged hydrocarbon residues such as the adamantyl residue, particularly the adamant-1-yl residue. Such residue is e.g. disclosed in compounds 9, 16, 46, 48, 49 as residue $R^1$.

The term "alkyl" also encompasses anellated ring systems such as the fluorene-9-yl residue such as the 9-phenyl-fluorene-9-yl residue.

The term "t-Bu" denotes a tertiary butyl group.

The term "alkoxy" refers to the group —O-alkyl, wherein alkyl has the meaning as defined above in connection with the term alkyl.

A preferred alkoxy residue is 9-phenylfluorene-9-yloxy as disclosed in compounds 28, 29, 30, 47, 49, 53, 58, 72 as residue $R^4$ and in compounds 49 and 72 as residues $R^4$ and $R^5$.

A further preferred alkoxy residue is triphenylmethyloxy (triphenylmethoxy) as disclosed in compound 23, 25, 27, 45, 52 as residue $R^4$.

A further preferred alkoxy residue is tri(4-methylphenyl) methyloxy [tri(4-methylphenyl)methoxy] as disclosed in compound 62 as residue $R^4$.

A further preferred alkoxy residue is 2-phenyl-1,1,1,3,3,3-hexafluoro-prop-2-yloxy as disclosed in compound 39 as residue $R^4$ and in compounds 38, 40 as residue $R^4$ and residue $R^5$.

A further preferred alkoxy residue is 2-methyl-1,1,1,3,3,3-hexafluoro-prop-2-yloxy as disclosed in compound 71 as residue $R^4$ and in compound 72 as residue $R^4$ and residue $R^5$.

A further preferred alkoxy residue is t-butyloxy as disclosed in compound 90 as residue $R^4$ and residue $R^5$.

A further preferred alkoxy residue is 9-phenyl-9-fluorene-9-yloxy as disclosed in compounds 29, 30, 47, 53, 58 as $R^4$ and in compound 49 and 81 as $R^4$ and $R^5$.

The term "alkenyl" refers to olefinic groups as described above. The alkenyl group may be optionally substituted with the substituents defined above.

The term "aryl" refers to aromatic carbocyclic groups, optionally substituted, having a single ring (e.g., phenyl), multiple rings (e.g., biphenyl), or multiple fused rings in which at least one is aromatic (e.g., 1,2,3,4-tetrahydronaphthyl, naphthyl, anthryl, or phenanthryl). That is, at least one ring may have a conjugated u electron system, while other, adjoining rings can be cycloalkyls, cycloalkenyls, cycloalkynyls, aryls, and/or heterocyclyls. The aryl group may be optionally substituted, as described herein.

The term "carbocyclic aryl groups" as used herein refers to aryl groups wherein the ring atoms on the aromatic ring are carbon atoms. Carbocyclic aryl groups include monocyclic carbocyclic aryl groups and polycyclic or fused compounds (e.g., two or more adjacent ring atoms are common to two adjoining rings) such as naphthyl groups. In some cases, the aryl groups may include monocyclic carbocyclic aryl groups and polycyclic or fused compounds (e.g., two or more adjacent ring atoms are common to two adjoining rings) such as naphthyl group. Non-limiting examples of aryl groups include phenyl, naphthyl, tetrahydronaphthyl, indanyl, indenyl, and the like.

A preferred aryl residue is 2,6-diisopropylphenyl as defined in compounds 1, 2, 6, 7, 8, 10, 11, 14, 17, 18, 19, 22, 23, 24, 25, 28, 29, 31, 32, 33, 34, 35, 36, 37, 38, 39, 41, 42, 43, 44, 50, 54, 56, 57, 58, 60 as residue $R^1$.

A further preferred aryl residue is 2,6-dichlorophenyl as defined in compounds 3, 4, 5, 20, 21, 26, 27, 30, 52, 53, 59, 62, 63, 64, 65, 66, 67, 68, 69, 70, 71 as residue $R^1$.

A further preferred aryl residue is 2,6-dimethylphenyl as defined in compounds 8, 12, 13, 15, 39, 40, 45, 47, 51, 55, 61 as residue $R^1$.

The term "phenoxy" refers to the group $C_6H_5O$—.

The term "thiophenoxy" refers to the group $C_6H_5S$—

This phenoxy or thiophenoxy residue may be substituted with up to five substituents independently selected from alkyl, preferably $C_1$-$C_4$ alkyl such as methyl, isopropyl or t-butyl, alkoxy, preferably $C_1$-$C_4$ alkoxy, phenoxy, phenyl, halogen.

A preferred phenoxy residue is 2,6-diphenylphenoxy as defined in compounds 1, 6, 8, 9 as residue $R^4$.

A further preferred phenoxy residue is 4-bromo-2,6-diphenylphenoxy as defined in compounds 14, 15, 33, 68 as residue $R^4$.

A further preferred phenoxy residue is 4-fluoro-2,6-diphenylphenoxy as e.g. disclosed in compounds 34, 36, 63, 67 as residue $R^4$.

A further preferred phenoxy residue is 4-methyl-2,6-diphenylphenoxy as defined in compounds 41, 42, 65 as residue $R^4$.

A further preferred phenoxy residue is 2,4,6-triphenylphenoxy as defined in compounds 43, 44, 64, 66 as residue $R^4$.

A further preferred phenoxy residue is 4-fluoro-2,6-dimesitylphenoxy as defined in compounds 35, 37, 69 as residue $R^4$.

A further preferred phenoxy residue is 2,6-di-tert.-butylphenoxy as defined in compounds 59, 62 as residue $R^4$.

A further preferred phenoxy residue is 4-bromo-2,6-di-tert.-butylphenoxy as defined in compounds 3, 17 as residue $R^4$.

A further preferred phenoxy residue is 4-methoxy-2,6-di-tert.-butylphenoxy as defined in compounds 5, 19 as residue $R^4$.

A further preferred phenoxy residue is 4-methyl-2,6-di-tert.-butylphenoxy as defined in compound 7 as residue $R^4$.

A further preferred phenoxy residue is 2,4,6-tri-tert.-butylphenoxy as defined in compounds 4, 18 as residue $R^4$.

A further preferred phenoxy residue is 2,3,5,6-tetraphenylphenoxy as defined in compounds 10, 12 as residue $R^4$.

A further preferred phenoxy residue is 4-bromo-2,3,5,6-tetraphenylphenoxy as defined in compounds 11, 13, 16 as residue $R^4$.

A further preferred phenoxy residue is 2,6-di(4-bromophenyl)-3,5-diphenylphenoxy as defined in compounds 53, 54 as residue $R^4$.

A further preferred phenoxy residue is 4-bromo-2,6-di(4-bromophenyl)-3,5-diphenylphenoxy as defined in compounds 32, 60 as residue $R^4$.

A further preferred phenoxy residue is

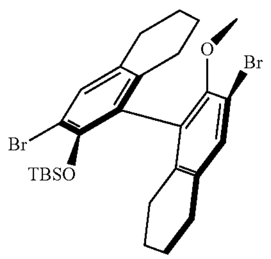

as defined in compound 56 as residue $R^4$. TBS denotes a t-butyldimethylsilyl group.

A further preferred phenoxy residue is

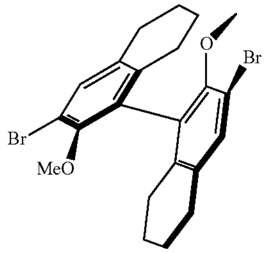

as defined in compound 58 as residue $R^4$. Me denotes a methyl group.

A further preferred phenoxy residue is 4-dimethylaminophenyl-2,6-diphenylphenoxy as residue $R^4$ as e.g. defined in structures 159, 160, 161, 162, 167, 168, 169, 170.

A further preferred phenoxy residue is 2,6-di(2,4,6-triisopropylphenyl)phenoxy as residue $R^4$ as e.g. defined in structure 174.

Another preferred residue is quinolone-8-oxy as residue $R^4$ as e.g. defined in structure 94 and 97.

A preferred thiophenoxy residue is 2,6-diphenylthiophenoxy, 4-bromo-2,6-diphenylthiophenoxy, 4-fluoro-2,6-diphenylthiophenoxy, 4-methyl-2,6-diphenylthiophenoxy, 2,4,6-triphenylthiophenoxy, 4-fluoro-dimesitylthiophenoxy, 2,6-di-tert.-butylthiophenoxy, 4-bromo-2,6-di-tert.-butylthiophenoxy, 4-methoxy-2,6-di-tert.butylthiophenoxy, 4-methyl-2,6-di-tert.-butylthiophenoxy, 2,4,6-tri-tert.-butylthiophenoxy, 2,3,5,6-tetraphenyithiophenoxy, 4-bromo-2,3,5,6-tetraphenylthiophenoxy, 2,6-di(4-bromophenyl)-3,5-diphenylthiophenoxy, 4-bromo-2,6-di(4-bromophenyl)-3,5-diphenylthiophenoxy as residue $R^4$.

The term "heteroaryl" as used herein refers to aryl groups as described herein in which one or more atoms is a heteroatom (e.g., oxygen, nitrogen, sulfur, and the like), optionally substituted. Examples of aryl and heteroaryl groups include, but are not limited to, phenyl, aryloxy, pyrrolyl, furanyl, thiophenyl, imidazolyl, oxazolyl, thiazolyl, triazolyl, pyrazolyl, pyridinyl, pyrazinyl, pyridazinyl and pyrimidinyl, and the like.

A preferred heteroaryl residue is the pyrrol-1-yl residue as e.g. disclosed in compounds 2, 3, 4, 5, 6, 7, 17, 18, 19, 20, 25, 28, 33, 34, 37, 41, 43, 51, 52, 58, 59, 62, 65, 66, 67, 68, 69, 70 as residue $R^5$.

A further preferred heteroaryl residue is the 2,5-dimethylpyrrol-1-yl residue as e.g. disclosed in compounds 1, 8, 9, 10, 11, 12, 13, 14, 15, 16, 21, 22, 23, 24, 26, 27, 29, 30, 31, 32, 35, 36, 39, 42, 45, 44, 47, 57, 61, 63, 64 as residue $R^5$.

The term "heteroalkyl" refers to alkyl groups as described herein in which one or more atoms is a heteroatom (e.g., oxygen, nitrogen, sulfur, and the like). Examples of heteroalkyl groups include, but are not limited to, alkoxy, poly(ethylene glycol)-, alkyl-substituted amino, tetrahydrofuranyl, piperidinyl, morpholinyl, etc.

The term "halogen" refers to F, Cl, Br, I.

The term "acyl" refers to H, alkyl, alkenyl, aryl, heteroalkyl and heteroaryl groups as defined above, which are linked to another atom or to another moiety such as a olefinic double bond via a carbonyl group.

The term "triphenylsilyloxy" refers to the preferred group $(C_6H_5)_3SiO$ which is e.g. disclosed in compounds 2, 20, 21, 22, 24, 46, 49, 50 as residue $R^4$ and in compounds 46, 50 additionally as residue $R^5$.

The term "triisopropylsilyloxy" refers to the preferred group $(CH_3)_2CHSiO$ as e.g. disclosed in compound 137.

The term "comprising" is used in the meaning of "including but not limited to".

The term "consisting of" is used in the meaning "including and limited to".

The term "feedstock" encompasses the compounds used as starting material in the reaction according to the invention, i.e. first olefin and/or said second olefin and further products accompanying said olefin(s). said further olefins are termed as "by-products". In one embodiment, the feedstock comprises at least 99% by weight of the first and/or the second olefin based on the total weight of the feedstock, the remainder being by-products, or at least 99.5% by weight. By-products are e.g. water, alcohols, aldehydes, peroxides, hydroperoxides.

The term "first or second olefin" is in one embodiment synonymously used with the term "first and second olefin".

The term "by-product" is synonymously used with the term "contaminant".

The term "physical purification" encompasses: distilling said by-products off, or distilling said feedstock, or adsorbing said by-products.

The term "chemical purification" encompasses: subjecting the by-products to a chemical reaction.

The term "chemical reaction" encompasses a reaction in which at least one compound such as a by-product accompanying said first and/or second olefin is converted into another compound. Thus, the term "chemical reaction" refers to a process in which in a compound a new bond is formed.

The term "substrate" encompasses the first and/or the second olefin, i.e. the olefin(s) to be converted in a metathesis reaction.

The term "protic material" encompasses any material that is suitable to release a proton, or from which protons may be removed.

The term "polar material" encompasses any material that has polar groups such as hydroxyl groups, carboxylic groups, aldehyde groups, cyano groups, nitrile groups, sulfonate groups, phosphate groups, ester groups.

The term "Lewis base catalyst poisons" encompasses any compound which has a free pair of electrons.

The term "means" in connection with purification encompasses any method or material which is/are suitable to at least partially destroy or remove a by-product that is contained in a feedstock comprising a first and a second olefin.

The term "optionally substituted" as used herein encompasses the substitution of a phenyl ring or an alkyl chain with one or more substituents selected from the group consisting of: halogen, hydroxyl, protected hydroxyl, $C_{1-4}$ dialkylamino, optionally substituted $C_{1-4}$ alkyl, optionally substituted $C_{1-4}$ alkyloxy, optionally substituted phenyl, optionally substituted phenyloxy.

The term "protected hydroxyl" encompasses the protection with Si-containing groups such as trimethylsilyl (TMS), triethylsilyl (TES), t-butyldimethylsilyl (TBS, TBDMS), triisopropylsilyl (TIPS), and t-butyldiphenylsilyl (TBDPS).

EXAMPLES

1. Synthesis of Catalysts

All reactions were carried out in owen-(120° C.) dried glassware under an inert atmosphere of N2 unless otherwise stated. Alcohols were dried by azeotropic distillation with $C_6D_6$ prior to use in reactions with Mo- or W-based reagents. $^1H$ NMR were recorded on a Varian XL-200 (200 MHz) spectrometer. Chemical shifts are reported in ppm from tetramethylsilane with the tetramethylsilane resonance as the internal reference (δ 0.00). Data are reported as follows: chemical shift, integration, multiplicity (s=singulet, d=doublet, t=triplet, hept=heptate, br=broad, m=multiplet).

Example 1: N-[(2,5-dimethyl-1H-pyrrol-1-yl)(2-methyl-2-phenylpropylidene)2,4,6-triphenylphenoxymolybdenumylidene]-2,6-bis(propan-2-yl)aniline (novel compound 44)

In a N2-filled glovebox, a 100 mL pear-shaped flask with magnetic stirbar was charged with N-[bis(2,5-dimethyl-1H-pyrrol-1-yl)(2-methyl-2-phenylpropylidene)molybdenumylidene]-2,6-bis(propan-2-yl)aniline (959.5 mg, 1.6 mmol) and $Et_2O$ (16 mL). A 30 mL vial was charged with 2,4,6-triphenylphenol (522.8 mg, 1.6 mmol) and $Et_2O$ (4 mL). The Mo-bis(pyrrolide) solution was allowed to stir and the phenol solution was added to it by pipet. The vial containing the phenol was rinsed with $Et_2O$ (2 mL), which was similarly transferred to the reaction mixture. After 2 h at 22° C., volatiles were removed under reduced pressure and the resulting red oil was triturated with n-pentane (10 mL) to afford an orange precipitate. The flask was sealed and allowed to cool to −38° C. (glovebox freezer) for 12 h. The orange precipitate was collected by vacuum filtration and washed with cold pentane (~5 mL) to afford the titled compound as an orange powder (1.1 g, 1.3 mmol, 82.8% yield). $^1H$ NMR (200 MHz, $C_6D_6$): δ 11.42 (1H, s), 7.63-7.56 (8H, m), 7.22-6.88 (17H, m), 6.10 (2H, s), 3.13 (2H, hept), 2.25 (6H, br s), 1.54 (3H, s), 1.21 (3H, s), 0.96 (6H, d), 0.84 (6H, d).

Example 2: 2,6-dichloro-N-[(2,5-dimethyl-1H-pyrrol-1-yl)(2,2-dimethylpropylidene)4-fluoro-2,6-diphenylphenoxytungstenylidene]aniline (novel compound 63)

In a N2-filled glovebox, a 100 mL pear-shaped flask with magnetic stirbar was charged with N-[bis(2,5-dimethyl-1H-pyrrol-1-yl)(2,2-dimethylpropylidene)tungstenylidene]-2,6-dichloroaniline (1.5 g, 2.5 mmol) and $Et_2O$ (19 mL). A 30 mL vial was charged with 4-fluoro-2,6-diphenylphenol (658.3 mg, 2.5 mmol) and $Et_2O$ (6 mL). The W-bis(pyrrolide) solution was allowed to stir and the phenol solution was added to it by pipet. The vial containing the phenol was rinse with $Et_2O$ (2 mL), which was similarly transferred to the reaction mixture. After 2 h at 22° C., volatiles were removed under reduced pressure and the resulting orange solid was triturated with n-pentane (15 mL) to afford a yellow precipitate. The flask was sealed and allowed to cool to −38° C. (glovebox freezer) for 12 h. The orange precipitate was collected by vacuum filtration and washed with cold pentane (~5 mL) to afford the titled compound as an orange powder (1.6 g, 2.1 mmol, 83.3% yield). $^1H$ NMR (200 MHz, $C_6D_6$): δ 8.06 (1H, s), 7.39-7.35 (4H, m), 7.10-6.78 (10H, m), 6.18 (1H, t), 6.13 (2H, s), 2.17 (6H, s), 1.00 (9H, s).

The compounds were characterized by means of 1H NMR spectroscopy and the respective shift (ppm) of the respective alkylidene H ($C_6D_6$) as set forth in the following Table 1:

TABLE 1

Compounds used as catalyst for metathesis reactions according to the invention

| Compound | Formula | ppm |
|---|---|---|
| 1 | C46H50MoN2O | 11.38 |
| 2 | C44H48MoN2OSi | 12.07 |

TABLE 1-continued

Compounds used as catalyst for metathesis reactions according to the invention

| Compound | Formula | ppm |
|---|---|---|
| 3 | C29H37BrCl2N2OW | 10.17 |
| 4 | C33H46Cl2N2OW | 10.36 |
| 5 | C30H40Cl2N2O2W | 10.33 |
| 6 | C44H46MoN2O | 11.96 |
| 7 | C41H56MoN2O | 13.04 |
| 8 | C42H42MoN2O | 11.31 |
| 9 | C44H48MoN2O | 10.98 |
| 10 | C58H58MoN2O | 11.42 |
| 11 | C58H57BrMoN2O | 11.51 |
| 12 | C54H50MoN2O | 11.22 |
| 13 | C54H49BrMoN2O | 11.28 |
| 14 | C46H49BrMoN2O | 11.27 |
| 15 | C42H41BrMoN2O | 11.24 |
| 16 | C56H55BrMoN2O | 11.03 |
| 17 | C40H53BrMoN2O | 12.94 |
| 18 | C44H62MoN2O | 13.00 |
| 19 | C41H56MoN2O2 | 13.03 |
| 20 | C33H32Cl2N2OSiW | 9.23 |
| 21 | C35H36Cl2N2OSiOW | 8.97 |
| 22 | C46H52N2OSiW | 9.00 |
| 23 | C47H52MoN2O | 10.69 |
| 24 | C46H52MoN2OSi | 11.93 |
| 25 | C45H48MoN2O | 11.34 |
| 26 | C38H42Br2Cl2N2O2W | 9.85 |
| 27 | C36H36Cl2N2OW | 7.73 |
| 28 | C45H46MoN2O | 11.02 |
| 29 | C47H50MoN2O | 10.92 |
| 30 | C36H34Cl2N2OW | 7.80 |
| 31 | C37H42F6MoN2O | 12.29 |
| 32 | C58H55Br3MoN2O | 11.77 |
| 33 | C44H45BrMoN2O | 11.85 |
| 34 | C44H45FMoN2O | 11.88 |
| 35 | C52H61FMoN2O | 11.57 |
| 36 | C46H49FMoN2O | 11.29 |
| 37 | C50H57FMoN2O | 11.62 |
| 38 | C40H39F12MoNO2 | 12.34 |
| 39 | C33H34F6MoN2O | 12.50 |
| 40 | C36H31F12MoNO2 | 12.28 |
| 41 | C45H48MoN2O | 11.96 |
| 42 | C47H52MoN2O | 11.40 |
| 43 | C50H50MoN2O | 11.98 |
| 44 | C52H54MoN2O | 11.41 |
| 45 | C43H44MoN2O | 10.95 |
| 46 | C56H57MoNO2Si2 | 11.08 |
| 47 | C43H42MoN2O | 11.08 |
| 48 | C58H53MoNO2 | 10.25 |
| 49 | C58H59NO2Si2W | 7.94 |
| 50 | C54H51MoNO2Si2 | 11.22 |
| 51 | C34H32Cl2N2OW | |
| 52 | C34H30Cl2N2OW | |
| 53 | C58H56Br2MoN2O | 11.63 |
| 54 | C54H48Br2MoN2O | 11.46 |
| 55 | C49H58Br2N2O2W | 9.82; 9.79 |
| 56 | C54H70Br2N2O2SiW | 9.46; 9.43 |
| 57 | C47H50N2OW | 7.94 |
| 58 | C36H38Br2Cl2N2O2W | 9.95; 9.74 |
| 59 | C40H54MoN2O | 13.01 |
| 60 | C54H47Br3MoN2O | 11.55 |
| 61 | C39H42Cl2N2OW | 7.68 |
| 62 | C29H38Cl2N2OW | 10.30 |
| 63 | C35H33Cl2FN2OW | 8.06 |
| 64 | C41H38Cl2N2OW | 8.17 |
| 65 | C34H32Cl2N2OW | 9.09 |
| 66 | C39H34Cl2N2OW | 9.13 |
| 67 | C33H29Cl2FN2OW | 8.98 |
| 68 | C33H29BrCl2N2OW | 8.98 |
| 69 | C39H41Cl2FN2OW | 8.64 |
| 70 | C30H40Cl2N2OW | 10.32 |
| 71 | $C_{32}H_{40}F_6MoN_2O$ | 12.40 |
| 72 | $C_{30}H_{35}F_{12}MoNO_2$ | 12.09 |
| 73 | $C_{36}H_{46}MoN_2O_3$ | 11.93 |
| 74 | $C_{34}H_{40}Cl_2MoN_2O$ | 12.54 |
| 75 | $C_{34}H_{37}F_5MoN_2O$ | 12.69 |
| 76 | $C_{54}H_{70}Br_2MoN_2O_2Si$ | |
| 77 | $C_{49}H_{58}Br_2MoN_2O_2$ | 12.78; 12.76 |

TABLE 1-continued

Compounds used as catalyst for metathesis reactions according to the invention

| Compound | Formula | ppm |
|---|---|---|
| 78 | $C_{54}H_{62}Br_2MoN_2O_2Si$ | 12.91; 11.58 |
| 79 | $C_{49}H_{50}Br_2MoN_2O_2$ | 12.83; 11.64 |
| 80 | $C_{52}H_{66}Br_2MoN_2O_2Si$ | 12.89; 12.87 |
| 81 | $C_{47}H_{54}Br_2MoN_2O_2$ | 12.80; 12.58 |
| 82 | $C_{42}H_{49}MoNO_2$ | 11.72 |
| 83 | $C_{42}H_{47}Br_2MoNO_2$ | 12.42 |
| 84 | $C_{44}H_{45}F_6MoNO_2$ | 11.62 |
| 85 | $C_{58}H_{55}MoNO_2$ | 11.48 |
| 86 | $C_{47}H_{53}Br_2F_6MoNO_3$ | 12.32; 12.25 |
| 87 | $C_{43}H_{54}Br_2Cl_2N_2O_2SiW$ | 9.78; 9.16 |
| 88 | $C_{40}H_{54}MoN_2O$ | 12.24 |
| 89 | $C_{48}H_{51}MoNO_4$ | 11.20 |
| 90 | $C_{30}H_{47}MoNO_2$ | 11.27 |
| 91 | $C_{51}H_{68}MoN_2O_2$ | 12.48 |
| 92 | $C_{54}H_{70}Br_2MoN_2O_2Si$ | 12.89; 12.41 |
| 93 | $C_{50}H_{62}Br_2MoN_2O_2Si$ | 12.98; 12.94 |
| 94 | $C_{37}H_{43}MoN_3O$ | 12.07 |
| 95 | $C_{56}H_{70}F_6MoN_2O_2Si$ | 12.90; 12.42 |
| 96 | $C_{60}H_{69}MoNO_2$ | 11.06 |
| 97 | $C_{35}H_{38}F_6MoN_2O_2$ | 13.66 |
| 98 | $C_{70}H_{88}MoN_2O_2Si$ | 11.6 |
| 99 | $C_{54}H_{56}F_8MoN_2O_2Si$ | 12.15; 12.09 |
| 100 | $C_{49}H_{44}F_8MoN_2O_2$ | 12.02; 11.99 |
| 101 | $C_{51}H_{66}Cl_2N_2OW$ | |
| 102 | $C_{52}H_{68}Br_2MoN_2O_2Si$ | 12.52; 12.87 |
| 103 | $C_{26}H_{27}F_{12}MoNO_2$ | 12.12 |
| 104 | $C_{45}H_{50}Br_2MoN_2O_2$ | 13.13; 12.75 |
| 105 | $C_{38}H_{39}Br_2MoNO_2$ | 12.87 |
| 106 | $C_{50}H_{54}Br_2MoN_2O_2Si$ | 12.85; 11.67 |
| 107 | $C_{65}H_{78}MoN_2O_2Si$ | 12.0; 11.57 |
| 108 | $C_{52}H_{62}F_6MoN_2O_2Si$ | 12.87; 12.8 |
| 109 | $C_{47}H_{56}Br_2MoN_2O_2$ | 13.00; 12.59 |
| 110 | $C_{52}H_{60}Br_2MoN_2O_2Si$ | 12.80; 12.47; 11.22 |
| 111 | $C_{60}H_{63}Br_4MoNO_4$ | 12.78 |
| 112 | $C_{28}H_{33}F_{12}MoNO_2$ | 11.85; 13.10 |
| 113 | $C_{54}H_{68}F_6MoN_2O_2Si$ | 12.63; 12.23; 12.93 |
| 114 | $C_{40}H_{45}Br_2MoNO_2$ | 12.97 |
| 115 | $C_{70}H_{90}MoN_2O_2Si$ | 11.23; 11.67 |
| 116 | $C_{62}H_{69}Br_4MoNO_4$ | 12.57 |
| 117 | $C_{72}H_{93}Br_4MoNO_4Si_2$ | 12.64 |
| 118 | $C_{62}H_{84}MoN_2O$ | 12.16 |
| 119 | $C_{41}H_{50}Br_2Cl_2N_2O_2SiW$ | 10.01; 9.98 |
| 120 | $C_{42}H_{41}FMoN_2O$ | 11.22 |
| 121 | $C_{48}H_{46}MoN_2O$ | 11.33 |
| 122 | $C_{48}H_{53}FMoN_2O$ | 11.51 |
| 123 | C47H41BrCl2N2OW | Overlap with aromatic protons |
| 124 | C47H39Br3Cl2N2OW | Overlap with aromatic protons |
| 125 | $C_{50}H_{52}MoN_2O$ | 10.95 |
| 126 | $C_{44}H_{47}BrMoN_2O$ | 10.85 |
| 127 | $C_{50}H_{59}FMoN_2O$ | 10.91 |
| 128 | $C_{24}H_{22}Cl_2F_6N_2OW$ | 9.58 |
| 129 | $C_{37}H_{42}F_6N_2OW$ | 9.23 |
| 130 | $C_{35}H_{33}BrCl_2N_2OW$ | 8.04 |
| 131 | $C_{41}H_{45}Cl_2FN_2OW$ | 8.37 |
| 132 | $C_{52}H_{54}N_2OW$ | 8.51 |
| 133 | $C_{46}H_{49}FN_2OW$ | 8.37 |
| 134 | $C_{46}H_{49}BrN_2OW$ | 8.4 |
| 135 | $C_{52}H_{61}FN_2OW$ | 8.63 |
| 136 | $C_{58}H_{55}Br_3N_2OW$ | 8.79 |
| 137 | $C_{26}H_{42}Cl_2N_2OSiW$ | 9.53 |
| 138 | $C_{37}H_{58}MoN_2OSi$ | 12.43 |
| 139 | $C_{56}H_{53}BrMoN_2O$ | 11.82 |
| 140 | $C_{43}H_{44}MoN_2O$ | 11.32 |
| 141 | $C_{45}H_{50}MoN_2O$ | 10.98 |
| 142 | $C_{36}H_{36}Cl_2N_2OW$ | 8.14 |
| 143 | C56H54MoN2O | 11.39 |
| 144 | C58H58N2OW | 8.42 |
| 145 | $C_{56}H_{51}Br_3MoN_2O$ | 11.59 |
| 146 | $C_{42}H_{39}F_3MoN_2O$ | 10.89 |
| 147 | $C_{49}H_{57}Br_2F_3MoN_2O_2Si$ | 12.37 |
| 148 | $C_{48}H_{53}Br_2F_5MoN_2O_2Si$ | 12.24 |
| 149 | $C_{41}H_{35}F_5MoN_2O$ | 10.92 |
| 150 | $C_{44}H_{47}FMoN_2O$ | 10.84 |
| 151 | C40H46N2OW | 8.72 |
| 152 | C29H30Cl2N2OW | 8.72 |

TABLE 1-continued

| Compounds used as catalyst for metathesis reactions according to the invention | | |
|---|---|---|
| Compound | Formula | ppm |
| 153 | C40H46MoN2O | 11.49 |
| 154* | C47H42Cl2N2OW | 7.86 |
| 155 | C41H56N2OW | 10.28 |
| 156 | C41H56N2O2W | 10.28 |
| 157 | C40H53BrN2OW | 10.18 |
| 158 | C44H62N2OW | 10.27 |
| 159 | C46H51N3OW | 9.23 |
| 160 | C48H55N3OW | 8.42 |
| 161 | C46H51MoN3O | 11.97 |
| 162 | C48H55MoN3O | 11.33 |
| 163 | C44H45FN2OW | 9.14 |
| 164 | C45H48N2OW | 9.22 |
| 165 | C50H57FN2OW | 8.94 |
| 166 | C50H50N2OW | 9.23 |
| 167 | C35H35Cl2N3OW | 9.1 |
| 168 | C37H39Cl2N3OW | 8.13 |
| 169 | C46H53MoN3O | 10.94 |
| 170 | C44H47MoN3O | 11.27 |
| 171 | C52H66Br2N2O2SiW | 10.26; 10.04 |
| 172 | C47H54Br2N2O2W | 9.97; 9.72 |
| 173 | C44H45BrN2OW | 9.11 |
| 174 | C62H82N2OW | 9.95 |
| 175 | C59H73F3MoN2O | 12.31 |
| 176 | C33H30Cl2N2OW | 9.08 |
| 177 | C44H46N2OW | 9.21 |
| 178 | C35H34Cl2N2OW | 8.15 |
| 179 | C46H50N2OW | 8.48 |

*In case of compound 154 a different chemical shift of the alkylidene signal of the complex (7.86 ppm) was detected than described in the literature US 20110077421, WO 2011040963 (11.04 ppm) which is unusually high for that kind of complexes.

Compounds 180 to 291 were also characterized by means of 1H NMR spectroscopy and the respective shift (ppm) of the respective alkylidene H ($C_6D_6$) as set forth in the respective formulas. Additionally, the formula weight is indicated.

2. Screening of Various Compounds in Ring Closure Metathesis (RCM) of Diethyl Diallylmalonate According to the Following Scheme 1

Scheme 1

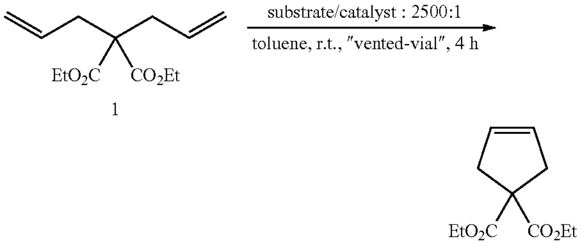

1

2

Metathesis catalysts were tested in RCM of diethyl diallylmalonate. The reaction was characterized by the conversion data. Compounds 1, 10 and 154 are known compounds, compounds 11, 42, 123, 142, 162, 168, 178 are novel. Results are summarized at Table 2.

TABLE 2

Results of diethyl diallylmalonate (1) self-metathesis in the presence of different metathesis catalysts at 760 Torr

| Entry | Cat. No. | Molar ratio Catalyst/ olefin | T (° C.) | Time [h] | Solvent | c (mol/L) | Conv. (%) |
|---|---|---|---|---|---|---|---|
| 1 | 10 | 1:2500 | 25° C. | 4 h | toluene | 1 | 85 |
| 2 | 11 | 1:2500 | 25° C. | 4 h | toluene | 1 | 87 |
| 3 | 154 | 1:2500 | 25° C. | 4 h | toluene | 1 | 99 |
| 4 | 123 | 1:2500 | 25° C. | 4 h | toluene | 1 | 98 |
| 5 | 1 | 1:2500 | 25° C. | 4 h | toluene | 1 | 51 |
| 6 | 178 | 1:2500 | 25° C. | 4 h | toluene | 1 | 97 |
| 7 | 42 | 1:2500 | 25° C. | 4 h | toluene | 1 | 58 |
| 8 | 142 | 1:2500 | 25° C. | 4 h | toluene | 1 | 99 |
| 9 | 162 | 1:2500 | 25° C. | 4 h | toluene | 1 | 71 |
| 10 | 168 | 1:2500 | 25° C. | 4 h | toluene | 1 | 98 |

Conversion = [(area of diethyl cyclopent-3-ene-1,1-dicarboxylate 2)/(area of diethyl cyclopent-3-ene-1,1-dicarboxylate 2) + (area of diethyl diallylmalonate 1)] without calibration.

Entry 1-2, 4-9: All manipulation was performed under the inert atmosphere of the glove-box. Diethyl diallylmalonate (2.5 mmol, 604 μL) (substrate) was measured into a 10 ml glass vial and dissolved in toluene (abs 1.9 mL). 0.1 M stock solution (1 μmol, 10 μL) of the catalyst was added at r.t. and the vial was capped with a perforated cap to vent out the evolving ethylene. The reaction mixture was stirred at the same temperature for 4 h then it was taken out from the glovebox and its volume was diluted to 10 mL with EtOAc. 1 mL of this solution was poured onto the top of a silica column (1.0 mL) and eluted with EtOAc (10 mL). The collected eluate was analyzed by GCMS.

Entry 3: The manipulation was performed under the inert atmosphere of the glovebox. Diethyl diallylmalonate (2.5 mmol, 604 μL) was measured into a 10 ml glass vial and dissolved in toluene (abs 1.9 mL). 0.05 M stock solution (1 μmol, 20 μL) of catalyst 154 was added at r.t. and the vial was capped with a perforated cap to vent out the evolving ethylene. The reaction mixture was stirred at the same temperature for 4 h then it was taken out from the glovebox and its volume was diluted to 10 mL with EtOAc. 1 mL of this solution was poured onto the top of a silica column (1.0 mL) and eluted with EtOAc (10 mL). The collected eluate was analyzed by GCMS.

Materials:

Diethyldiallylmalonate was purchased from Sigma-Aldrich. It was purged with nitrogen and transferred to the glovebox. It was percolated twice on 2×25 weight % activated alumina, and stored on molecular sieve.

All reactions under the glovebox were carried out in ovendried (140° C.) glassware under an inert atmosphere of N2 unless otherwise stated. All catalyst was used as 0.1 M stock solution in $C_6D_6$ or benzene except 154 which was used as a 0.05M solution in $C_6D_6$. GCMS chromatograms were recorded on a Shimadzu GC2010 Plus instrument

3. Screening of Various Compounds in Homo Cross Metathesis (HCM) of 2-Allylphenylacetate

Preparation of 2-allylphenylacetate according to Scheme 2

Scheme 2

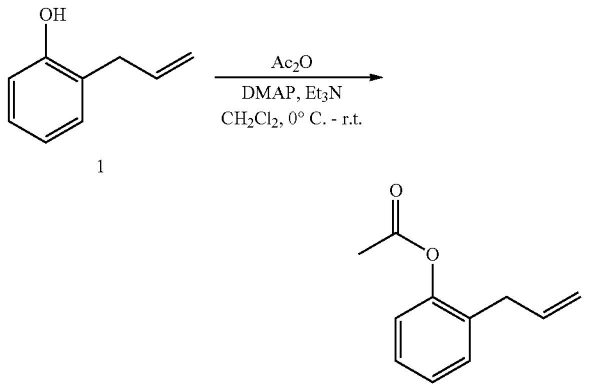

1

2

2-allylphenol (0.5 mol) was dissolved in $CH_2Cl_2$ (10 under nitrogen. $Et_3N$ (139 mL, 1 mol,) and DMAP (1.83 g, 0.015 mol) were added in one portion. The mixture was cooled to 0° C. with an ice bath and acetic anhydride was added to it drop-wise, keeping the temperature below 10° C. The reaction mixture was stirred for 2 h at 0-5° C. and monitored by TLC (10% EtOAc in heptane). The ice bath was removed, the reaction mixture was extracted with water (2×500 mL) and brine (300 mL). The solvent was evaporated and the product was purified by vacuum distillation (bp: 101° C. at 11 torr). The main fraction was purged with nitrogen; transferred into a nitrogen filled glovebox and filtered through on activated alumina pad (20 weight %) to afford 2 as a transparent liquid. (50 mL, 58.6%). GC-MS: 99.6%, [allylphenol traces (0.037%) are also detected], $^1$H NMR (200 MHz, Chloroform-d): δ 2.23 (s, 3H), 3.23 (s, 2H), 4.94-4.98 (m, 1H), 5.03-5.04 (m, 1H), 5.73-5.93 (m, 1H), 6.94-7.22 (m, 4H), consistent.

Before metathesis reaction the substrate was further stirred with 0.037-0.1 mol % triethylaluminium (r.t. during 1 h) to deactivate free phenol and water traces.

2-allylphenylacetate was subjected to HCM according to Scheme 3

Scheme 3

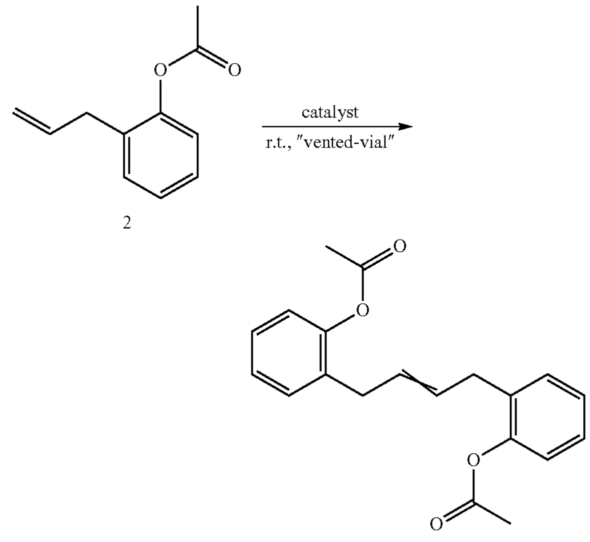

2

3

Metathesis catalysts were tested in HCM of 2-allylphenylacetate using different substrate/catalyst ratios. The reaction was characterized by the conversion data. Catalysts according to the invention were compared to known compounds 1 and 10. Prior to the metathesis reaction, novel compound 2 was purified by means of $Et_3Al$.

Compound 162 gave a remarkable result. A higher conversion was detected than in case of the known compound 1 for a high loading with olefin. Compounds 11, 42 and 162 are novel. Results are summarized at Table 3.

TABLE 3

Results of allylphenylacetate (2) self-metathesis in the presence of different metathesis catalysts at 760 Torr

| Entry | Cat. | $Et_3Al$ Additive (mol %) | Molar ratio cat/olefin | T (° C.) | Time [h] | [b]Conv. [%] | TON | [c]Z/E Isomer ratio |
|---|---|---|---|---|---|---|---|---|
| 1 | 11 | 0.1 | 1:1 000 | r.t. | 2.5 | 93 | 456 | 17/83 |
| 2 | 1 | 0.085 | 1:1 000 | r.t. | 2.5 | 92 | 453 | 20/80 |
| 3 | 42 | 0.085 | 1:1 000 | r.t. | 2.5 | 90 | 441 | 20/80 |
| 4 | 162 | 0.085 | 1:1 000 | r.t. | 2.5 | 95 | 464 | 16/84 |
| 5 | 10 | 0.085 | 1:10 000 | r.t. | 2.5 | 64 | 3144 | 19/81 |
| 6 | 11 | 0.085 | 1:10 000 | r.t. | 2.5 | 66 | 3218 | 21/79 |
| 7 | 1 | 0.085 | 1:10 000 | r.t. | 2.5 | 48 | 2340 | 24/76 |
| 8 | 42 | 0.085 | 1:10 000 | r.t. | 2.5 | 44 | 2161 | 22/78 |
| 9 | 162 | 0.085 | 1:10 000 | r.t. | 2.5 | 67 | 3299 | 18/82 |

[b]Conversion = [area of (1,4-di(2-acetyloxyphenyl)-2-butene 3) x 2)/area of ((1,4-di(2-acetyloxyphenyl)-2-butene 3) x 2 + area of 2-allylphenylacetate 2)]. (based on calibrated GCMS data)

[c]The E/Z isomers were separable in GC. The E isomer could be isolated by flash chromatography and characterized by NMR.

TON = Turn Over Number.

Experimental:

Entry 1. All manipulation was performed under the inert atmosphere of the glovebox. 2-allylphenylacetate was pretreated with 0.1 mol % $Et_3Al$ (25 weight % in toluene). The pretreated substrate stock solution (171 μl, 1 mmol) was measured into a 4 ml glass vial. 0.1 M stock solution of catalyst 11 (1 μmol, 10 μL) was added at r.t. and the vial was capped with a perforated cap to vent out the evolving ethylene. The reaction mixture was stirred at the same temperature for 2.5 h. The reaction mixture was taken out from the glovebox and quenched with ethyl acetate. Internal standards, mesitylene (c=60 mg/mL) and pentadecane (c=60 mg/mL) were added, the solution was poured onto the top of a silica column (1.0 mL) and eluted with EtOAc (10 mL). The collected eluate was analyzed by GCMS. Conversion: 93%, TON: 456, Z/E Isomer ratio: 17/83

Entry 9. All manipulation was performed under the inert atmosphere of the glovebox. 2-Allylphenylacetate was pretreated with 0.085 mol % $Et_3Al$ (25 weight % in toluene). The pretreated substrate stock solution (1711 μl, 10 mmol) was measured into a 10 ml glass vial. 0.1 M stock solution of compound 162 (1 μmol, 10 μL) was added at r.t. and the vial was capped with a perforated cap to vent out the evolving ethylene. The reaction mixture was stirred at the same temperature for 2.5 h. The reaction mixture was taken out from the glovebox and quenched with ethyl acetate. Internal standards, mesitylene (c=60 mg/mL) and pentadecane (c=60 mg/mL) were added and the volume of the mixture was diluted to 10 mL. 1 mL of the solution was poured onto the top of a silica column (1.0 mL) and eluted with EtOAc (10 mL). The collected eluate was analyzed by GCMS. Conversion: 67%, TON: 3299, Z/E Isomer ratio: 18/82

General:

All reactions under the glovebox were carried out in owendried (140° C.) glassware under an inert atmosphere of $N_2$ unless otherwise stated. All catalyst was used as 0.1 M stock solution in $C_6D_6$ or benzene.

TLC was performed on 0.25 mm Merck silica gel 60 $F_{254}$ plates and visualized under UV light (254 nm) and iodine vapor. GCMS chromatograms were recorded on a Shimadzu GC2010 Plus instrument. $^1H$ NMR were recorded on a Varian XL-200 (200 MHz) spectrometer. Chemical shifts are reported in ppm from tetramethylsilane with the tetramethylsilane resonance as the internal reference (δ 0.00). Data are reported as follows: chemical shift, integration, multiplicity (s=singulet, d=doublet, t=triplet, hept=heptate, br=broad, m=multiplet).

4. Screening of Various Compounds in a Homo Cross Metathesis Reaction (HCM) of Allylbenzene at Different Catalyst Loadings According to the Following Scheme 4

Scheme 4

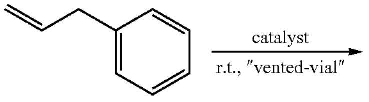

1

-continued

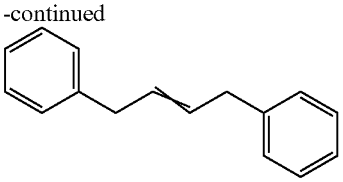

2

4.1 Purification of Crude Allylbenzene by Physicochemical Pretreatment

Crude allylbenzene (substrate) was distilled under atmospheric pressure. Its peroxide content was determined by titration and found to be 0.01 mol %. Then the substrate was percolated on 20 weight % activated aluminum oxide 90 (active basic). By that method hydroperoxide content could be decreased under the detection limit and water content under 5 ppms. The percolated substrate was stored over molecular sieve and applied in self-metathesis reaction using different catalysts.

The reaction was tested with novel compound 11 using different molar ratios of catalyst/substrate. Results are summarized at Table 4. The selected catalyst gives practically complete conversion after 1 h.

TABLE 4

Results of allylbenzene (1) self-metathesis in the presence of novel compound 11

| Entry | Cat./ Subs. | T (° C.) | Time [h] | Conv.[a] [%] | E/Z ratio[b] |
|---|---|---|---|---|---|
| 1 | 1:1 000 | r.t. | 1 | 97 | 85/15 |
| 2 | 1:1 000 | r.t. | 18 | >99 | 86/14 |
| 3 | 1:5 000 | r.t. | 1 | 97 | 86/14 |
| 4 | 1:5 000 | r.t. | 4 | 100 | 87/13 |
| 5 | 1:10 000 | r.t. | 1 | 94 | 86/14 |
| 6 | 1:10 000 | r.t. | 4 | 97 | 87/13 |
| 7 | 1:20 000 | r.t. | 1 | 93 | 89/11 |
| 8 | 1:20 000 | r.t. | 2 | 95 | 88/12 |
| 9 | 1:20 000 | r.t. | 4 | 96 | 89/11 |

[a] Conversion = [(area of 1,4-diphenylbutene 2) x 2/((area of 1,4-diphenylbutene 2) x) 2 + area of allylbenzene 1].

[b] The E/Z isomers were separable in GC. The mixture was measured by $^1H$ NMR, and the chemical shifts of isomers were compared to the literature data. The major component was found to be the E isomer.

[d] the catalyst was used from 0.1M stock solution in $C_6D_6$ or benzene

The reaction was carried out with further catalysts as presented at Table 5 below. Compound 10 is known, compounds 11, 21, 30, 32, 36, 42 are novel.

TABLE 5

Selected results of allylbenzene (1) self-metathesis in the presence of various catalyst

| Entry | Cat. | Cat./Subs. | T (° C.) | Time [h] | Conv.[a] [%] | E/Z ratio[b] |
|---|---|---|---|---|---|---|
| 1 | 10 | 1:20 000 | r.t. | 2 | 90 | 91/9 |
| 2 | 11 | 1:20 000 | r.t. | 2 | 95 | 88/12 |
| 3 | 21 | 1:20 000 | r.t. | 2 | 63 | 57/43 |
| 4 | 30 | 1:20 000 | r.t. | 2 | 41 | 26/74 |
| 5 | 32 | 1:20 000 | r.t. | 2 | 83 | 90/10 |
| 6 | 36 | 1:20 000 | r.t. | 2 | 92 | 87/13 |
| 7 | 42 | 1:20 000 | r.t. | 2 | 85 | 89/11 |

[a] Conversion = [(area of 1,4-diphenylbutene 2) x 2/((area of 1,4-diphenylbutene 2) x) 2 + area of allylbenzene 1].

[b] The E/Z isomers were separable in GC. The mixture was measured by $^1H$ NMR, and the chemical shifts of isomers were compared to the literature data.
The major component was found to be the E isomer.

Experimental:

Reactions in Table 5 were performed according to the following protocol: All manipulation was performed under the inert atmosphere of the Glove-Box. Allylbenzene (20 mmol, 2650 μL) was measured into a 10 ml glass vial. 0.1 M stock solution (1 μmol, 10 μL) of the catalyst was added at r.t. and the reaction mixture is stirred at the same temperature for 2 h. 100 μl sample was taken out from the Glove-Box and quenched with 2 mL EtOAc. The solution was poured onto the top of a silica column (1.0 mL) and eluted with EtOAc (10 mL). From the collected elute 200 μL was analyzed by GCMS.

4.2 Purification of Allylbenzene by a Chemical Purification Step: Reaction of by-Products with Trioctyl Aluminum Allylbenzene was purchased from Sigma-Aldrich (A29402-100ML, Lot No.: 55496LMV, Certificate of analysis: 99.9%). In house GCMS analysis: 99.64% allylbenzene, 0.27% cinnamaldehyde, 0.07% unknown impurities. Hydroperoxide content: 0.68 mol % by titration. Water content by KF titration: 973 ppm, 0.63 mol %.

Crude allylbenzene was pretreated with different amount of $Oc_3Al$. After pretreatment the crude substrate was applied in metathesis reaction. The reaction was characterized by the conversion data and the necessary amount of $Oc_3Al$ could be optimized.

0.8-1.2 mol % $Oc_3Al$ efficiently removed impurities. The optimum was not determined because of the high conversion in each point. Results with known catalyst 1 are listed at Table 6.

TABLE 6

Application of $Oc_3Al$ pretreatment in allylbenzene self-metathesis in the presence of 100 mol ppm of catalyst 1

| Entry | $Oc_3Al$ [mol %] | Conv. [%][a] | TON | E/Z ratio[b] |
|---|---|---|---|---|
| 1 | 0.2 | 0 | 0 | — |
| 2 | 0.4 | 0 | 0 | — |
| 3 | 0.5 | 0 | 0 | — |
| 4 | 0.6 | 2 | 78 | 67/33 |
| 5 | 0.7 | 37 | 1872 | 89/11 |
| 6 | 0.8 | 88 | 4407 | 88/12 |
| 7 | 0.9 | 96 | 4810 | 87/13 |
| 8 | 1 | 95 | 4753 | 86/14 |
| 9 | 1.1 | 96 | 4800 | 86/14 |
| 10 | 1.2 | 96 | 4817 | 86/14 |
| 11 | 1.3 | 12 | 608 | 85/15 |
| 12 | 1.4 | 2 | 98 | 75/25 |
| 13 | 1.5 | 0 | 0 | — |

Allylbenzene quality: crude, hydroperoxide/water content = 0.68%/0.63%,
Additive: $Oc_3Al$ (25 weight % in hexane),
Pretreatment conditions: 18 h stirring at r.t,
Catalyst: 1, S/C = 10 000,
Metathesis conditions: 4 h, r.t.
[a]Conversion = [(area of 1,4-diphenylbutene 2) × 2/((area of 1,4-diphenylbutene 2) ×) 2 + area of allylbenzene 1].
[b]The E/Z isomers were separable in GC.

Table 7 presents the application of $Oc_3Al$ pretreatment in allylbenzene self-metathesis in the presence of 50 mol ppm of known catalyst 1 and novel catalysts 178, 162, 168, 183, 184 and 123:

TABLE 7

Application of $Oc_3Al$ pretreatment in allylbenzene (1) self-metathesis in the presence of 50 mol ppm catalysts

| | $Oc_3Al$ | Conversion [%][a] | | | | | | | |
|---|---|---|---|---|---|---|---|---|---|
| Entry | [mol %] | 1 | 178 | 162 | 168 | 183 | 184 | 11 | 123 |
| 1 | 0.9 | 91 | 18 | 48 | 64 | 48 | 85 | 34 | 90 |
| 2 | 1 | 95 | 83 | 91 | 92 | 58 | 94 | 88 | 92 |
| 3 | 1.10 | 85 | 91 | 90 | 92 | 85 | 93 | 91 | 91 |
| 4 | 1.20 | 12 | 90 | 11 | 87 | 77 | 87 | 82 | 93 |

Pretreatment conditions: 18 h stirring at r.t, Catalyst/substrate = 1:20 000,
Metathesis conditions: 4 h, r.t.

Table 8 presents the effect of the pretreatment time. It was found that under the given conditions the reaction goes to completion practically in 2-4 h.

TABLE 8

Study of the effect of pretreatment time of crude allylbenzene in self-metathesis catalyzed by known catalyst 1

| Purification time [h] | Conv. [%][b] | TON | E/Z ratio[c] |
|---|---|---|---|
| 1 | 74 | 3677 | 88/12 |
| 2 | 91 | 4531 | 87/13 |
| 3 | 90 | 4524 | 87/13 |
| 4 | 92 | 4605 | 87/13 |
| 18 | 96 | 4810 | 87/13 |

Allylbenzene quality: crude, hydroperoxide/water content = 0.68%/0.63%,
Additive: 0.9 ml % $Oc_3Al$ (25 weight % in hexane),
catalyst: 1, Catalyst/Substrate = 1:10 000,
Metathesis conditions: 4 h, r.t.
[a]Conversion = [(area of 1,4-diphenylbutene 2) × 2/((area of 1,4-diphenylbutene 2) ×) 2 + area of allylbenzene 1].
[c]The E/Z isomers were separable in GC.

Experimental:

If catalyst/substrate=1:10 000, (100 mol ppm catalyst), reactions in Table 7 and Table 8 were performed according to the following protocol: All manipulation was performed under the inert atmosphere of the Glove-Box. 662 μl (5 mmol) of allylbenzene ($H_2O$ content 973 ppm, 0.63%, peroxide content 0.68%) was measured into a 5 ml glass vial. $Oc_3Al$ (25% sol. in hexane) was added to it and the mixture was stirred for 1-18 h. Then 0.1 M stock solution (5 μl, 1 μmol, 100 mol ppm) of the catalyst was added at r.t. and the reaction mixture is stirred at the same temperature for 4 h. Then the reaction mixture was taken out of the glovebox and quenched with 100 μL MeOH. Internals standards were added: mesitylene in EtOAc and pentadecane (1 mL, c=60 mg/mL). The volume was diluted to 5 mL. 1 mL of this solution was poured onto the top of silica column 1 (mL) and eluted with EtOAc (10 mL). From the collected elute 100 μL is analyzed by GC or GCMS.

If catalyst/substrate=1:20 000, (50 mol ppm catalyst), reactions in Table 7 were performed according to the following protocol: All manipulation was performed under the inert atmosphere of the Glove-Box. 1362 μl (10 mmol) of allylbenzene ($H_2O$ content 973 ppm, 0.63%, peroxide content 0.68%) was measured into a 10 ml glass vial. $Oc_3Al$ (25% sol. in hexane) was added to it and the mixture was stirred for 18 h. Then 0.1 M stock solution (5 μl, 0.5 μmol, 50 mol ppm) of the catalyst was added at r.t. and the reaction mixture is stirred at the same temperature for 4 h. Then the reaction mixture was taken out of the glovebox and quenched with 100 μL MeOH. Internals standards were added: mesitylene in EtOAc and pentadecane (1 mL, c=60 mg/ml). The volume was diluted to 10 mL. 1 mL of this solution was poured onto the top of silica column 1 (mL) and eluted with EtOAc (10 mL). From the collected elute 100 μL is analyzed by GC or GCMS.

Trioctylaluminum, which allows a safe handling, efficiently destroys impurities in allylbenzene substrate and allows to reach high conversion even at such a low catalyst loading as of 50 mol ppm.

5. Screening of Compounds in Ring Closing Metathesis (RCM) of Diethyl Diallylmalonate (DEDAM) Depending on Purification Crude diethyl diallylmalonate was purchased from Sigma-Aldrich, its water content by Karl-Fischer titration was 346 weight ppm (0.46 mol %). The solution of the crude substrate was pretreated (stirred) with $Oc_3Al$ then applied in RCM reaction using novel compound 11 as catalyst under standard conditions.

Diethyl diallylmalonate was pre-dried on 20 weight % molecular sieve for 24 h. Its water content was decreased from 346 weight ppm (0.46 mol %) to 14.7 weight ppm, 0.019 mol %. Without $Oc_3Al$ purification no metathesis reaction could be performed (Table 9, entry 1). After 0.175 mol % trioctyl aluminum treatment the metathesis could be performed at high conversion (Table 9, entry 8)

TABLE 9

Results of diethyl diallylmalonate (1) RCM reaction after predrying the substrate on molecular sieve and subsequent $Oc_3Al$ pretreatment (purification)

| Entry | Water content of substrate [mol %] | Amount of $Oc_3Al$ [mol %] | Purification time [h] | Cat. No. | Conv. [%][b] |
|---|---|---|---|---|---|
| 1 | 0.019 | 0 | 1 | 11 | 3 |
| 2 | 0.019 | 0.025 | 1 | 11 | 5 |
| 3 | 0.019 | 0.05 | 1 | 11 | 6 |
| 4 | 0.019 | 0.075 | 1 | 11 | 2 |
| 5 | 0.019 | 0.1 | 1 | 11 | 9 |
| 6 | 0.019 | 0.125 | 1 | 11 | 51 |
| 7 | 0.019 | 0.15 | 1 | 11 | 62 |
| 8 | 0.019 | 0.175 | 1 | 11 | 74 |
| 9 | 0.019 | 0.2 | 1 | 11 | 66 |

[b]Conversion = [(area of diethyl cyclopent-3-ene-1,1-dicarboxylate 2)/(area of diethyl cyclopent-3-ene-1,1-dicarboxylate 2) + (area of diethyl diallylmalonate (1)] without calibration.

Pretreatment conditions: $C_{DEDAM}$ = 1M in toluene, 0-0.2% $Oc_3Al$, 1 h, r.t.

Metathesis conditions: catylst/substrate = 1:2500, catalyst 11 loading = 400 mole ppm, 4 h, r.t.

Table 10 shows the results of the improved conversion if purification period is prolonged:

TABLE 10

Results of diethyl diallylmalonate (1) RCM reaction after $Oc_3Al$ purification time using 24 h purification time

| Entry | Water content of substrate [mol %] | Additive | Amount of additive [mol %] | Purification time [h] | Cat. No. | Conv. [%] |
|---|---|---|---|---|---|---|
| 1 | 0.82 | $Oct_3Al$ | 0 | 24 | 11 | 0 |
| 2 | 0.82 | $Oct_3Al$ | 0.25 | 24 | 11 | 3 |
| 3 | 0.82 | $Oct_3Al$ | 0.5 | 24 | 11 | 89 |
| 4 | 0.82 | $Oct_3Al$ | 0.75 | 24 | 11 | 90 |
| 5 | 0.82 | $Oct_3Al$ | 1 | 24 | 11 | 96 |

TABLE 10-continued

Results of diethyl diallylmalonate (1) RCM reaction after $Oc_3Al$ purification time using 24 h purification time

| Entry | Water content of substrate [mol %] | Additive | Amount of additive [mol %] | Purification time [h] | Cat. No. | Conv. [%] |
|---|---|---|---|---|---|---|
| 6 | 0.82 | $Oct_3Al$ | 1.25 | 24 | 11 | 95 |
| 7 | 0.82 | $Oct_3Al$ | 1.5 | 24 | 11 | 52 |
| 8 | 0.82 | $Oct_3Al$ | 1.75 | 24 | 11 | 1 |

[b]Conversion = [(area of diethyl cyclopent-3-ene-1,1-dicarboxylate 2)/(area of diethyl cyclopent-3-ene-1,1-dicarboxylate 2) + (area of diethyl diallylmalonate (1)] without calibration.

Purification conditions: $C_{DEDAM}$ = 1M in toluene, 0-1.75% $Oc_3Al$; 24 h, r.t.

Metathesis conditions: catalyst/substrate = 1:2500, 11 catalyst loading = 400 mole ppm, 4 h, r.t.

6. Screening of Compound 11 in Homo Cross Metathesis (HCM) of Allyl Benzene, Depending on Purification and Addition Mode of Catalyst Allyl benzene containing 973 ppm (0.6 mol %) of water was pretreated with 1 mole % of $Oc_3Al$ for a period of 18 h. Subsequent to the purification, 33 mole % of novel compound 11 was added in one batch. After a period of 4 h, the conversion was 81%.

The experiment was repeated with the difference that the pretreatment time was extended to 60 h, and that the catalyst was added in four portions of 8.25 mole %, respectively. After a period of 2 h subsequent to the addition of the first portion, the conversion was 38%. Then the second portion was added. After further 2 h, the conversion was 84%. Then the third portion was added. After further 2 h, the conversion was 93%. Then the last portion was added. After further 2 h, the conversion was 94%.

7. Screening of Various Compounds in Ethenolysis

Performance of catalysts was compared in ethenolysis of purified unsaturated triglycerides. The purification method was a chemical pretreatment with trialkylaluminum. Triglyceride was subjected to ethylene at a temperature of 50° C. and a pressure of 10 bar for 18 hours using various amounts of catalyst.

Metathesis reaction was characterized by the conversion data. As the catalysts were used in the same amount [1000 ppm (weight)–250 ppm (weight)–25 ppm (weight) respectively], their molar ratio is depending on their molecular weight. Normalized conversion was obtained by linear extrapolation of real conversion calculated from real molar quantity.

Table 11 shows the superior results of novel catalysts 123 and 124 in which $R^6$ is phenyl substituted with phenyl in 2-, 3-, 5- and 6-position, and 4-position is substituted with bromine compared to known catalyst 154, which bears hydrogen in 4-position of the phenyl moiety.

TABLE 11

| Compound | 154 | 123 | 124 |
|---|---|---|---|
| $C_{1000\ ppm\ (weight)\ catalyst}$ [%] | 61 | 84 | 79 |
| $C_{norm\ 1000\ ppm\ (weight)\ catalyst}$ [%] | 63 | 94 | 102 |
| $C_{250\ ppm\ (weight)\ catalyst}$ [%] | | 39 | 49 |
| $C_{norm\ 250\ ppm\ (weight)\ catalyst}$ [%] | | 44 | 63 |

Table 12 shows the results of catalysts in which $R^6$ is a phenyl ring which is substituted in 2-, 4- and 6-position, wherein the 2- and 6-position are substituted by substituents via a carbon atom, and the substituent in 4-position may be attached to the phenyl ring via any atom. Compound 113 is known, the other compounds are novel.

TABLE 12

| Compound | 130 | 188 | 113 | 131 | 184 | 114 | 142 | 168 |
|---|---|---|---|---|---|---|---|---|
| $C_{1000\ ppm\ (weight)\ catalyst}$ [%] | 49 | 85 | 65 | 93 | 97 | 47 | 82 | 84 |
| $C_{norm\ 1000\ ppm\ (weight)\ catalyst}$ [%] | 69 | 76 | 57 | 90 | 90 | 44 | 72 | 76 |
| $C_{250\ ppm\ (weight)\ catalyst}$ [%] |  |  |  | 92 | 55 |  | 49 | 51 |
| $C_{norm\ 250\ ppm\ (weight)\ catalyst}$ [%] |  |  |  | 89 | 51 |  | 42 | 46 |

Table 13 shows the results of further catalysts in which $R^6$ is a phenyl ring which is substituted in 2-, 4- and 6-position, wherein the 2- and 6-position are substituted by substituents via a carbon atom, and the substituent in 4-position is fluorine. Compounds 35, 122, 127, 131 and 135 are novel

TABLE 13

| Compound | 127 | 122 | 35 | 135 | 131 |
|---|---|---|---|---|---|
| $C_{1000\ ppm\ (weight)\ catalyst}$ [%] | 87 | 87 | 77 | 76 | 93 |
| $C_{norm\ 1000\ ppm\ (weight)\ catalyst}$ [%] | 81 | 78 | 74 | 80 | 90 |

Table 14 shows the results of novel catalysts 178 and 233 in which $R^6$ is a phenyl ring which is substituted in 2- and 6-position via a phenyl moiety.

TABLE 14

| Compound | 178 | 233 |
|---|---|---|
| $C_{1000\ ppm\ (weight)\ catalyst}$ [%] | 82 | 87 |
| $C_{norm\ 1000\ ppm\ (weight)\ catalyst}$ [%] | 70 | 87 |
| $C_{250\ ppm\ (weight)\ catalyst}$ [%] | 46 |  |
| $C_{norm\ 250\ ppm\ (weight)\ catalyst}$ [%] | 39 |  |

8. Screening of Various Compounds Bearing a [8-(naphthalene-1-yl)naphthalene-1-yl]oxy ligand or a (8-phenlynaphthalene-1-yl)oxy ligand as $R^4$ Table 15 shows the efficacy of the novel compounds 192, 196, 214, 216, 217, 220, 246, 247, 269, 288 in the homo cross metathesis of methyldecenoate (HCM of DAME), in the homo cross metathesis of allylbenzene (HCM of AB), in the ring closing metathesis of diethyl diallylmalonate (RCM of DEDAM) and in ethenolysis of unsaturated glycerides. S/C is molar ratio of the substrate to catalyst):

TABLE 15

| | Catalyst activity in different metathesis reactions | | | |
|---|---|---|---|---|
| | Conversion (%) in HCM of DAME, loading: 50 ppm mole (S/C = 20000/1) | Conversion (%) in HCM of AB 50 ppm mole (S/C = 20000/1) | Conversion (%) in RCM of DEDAM 400 ppm mole (S/C = 2500/1) | Conversion (%) in TG ethenolysis 1000 ppm weight |
| 192 | 26 | 12 | 87 | 54 |
| 196 | 81 | 3 | >99 | 93 |
| 220 | 73 | 68 | >99 |  |
| 217 | 13 | 25 | >99 | 44 |
| 214 | 76 | 81 | >99 | 97 |

TABLE 15-continued

| | Catalyst activity in different metathesis reactions | | | |
|---|---|---|---|---|
| | Conversion (%) in HCM of DAME, loading: 50 ppm mole (S/C = 20000/1) | Conversion (%) in HCM of AB 50 ppm mole (S/C = 20000/1) | Conversion (%) in RCM of DEDAM 400 ppm mole (S/C = 2500/1) | Conversion (%) in TG ethenolysis 1000 ppm weight |
| 218 | 20 | 35 | 42 | 58 |
| 216 | 88 | 72 | >99 | 97 |
| 247 |  |  | 14 | 8 |
| 246 | not tested | 20 | 11 | 20 |
| 288 | not tested | not tested | not tested | not tested |
| 269 | not tested | 5 | 9 | 36 |

Table 16 shows the efficacy of novel catalysts 207, 208, 214, 216, 220 in HCM of allylbenzene. Allylbenzene was physicochemically treated before metathesis reaction, which means that it was percolated on an activated basic alumina layer (20 weight %). Then it was allowed to stand on 20% molecular sieve at least 1 day before metathesis reaction.

TABLE 16

| Compound | 207 | 214 | 208 | 220 | 216 |
|---|---|---|---|---|---|
| $C_{50\ ppm\ (mole\ catalyst\ loading)}$ [%] | 82 | 81 | 83 | 68 | 72 |

9. Screening of Compounds Bearing 2,6-Diphenyl Phenols and 2-Br-6-Arylphenols as Ligand $R^4$ in HCM of Allylbenzene Using a Chemically Treated Substrate HCM reactions were carried out in a glovebox atmosphere at r.t. for 4 h in a vented vial. Typical substrate/catalyst ratios are: 20 000=50 ppm mole catalyst loading, 30 000=33 ppm mole catalyst loading. After the reaction was quenched by "wet" EtOAc samples were filtered through on a silica layer and analysed by GCMS-FID. The used catalysts are all novel.

Results are summarized at Table 17:

TABLE 17

| Compound | 162 | 183 | 178 | 168 | 184 |
|---|---|---|---|---|---|
| $C_{50\ ppm\ (mole\ catalyst\ loading)}$ [%] | 91 | 58 | 83 | 92 | 94 |
| $C_{33\ ppm\ (mole\ catalyst\ loading)}$ [%] | 21 | 9 | 63 | 60 | 79 |

10. Screening of Compounds Bearing a 2,3,5,6-Tetraphenylphenoxy Moiety as Ligand $R^4$ in HCM of Methyl Decenoate (DAME) Using a Physically Pretreated Substrate According to Scheme 5

Scheme 5

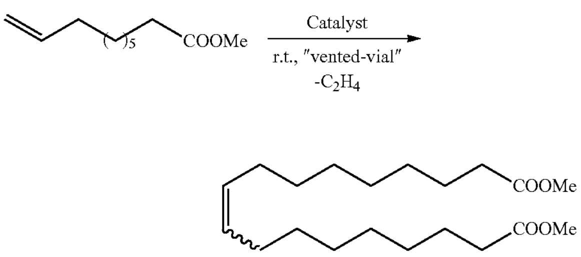

The substrate was purified by a physical treatment method, i.e. percolation on activated alumina layer. The reaction was characterized by the conversion data. Data are summarized in Table 18.

TABLE 18

| Compound | 10 | 11 | 32 | 154 | 123 | 124 |
|---|---|---|---|---|---|---|
| $C_{50\ ppm\ (mole\ catalyst\ loading)}$ [%] | not tested | 94 | 75 | 60 | 90 | 80 |
| $C_{33\ ppm\ (mole\ catalyst\ loading)}$ [%] | 79 | 80 | 77 | not tested | 68 | 67 |

Compounds 10, 11 and 32 are Mo-complexes, whereas compounds 154, 123 and 124 are W-complexes. Compounds 10 and 154 are known, compounds 11, 32, 123 and 124 are novel.

Compound 10 has a 2,3,5,6-tetraphenlyphenoxy compound as ligand $R^4$, whereas compound 11 is the respective 4-bromo-2,3,5,6-tetraphenylphenoxy compound and compound 32 is the 4-bromo-2,6-di(4-bromophenyl)-3,5-diphenylphenoxy analogue. $R^1$ in each case is 2,6-diisopropylphenyl.

Compound 154 bears a 2,3,5,6-tetraphenylphenoxy residue as ligand $R^4$, whereas compound 123 is the respective 4-bromo-2,3,5,6-tetraphenylphenoxy compound and compound 124 the 4-bromo-2,6-di(4-bromophenyl)-3,5-diphenylphenoxy analogue. $R^1$ in each case is 2,6-dichlorophenyl.

The new catalysts exhibit excellent activity.

The invention claimed is:

1. A composition, comprising:

a compound of Formula (A):

Formula (A)

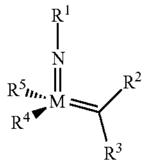

wherein

M=Mo or W;

$R^1$ is aryl, heteroaryl, alkyl, or heteroalkyl; optionally substituted;

$R^2$ and $R^3$ can be the same or different and are hydrogen, alkyl, alkenyl, heteroalkyl, heteroalkenyl, aryl, or heteroaryl; optionally substituted;

$R^5$ is optionally substituted pyrrol-1-yl; and $R^4$ is a residue $R^6$—X—, wherein X═O and $R^6$ is aryl, optionally substituted;

wherein $R^6$ is a phenyl ring which is at least substituted in 4-position with respect to O, wherein $R^6$ is substituted in 2- and 4-position with respect to O; or $R^6$ is substituted in 3- and 4-position; or $R^6$ is substituted in 2-, 3- and 4-position; or $R^6$ is substituted in 2-, 5- and 4-position; or $R^6$ is substituted in 3-, 5- and 4-position; or $R^6$ is substituted in 2-, 6- and 4-position; or $R^6$ is substituted in 2-, 3-, 5- and 4-position; or $R^6$ is substituted in 2-, 3-, 5-, 6- and 4-position;

and a first and a second olefin or a first or a second olefin, which are comprised in a feedstock.

2. The composition of claim 1, wherein in the compound of Formula (A)

$R^1$ is aryl or adamant-1-yl; optionally substituted;

$R^2$ is —$C(CH_3)_2C_6H_5$ or —$C(CH_3)_3$;

$R^3$ is H;

$R^4$ is a residue $R^6$—X—, wherein

X═O and $R^6$ is phenyl substituted with up to five substituents independently selected from alkyl, preferably $C_1$-$C_4$ alkyl, such as methyl, isopropyl or t-butyl, alkoxy, preferably $C_1$-$C_4$ alkoxy, phenoxy, phenyl, halogen, optionally substituted.

3. The composition of claim 1, wherein in the compound of Formula (A)

$R^1$ is selected from 1-(2,6-dimethylphenyl), 1-(2,6-diisopropylphenyl), 1-(2,6-di-t-butylphenyl), 1-(2,6-dichlorophenyl), adamant-1-yl;

$R^2$ is —$C(CH_3)_2C_6H_5$ or —$C(CH_3)_3$;

$R^3$ is H;

$R^5$ is selected from pyrrol-1-yl; 2,5-dimethyl-pyrrol-1-yl; and $R^4$ is $R^6$—X—, wherein X═O and $R^6$ is phenyl substituted with up to five substituents independently selected from alkyl, preferably $C_1$-$C_4$ alkyl such as methyl, isopropyl or t-butyl, alkoxy, preferably $C_1$-$C_4$ alkoxy, phenoxy, phenyl, halogen, optionally substituted.

4. The composition of claim 1, wherein in the compound of Formula (A)

$R^1$ is selected from 2,6-dimethylphenyl, 2,6-diisopropylphenyl, 2,6-dichlorophenyl, adamant-1-yl;

$R^2$ is —$C(CH_3)_2C_6H_5$ or —$C(CH_3)_3$;

$R^3$ is H;

$R^5$ is selected from pyrrol-1-yl; 2,5-dimethyl-pyrrol-1-yl; and $R^4$ is $R^6$—X—, wherein X═O and $R^6$ is phenyl which bears at least three substituents, from which two substituents are in ortho position with respect to O and one substituent is in para position with respect to O.

5. The composition of claim 4, wherein $R^4$ is selected from 4-bromo-2,6-diphenylphenoxy, 4-fluoro-2,6-diphenylphenoxy, 4-methyl-2,6-diphenylphenoxy, 4-methoxy-2,6-diphenylphenoxy, 4-dimethylamino-2,6-diphenylphenoxy, 2,4,6-triphenylphenoxy, 4-fluoro-2,6-dimesitylphenoxy, 4-bromo-2,6-di-tert.-butylphenoxy, 4-methoxy-2,6-di-tert.-butylphenoxy, 4-methyl-2,6-di-tert.-butylphenoxy, 2,4,6-tri-tert.-butylphenoxy, 4-bromo-2,3,5,6-tetraphenylphenoxy; 4-bromo-2,6-di(4-bromophenyl)-3,5-diphenylphenoxy.

6. The composition of claim 1, wherein the compound is selected from the following structures:

3

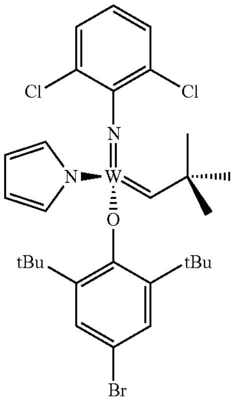

4

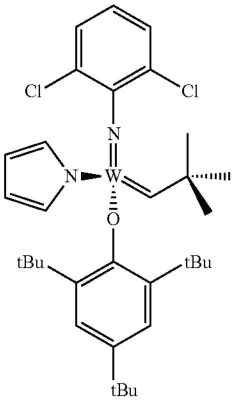

-continued

5

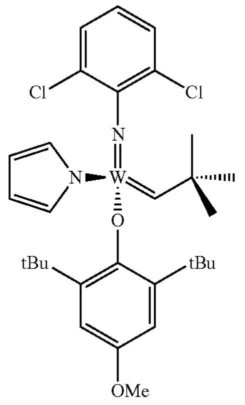

7

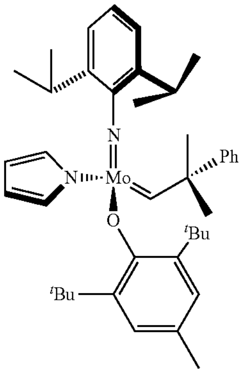

11

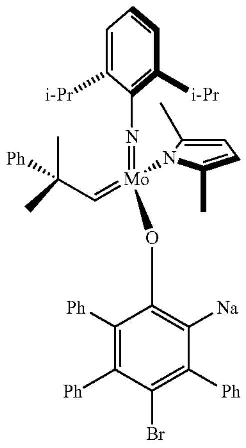

-continued
13
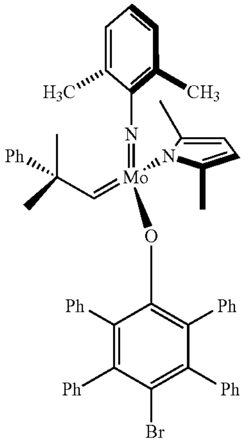
14
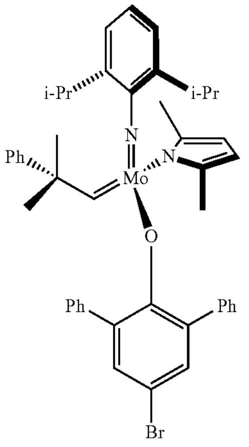
15
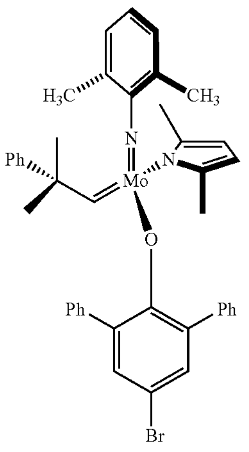
-continued
16
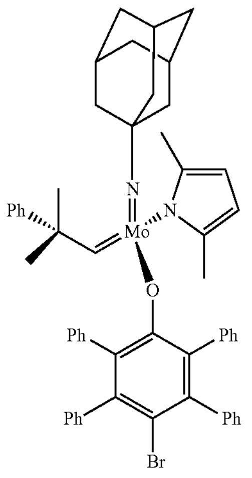
17
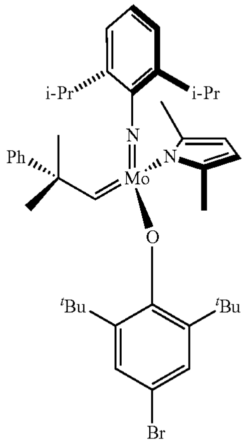
18
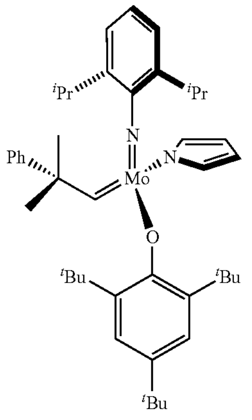

-continued
19
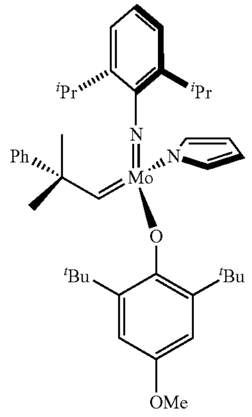
32
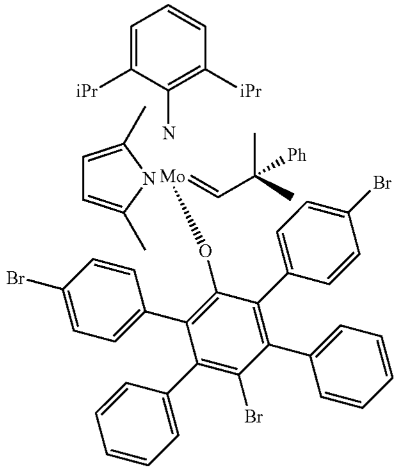
33
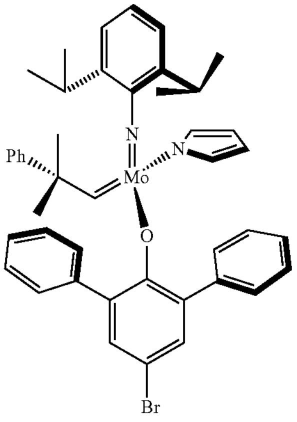
-continued
34
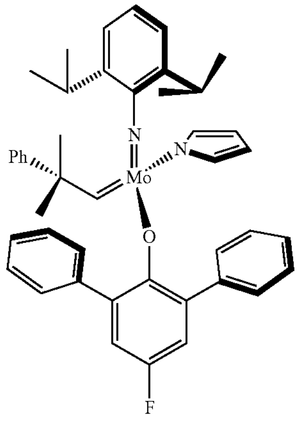
35
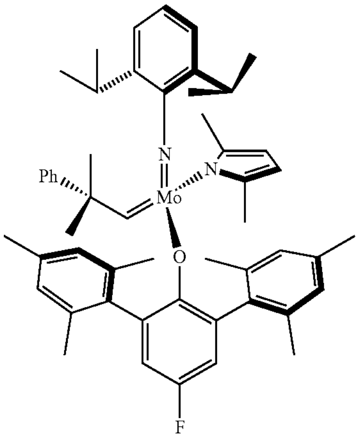
36
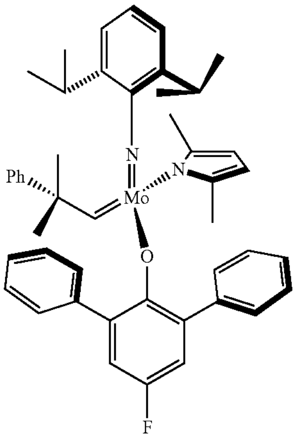

37
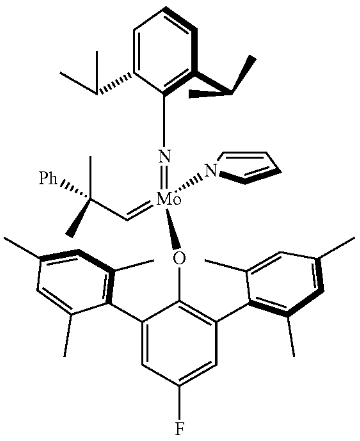
41
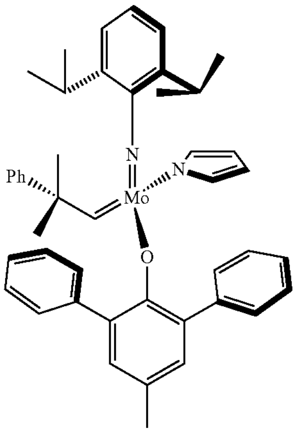
42
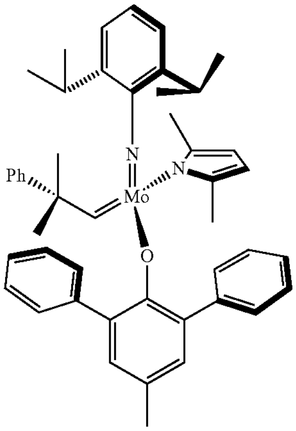
43
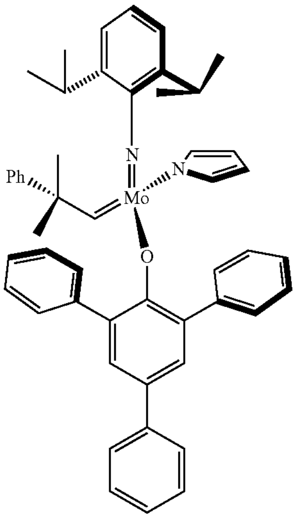
44
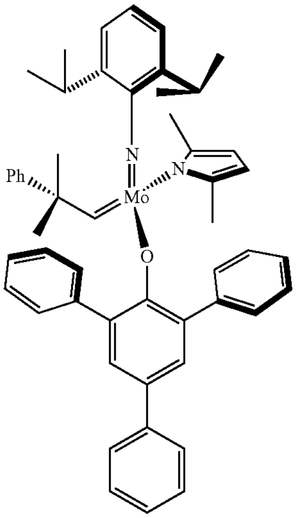
60
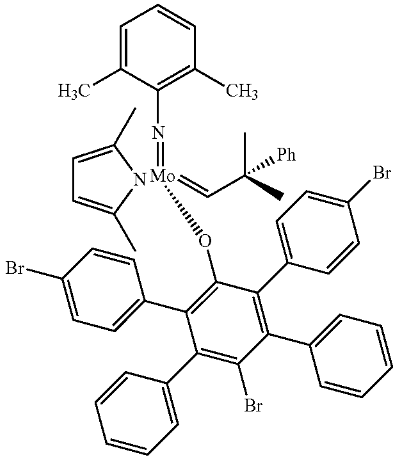

-continued
63
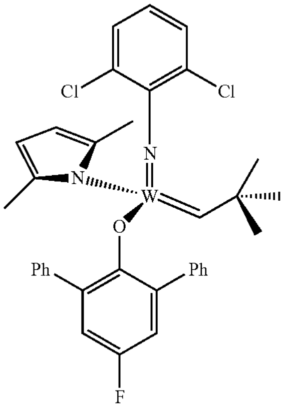
64
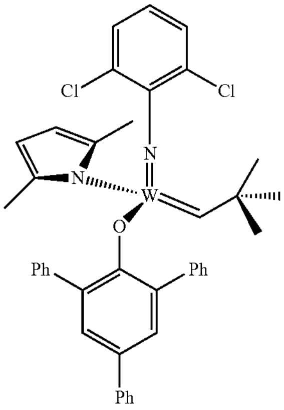
65
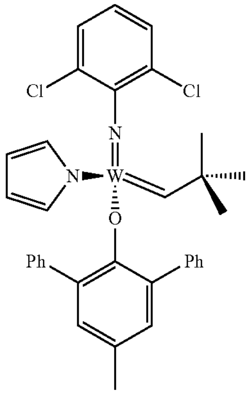
66
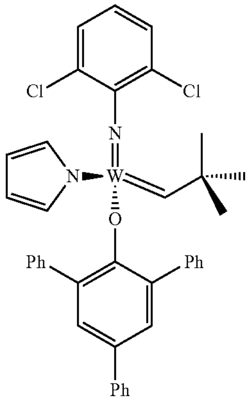
-continued
67
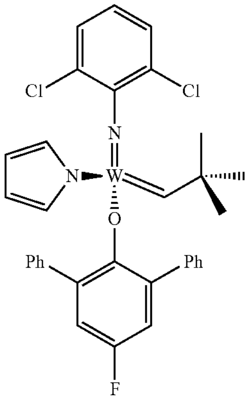
68
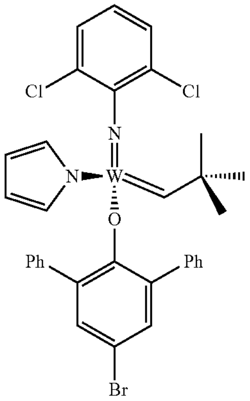
69
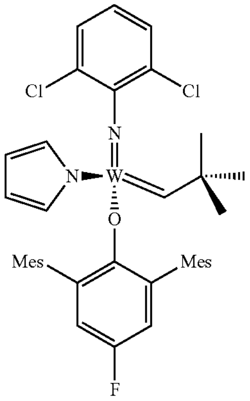
70
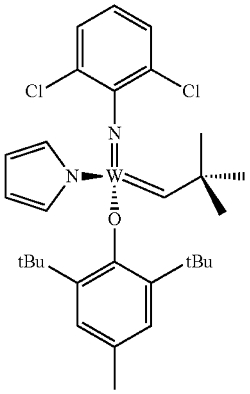

-continued
75
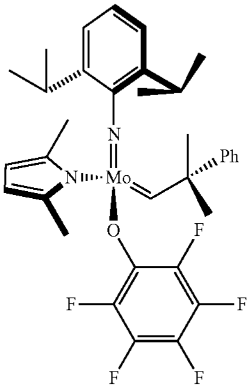
99
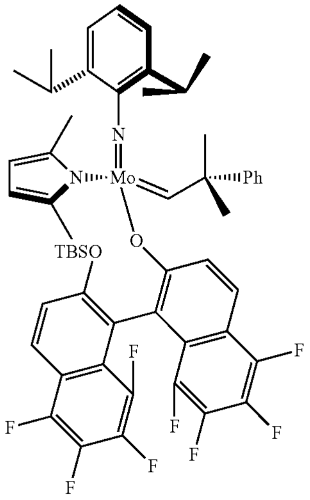
100
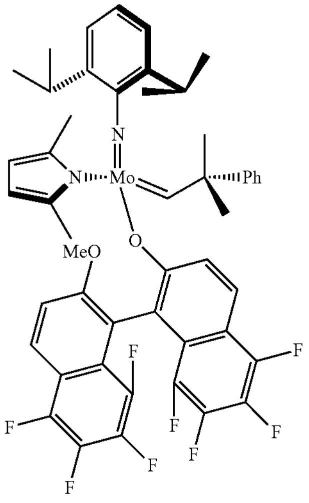
120
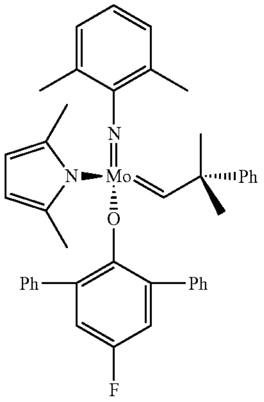
121
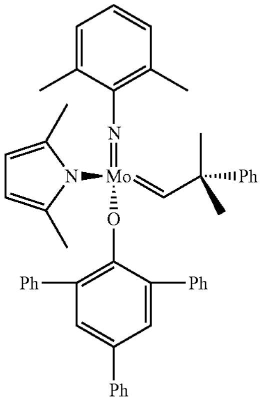
122
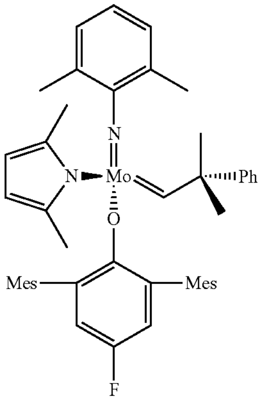
123
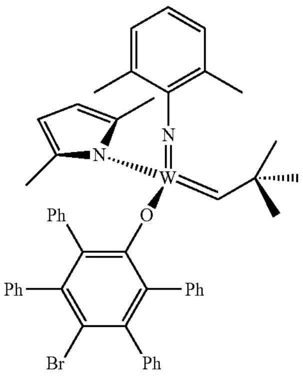

-continued
124
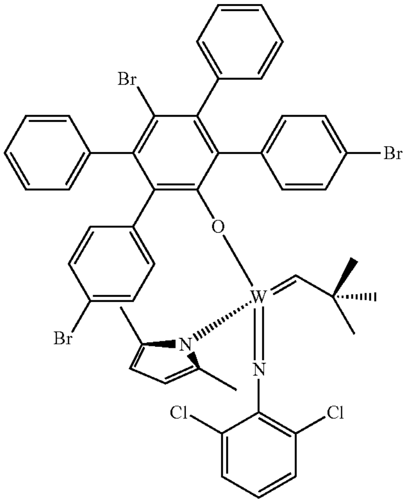
125
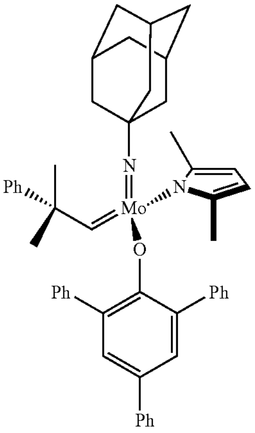
126
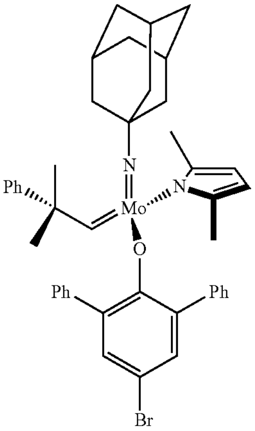
-continued
127
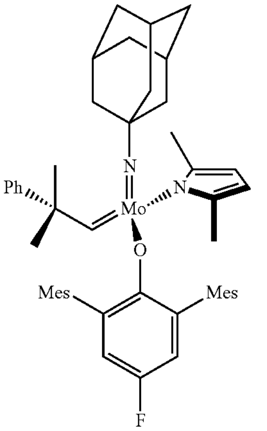
130
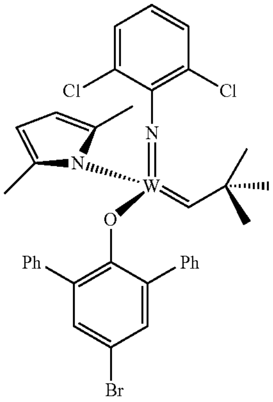
131
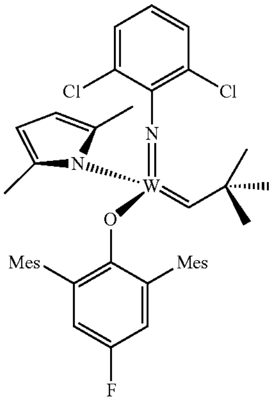
132
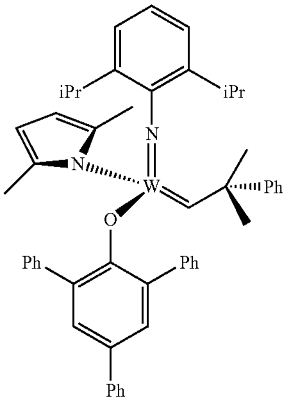

-continued
133
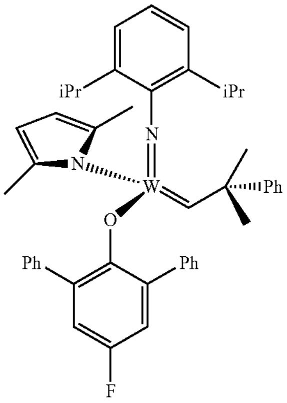
134
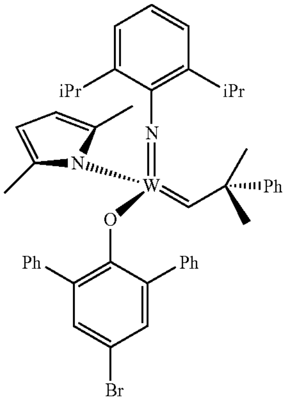
135
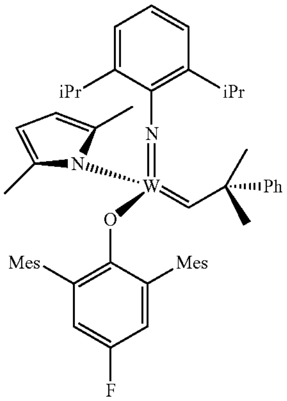
136
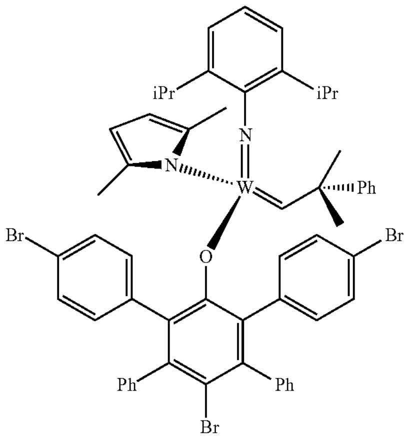
-continued
139
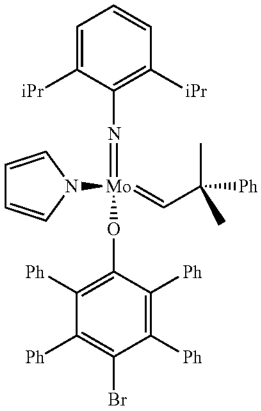
140
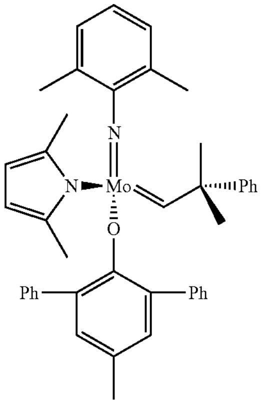
141
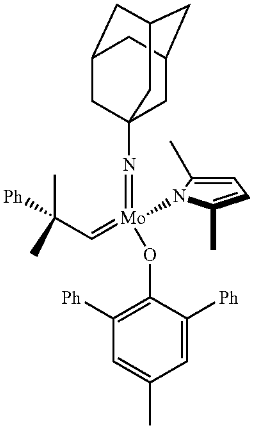
142
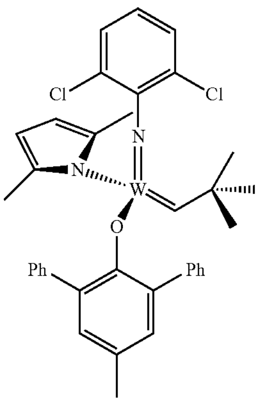

-continued
145
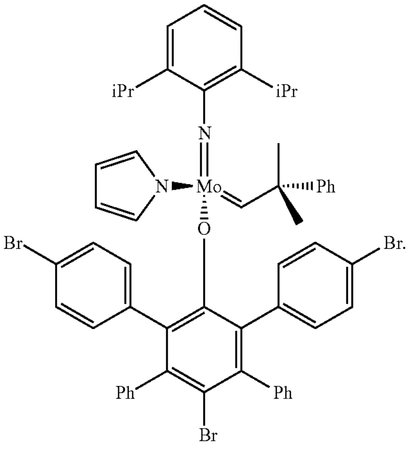
146
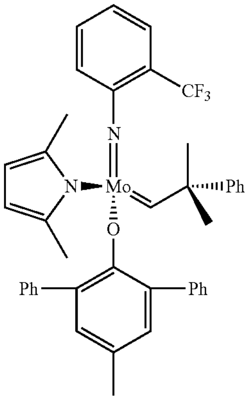
149
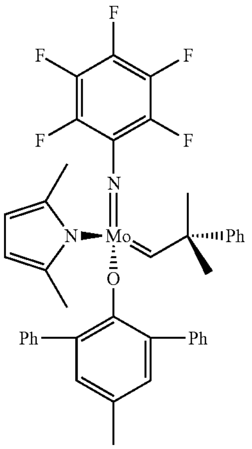
-continued
150
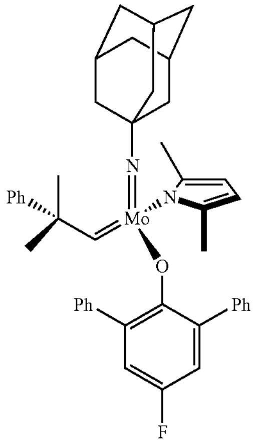
155
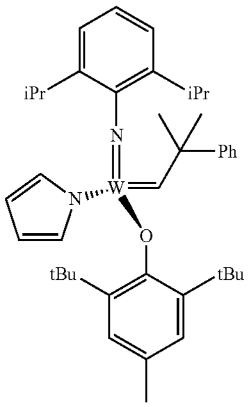
156
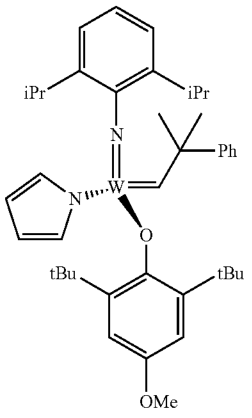

-continued
157
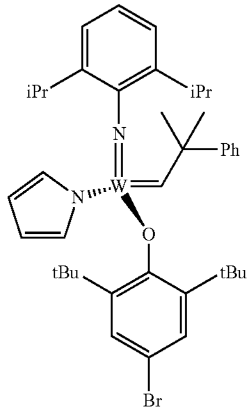
158
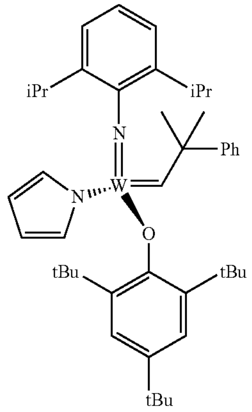
159
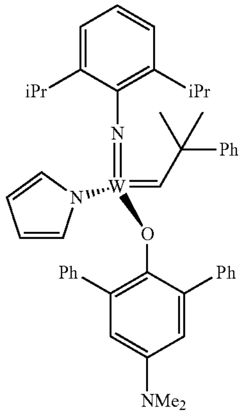
160
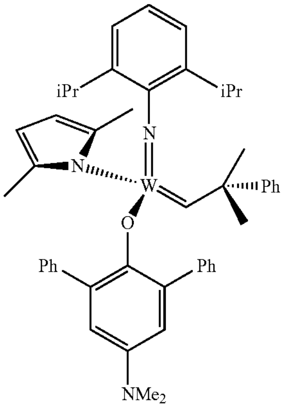
-continued
161
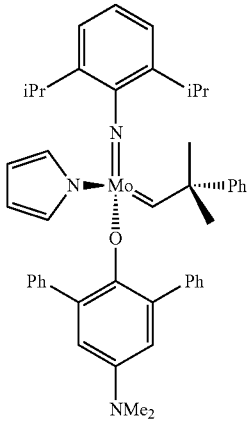
162
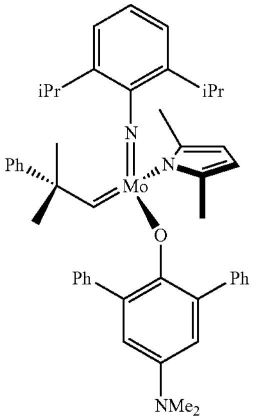
163
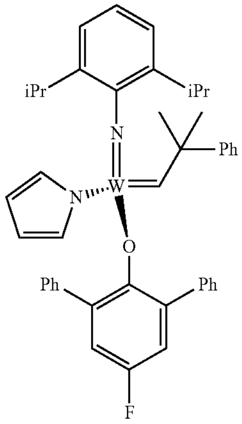

-continued
164
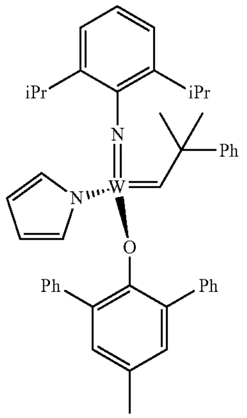
165
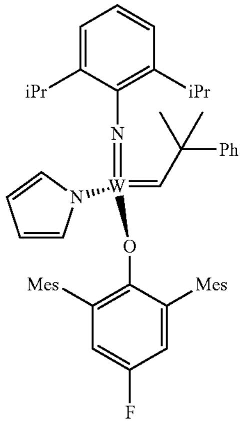
166
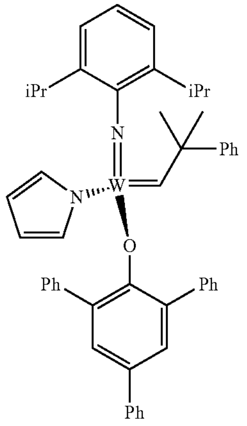
-continued
167
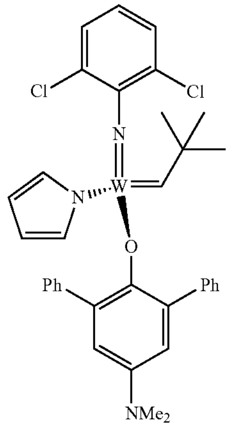
168
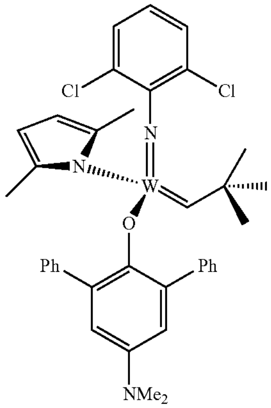
169
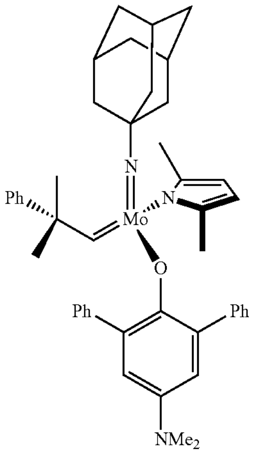

170
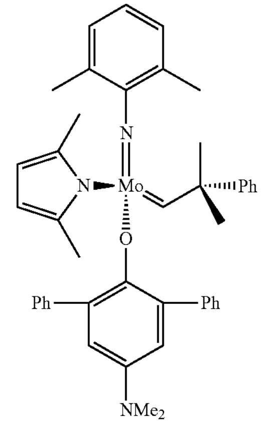
173
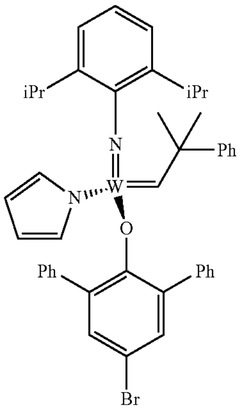
181
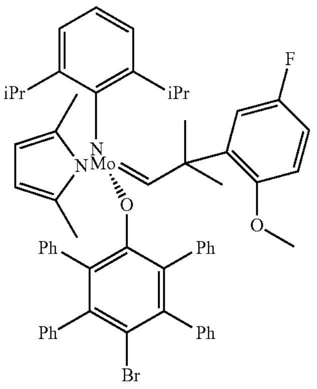
183
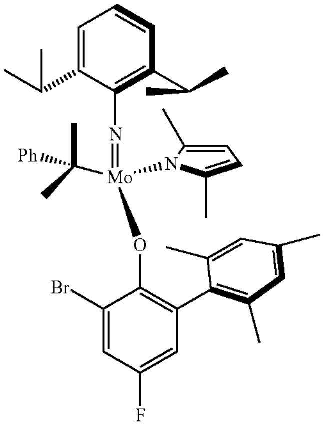
184
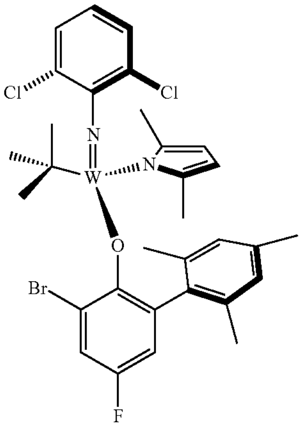
187
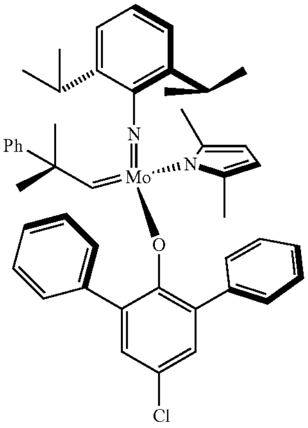

-continued
188
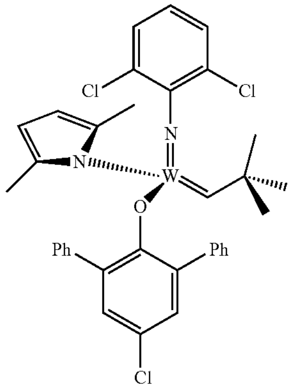
189
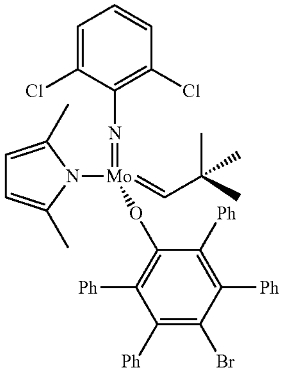
190
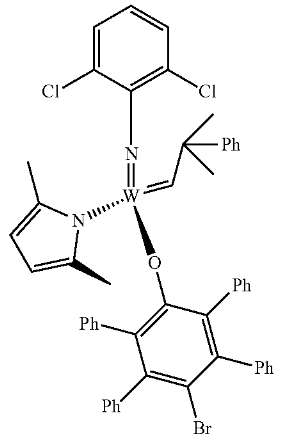
201
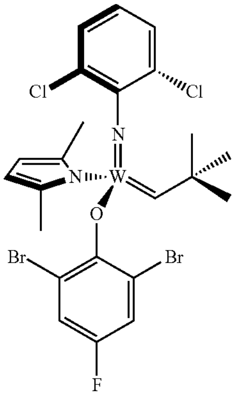
-continued
209
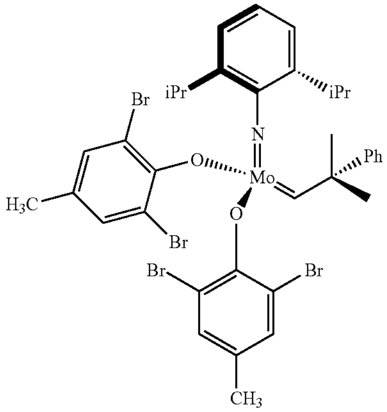
210
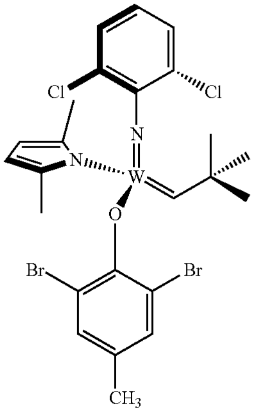
261
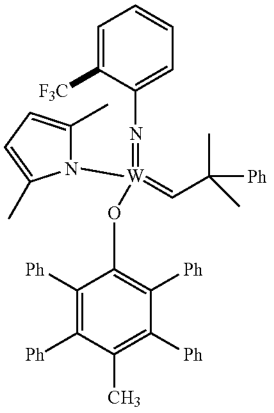
and -continued

263

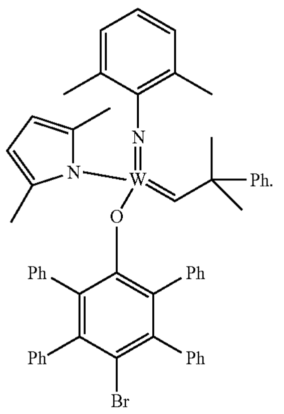

7. The composition of claim 1, wherein in the compound of Formula (A)

$R^1$ is selected from 2,6-dimethylphenyl, 2,6-diisopropylphenyl, 2,6-di-t-butylphenyl, 2,6-dichlorophenyl, adamant-1-yl;

$R^2$ is —$C(CH_3)_2C_6H_5$ or —$C(CH_3)_3$;

$R^3$ is H;

$R^5$ is selected from pyrrol-1-yl; 2,5-dimethyl-pyrrol-1-yl; and $R^4$ is $R^6$—X—, wherein X═O and $R^6$ is phenyl which bears two substituents in ortho position with respect to O and a substituent in para position with respect to O.

8. The composition of claim 7, wherein $R^1$ is selected from 2,6-dimethylphenyl, 2,6-diisopropylphenyl, 2,6-dichlorophenyl, adamant-1-yl;

$R^2$ is —$C(CH_3)_2C_6H_5$ or —$C(CH_3)_3$;

$R^3$ is H;

$R^4$ is selected from 4-bromo-2,6-diphenylphenoxy, 4-fluoro-2,6-diphenylphenoxy, 4-methyl-2,6-diphenylphenoxy, 4-methoxy-2,6-diphenylphenoxy, 4-dimethylaminophenyl-2,6-diphenylphenoxy; 2,4,6-triphenylphenoxy, 4-fluoro-2,6-dimesitylphenoxy, 4-bromo-2,6-di-tert.-butylphenoxy, 4-methoxy-2,6-di-tert.-butylphenoxy, 4-methyl-2,6-di-tert.-butylphenoxy, 2,4,6-tri-tert.-butylphenoxy, 4-bromo-2,3,5,6-tetraphenylphenoxy; 4-bromo-2,6-di(4-bromophenyl)-3,5-diphenylphenoxy.

9. The composition of claim 1, wherein the substituent of residue $R^6$ in 4-position is selected from the group consisting of: halogen, dialkylamino, cyano, optionally substituted alkyl, optionally substituted alkyloxy, optionally substituted aryl, optionally substituted aryloxy; or wherein the further substituents of residue $R^6$ may be the same or may be different from the substituent in 4-position and may be independently selected from the group consisting of: halogen, dialkylamino, cyano, optionally substituted alkyl, optionally substituted alkyloxy, optionally substituted aryl, optionally substituted aryloxy; or wherein $R^1$ is phenyl or alkyl, optionally independently substituted with halogen, $C_{1-4}$ dialkylamino, $C_{1-4}$ alkyl, $C_{1-4}$ alkyloxy, phenyl, optionally substituted, phenyloxy, optionally substituted;

$R^2$ and $R^3$ can be the same or different and are hydrogen, $C(CH_3)_3$, or $C(CH_3)_2C_6H_5$;

$R^5$ is selected from pyrrol-1-yl; 2,5-dimethyl-pyrrol-1-yl;

the substituent of residue $R^6$ in 4-position is selected from the group consisting of: halogen, $C_{1-4}$ dialkylamino, $C_{1-4}$ alkyl, optionally substituted, $C_{1-4}$ alkyloxy, optionally substituted, phenyl, optionally substituted, phenyloxy, optionally substituted;

and the further substituents of residue $R^6$ may be the same or may be different from the substituent in 4-position and may be independently selected from the group consisting of halogen, $C_{1-4}$ dialkylamino, $C_{1-4}$ alkyl, optionally substituted, $C_{1-4}$ alkyloxy, optionally substituted, phenyl, optionally substituted, phenyloxy, optionally substituted; or wherein $R^6$ is a phenyl ring which is substituted in 2- and 4-position independently with halogen and in 6-position with phenyl, which optionally may be substituted with halogen, alkyl, alkyloxy, phenyl, phenoxy; or phenyl or phenoxy optionally substituted with halogen, alkyl, alkyloxy, phenyl, phenoxy, respectively; or wherein $R^6$ is a phenyl ring which is substituted in 2- and 6-position by substituents via carbon atoms, and in 4-position by a substituent via any atom; or wherein $R^6$ is a phenyl ring which is substituted in 4-position with bromine and in 2-, 3-, 5- and 6-position with phenyl, respectively, wherein said phenyl residues may be independently substituted with fluoro, chloro, bromo, dimethylamino, diethylamino, methyl, ethyl, propyl, isopropyl, butyl, t-butyl, methoxy, ethoxy, propyloxy, butyloxy, t-butyloxy, trifluoromethyl, phenyl optionally substituted with halogen, alkyl, alkyloxy, phenyl, phenoxy; phenoxy optionally substituted with halogen, alkyl, alkyloxy, phenyl, phenoxy.

10. A composition comprising a compound of Formula (A)

Formula (A)

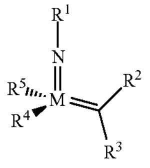

wherein

M=Mo or W;

$R^1$ is aryl, heteroaryl, alkyl, or heteroalkyl; optionally substituted;

$R^2$ and $R^3$ can be the same or different and are hydrogen, alkyl, alkenyl, heteroalkyl, heteroalkenyl, aryl, or heteroaryl; optionally substituted;

$R^5$ is optionally substituted pyrrol-1-yl;

$R^4$ is [8-(naphthalene-1-yl)-naphthalene-1-yl]oxy, optionally substituted; or $R^4$ is (8-phenylnaphthalene-1-yl)oxy, optionally substituted.

11. The composition of claim 10, wherein in the compound of Formula (A)

$R^1$ is aryl or adamant-1-yl; optionally substituted;

$R^2$ is —$C(CH_3)_2C_6H_5$ or —$C(CH_3)_3$; and $R^3$ is H.

12. The composition of claim 10, wherein in the compound of Formula (A)

$R^1$ is selected from 1-(2,6-dimethylphenyl), 1-(2,6-diisopropylphenyl), 1-(2,6-di-t-butylphenyl), 1-(2,6-dichlorophenyl), adamant-1-yl;

$R^2$ is —$C(CH_3)_2C_6H_5$ or —$C(CH_3)_3$;

$R^3$ is H; and $R^5$ is selected from pyrrol-1-yl; 2,5-dimethyl-pyrrol-1-yl.

13. The composition of claim 10, wherein in the compound is selected from the following structures:
192
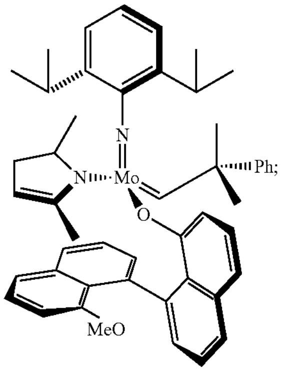
196
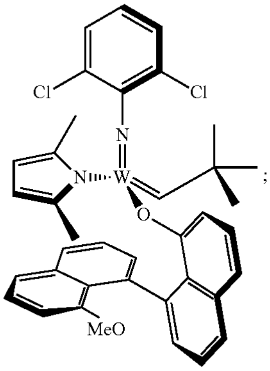
214
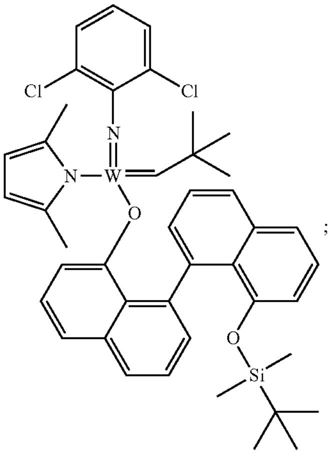
-continued
216
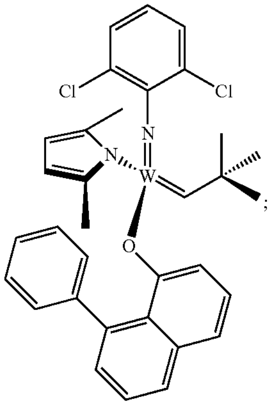
217
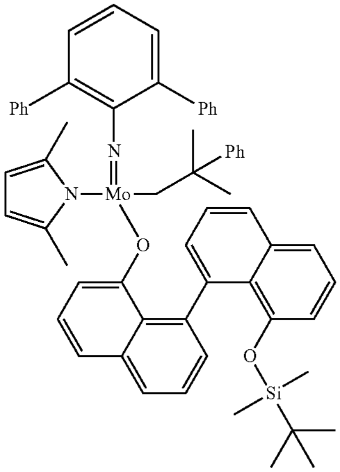
218
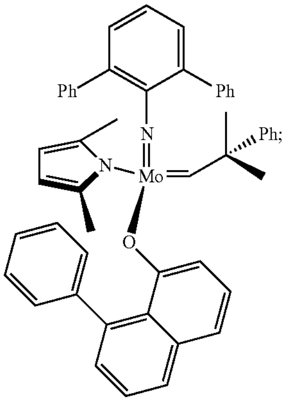

-continued

220

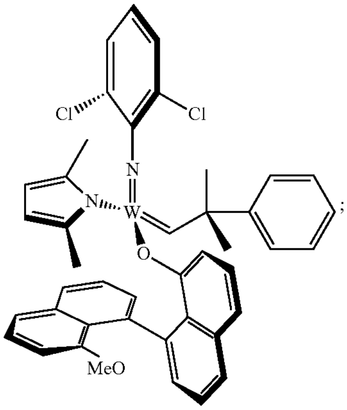
;

246

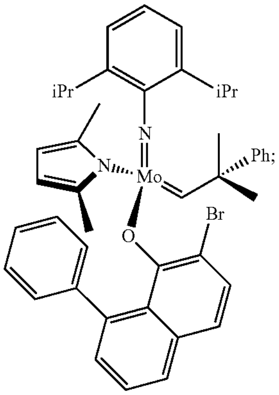

269

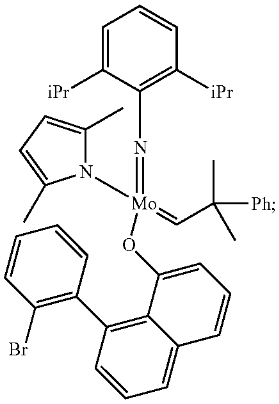
and

288

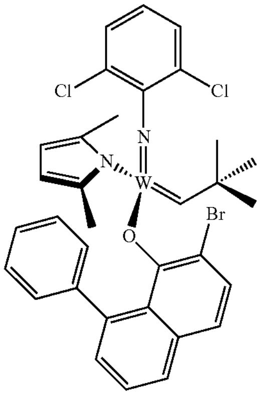
.

14. A compound of Formula (A):

Formula (A)

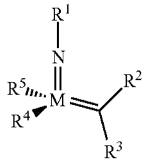

wherein

M=Mo or W;

$R^1$ is aryl, heteroaryl, alkyl, or heteroalkyl; optionally substituted;

$R^2$ and $R^3$ can be the same or different and are hydrogen, alkyl, alkenyl, heteroalkyl, heteroalkenyl, aryl, or heteroaryl; optionally substituted;

$R^5$ is optionally substituted pyrrol-1-yl; and $R^4$ is a residue $R^6$—X—, wherein X═O and $R^6$ is aryl, optionally substituted;

wherein $R^6$ is a phenyl ring which is at least substituted in 4-position with respect to O, $R^6$ is substituted in 2- and 4-position with respect to O; or $R^6$ is substituted in 3- and 4-position; or $R^6$ is substituted in 2-, 3- and 4-position; or $R^6$ is substituted in 2-, 5- and 4-position; or $R^6$ is substituted in 3-, 5- and 4-position; or $R^6$ is substituted in 2-, 6- and 4-position; or $R^6$ is substituted in 2-, 3-, 5- and 4-position; or $R^6$ is substituted in 2-, 3-, 5-, 6- and 4-position;

or wherein

M=Mo or W;

$R^1$ is aryl, heteroaryl, alkyl, or heteroalkyl; optionally substituted;

$R^2$ and $R^3$ can be the same or different and are hydrogen, alkyl, alkenyl, heteroalkyl, heteroalkenyl, aryl, or heteroaryl; optionally substituted;

$R^5$ is optionally substituted pyrrol-1-yl;

$R^4$ is [8-(naphthalene-1-yl)-naphthalene-1-yl]oxy, optionally substituted; or $R^4$ is (8-phenylnaphthalene-1-yl)oxy, optionally substituted.

15. The compound of claim 14, wherein the compound is selected from the following structures:

3

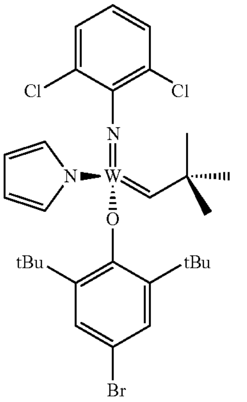

-continued
4
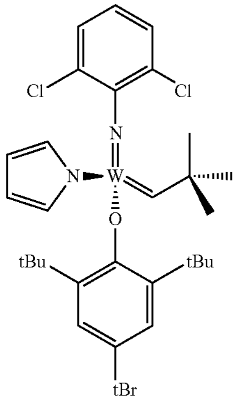
5
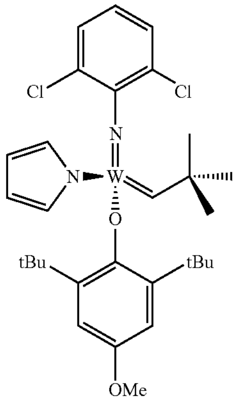
7
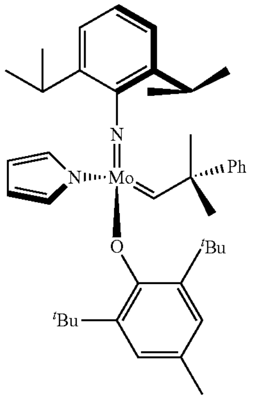
11
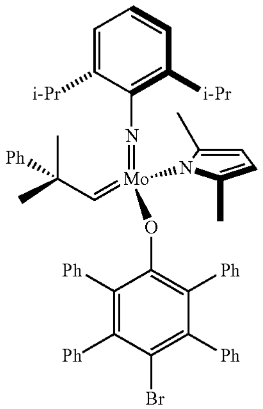
-continued
13
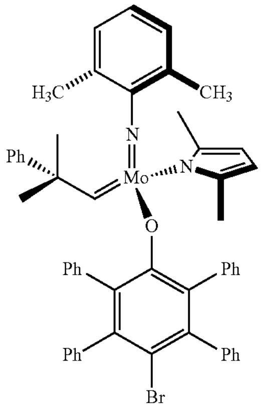
14
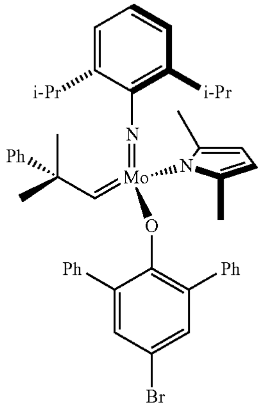
15
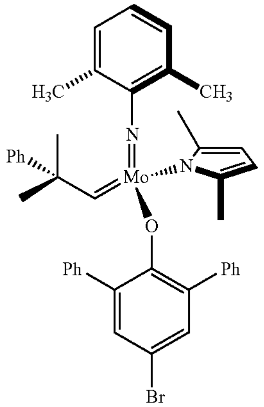

-continued
-continued
16
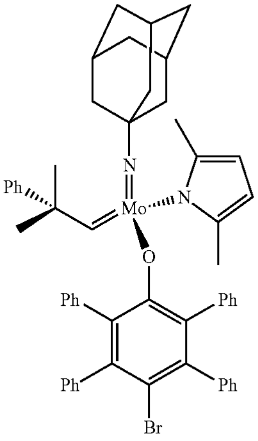
17
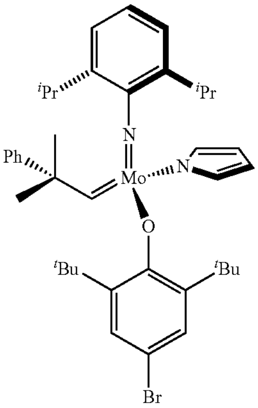
18
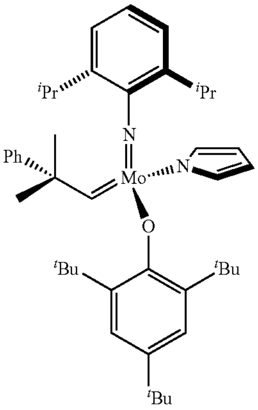
19
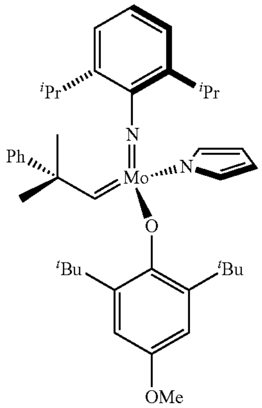
32
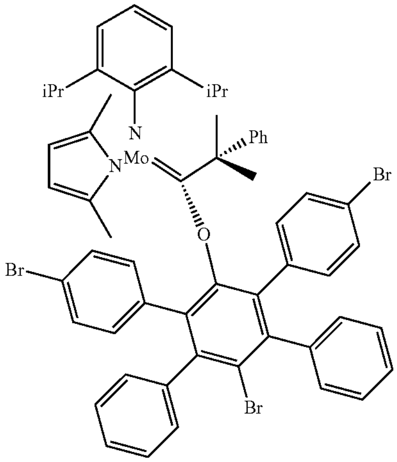
33
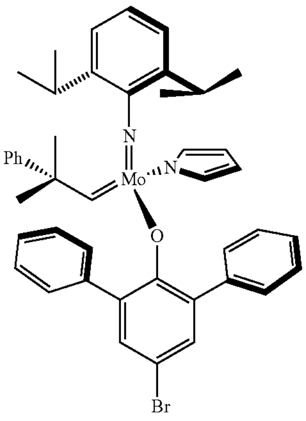

-continued
34
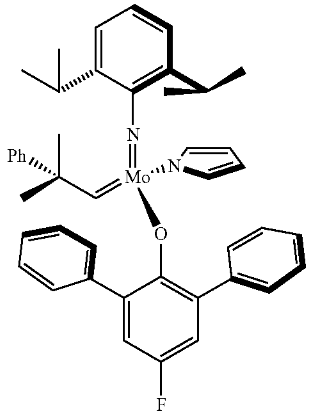
35
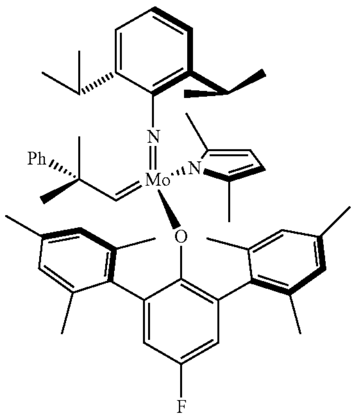
36
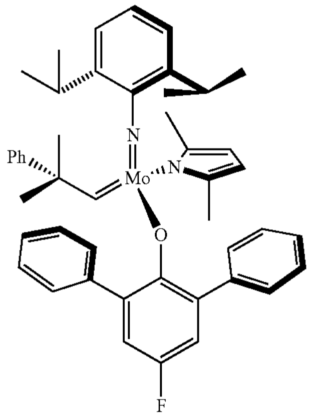
-continued
37
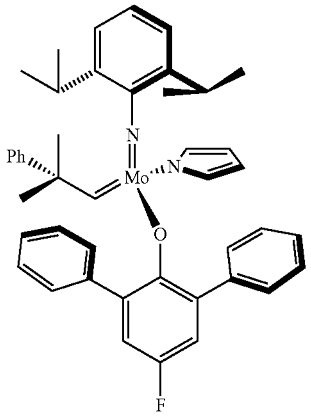
41
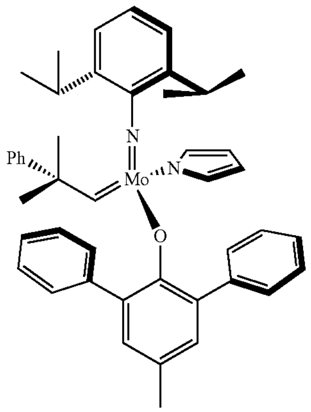
42
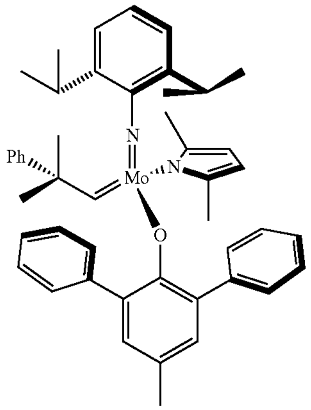

-continued
43
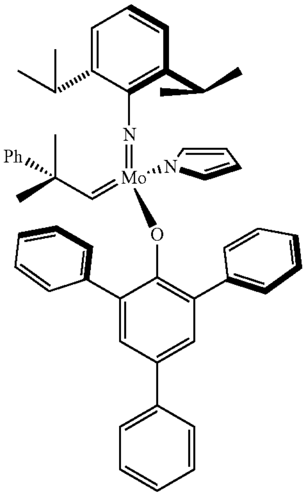
44
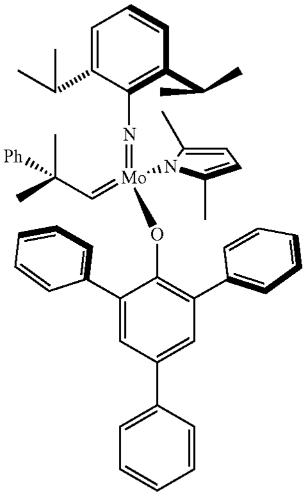
60
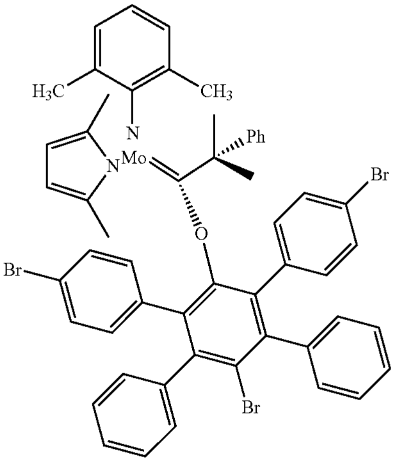
-continued
63
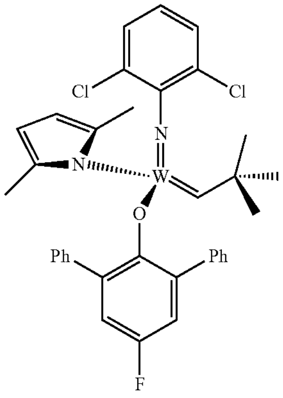
64
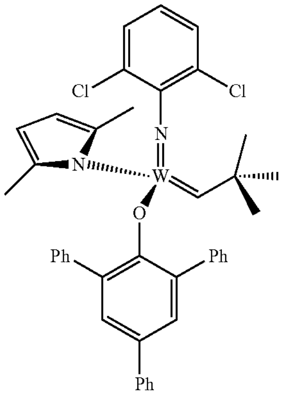
65
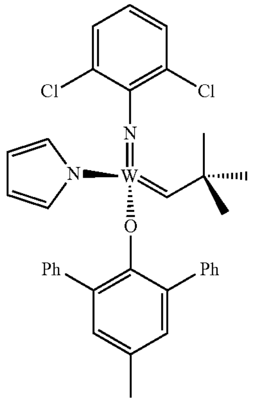
66
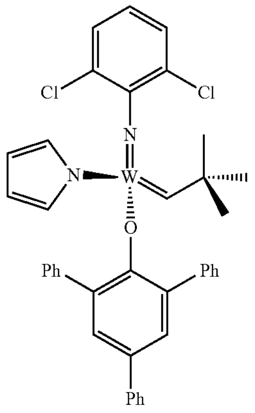

-continued
67
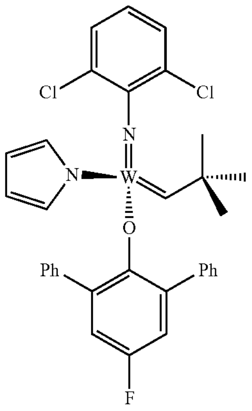
68
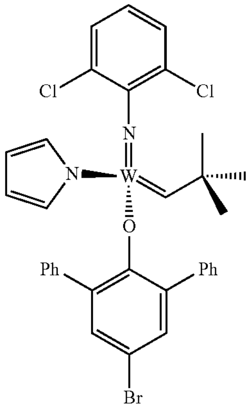
69
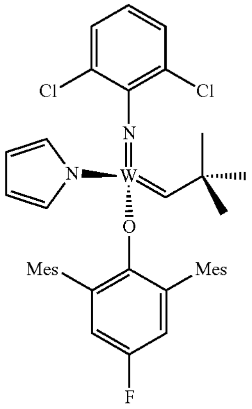
70
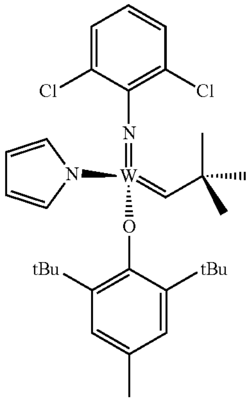
-continued
75
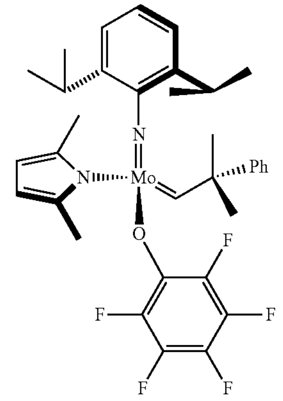
100
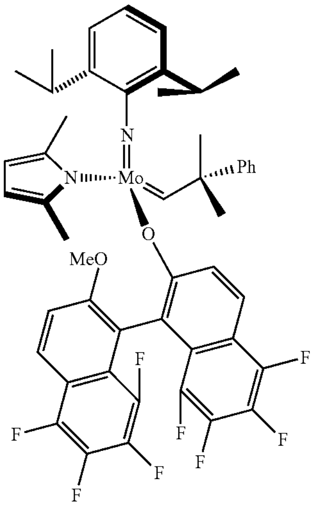
99
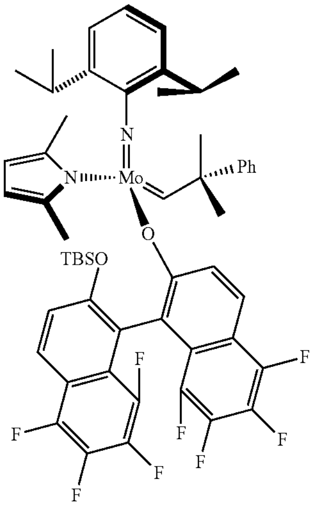

-continued
120
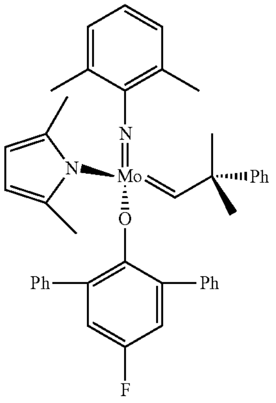
121
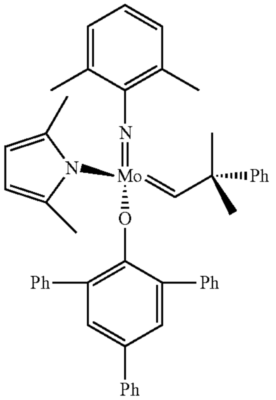
122
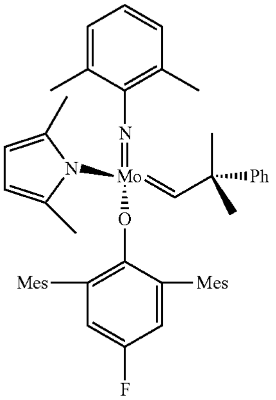
123
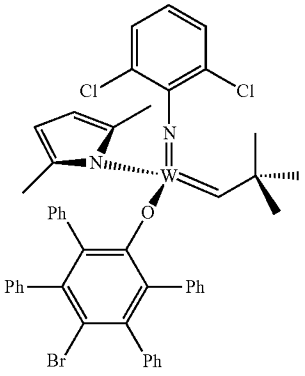
-continued
124
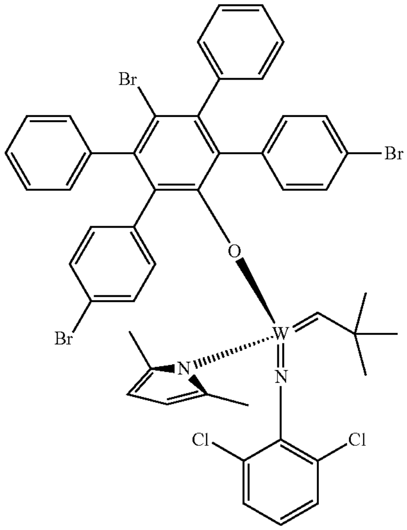
125
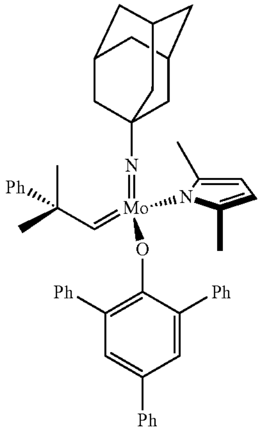
126
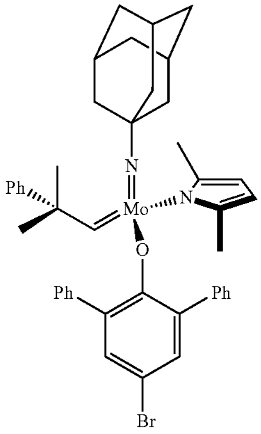

127
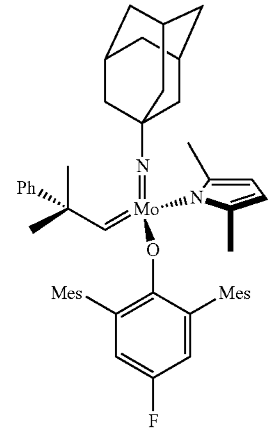
130
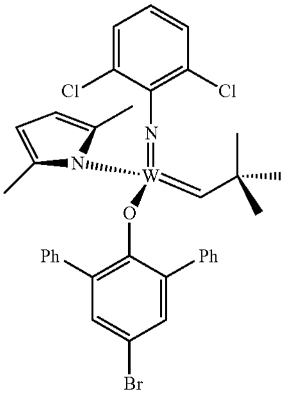
131
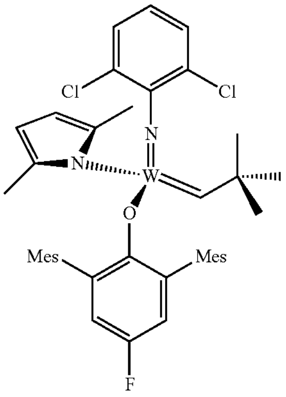
132
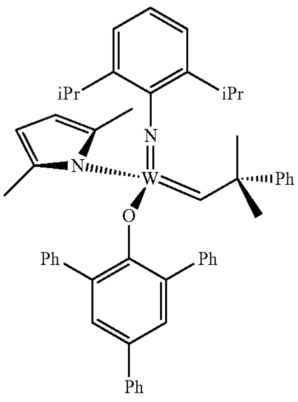
133
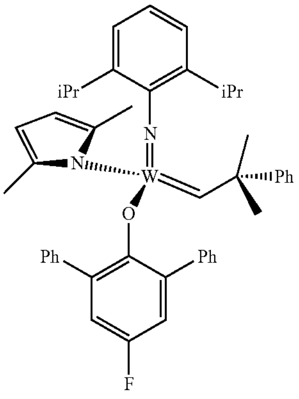
134
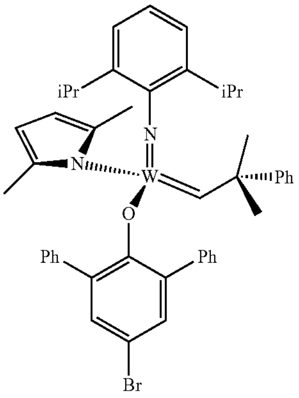
135
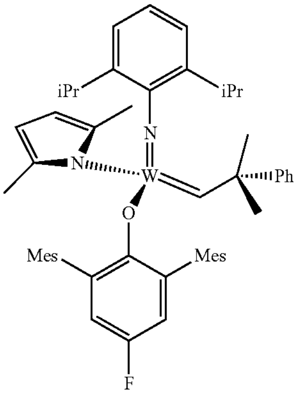
136
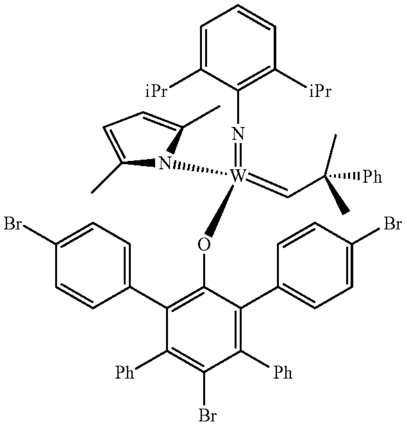

-continued
139
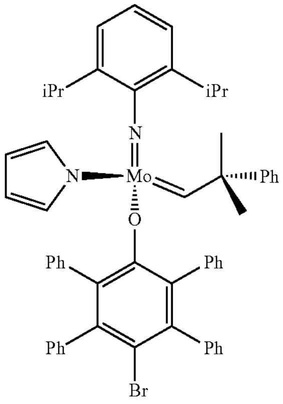
140
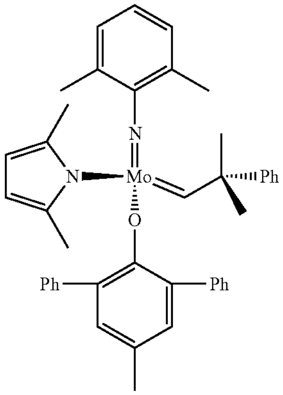
141
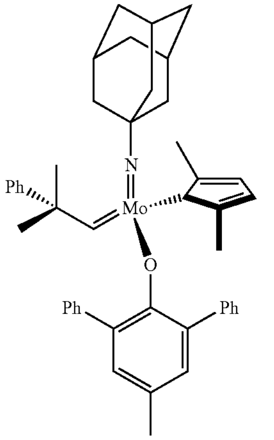
142
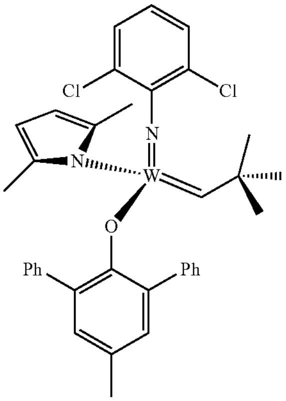
-continued
145
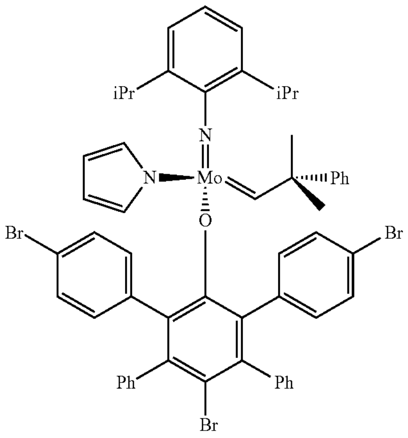
146
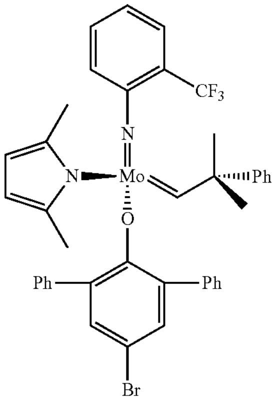
149
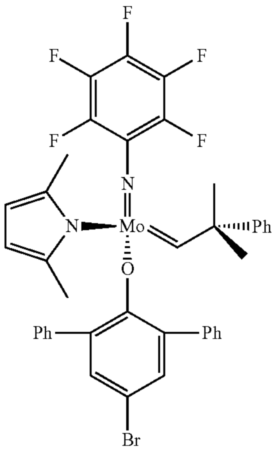

-continued
150
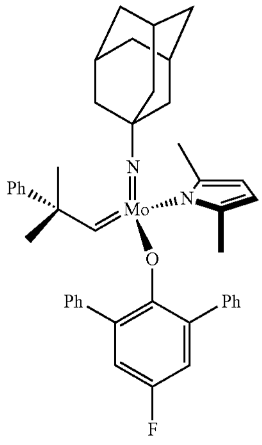
155
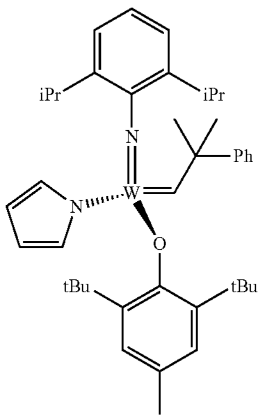
156
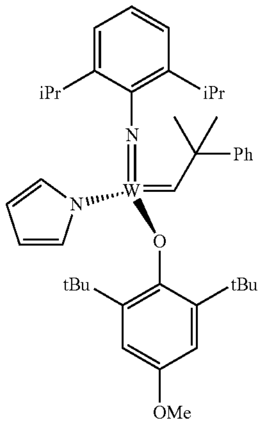
-continued
157
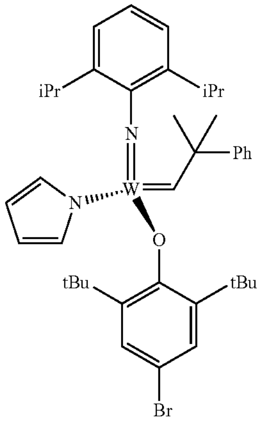
158
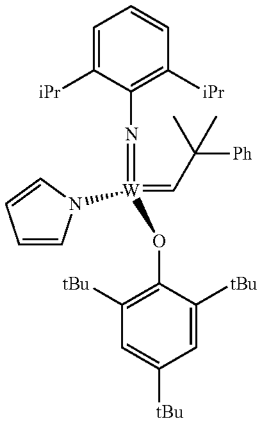
159
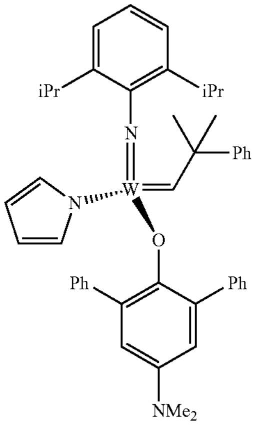

-continued
160
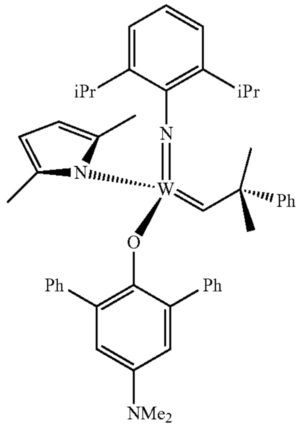
161
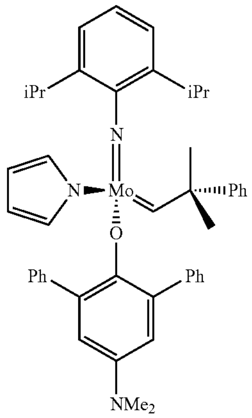
162
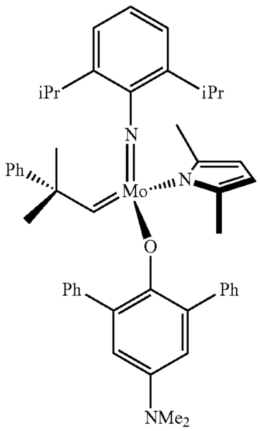
-continued
163
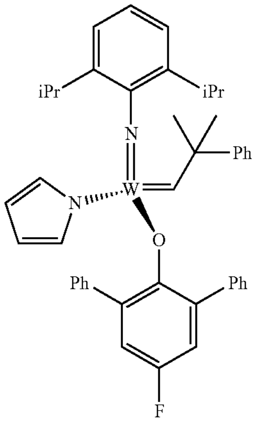
164
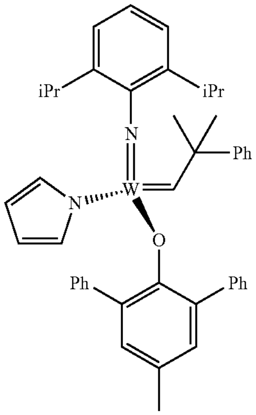
165
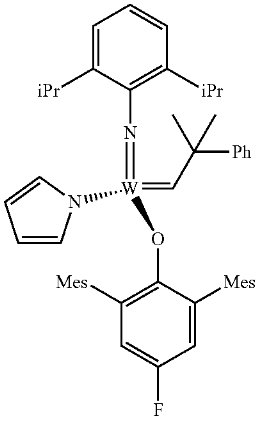

-continued
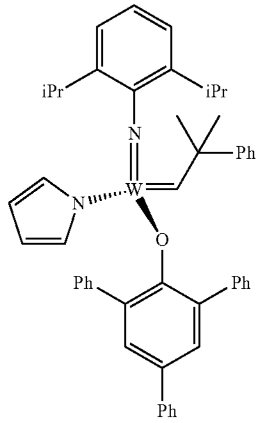
166
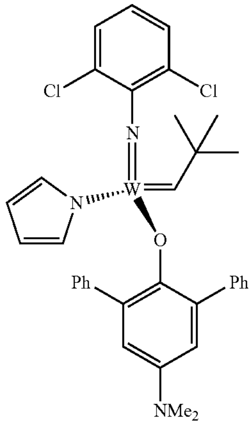
167
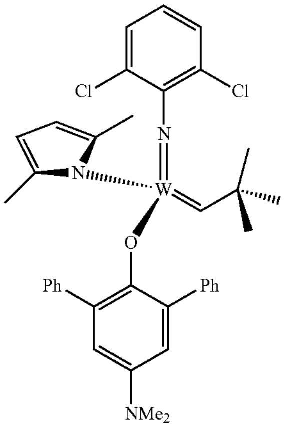
168
-continued
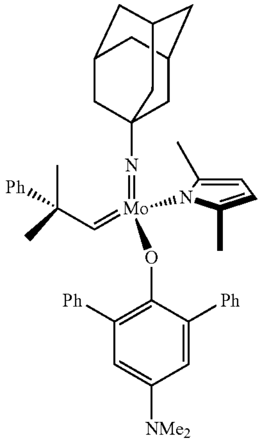
169
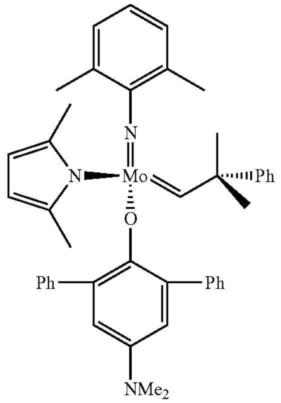
170
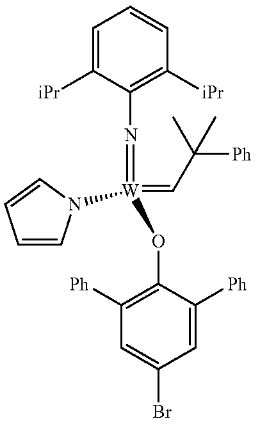
173

-continued
181
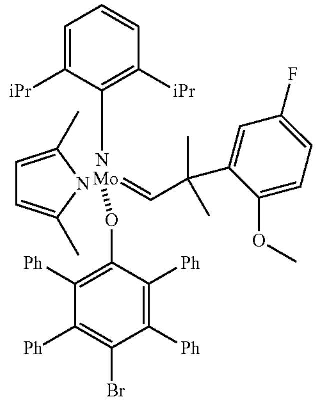
183
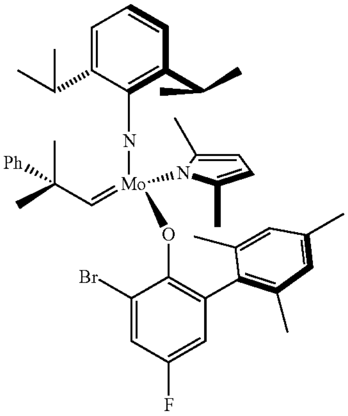
184
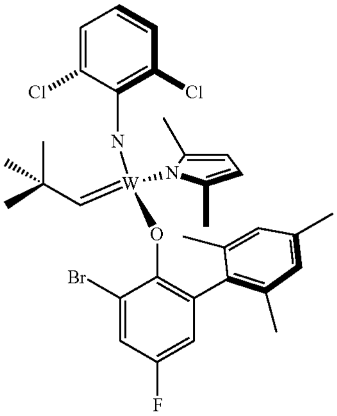
187
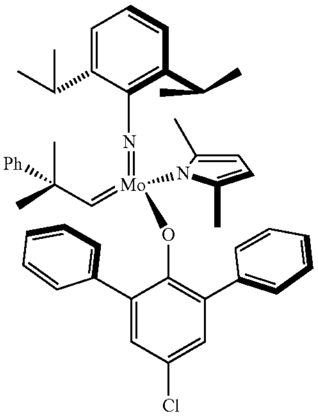
-continued
188
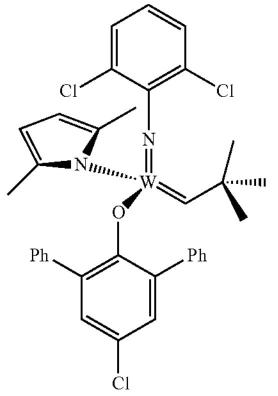
189
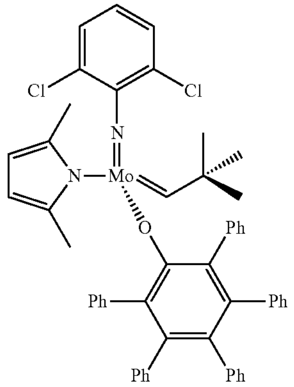
190
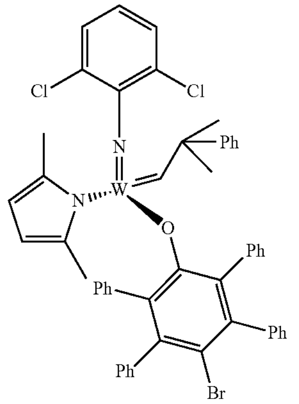
192
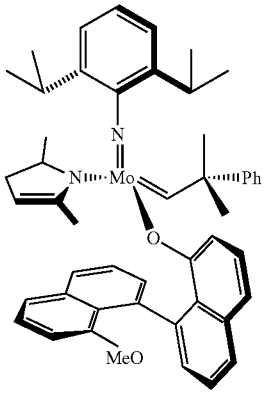

196
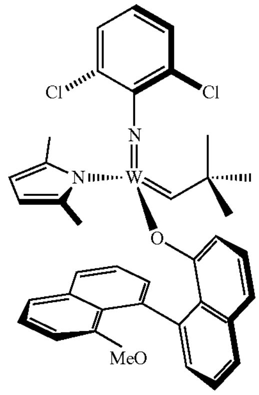
201
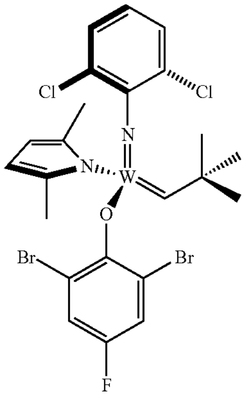
209
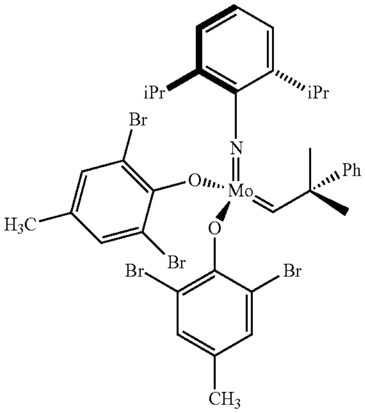
210
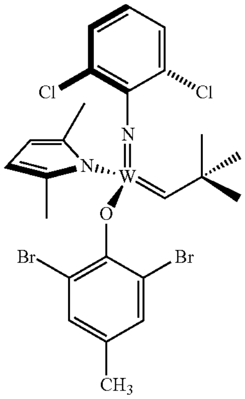
214
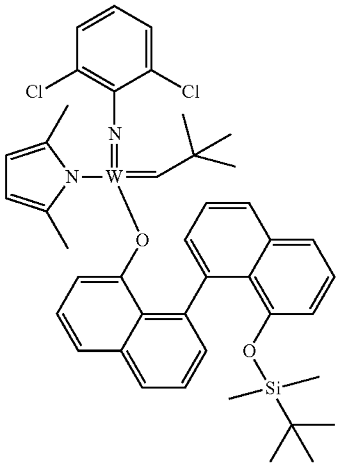
216
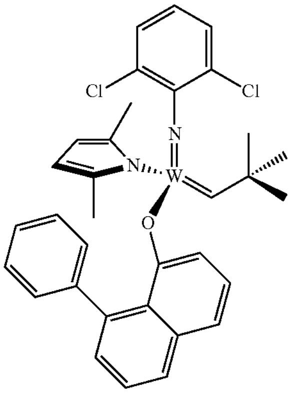
217
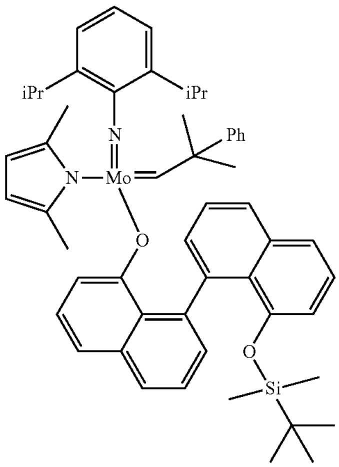

-continued
218
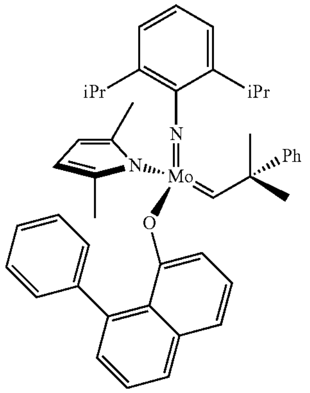
220
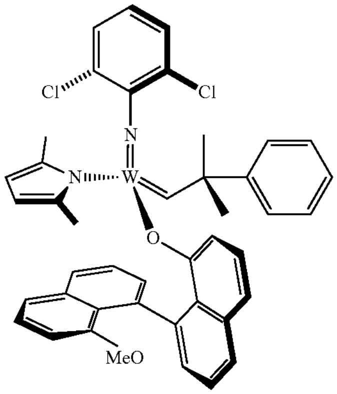
246
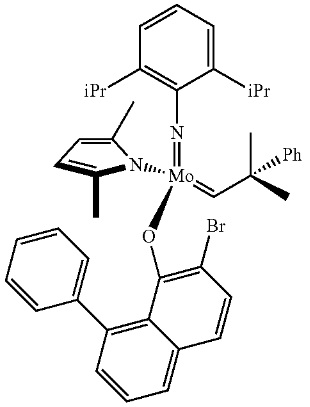
261
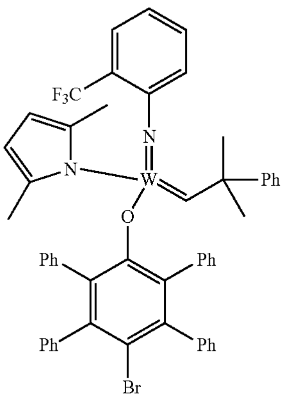
-continued
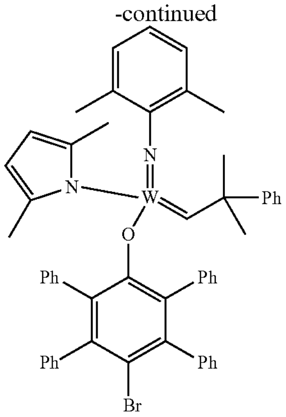
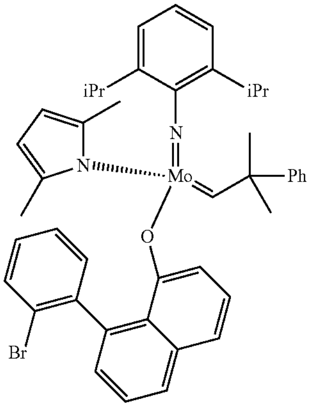
and
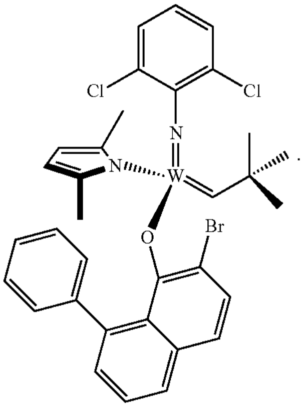
* * * * *

UNITED STATES PATENT AND TRADEMARK OFFICE

CERTIFICATE OF CORRECTION

PATENT NO. : 9,919,299 B2
APPLICATION NO. : 14/774404
DATED : March 20, 2018
INVENTOR(S) : Levente Ondi et al.

It is certified that error appears in the above-identified patent and that said Letters Patent is hereby corrected as shown below:

In the Specification

Column 85, Line 16 reads, "... preferably 1 to 0.2" which should read, "... preferably 1 to 2"

Column 99, Line 16 reads, "... or W; is selected ..." which should read, "... or W; $R^1$ is selected ..."

Column 100, Lines 32-33 read, "... 6-dimesityiphenoxy, ..." which should read, "... 6-dimesitylphenoxy, ..."

Column 105, Line 24 reads, "... 6- and 5-position, ..." which should read, "... 3- and 5-position, ..."

Column 108, Line 46 reads, "... 2-, band 4-position ..." which should read, "... 2-, 6- and 4-position, ..."

Column 111, Line 22 reads, "... [8-(naphthalene-1-yl)naphthalene-1-yl]oxy, ..." which should read, "... [8-(naphthalene-1-yl)-naphthalene-1-yl]oxy, ..."

Column 114, Line 13 delete the line break after "substituted"

Column 116, Line 45 reads, "... may have a conjugated u electron system, ..." which should read, "... may have a conjugated π electron system, ..."

Column 118, Line 31 reads, "... 6-tetraphenyithiophenoxy ..." which should read, "... 6-tetraphenylthiophenoxy ..."

Column 125, Line 28 reads, "... (10" which should read, "... (1L)"

Signed and Sealed this
Third Day of July, 2018

Andrei Iancu
*Director of the United States Patent and Trademark Office*